US011490995B2

(12) United States Patent
Wratten, Jr. et al.

(10) Patent No.: US 11,490,995 B2
(45) Date of Patent: Nov. 8, 2022

(54) ORTHODONTIC TREATMENT AND ASSOCIATED DEVICES, SYSTEMS, AND METHODS

(71) Applicant: Brius Technologies, Inc., Carrollton, TX (US)

(72) Inventors: James Sylvester Wratten, Jr., Waterville, NY (US); Seyed Mehdi Roein Peikar, Addison, TX (US)

(73) Assignee: Brius Technologies, Inc., Carrollton, TX (US)

(*) Notice: Subject to any disclaimer, the term of this patent is extended or adjusted under 35 U.S.C. 154(b) by 0 days.

(21) Appl. No.: 17/518,549

(22) Filed: Nov. 3, 2021

(65) Prior Publication Data

US 2022/0304774 A1 Sep. 29, 2022

Related U.S. Application Data

(60) Provisional application No. 63/165,747, filed on Mar. 25, 2021.

(30) Foreign Application Priority Data

May 1, 2021 (WO) ................ PCT/US2021/030377

(51) Int. Cl.
*A61C 7/00* (2006.01)
*A61C 7/14* (2006.01)

(52) U.S. Cl.
CPC .............. *A61C 7/002* (2013.01); *A61C 7/145* (2013.01)

(58) Field of Classification Search
CPC ................................................. A61C 7/002
See application file for complete search history.

(56) References Cited

U.S. PATENT DOCUMENTS

| 659,577 A | 10/1900 | Cederstrom |
| 1,292,702 A | 1/1919 | Canning |

(Continued)

FOREIGN PATENT DOCUMENTS

| CA | 2511247 C | 6/2009 |
| CN | 201079455 Y | 7/2008 |

(Continued)

OTHER PUBLICATIONS

International Preliminary Report on Patentability dated Jun. 21, 2018, International Application No. PCT/US2016/065174, 10pages.

(Continued)

*Primary Examiner* — Ralph A Lewis
(74) *Attorney, Agent, or Firm* — Fortem IP LLP; Katrina Marcelo; Mary Fox

(57) ABSTRACT

Devices, systems, and methods for orthodontic treatment planning and orthodontic treatment are disclosed herein. Various embodiments of the present technology, for example, are directed to a method of obtaining data characterizing movements of a patient's teeth from original positions to desired, final positions. In some embodiments, the method can include identifying one or more components of the movements, evaluating the movements, and/or modifying the movements. A method in accordance with several embodiments of the present technology can comprise obtaining an orthodontic treatment plan, which can include one or more suggested interventions to accomplish the tooth movements, a design of such intervention(s), and/or other useful information regarding the orthodontic treatment. In some embodiments, a method of the present technology comprises evaluating an orthodontic treatment during and/or after implementation of the treatment, which can include obtaining data characterizing current positions of the patient's teeth. Based on the evaluation, the method can (Continued)

include obtaining another orthodontic treatment plan and movement data characterizing movements of a patient's teeth from their current positions to desired, final positions.

19 Claims, 65 Drawing Sheets

(56) References Cited

U.S. PATENT DOCUMENTS

| | | | |
|---|---|---|---|
| 1,369,665 A | 2/1921 | Johnson | |
| 2,259,160 A | 10/1941 | Glaser | |
| 2,266,860 A | 12/1941 | Griesinger | |
| 2,305,916 A | 12/1942 | Atkinson | |
| 3,235,965 A | 2/1966 | Muir | |
| 3,256,602 A | 6/1966 | Broussard et al. | |
| 3,416,228 A | 12/1968 | Grimmett | |
| 3,505,736 A | 4/1970 | Brader et al. | |
| 3,510,340 A | 5/1970 | Blake et al. | |
| 3,593,421 A | 7/1971 | Brader | |
| 3,618,214 A | 11/1971 | Armstrong | |
| 3,738,005 A | 6/1973 | Cohen et al. | |
| 3,762,050 A | 10/1973 | Dal | |
| 3,792,529 A | 2/1974 | Goshgarian | |
| 3,815,237 A | 6/1974 | Wallshein | |
| 4,037,324 A | 7/1977 | Andreasen | |
| 4,197,643 A | 4/1980 | Burstone et al. | |
| 4,354,834 A | 10/1982 | Wilson | |
| 4,360,342 A | 11/1982 | Salvo | |
| 4,433,960 A | 2/1984 | Garito et al. | |
| 4,468,196 A | 8/1984 | Keller | |
| 4,479,779 A | 10/1984 | Wool | |
| 4,516,938 A | 5/1985 | Hall | |
| 4,533,320 A | 8/1985 | Piekarsky | |
| 4,571,179 A | 2/1986 | Balenseifen | |
| 4,731,018 A | 3/1988 | Adell | |
| 4,815,968 A | 3/1989 | Keller | |
| 4,932,866 A | 6/1990 | Guis | |
| 4,976,614 A | 12/1990 | Tepper | |
| 5,022,855 A | 6/1991 | Jeckel | |
| 5,120,218 A | 6/1992 | Hanson | |
| 5,167,499 A | 12/1992 | Arndt et al. | |
| 5,255,352 A | 10/1993 | Falk | |
| 5,295,886 A | 3/1994 | Wildman | |
| 5,310,340 A | 5/1994 | Zedda | |
| 5,312,247 A | 5/1994 | Sachdeva et al. | |
| 5,380,197 A | 1/1995 | Hanson | |
| 5,429,501 A | 7/1995 | Farzin-Nia et al. | |
| 5,431,562 A | 7/1995 | Andreiko et al. | |
| 5,435,721 A | 7/1995 | Vogt | |
| 5,536,169 A | 7/1996 | Yousefian | |
| 5,580,243 A | 12/1996 | Bloore | |
| 5,645,423 A | 7/1997 | Collins | |
| 5,791,897 A | 8/1998 | Wildman | |
| 5,829,980 A | 11/1998 | Sheridan et al. | |
| 5,975,893 A | 11/1999 | Chishti et al. | |
| 6,053,730 A | 4/2000 | Cleary | |
| 6,086,364 A | 7/2000 | Brunson | |
| 6,174,163 B1 | 1/2001 | Hiro | |
| 6,190,166 B1 | 2/2001 | Sasakura | |
| 6,220,856 B1 | 4/2001 | Carano et al. | |
| 6,254,384 B1 | 7/2001 | Rosenberg | |
| 6,302,688 B1 | 10/2001 | Jordan et al. | |
| 6,406,292 B1 | 6/2002 | Chishti et al. | |
| 6,471,511 B1 * | 10/2002 | Chishti | A61C 7/00 |
| 6,582,226 B2 | 6/2003 | Jordan et al. | |
| 6,685,469 B2 | 2/2004 | Chishti et al. | |
| 6,688,886 B2 * | 2/2004 | Hughes | A61C 7/00 |
| | | | 433/24 |
| 6,732,558 B2 | 5/2004 | Butscher et al. | |
| 6,739,870 B2 | 5/2004 | Lai et al. | |
| 6,755,064 B2 | 6/2004 | Butscher et al. | |
| 6,860,132 B2 | 3/2005 | Butscher et al. | |
| 6,884,067 B2 | 4/2005 | Tuneberg | |
| 6,908,306 B2 | 6/2005 | Bowman et al. | |
| 6,928,733 B2 | 8/2005 | Rubbert et al. | |
| 6,935,858 B2 | 8/2005 | Cleary | |
| 6,984,127 B2 | 1/2006 | Lai | |
| 7,020,963 B2 | 4/2006 | Cleary et al. | |
| 7,056,115 B2 | 6/2006 | Phan et al. | |
| 7,063,531 B2 | 6/2006 | Maijer et al. | |
| 7,074,039 B2 * | 7/2006 | Kopelman | A61C 7/00 |
| | | | 433/213 |
| 7,076,980 B2 | 7/2006 | Butscher et al. | |
| 7,077,647 B2 | 7/2006 | Choi et al. | |
| 7,112,065 B2 | 9/2006 | Kopelman et al. | |
| 7,131,836 B1 | 11/2006 | Kesling | |
| 7,156,661 B2 * | 1/2007 | Choi | A61C 7/002 |
| | | | 433/213 |
| 7,210,929 B2 | 5/2007 | Raby et al. | |
| 7,234,934 B2 | 6/2007 | Rosenberg | |
| 7,240,528 B2 | 7/2007 | Weise et al. | |
| 7,283,891 B2 | 10/2007 | Butscher et al. | |
| 7,291,011 B2 | 11/2007 | Stark et al. | |
| 7,335,021 B2 | 2/2008 | Nikodem | |
| 7,347,688 B2 | 3/2008 | Kopelman et al. | |
| 7,354,268 B2 | 4/2008 | Raby et al. | |
| 7,357,634 B2 | 4/2008 | Knopp | |
| 7,377,778 B2 | 5/2008 | Chishti et al. | |
| 7,416,407 B2 | 8/2008 | Cronauer | |
| 7,433,810 B2 | 10/2008 | Pavloskaia et al. | |
| 7,556,496 B2 | 7/2009 | Cinader et al. | |
| 7,578,673 B2 | 8/2009 | Wen et al. | |
| 7,580,846 B2 | 8/2009 | Chishti et al. | |
| 7,600,999 B2 | 10/2009 | Knopp | |
| 7,613,527 B2 | 11/2009 | Raby et al. | |
| 7,641,473 B2 | 1/2010 | Sporbert et al. | |
| 7,658,610 B2 | 2/2010 | Knopp | |
| 7,708,557 B2 | 5/2010 | Rubber | |
| 7,726,968 B2 | 6/2010 | Raby et al. | |
| 7,837,466 B2 | 11/2010 | Griffith et al. | |
| 7,837,469 B2 | 11/2010 | Chishti et al. | |
| 7,844,356 B2 | 11/2010 | Matov et al. | |
| 7,869,983 B2 | 1/2011 | Raby et al. | |
| 7,878,804 B2 | 2/2011 | Korytov et al. | |
| 7,880,751 B2 | 2/2011 | Kuo et al. | |
| 7,904,308 B2 | 3/2011 | Arnone et al. | |
| 7,930,189 B2 | 4/2011 | Kuo | |
| 7,940,258 B2 | 5/2011 | Stark et al. | |
| 7,987,099 B2 | 7/2011 | Kuo et al. | |
| 7,993,133 B2 | 8/2011 | Cinader et al. | |
| RE42,815 E | 10/2011 | Rubbert et al. | |
| 3,075,306 A1 | 12/2011 | Kitching et al. | |
| 3,092,215 A1 | 1/2012 | Stone-Collonge et al. | |
| 3,131,393 A1 | 3/2012 | Matov et al. | |
| 8,192,196 B2 | 6/2012 | Singh | |
| 8,194,067 B2 | 6/2012 | Raby et al. | |
| 8,266,940 B2 | 9/2012 | Riemeier et al. | |
| 8,292,617 B2 | 10/2012 | Brandt et al. | |
| 8,308,478 B2 | 11/2012 | Primus et al. | |
| 8,326,647 B2 | 12/2012 | Chishti et al. | |
| 8,356,993 B1 | 1/2013 | Marston | |
| 8,382,917 B2 | 2/2013 | Johnson | |
| 8,401,686 B2 | 3/2013 | Moss et al. | |
| 8,417,366 B2 | 4/2013 | Getto et al. | |
| 8,439,673 B2 | 5/2013 | Korytov et al. | |
| 8,496,473 B2 | 7/2013 | Phan et al. | |
| 8,517,726 B2 | 8/2013 | Kakavand et al. | |
| 8,517,727 B2 | 8/2013 | Raby et al. | |
| 8,529,253 B2 | 9/2013 | Jasper | |
| 8,545,221 B2 | 10/2013 | Stone-Collonge et al. | |
| 8,562,338 B2 | 10/2013 | Kitching et al. | |
| 8,573,972 B2 | 11/2013 | Matov et al. | |
| 8,591,225 B2 | 11/2013 | Wu et al. | |
| RE44,668 E | 12/2013 | Rubbert et al. | |
| 8,606,598 B2 | 12/2013 | Chishti et al. | |
| 8,636,510 B2 | 1/2014 | Kitching et al. | |
| 8,651,859 B2 | 2/2014 | Chishti et al. | |
| 8,685,184 B2 | 4/2014 | Johnson et al. | |
| 8,734,149 B2 | 5/2014 | Phan et al. | |
| 8,801,633 B2 | 8/2014 | Fox et al. | |
| 8,827,697 B2 | 9/2014 | Cinader et al. | |
| 8,899,978 B2 | 12/2014 | Kitching et al. | |
| 8,932,054 B1 | 1/2015 | Rosenberg | |

(56) References Cited

U.S. PATENT DOCUMENTS

| | | |
|---|---|---|
| 8,944,812 B2 | 2/2015 | Kuo |
| 8,992,215 B2 | 3/2015 | Chapoulaud et al. |
| 9,017,070 B2 | 4/2015 | Parker |
| 9,017,072 B2 | 4/2015 | Kitching et al. |
| 9,060,829 B2 | 6/2015 | Sterental et al. |
| 9,061,124 B2 | 6/2015 | Fox et al. |
| 9,127,338 B2 | 9/2015 | Johnson |
| 9,144,472 B2 * | 9/2015 | Isaacson ............... A61C 7/002 |
| 9,149,344 B2 | 10/2015 | Gautam |
| 9,161,823 B2 * | 10/2015 | Morton .................. A61C 7/00 |
| 9,168,113 B2 | 10/2015 | Wu et al. |
| 9,204,942 B2 | 12/2015 | Phan et al. |
| 9,220,580 B2 | 12/2015 | Borovinskih et al. |
| 9,271,809 B2 | 3/2016 | Korytov et al. |
| 9,320,575 B2 | 4/2016 | Chishti et al. |
| 9,326,831 B2 | 5/2016 | Cheang |
| 9,328,406 B2 | 5/2016 | Johnson et al. |
| 9,364,297 B2 | 6/2016 | Kitching et al. |
| 9,375,300 B2 | 6/2016 | Matov et al. |
| 9,427,291 B2 | 8/2016 | Khoshnevis et al. |
| 9,433,479 B2 | 9/2016 | Phan et al. |
| 9,492,245 B2 | 11/2016 | Sherwood et al. |
| 9,498,302 B1 | 11/2016 | Patel |
| 9,504,544 B2 | 11/2016 | Conley et al. |
| 9,532,854 B2 | 1/2017 | Cinader et al. |
| 9,554,875 B2 | 1/2017 | Gualano |
| 9,566,132 B2 | 2/2017 | Stone-Collonge et al. |
| 9,566,133 B2 | 2/2017 | Vu |
| 9,572,971 B2 | 2/2017 | Su |
| 9,610,628 B2 | 4/2017 | Riemeier et al. |
| 9,642,678 B2 | 5/2017 | Kuo |
| 9,707,054 B2 | 7/2017 | Chishti et al. |
| 9,757,211 B2 | 9/2017 | Ward |
| 9,770,217 B2 | 9/2017 | Sandholm et al. |
| 9,844,420 B2 | 12/2017 | Cheang |
| 9,925,019 B2 | 3/2018 | Cinader et al. |
| 9,925,025 B2 | 3/2018 | Conley et al. |
| 9,937,018 B2 | 4/2018 | Martz et al. |
| 10,022,204 B2 | 7/2018 | Cheang |
| 10,052,174 B2 | 8/2018 | Kitching et al. |
| 10,154,890 B2 | 12/2018 | Johnson et al. |
| 10,226,312 B2 | 3/2019 | Khoshnevis et al. |
| 10,231,801 B2 | 3/2019 | Korytov et al. |
| 10,248,883 B2 | 4/2019 | Borovinskih et al. |
| 10,278,791 B2 | 5/2019 | Schumacher |
| 10,342,638 B2 * | 7/2019 | Kitching ................. A61C 7/00 |
| 10,363,116 B2 | 7/2019 | Boronkay |
| 10,368,960 B2 | 8/2019 | Wu et al. |
| 10,383,707 B2 | 8/2019 | Roein Peikar et al. |
| 10,413,385 B2 | 9/2019 | Sherwood et al. |
| 10,413,386 B2 | 9/2019 | Moon et al. |
| 10,512,524 B2 | 12/2019 | Kuo |
| 10,517,696 B2 | 12/2019 | Kitching et al. |
| 10,548,690 B2 * | 2/2020 | Wen ....................... G16H 30/20 |
| 10,610,332 B2 | 4/2020 | Wu et al. |
| 10,624,716 B2 | 4/2020 | Kitching et al. |
| 10,758,321 B2 | 9/2020 | Stone-Collonge et al. |
| 10,792,127 B2 | 10/2020 | Kopelman et al. |
| 10,799,321 B2 * | 10/2020 | Salah .................... A61B 5/6898 |
| 10,813,721 B2 | 10/2020 | Sterental et al. |
| 10,905,527 B2 | 2/2021 | Roein Peikar et al. |
| 10,980,614 B2 | 4/2021 | Roein Peikar et al. |
| 10,993,785 B2 | 5/2021 | Roein Peikar et al. |
| 11,000,350 B2 | 5/2021 | Kuo |
| 11,024,431 B2 | 6/2021 | Stone-Collonge et al. |
| 11,042,774 B2 | 6/2021 | Borovinskih et al. |
| 11,058,518 B2 | 7/2021 | Roein Peikar et al. |
| 11,071,608 B2 | 7/2021 | Derakhshan et al. |
| 11,096,763 B2 | 8/2021 | Akopov et al. |
| 11,317,994 B2 | 5/2022 | Roein Peikar et al. |
| 11,317,995 B2 | 5/2022 | Roein Peikar et al. |
| 11,324,572 B2 | 5/2022 | Roein Peikar et al. |
| 2003/0075186 A1 | 4/2003 | Florman |
| 2003/0096210 A1 | 5/2003 | Rubbert et al. |
| 2004/0009449 A1 | 1/2004 | Mah et al. |
| 2004/0048222 A1 | 3/2004 | Forster et al. |
| 2004/0067463 A1 | 4/2004 | Rosenberg |
| 2004/0072120 A1 | 4/2004 | Lauren |
| 2004/0131989 A1 | 7/2004 | Dellinger |
| 2005/0048432 A1 | 3/2005 | Choi et al. |
| 2005/0130094 A1 | 6/2005 | Graham |
| 2005/0227196 A1 | 10/2005 | Von |
| 2005/0244780 A1 | 11/2005 | Abels et al. |
| 2006/0073436 A1 | 4/2006 | Raby et al. |
| 2006/0234179 A1 | 10/2006 | Wen et al. |
| 2008/0032258 A1 | 2/2008 | Kyung et al. |
| 2008/0057460 A1 | 3/2008 | Hicks |
| 2008/0254403 A1 | 10/2008 | Hilliard |
| 2008/0311535 A1 | 12/2008 | Andreiko |
| 2009/0098500 A1 | 4/2009 | Diaz |
| 2010/0068671 A1 | 3/2010 | Kakavand et al. |
| 2010/0075268 A1 | 3/2010 | Duran |
| 2010/0279245 A1 | 11/2010 | Navarro |
| 2011/0027743 A1 | 2/2011 | Cinader et al. |
| 2011/0269095 A1 | 11/2011 | Singh |
| 2012/0015316 A1 | 1/2012 | Sachdeva et al. |
| 2012/0048432 A1 | 3/2012 | Johnson et al. |
| 2012/0123577 A1 | 5/2012 | Chapoulaud et al. |
| 2012/0225398 A1 | 9/2012 | Fallah |
| 2012/0322019 A1 | 12/2012 | Lewis |
| 2014/0120491 A1 | 5/2014 | Khoshnevis et al. |
| 2014/0154637 A1 | 6/2014 | Hansen et al. |
| 2014/0302448 A1 | 10/2014 | Cassalia |
| 2014/0356799 A1 | 12/2014 | Cinader et al. |
| 2015/0157421 A1 | 6/2015 | Martz et al. |
| 2015/0245888 A1 | 9/2015 | Hasegawa |
| 2015/0257856 A1 | 9/2015 | Martz et al. |
| 2016/0058527 A1 | 3/2016 | Schumacher |
| 2016/0095670 A1 | 4/2016 | Witte et al. |
| 2016/0095672 A1 | 4/2016 | Izadi |
| 2016/0106520 A1 | 4/2016 | Borovinskih et al. |
| 2016/0135925 A1 * | 5/2016 | Mason ..................... A61C 7/08 703/2 |
| 2016/0135926 A1 | 5/2016 | Djamchidi |
| 2016/0302890 A1 | 10/2016 | Hamilton |
| 2016/0324601 A1 | 11/2016 | Phan et al. |
| 2016/0346064 A1 | 12/2016 | Schulhof et al. |
| 2017/0007365 A1 | 1/2017 | Kopelman et al. |
| 2017/0100215 A1 | 4/2017 | Khouri |
| 2017/0156823 A1 | 6/2017 | Roein Peikar et al. |
| 2017/0296304 A1 | 10/2017 | Tong et al. |
| 2018/0014916 A1 | 1/2018 | Cinader et al. |
| 2018/0021108 A1 | 1/2018 | Cinader et al. |
| 2018/0049847 A1 | 2/2018 | Oda et al. |
| 2018/0071057 A1 | 3/2018 | Rudman |
| 2018/0142377 A1 | 5/2018 | Gao et al. |
| 2018/0153651 A1 | 6/2018 | Tong et al. |
| 2018/0185125 A1 | 7/2018 | Salah et al. |
| 2018/0189434 A1 | 7/2018 | Zhou et al. |
| 2018/0221113 A1 | 8/2018 | Tong et al. |
| 2018/0303583 A1 | 10/2018 | Tong et al. |
| 2018/0338564 A1 | 11/2018 | Oda et al. |
| 2018/0353265 A1 | 12/2018 | Paehl et al. |
| 2019/0015178 A1 | 1/2019 | Wiechmann |
| 2019/0069974 A1 | 3/2019 | Schumacher |
| 2019/0090985 A1 | 3/2019 | Jo |
| 2019/0090988 A1 | 3/2019 | Schumacher et al. |
| 2019/0321136 A1 | 10/2019 | Martz et al. |
| 2019/0321138 A1 | 10/2019 | Roein Peikar et al. |
| 2020/0078140 A1 | 3/2020 | Roein Peikar et al. |
| 2020/0085540 A1 | 3/2020 | Roein Peikar et al. |
| 2020/0085541 A1 | 3/2020 | Roein Peikar et al. |
| 2020/0093569 A1 | 3/2020 | Kitching et al. |
| 2020/0100866 A1 | 4/2020 | Medvinskaya et al. |
| 2020/0107911 A1 | 4/2020 | Roein Peikar |
| 2020/0129272 A1 | 4/2020 | Roein Peikar et al. |
| 2020/0345455 A1 | 11/2020 | Roein Peikar et al. |
| 2020/0345460 A1 | 11/2020 | Roein Peikar et al. |
| 2020/0375699 A1 | 12/2020 | Roein Peikar et al. |
| 2020/0390524 A1 | 12/2020 | Roein Peikar et al. |
| 2021/0007830 A1 | 1/2021 | Roein Peikar et al. |
| 2021/0007832 A1 | 1/2021 | Roein Peikar et al. |
| 2021/0169616 A1 | 6/2021 | Jo |
| 2021/0177551 A1 | 6/2021 | Roein Peikar et al. |

(56) References Cited

U.S. PATENT DOCUMENTS

| | | |
|---|---|---|
| 2021/0186662 A1 | 6/2021 | Roein Peikar et al. |
| 2021/0353389 A1 | 11/2021 | Roein Peikar et al. |
| 2022/0015868 A1 | 1/2022 | Mason et al. |
| 2022/0023009 A1 | 1/2022 | Tong et al. |
| 2022/0054232 A1 | 2/2022 | Wen et al. |
| 2022/0226076 A1 | 7/2022 | Roein Peikar et al. |
| 2022/0226077 A1 | 7/2022 | Roein Peikar et al. |

FOREIGN PATENT DOCUMENTS

| | | |
|---|---|---|
| CN | 101277658 A | 10/2008 |
| CN | 104146786 A | 11/2014 |
| CN | 104887332 A | 9/2015 |
| CN | 106491221 A | 3/2017 |
| CN | 207949917 U | 10/2018 |
| DE | 102015009345 A1 | 1/2016 |
| EP | 0400932 A3 | 1/1991 |
| EP | 0551800 A1 | 7/1993 |
| EP | 1379193 B1 | 2/2007 |
| EP | 1301140 B1 | 11/2010 |
| GB | 974100 A | 11/1964 |
| GB | 2521046 A | 6/2015 |
| JP | H0634607 U | 5/1994 |
| JP | H08280711 A | 10/1996 |
| JP | 2002102256 A | 4/2002 |
| JP | 2003204973 A | 7/2003 |
| JP | 2005110830 A | 4/2005 |
| JP | 2005177161 A | 7/2005 |
| JP | 2006246978 A | 9/2006 |
| JP | 2009504247 A | 2/2009 |
| JP | 2011517603 A | 6/2011 |
| KR | 20180107481 A | 10/2018 |
| SU | 1502023 A1 | 8/1989 |
| WO | 01/80761 A2 | 11/2001 |
| WO | 2007021468 A2 | 2/2007 |
| WO | 2009126433 A2 | 10/2009 |
| WO | 2010146192 A1 | 12/2010 |
| WO | 2011103669 A1 | 9/2011 |
| WO | 2014088422 A1 | 6/2014 |
| WO | 2014140013 A1 | 9/2014 |
| WO | 2015032918 A1 | 3/2015 |
| WO | 2016149007 A1 | 9/2016 |
| WO | 2016149008 A1 | 9/2016 |
| WO | 2017100198 A1 | 6/2017 |
| WO | 2018215863 A1 | 11/2018 |
| WO | 2019043005 A1 | 3/2019 |
| WO | 2019064127 A1 | 4/2019 |
| WO | 2020069446 A1 | 4/2020 |
| WO | 2020223714 A1 | 11/2020 |
| WO | 2020223744 A1 | 11/2020 |
| WO | 2020223745 A1 | 11/2020 |
| WO | 2020223745 A9 | 11/2020 |
| WO | 2021225916 A2 | 11/2021 |
| WO | 2021225916 A3 | 11/2021 |
| WO | 2021226618 A1 | 11/2021 |

OTHER PUBLICATIONS

International Search Report and Written Opinion dated Aug. 6, 2020, International Application No. PCT/US2020/031211, 28 pages.
International Search Report and Written Opinion dated Aug. 26, 2020, International Application No. PCT/US2020/070017, 12 pages.
International Search Report and Written Opinion dated Jul. 19, 2021, International Application No. PCT/US2021/070469, 14 pages.
International Search Report and Written Opinion dated Mar. 13, 2017, International Application No. PCT/US2016/065174, 13 pages.
International Search Report and Written Opinion dated Nov. 11, 2021, International Application No. PCT/US2021/030377, 24 pages.
International Search Report and Written Opinion dated Oct. 8, 2020, International Application No. PCT/US2020/070016, 18 pages.
Baron Pascal, et al., "Customized Brackets and the Straight Arch Technique Combined in One Appliance to Simplify Lingual Orthodontics", J. Dentofacial Anom Orthod, 2012, pp. 1-16.
Faber Zackary, "Incognito Customized Orthodontic Appliance: A Giant Leap Forward in Orthodontic Technology", Dentistry iQ, 2012, pp. 1-5.
Gracco Antonio, et al., "The Insignia System of Customized Orthodontics", JCO, Inc., 2011, pp. 442-451.
Khosravi, Rooz , "Biomechanics in lingual orthodontics: What the future holds", Seminars in Orthodontics, vol. 24, No. 3, 2018, pp. 363-371.
Kusy Robert, "Orthodontic Biomaterials: From the Past to the Present", The Angle Orthodontist, 2002, pp. 501-512.
Mankar Mugdha, et al., "Precision Multiloop (PM Design) with Space Closing Circles for Lingual Orhodontics", Journal of Indian Orthodontic Society, 2016, pp. S88-S93.
Miura Fujio, et al., "New Application of Superelastic NiTi Rectangular Wire", J. Clin. Orthod., 1990, pp. 544-548.
Raboud D.W., "Superelastic Response to NiTi Shape Memory Alloy Wires for Orthodontic Applications", Smart Materials and Stuctures, 2000, pp. 684-692.
Ribeiro Gerson Luiz Ulema, et al., "Multiloop Edgewise Archwire in the Treatment of a Patient with an Anterior Open Bite and a Long Face", American Journal of Orthodontics and Dentofacial Orthopedics, 2010, pp. 89-95.
Sanjay N., et al., "Space Closure with Loop Mechanics for Treatment of Bimaxillary Protrusion: A Case Report", Journal of International Oral Health, 2015, pp. 65-67.
Siatkowski Raymond, "Continuous Arch Wire Closing Loop Design, Optimization, and Verification. Part I", American Journal of Orthodontics and Dentofacial Orthopedics, 1997, pp. 393-408.
Teramoto Alberto, "SENTALLOY the Story of Superelasticity", Materials Science, 2012, pp. 1-12.
Viecilli Amanda, et al., "The T-Loop in Details", Dental Press J. Orthod., 2018, pp. 108-117.
Werner Alison, "MEAW Therapy", Orthodontic Products, https://orthodonticproductsonline.com/clinical-tips/meaw-therapy/, 2012, pp. 1-7.
Wiechmann Dirk, et al., "Customized Brackets and Archwire for Lingual Orthodontic Treatment", American Journal of Orthodontics and Dentofacial Orthopedics, 2003, pp. 593-599.
Yang Won-Sik, et al., "A Study of the Regional Load Deflection Rate of Multiloop Edgewise Arch Wire", The Angle Orthodontist, 2001, pp. 103-109.
KR20180107481A (Yoon Sung Hee; Oh Yoon Joon) (Biocetec Co Ltd) Self ligation orthodontic bracket assembly, Oct. 2, 2018. [retrieved on May 26, 2022], Translation retrieved from: Espacenet (Year: 2018).

* cited by examiner

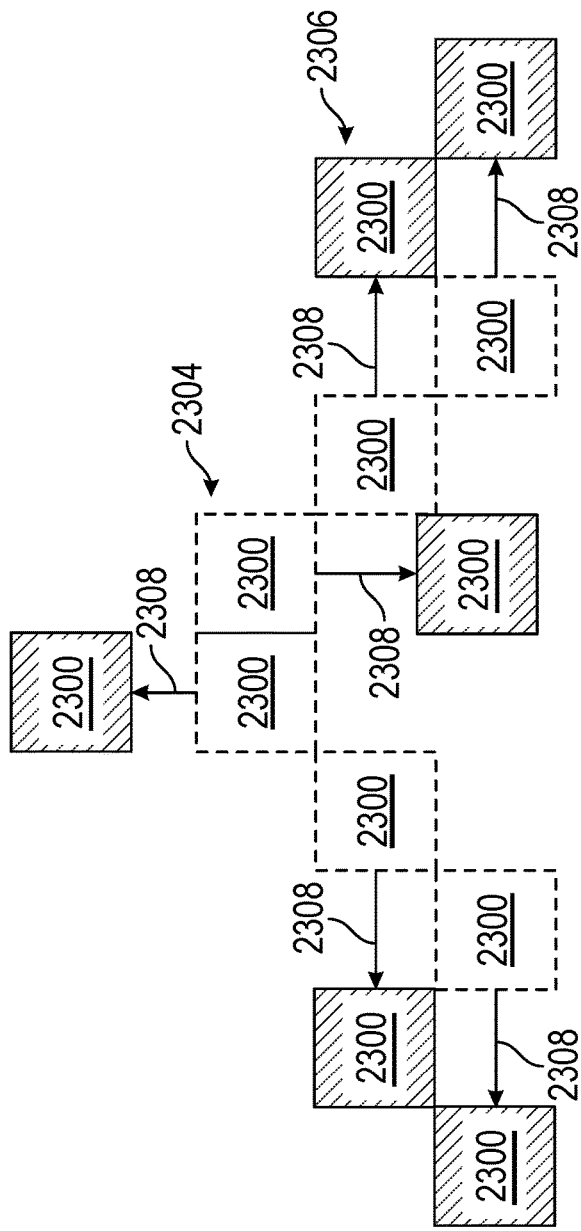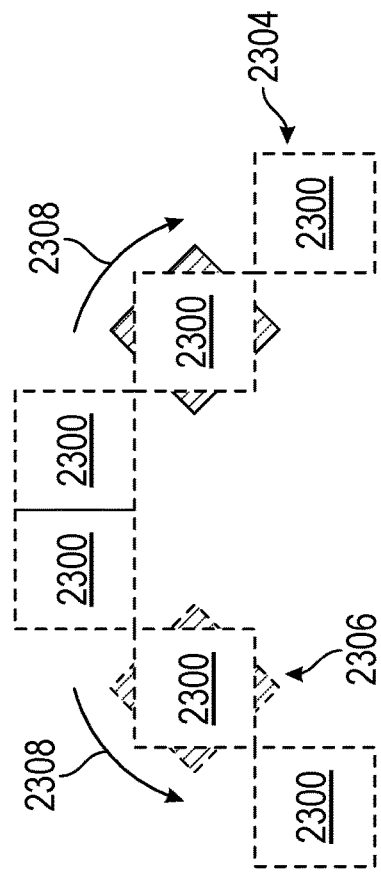
FIG. 23A
FIG. 23B

Anterior ←-------------→ Posterior

Posterior ◄-------------------------------► Anterior
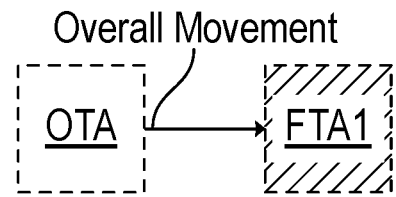
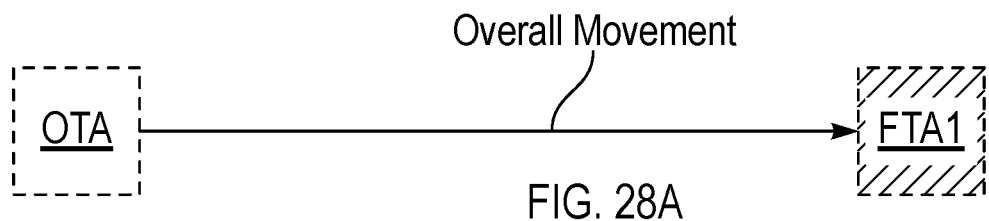
FIG. 28A
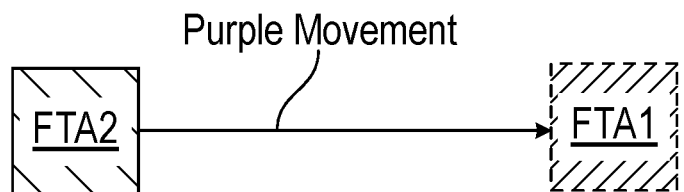
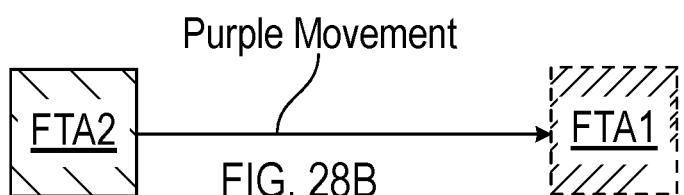
FIG. 28B
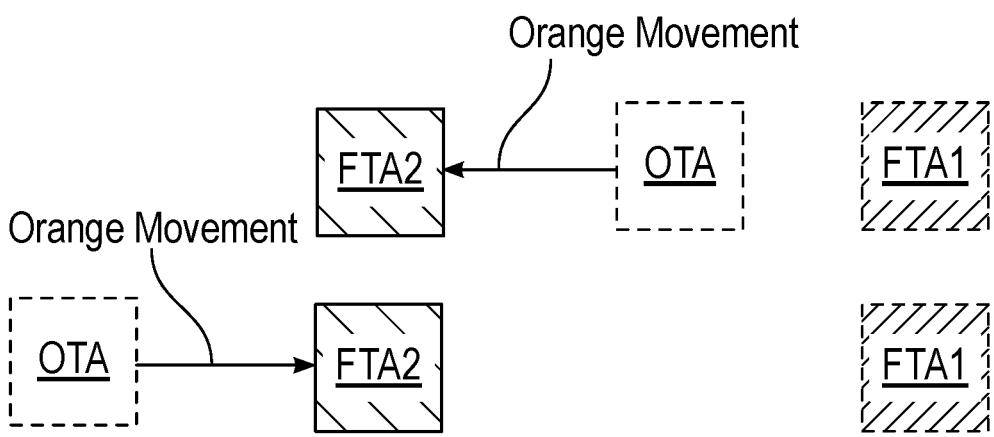
FIG. 28C

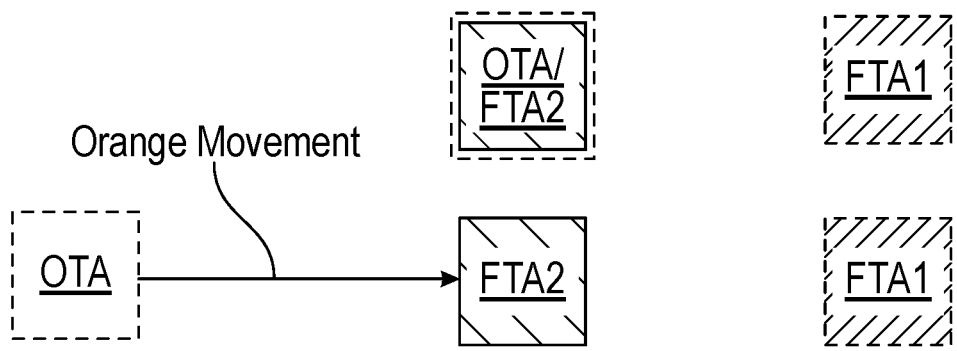
FIG. 29A
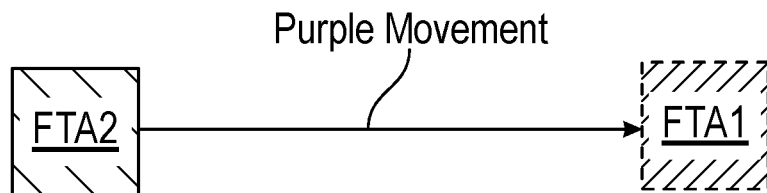
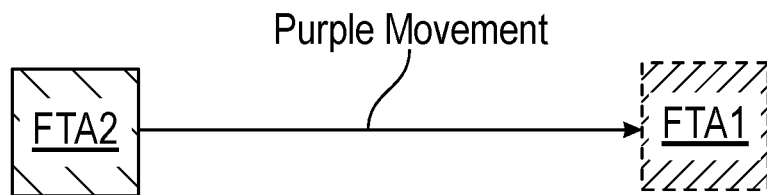
FIG. 29B
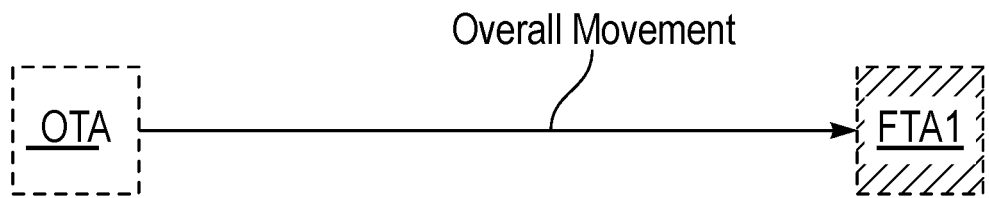
FIG. 29C

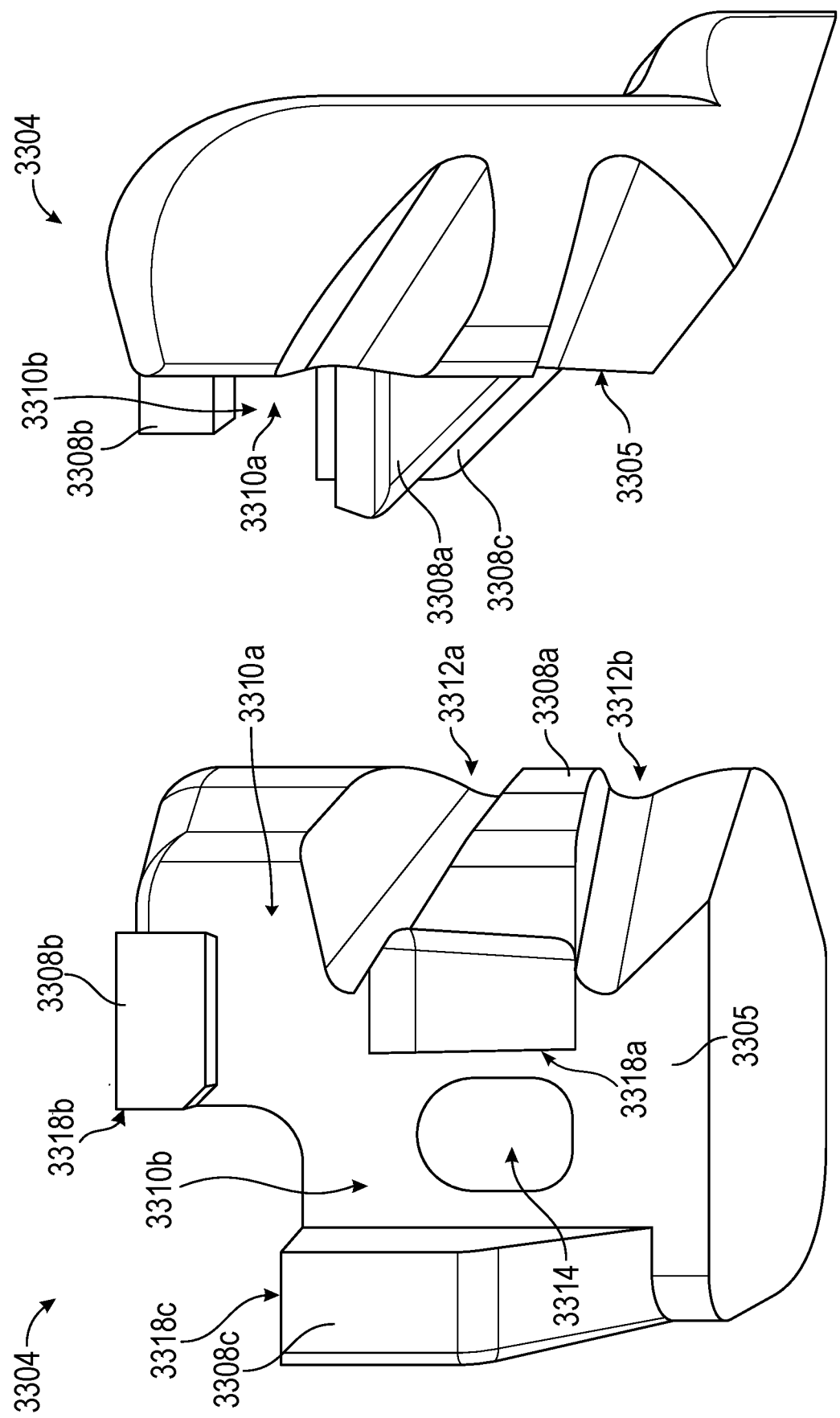

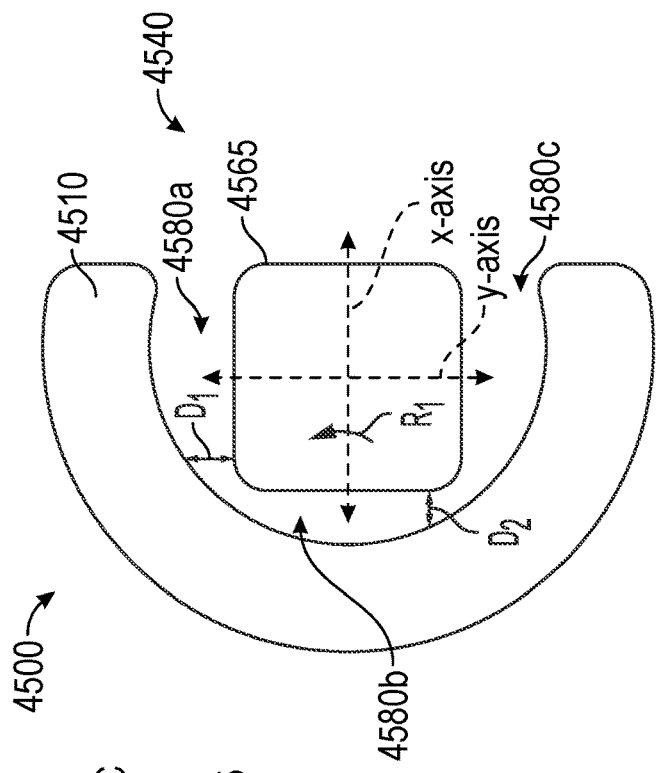
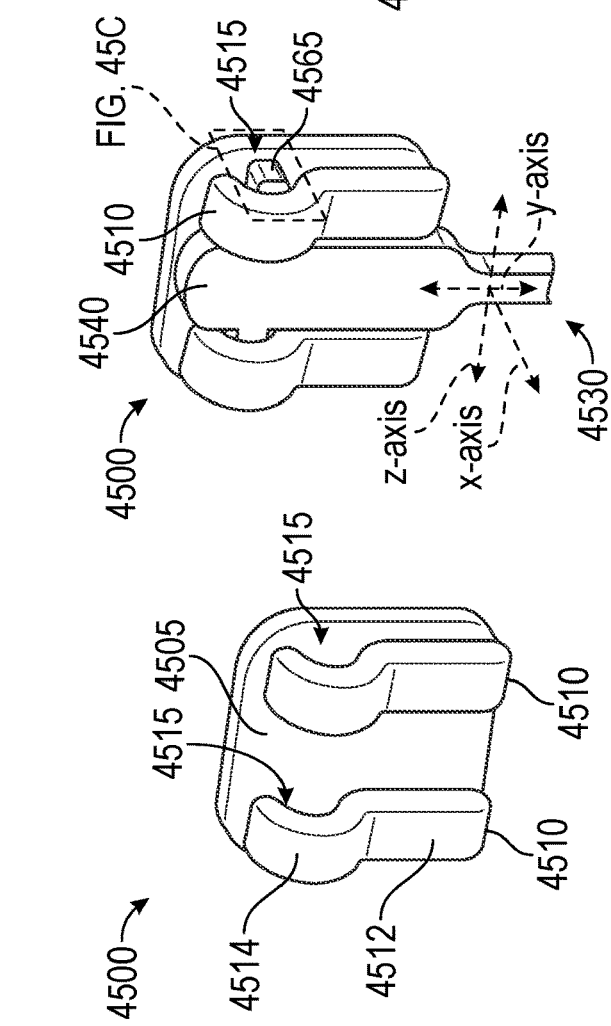
FIG. 45C
FIG. 45B
FIG. 45A

ORTHODONTIC TREATMENT AND ASSOCIATED DEVICES, SYSTEMS, AND METHODS

CROSS-REFERENCE TO RELATED APPLICATION(S)

The present application claims the benefit of priority to International Patent Application No. PCT/US21/30377, titled DENTAL APPLIANCES AND ASSOCIATED METHODS OF MANUFACTURING, filed May 1, 2021, and U.S. Provisional Patent Application No. 63/165,747, titled ORTHODONTIC TREATMENT PLANNING AND ASSOCIATED DEVICES, SYSTEMS, AND METHODS, filed Mar. 25, 2021, each of which is incorporated by reference herein in its entirety.

The present application is related to the following applications, each of which is incorporated by reference herein in its entirety: U.S. Provisional Patent Application No. 62/842,391, filed May 2, 2019; U.S. patent application Ser. No. 16/865,323, titled DENTAL APPLIANCES, SYSTEMS AND METHODS, filed May 2, 2020; International Patent Application No. PCT/US20/31211, titled DENTAL APPLIANCES, SYSTEMS AND METHODS, filed May 2, 2020; U.S. Provisional Patent Application No. 62/956,290, filed Jan. 1, 2020; U.S. patent application Ser. No. 15/929,443, titled DENTAL APPLIANCES AND ASSOCIATED SYSTEMS AND METHODS OF USE, filed May 2, 2020; U.S. patent application Ser. No. 15/929,444, titled DENTAL APPLIANCES AND ASSOCIATED SYSTEMS AND METHODS OF USE, filed May 2, 2020; U.S. Patent Application No. PCT/US20/70017, titled DENTAL APPLIANCES AND ASSOCIATED SYSTEMS AND METHODS OF USE, filed May 2, 2020; U.S. patent application Ser. No. 15/929,442, titled DENTAL APPLIANCES AND ASSOCIATED METHODS OF MANUFACTURING, filed May 2, 2020; International Application No. PCT/US20/70016, titled DENTAL APPLIANCES AND ASSOCIATED METHODS OF MANUFACTURING, filed May 2, 2020; U.S. Provisional Patent Application No. 62/704,545, titled DENTAL APPLIANCES AND ASSOCIATED SYSTEMS AND METHODS OF USE, filed May 15, 2020; U.S. patent application Ser. No. 17/302,227, titled DENTAL APPLIANCES AND ASSOCIATED SYSTEMS AND METHODS OF USE, filed Apr. 27, 2021; International Patent Application No. PCT/US21/70469, titled DENTAL APPLIANCES AND ASSOCIATED SYSTEMS AND METHODS OF USE, filed Apr. 27, 2021; U.S. Provisional Patent Application No. 63/275,401, titled DENTAL APPLIANCES AND ASSOCIATED METHODS OF MANUFACTURING, filed concurrently herewith; and U.S. patent application Ser. No. 17/518,547, titled ORTHODONTIC TREATMENT AND ASSOCIATED DEVICES, SYSTEMS, AND METHODS, filed concurrently herewith.

TECHNICAL FIELD

The present technology relates to orthodontic treatment and associated devices, systems, and methods.

BACKGROUND

A common objective in orthodontics is to move a patient's teeth to positions where the teeth function optimally and aesthetically. To move the teeth, the orthodontist may begin by obtaining multiple scans and/or impressions of the patient's teeth to determine a series of corrective paths between the initial positions of the teeth and the desired ending positions. The orthodontist then fits the patient to one of two main appliance types: braces or aligners.

Traditional braces consist of brackets and an archwire placed across a front side of the teeth, with elastic ties or ligature wires to secure the archwire to the brackets. In some cases self-ligating brackets may be used in lieu of ties or wires. The shape and stiffness of the archwire as well as the archwire-bracket interaction governs the forces applied to the teeth and thus the direction and degree of tooth movement. To exert a desired force on the teeth, the orthodontist often manually bends the archwire. The orthodontist monitors the patient's progress through regular appointments, during which the orthodontist visually assesses the progress of the treatment and makes manual adjustments to the archwire (such as new bends) and/or replaces or repositions brackets. The adjustment process is both time consuming and tedious for the patient and more often than not results in patient discomfort for several days following the appointment. Moreover, braces are not aesthetically pleasing and make brushing, flossing, and other dental hygiene procedures difficult.

Aligners comprise clear, removable, polymeric shells having cavities shaped to receive and reposition teeth to produce a final tooth arrangement. Aligners offer patients significantly improved aesthetics over braces. Aligners do not require the orthodontists to bend wires or reposition brackets and are generally more comfortable than braces. However, unlike braces, aligners cannot effectively treat all malocclusions. Certain tooth repositioning steps, such as extrusion, translation, and certain rotations, can be difficult or impossible to achieve with aligners. Moreover, because the aligners are removable, success of treatment is highly dependent on patient compliance, which can be unpredictable and inconsistent.

Lingual braces are an alternative to aligners and traditional (buccal) braces and have been gaining popularity in recent years. Two examples of existing lingual braces are the Incognito™ Appliance System (3M United States) and INBRACE® (Swift Health Systems, Irvine, Calif., USA), each of which consists of brackets and an archwire placed on the lingual, or tongue side, of the teeth. In contrast to traditional braces, lingual braces are virtually invisible, and, unlike aligners, lingual braces are fixed to the patient's teeth and force compliance. These existing lingual technologies, however, also come with several disadvantages. Most notably, conventional lingual appliances still rely on a bracket-archwire system to move the teeth, thus requiring multiple office visits and painful adjustments. For example, lingual technologies have a relatively short inter-bracket distance, which generally makes compliance of the archwire stiffer. As a result, the overall lingual appliance is more sensitive to archwire adjustments and causes more pain for the patient. Moreover, the lingual surfaces of the appliance can irritate the tongue and impact speech, and make the appliance difficult to clean.

Therefore, a need exists for improved orthodontic appliances.

SUMMARY

The present technology is directed to orthodontic treatment and associated devices, systems, and methods. For example, some aspects of the present technology are directed to methods of determining proposed movements of the patient's teeth from original positions (e.g., positions in which the teeth are maloccluded, misaligned, or otherwise in need of orthodontic correction) to final positions (e.g., positions in which occlusion and/or alignment of the patient's teeth is improved). Various embodiments of the present technology are directed to novel methods of evaluating the proposed movements of the patient's teeth. For example, a method in accordance with some embodiments of the present technology includes decomposing overall movements of the patient's teeth into component movements. Such component movements can include movements of all of a patient's teeth within one of the patient's dental arches according to the same transformation, movement of the patient's teeth within one dental arch relative to one another, etc. Moreover, various embodiments of the present technology include methods for modifying the proposed final positions and/or movements of the patient's teeth such that the orthodontic treatment is more realistic, more achievable, faster, less painful, and/or has another more desirable property.

Some aspects of the present technology are directed to methods of obtaining an orthodontic treatment plan. The treatment plan can include final positions of the patient's teeth and/or movements of the patient's teeth. Additionally or alternatively, the treatment plan can include one or more suggestions or indications of orthodontic interventions to accomplish the tooth movements. In some embodiments, the treatment plan includes a design of an appliance configured to accomplish intraarch movements. Various aspects of the present technology are directed to such appliance designs and methods of manufacturing. Moreover, the treatment plan can include useful information such as an estimated duration of the treatment, a complexity of the treatment, a number of orthodontic intervention required, etc. The treatment plan or any portion thereof can be communicated to a human operator (e.g., an orthodontist, a patient, etc.). Once a treatment plan has been generated, reviewed, and/or modified, the treatment can be implemented (e.g., by installation of an appliance in the patient's mouth).

It can be useful to evaluate progress of an orthodontic treatment during and/or after implementation of the orthodontic treatment. For example, an orthodontic treatment can be adjusted if it is determined during the treatment that the patient's teeth are not moving as planned. Additionally or alternatively, if the treatment concludes and the patient's teeth are still misaligned, maloccluded, or otherwise in need of further orthodontic correction, the treatment can be extended and/or a new treatment can be implemented. Various methods of the present technology are directed to evaluating an orthodontic treatment and comprise obtaining data characterizing current positions of the patient's teeth during and/or after implementation of the orthodontic treatment and comparing the current positions to corresponding desired positions of the patient's teeth. In some embodiments, evaluating an orthodontic treatment comprises obtaining an overall displacement of a tooth from its current position to its desired position and decomposing the overall displacement into one or more component displacements, which can be compared to planned component displacements associated with movement of the tooth from its original position to its desired position. Based on an evaluation of an orthodontic treatment, further repositioning of the patient's teeth may be beneficial and/or necessary to accomplish certain objectives of the treatment (e.g., improved aesthetics, improved occlusion of the patient's teeth, etc.). Various embodiments of the present technology are directed to methods of obtaining a treatment plan and/or planned movements of a patient's teeth from their current positions following a first orthodontic treatment to desired positions following an additional orthodontic treatment. In some embodiments, the desired positions of the patient's teeth after the additional orthodontic treatment may be the same as the originally planned desired positions.

The subject technology is illustrated, for example, according to various aspects described below, including with reference to FIGS. 1A-58. Various examples of aspects of the subject technology are described as numbered clauses (1, 2, 3, etc.) for convenience. These are provided as examples and do not limit the subject technology.

1. A method of obtaining an orthodontic treatment plan for a patient, the method comprising:
   obtaining first data characterizing an original position of a tooth of the patient;
   obtaining second data characterizing a final position of the patient's tooth;
   based on the first and second data, determining a movement of the patient's tooth from the original position to the final position; and
   decomposing the movement into an intraarch movement and an interarch movement.

2. The method of Clause 1, wherein the intraarch movement comprises a movement of one or more of the patient's teeth in a first dental arch relative to the other ones of the patient's teeth in the first dental arch.

3. The method of Clause 1 or Clause 2, wherein the interarch movement comprises a movement of all of the patient's teeth in a first dental arch relative to a second dental arch of the patient.

4. The method of any one of Clauses 1 to 3, wherein the interarch movement is non-zero.

5. The method of any one of Clauses 1 to 4, further comprising indicating a first orthodontic intervention to move the tooth according to the intraarch movement and a second orthodontic intervention to move the tooth according to the interarch movement.

6. The method of any one of Clauses 1 to 5, wherein obtaining the second data comprises obtaining instructions from a clinician.

7. The method of Clause 6, wherein obtaining the first data comprises obtaining intraoral scan data of the patient's teeth.

8. The method of any one of Clauses 1 to 7, wherein the intraarch movement has six directions of movement.

9. The method of any one of Clauses 1 to 8, wherein the interarch movement has six directions of movement.

10. The method of Clause 8 or Clause 9, wherein the six components comprise three translational directions of movement and three rotational directions of movement.

11. The method of any one of Clauses 1 to 10, further comprising, based on the first and second data and the intraarch and interarch movements, determining third data characterizing an intermediate position of the patient's tooth.

12. The method of Clause 11, wherein the intermediate position of the patient's tooth corresponds to a position of the patient's tooth after it has been moved from the original position according to the intraarch movement.

13. The method of any one of Clauses 1 to 12, wherein decomposing the movement into an intraarch movement and an interarch movement comprises applying a transformation to the second data.

14. The method of Clause 13, wherein the transformation is rigid and/or affine.

15. The method of any one of Clauses 11 to 14, wherein decomposing the movement into an intraarch movement and an interarch movement comprises registering the third data to the first data.

16. The method of any one of Clauses 5 to 15, further comprising indicating a relative timing of implementation of the first orthodontic intervention with respect to the second orthodontic intervention.

17. A method of obtaining an orthodontic treatment plan comprising:
   obtaining first data characterizing an original position of a tooth in a dental arch of a patient;
   obtaining second data characterizing a final position of the patient's tooth;
   based on the first and second data, determining movement data characterizing a movement of the patient's tooth from the original position to the final position; and
   decomposing the movement data into first movement data and second movement data,
   wherein the first movement data characterizes a first component of the movement achievable by a first orthodontic intervention, and
   wherein the second movement data characterizes a second component of the movement achievable by a second orthodontic intervention different than the first orthodontic intervention.

18. The method of Clause 17, wherein the first component of the movement comprises a movement of the tooth with respect to other teeth in the dental arch of the patient.

19. The method of Clause 17 or Clause 18, wherein the dental arch is a first dental arch, and wherein the second component of the movement comprises a movement of the tooth with respect to a second dental arch of the patient.

20. The method of any one of Clauses 17 to 19, wherein the first orthodontic intervention comprises moving the tooth via an orthodontic device.

21. The method of any one of Clauses 17 to 20, wherein the second orthodontic intervention comprises moving the tooth via orthognathic surgery.

22. The method of any one of Clauses 17 to 21, wherein the second orthodontic intervention comprises moving the tooth via an orthodontic device.

23. The method of any one of Clauses 20 to 22, wherein the orthodontic device comprises an orthodontic appliance configured to be secured to one or more of the patient's teeth and, once secured, apply forces to the teeth to move the patient's teeth from an original position to a final desired position.

24. The method of any one of Clauses 20 to 23, wherein the orthodontic device comprises an elastic, a temporary anchorage device, or a platform.

25. A method for obtaining an orthodontic treatment plan comprising:
   obtaining first data characterizing an initial position of a tooth of a patient;
   obtaining second data characterizing a preferred position of the patient's tooth;
   based on the first and second data, obtaining third data characterizing a movement of the patient's tooth from the initial position to the preferred position;
   based on the first, second, and third data, identifying a component of the third data, wherein the component of the third data characterizes a portion of the movement of the patient's tooth from the initial position to the preferred position such that, after the patient's tooth is moved according to the portion of the movement, the patient's tooth is located at an intermediate position; and
   suggesting an orthodontic treatment to move the tooth according to the portion of the movement.

26. The method of Clause 25, wherein the portion of the movement comprises an intraarch movement.

27. The method of Clause 25 or Clause 26, wherein the portion of the movement comprises interarch movement.

28. The method of any one of Clauses 25 to 27, wherein the portion of the movement comprises an entirety of the movement.

29. The method of any one of Clauses 25 to 28, further comprising, based on the component of the third data, suggesting a parameter of the orthodontic treatment.

30. The method of any one of Clauses 25 to 29, wherein the orthodontic treatment comprises moving the patient's tooth with an orthodontic appliance according to the portion of the movement.

31. The method of Clause 29 or Clause 30, wherein the parameter comprises a stiffness of one or more portions of the appliance.

32. The method of any one of Clauses 29 to 31, wherein the parameter comprises a pre-set shape of one or more portions of the appliance.

33. The method of any one of Clauses 25 to 32, wherein the component is a first component characterizing a first portion of the movement and the orthodontic treatment is a first orthodontic treatment, the method further comprising:
   based on the first, second, and third data, identifying a second component of the third data, wherein the second component of the third data characterizes a second portion of the movement of the patient's tooth from the initial position to the preferred position; and
   suggesting a second orthodontic treatment to move the tooth according to the second portion of the movement.

34. The method of any one of Clauses 25 to 33, further comprising communicating the orthodontic treatment plan to a human operator.

35. The method of Clause 34, wherein communicating the orthodontic treatment plan comprises visually displaying an animation of the patient's tooth moving according to the portion of the movement characterized by the component of the third data.

36. The method of Clause 34 or Clause 35, wherein communicating the orthodontic treatment plan comprises visually displaying the initial position, the preferred position, and/or the intermediate position.

37. One or more tangible, non-transitory computer-readable media storing instructions that, when executed by one or more processors, cause the one or more processors to perform the method of any one of the Clauses herein.

38. A device comprising:
   one or more processors; and
   one or more tangible, non-transitory, computer-readable media storing instructions that, when executed by the one or more processors, cause the one or more processors to perform the method of any one of the Clauses herein.

39. A method for designing an orthodontic appliance comprising:
   obtaining an anatomy digital model representing a patient's gingiva and teeth in an arrangement;
   obtaining an appliance digital model representing an orthodontic appliance design configured to use with the patient's teeth;

virtually deforming the appliance digital model into a configuration in which the appliance is coupled to the patient's teeth in the arrangement; and evaluating the deformed configuration of the appliance digital model.

40. The method of Clause 39, wherein the orthodontic appliance comprises an appliance for repositioning one or more teeth of the patient.

41. The method of Clause 39 or Clause 40, wherein the orthodontic appliance comprises an anchor configured to be disposed adjacent the patient's teeth and one or more arms extending away from the anchor, each of the one or more arms being configured to couple to a respective one or more of the patient's teeth.

42. The method of any one of Clauses 39 to 41, wherein the arrangement comprises an original tooth arrangement.

43. The method of any one of Clauses 39 to 41, wherein the arrangement comprises an intermediate tooth arrangement.

44. The method of any one of Clauses 39 to 41, wherein the arrangement comprises a final tooth arrangement.

45. The method of any one of Clauses 39 to 44, wherein evaluating the deformed configuration comprises determining whether the deformed appliance digital model impinges on the gingiva.

46. The method of any one of Clauses 39 to 45, wherein evaluating the deformed configuration comprises evaluating relative positions of the appliance digital model and the gingiva.

47. The method of any one of Clauses 39 to 46, wherein evaluating the deformed configuration comprises determining whether appliance is spaced apart from gingiva by greater than a predetermined threshold.

48. The method of any one of Clauses 39 to 47, wherein evaluating the deformed configuration comprises determining whether any portion of the deformed appliance digital model exceeds an elastic strain limit.

49. The method of any one of Clauses 39 to 48, wherein evaluating the deformed configuration comprises determining a difference between a force and/or moment applied to the teeth by the deformed appliance and an intended force and/or moment.

50. The method of Clause 49, wherein evaluating the deformed configuration comprises determining whether the difference between a force and/or moment applied to the teeth by the deformed appliance and an intended force and/or moment exceeds a predetermined accuracy limit.

51. The method of any one of Clauses 39 to 50, wherein evaluating the deformed configuration comprises determining if a force and/or moment applied to the teeth by the deformed appliance exceeds a predetermined maximum force and/or moment.

52. The method of any one of Clauses 39 to 51, further comprising, based on the evaluation, modifying the appliance digital model.

53. The method of Clause 52, wherein modifying the appliance digital model comprises changing a configuration of at least one arm of the appliance digital model.

54. The method of Clause 52 or Clause 53, wherein modifying the appliance digital model comprises changing a geometry of a shape-set configuration for the appliance digital model.

55. The method of any one of Clauses 52 to 54, wherein modifying the appliance digital model comprises changing a configuration of an anchor of the appliance digital model.

56. The method of any one of Clauses 52 to 55, further comprising, after modifying the appliance digital model:

virtually deforming the modified appliance digital model into a configuration in which the appliance is mated to the patient's teeth; and evaluating the deformed configuration of the modified appliance digital model.

57. The method of any one of Clauses 39 to 56, wherein virtually deforming the appliance comprises performing a finite element analysis (FEA) using the appliance digital model.

58. A method for designing an orthodontic appliance for repositioning a tooth of a patient, the orthodontic appliance having an anchor and an arm extending away from the anchor, the method comprising:

obtaining an anatomy digital model characterizing the patient's gingiva and teeth in an arrangement;

obtaining an appliance digital model characterizing an orthodontic appliance design; and virtually deforming the appliance digital model based on the anatomy digital model.

59. The method of Clause 58, wherein virtually deforming the appliance model includes performing a finite element analysis (FEA).

60. The method of Clause 58 or Clause 59, further comprising obtaining an output from virtually deforming the appliance digital model based on the anatomy digital model.

61. The method of Clause 60, wherein the output is a deformed appliance digital model.

62. The method of Clause 60 or Clause 61, wherein the output comprises a position of a first portion of the appliance digital model corresponding to the anchor of the orthodontic appliance relative to a position of the patient's gingiva of the anatomy digital model.

63. The method of any one of Clauses 60 to 62, wherein the output comprises a measure of strain in the appliance digital model.

64. The method of any one of Clauses 60 to 63, further comprising determining if the output is greater than a predetermined threshold.

65. The method of any one of Clauses 60 to 64, further comprising determining if the output is less than a predetermined threshold.

66. The method of Clause 64 or Clause 65, wherein the predetermined threshold is an elastic strain limit.

67. The method of Clause 64 or Clause 65, wherein the predetermined threshold is a distance between the anatomy digital model and the appliance digital model.

68. The method of any one of Clauses 60 to 67, further comprising modifying the appliance digital model based on the output.

69. The method of any one of Clauses 60 to 68, further comprising modifying the anatomy digital model based on the output.

70. The method of any one of Clauses 58 to 69, wherein the arrangement is an original tooth arrangement.

71. The method of any one of Clauses 58 to 70, wherein the arrangement is a desired final tooth arrangement.

72. The method of any one of Clauses 58 to 71, wherein the arrangement is an intermediate tooth arrangement.

73. The method of any one of Clauses 58 to 72, wherein the appliance digital model comprises a planar appliance digital model virtually representing the orthodontic appliance in a substantially planar form.

74. The method of any one of Clauses 58 to 72, wherein the appliance digital model comprises an intended appliance digital model virtually representing a geometry of the orthodontic appliance in a shape-set form.

75. The method of any one of Clauses 58 to 72, wherein the appliance digital model comprises a deformed intended appliance digital model virtually representing the geometry of the orthodontic appliance in an installed form.

76. A method for designing an orthodontic appliance for repositioning a tooth of a patient, the orthodontic appliance having an anchor and at least one arm extending away from the anchor, the method comprising:
　obtaining a planar appliance digital model, the planar appliance digital model virtually representing the appliance in a substantially planar configuration;
　obtaining a heat treatment fixture digital model, the heat treatment fixture digital model characterizing a geometry of a heat treatment fixture for shape-setting an appliance;
　performing a first FEA using the planar appliance digital model and the heat treatment fixture digital model;
　obtaining an intended appliance digital model, the intended appliance digital model virtually representing the appliance in a three-dimensional configuration with a geometry based at least in part on the heat treatment fixture digital model;
　obtaining an original tooth arrangement (OTA) digital model, the OTA digital model virtually representing a patient's teeth and gingiva in an original arrangement;
　performing a second FEA using the intended appliance digital model and the OTA digital model; and
　obtaining a deformed intended appliance digital model and an analysis result.

77. The method of Clause 76, further comprising modifying the planar appliance digital model based on the analysis result.

78. The method of Clause 76 or Clause 77, further comprising modifying the heat treatment fixture digital model based on the analysis result.

79. The method of any one of Clauses 76 to 78, wherein performing the first FEA comprises:
　discretizing at least one of the planar appliance digital model and the heat treatment fixture digital model into a plurality of finite elements and a plurality of nodes;
　assigning material properties to at least one of the planar appliance digital model and the heat treatment fixture digital model;
　defining a contact interaction between the planar appliance digital model and the heat treatment fixture digital model;
　assigning boundary conditions to at least one of the planar appliance digital model and the heat treatment fixture digital model;
　defining an analysis parameter; and
　running the FEA until an exit condition is reached.

80. The method of Clause 79, wherein assigning the boundary conditions includes assigning a non-zero displacement to an anchor portion of the planar appliance digital model.

81. The method of Clause 79 or Clause 80, wherein assigning the boundary conditions includes defining a relationship between an orientation of an arm of the planar appliance digital model and a base plane of a securing portion of the heat treatment fixture.

82. The method of Clause 81, wherein the arm of the planar appliance digital model is tangent to the base plane of the securing portion of the heat treatment fixture.

83. The method of any one of Clauses 79 to 82, wherein assigning the boundary conditions includes assigning a displacement to an attachment portion of the planar appliance digital model.

84. The method of Clause 83, wherein the displacement assigned to the attachment portion has a magnitude of zero.

85. The method of Clause 83, wherein the displacement assigned to the attachment portion has a non-zero magnitude.

86. The method of any one of Clauses 76 to 85, wherein performing the second FEA comprises:
　discretizing at least one of the intended appliance digital model and the OTA digital model into a plurality of finite elements and a plurality of nodes;
　assigning material properties to at least one of the intended appliance digital model and the OTA digital model;
　defining a contact interaction between the intended appliance digital model and the OTA digital model;
　assigning boundary conditions to at least one of the intended appliance digital model and the OTA digital model;
　defining an analysis parameter; and
　running the FEA until an exit condition is reached.

87. A method for designing an orthodontic appliance for repositioning a tooth of a patient, the orthodontic appliance having an anchor and an arm extending away from the anchor, the method comprising:
　obtaining an OTA digital model of a patient's teeth and gingiva in an original arrangement, the OTA digital model comprising original position data of a tooth to be repositioned by the orthodontic appliance when installed in the patient's mouth;
　obtaining an FTA digital model characterizing the patient's teeth and gingiva in a desired final arrangement, the FTA digital model comprising final position data of the tooth;
　determining displacement data characterizing a displacement between the original position data of the tooth and the final position data of the tooth;
　obtaining a heat treatment fixture digital model based on the FTA digital model;
　obtaining a 3D template digital model based on the heat treatment fixture digital model comprising a first portion corresponding to the anchor of the orthodontic appliance in the treatment configuration and a second portion corresponding to the arm in the treatment configuration;
　obtaining a planar template digital model, wherein the planar template digital model is a substantially planar configuration of the 3D template digital model;
　obtaining a planar appliance digital model based on the planar template digital model;
　obtaining an intended appliance digital model, wherein the intended appliance digital model characterizes the orthodontic appliance in 3D configuration based on the heat treatment fixture digital model; and
　performing an FEA on the OTA and intended appliance digital models to deform the intended appliance digital model based on the displacement data.

88. The method of Clause 87, wherein obtaining the OTA digital model includes scanning the patient's teeth and gingiva.

89. The method of Clause 88, wherein scanning the patient's teeth and gingiva comprises optical scanning.

90. The method of Clause 88 or Clause 89, wherein scanning the patient's teeth and gingiva comprises computed tomography scanning.

91. The method of any one of Clauses 88 to 90, wherein scanning the patient's teeth and gingiva comprises scanning an impression of the patient's teeth and gingiva.

92. The method of any one of Clauses 87 to 91, further comprising segmenting the OTA digital model into a plurality of digital models of each tooth and at least one gingiva.

93. The method of any one of Clauses 87 to 92, further comprising obtaining a securing member digital model representing a securing member, the securing member configured to be adhered to a surface of the tooth and detachably couple with a portion of the orthodontic appliance to secure the orthodontic appliance to the tooth.

94. The method of Clause 93, further comprising obtaining an OTA with securing member digital model comprising a combination of the OTA digital model and the securing member digital model, wherein the combination is based on a desired placement of the securing member on the patient's tooth when the orthodontic appliance is installed in the patient's mouth during treatment.

95. The method of Clause 93 or Clause 94, further comprising obtaining an FTA with securing member digital model comprising a combination of the FTA digital model and the securing member digital model, wherein the combination is based on a desired placement.

96. The method of Clause 94 or Clause 95, wherein the desired placement of the securing member is on a lingual surface of the patient's tooth.

97. The method of any one of Clauses 87 to 96, wherein the displacement data comprises three translations and three rotations.

98. The method of any one of Clauses 87 to 97, wherein obtaining the intended appliance digital model comprises performing an FEA with the planar appliance digital model and the heat treatment fixture digital model.

99. The method of any one of Clauses 87 to 98, wherein the method further comprises modifying the heat treatment fixture digital model based on the intended appliance digital model.

100. The method of Clause 97, wherein modifying the heat treatment fixture digital model comprises defining a tangent relationship between a gingival surface of the heat treatment fixture digital model and a gingival-facing surface of the intended appliance digital model.

101. The method of any one of Clauses 99 to 100, further comprising manufacturing the planar template digital model.

102. The method of any one of Clauses 1 to 101, further comprising manufacturing the heat treatment fixture digital model.

103. The method of any one of Clauses 39 to 102, further comprising manufacturing the intended appliance digital model.

104. An orthodontic appliance manufactured in accordance with a method of any one of the Clauses herein.

105. A fixture manufactured in accordance with a method of any one of the Clauses herein.

106. A tangible, non-transitory computer-readable medium configured to store instructions that, when executed by one or more processors, cause the one or more processors to perform the method of any one of the Clauses herein.

107. A device comprising:
one or more processors; and
a tangible, non-transitory computer-readable medium configured to store instructions that, when executed by one or more processors, cause the one or more processors to perform the method of any one of the Clauses herein.

108. A method for determining an arrangement of an orthodontic device, the method comprising:
obtaining position data corresponding to an original tooth arrangement (OTA) of a patient;
obtaining position data corresponding to a first final tooth arrangement (FTA) of the patient, the first FTA differing from the OTA; and
determining position data corresponding to a second FTA, the second FTA being based at least in part on the first FTA and a predetermined parameter, the second FTA differing from the first FTA,
wherein the second FTA can be used to form a fixture and/or an orthodontic appliance, the appliance being configured to move teeth of the patient from the OTA toward the first FTA or the second FTA.

109. The method of Clause 108, further comprising manufacturing the fixture and/or the appliance according to at least the data corresponding to the second FTA.

110. The method of Clause 108 or Clause 109, wherein the appliance is configured to move teeth of the patient generally from the OTA to the first FTA or to the second FTA.

111. The method of any one of Clause 108 to Clause 110, wherein the appliance is configured to have an arrangement generally corresponding to the second FTA in which the appliance is in a substantially unloaded state.

112. The method of any one of Clauses 108 to 111, wherein the appliance is configured to have a first arrangement generally corresponding to the second FTA and a second arrangement generally corresponding to the OTA, the first arrangement corresponding to a substantially unloaded state and the second arrangement corresponding to a loaded state.

113. The method of any one of Clauses 108 to 112, wherein the predetermined parameter is associated with an expected movement of at least one tooth of the patient after repositioning of the at least one tooth via the appliance to the second FTA.

114. The method of Clause 113, wherein the expected movement is in at least one of the mesial-distal direction, lingual-facial direction, or occlusal-gingival direction.

115. The method of Clause 113 or 114, wherein the expected movement is a rotation about an axis defined by at least one of the mesial-distal direction, lingual-facial direction, or occlusal-gingival direction.

116. The method of any one of Clauses 108 to 115, further comprising manufacturing the appliance such that the appliance in a substantially unloaded configuration generally corresponds to the second FTA, wherein the first FTA corresponds to a predetermined desired position of the patient's teeth.

117. The method of any one of Clauses 108 to 116, wherein the expected relapse corresponds to a positional difference between the first FTA and the second FTA.

118. A method for determining an arrangement of an orthodontic device, the method comprising:
obtaining data corresponding to an original tooth arrangement (OTA) of a patient; and
determining data corresponding to a final tooth arrangement (FTA) based on the OTA and a predetermined parameter,
wherein the FTA can be used to form a fixture and/or an orthodontic appliance, the appliance being configured to move a patient's teeth from the OTA toward the FTA, and
wherein the predetermined parameter is based at least in part on an expected relapse after repositioning the patient's teeth from the OTA.

119. The method of Clause 118, wherein a minimum threshold force is needed to move at least one tooth of the patient via the appliance, and wherein the predetermined parameter is associated with the minimum threshold force.

120. The method of Clause 118 or Clause 119, wherein the appliance has a configuration in an unloaded state that generally corresponds to the second FTA.

121. The method of any one of Clauses 118 to 120, wherein the appliance has a configuration in an unloaded state that generally corresponds to the second FTA, and wherein the appliance is configured to move the patient's teeth to the first FTA.

122. The method of any one of Clauses 118 to 121, wherein the appliance has a configuration in an unloaded state that generally corresponds to the second FTA, and wherein the appliance is configured to move the patient's teeth to the first FTA and not to the second FTA.

123. The method of any one of Clauses 118 to 122, wherein:
a minimum threshold force is needed to move at least one tooth of the patient via the appliance;
the predetermined parameter is associated with the minimum threshold force; and
the appliance is configured to provide a non-zero force greater than the minimum threshold along a path defined by at least the OTA and the first FTA.

124. The method of any one of Clauses 118 to 123, wherein:
a minimum threshold force is needed to move at least one tooth of the patient via the appliance;
the predetermined parameter is associated with the minimum threshold force; and
the appliance, when in a configuration generally corresponding to the first FTA, is configured to provide a non-zero force less than the minimum threshold.

125. A method for determining an arrangement of an orthodontic device, the method comprising:
obtaining data corresponding to an original tooth arrangement (OTA) of a patient; and
determining data corresponding to a final tooth arrangement (FTA) based on the OTA and a predetermined parameter,
wherein the FTA can be used to form a fixture and/or an orthodontic appliance, the appliance being configured to move a patient's teeth from the OTA toward the FTA, and
wherein a minimum threshold force is needed to move at least one tooth of the patient via the appliance, and
wherein the predetermined parameter is associated with the minimum threshold force.

126. The method of Clause 125, wherein the appliance is configured to be coupled to a securing member fixed to a patient's tooth, and wherein the predetermined parameter is associated with an expected free play between the appliance and the securing member.

127. The method of Clause 125 or Clause 126, wherein the appliance includes an attachment portion configured to be coupled to a securing member fixed to a patient's tooth, and wherein the predetermined parameter is associated with an expected free play between the attachment portion and the securing member.

128. The method of any one of the Clauses herein, wherein:
the appliance includes an arm having an attachment portion configured to be coupled to a securing member fixed to a patient's tooth,
the predetermined parameter is associated with a free play between the attachment portion and the securing member, the free play corresponding to an angle of rotation in which the attachment portion is able to rotate relative to the securing member, and
the second FTA differs from the first FTA at least by the angle of rotation.

129. The method of Clause 128, wherein the angle of rotation is in a direction corresponding to at least one of the mesial, distal, occlusal, gingival, facial, and/or lingual directions.

130. The method of any one of the Clauses herein, wherein:
the appliance includes an arm having an attachment portion configured to be coupled to a securing member fixed to a patient's tooth,
the predetermined parameter is associated with a free play between the attachment portion and the securing member, the free play corresponding to a dimension in which the attachment portion is able to move relative to the securing member, and
the second FTA differs from the first FTA at least by the dimension.

131. The method of Clause 130, wherein the dimension extends in a direction corresponding to at least one of the mesial-distal, occlusal-gingival, and/or facial-lingual directions.

132. The method of any one of the Clauses herein, wherein an arm of the appliance is configured to be coupled to a securing member fixed to a patient's tooth, and wherein the predetermined parameter is associated with an expected free play between the arm and the securing member.

133. A method for determining an arrangement of an orthodontic device, the method comprising:
obtaining data corresponding to an original tooth arrangement (OTA) of a patient; and
determining data corresponding to a final tooth arrangement (FTA) based on the OTA and a predetermined parameter,
wherein the FTA can be used to form a fixture and/or an orthodontic appliance, the appliance having a plurality of arms that, when coupled to a patient's teeth via corresponding securing members, are configured to be move a patient's teeth from the OTA toward the FTA, and
wherein the predetermined parameter is based at least in part on an expected free play between at least one of the arms and corresponding securing member.

134. The method of any one of the Clauses herein, wherein the predetermined parameter is associated with a positional difference between the first FTA and the second FTA.

135. The method of any one of the Clauses herein, wherein the appliance is configured to have a first arrangement corresponding to the first FTA and the fixture is configured to have a second configuration corresponding to the second FTA, and wherein the predetermined parameter is associated with the difference between the first and second arrangements.

136. The method of any one of the Clauses herein, further comprising:
manufacturing the fixture to have an arrangement corresponding to the second FTA;
treating the appliance disposed over the fixture, thereby causing the appliance to have an arrangement corresponding to the first FTA.

137. The method of any one of the Clauses herein, further comprising:
manufacturing the fixture to have an arrangement corresponding to the second FTA;

manufacturing the appliance to have a 2D configuration;
coupling the appliance over the fixture;
treating the appliance disposed over the fixture, thereby causing the appliance to assume an arrangement corresponding to the second FTA; and
decoupling the appliance from the fixture, thereby causing the appliance to assume an arrangement corresponding to the first FTA.

138. A method for determining an arrangement of an orthodontic device, the method comprising:
obtaining data corresponding to an original tooth arrangement (OTA) of a patient; and
determining data corresponding to a final tooth arrangement (FTA) based on the OTA and a predetermined parameter,
wherein the FTA can be used to form a fixture and/or an orthodontic appliance, the appliance being configured to move a patient's teeth from the OTA toward the FTA, and
wherein the predetermined parameter is associated with an expected plastic deformation threshold of the appliance.

139. The method of any one of the Clauses herein, wherein the predetermined parameter is associated with a stress experienced by the appliance when in the OTA.

140. The method of any one of the Clauses herein, wherein the predetermined parameter is associated with a material property of the appliance.

141. The method of any one of the Clauses herein, wherein the appliance comprises a superelastic material, and wherein the predetermined parameter is associated with plastic deformation associated with the superelastic material.

142. The method of any one of the Clauses herein, wherein the appliance comprises nitinol, and wherein the predetermined parameter is associated with plastic deformation associated with nitinol.

143. The method of any one of the Clauses herein, wherein the appliance comprises nitinol, and wherein the predetermined parameter is associated with hysteresis of nitinol.

144. The method of any one of the Clauses herein, wherein the predetermined parameter is associated with a stress experienced by the appliance when in a configuration corresponding to at least one of the OTA or the FTA.

145. The method of any one of the Clauses herein, wherein:
the predetermined parameter is associated with an expected plastic deformation threshold of the appliance,
the appliance includes an anchor portion and an arm extending from the anchor portion, and
the plastic deformation threshold is associated with the arm of the appliance.

146. The method of any one of the Clauses herein, wherein:
the predetermined parameter is associated with an expected plastic deformation threshold of the appliance,
the appliance includes an anchor portion and an arm extending from the anchor portion, the arm including a biasing portion, and
the plastic deformation threshold is associated with the biasing portion of the appliance.

147. The method of any one of the Clauses herein, wherein the appliance, when coupled to the patient's teeth, is configured to transition from a first configuration corresponding to the OTA, and wherein determining the data corresponding to the FTA comprises determining whether a portion of the appliance in the first configuration exceeds a yield strength of a material of the appliance.

148. The method of any one of the Clauses herein, wherein:
the appliance, when coupled to the patient's teeth, is configured to transition from a first configuration corresponding to the OTA, and
determining the data corresponding to the FTA comprises determining whether a portion of the appliance in the first configuration exceeds a yield strength of a material of the appliance.

149. The method of any one of the Clauses herein, wherein the appliance, when coupled to the patient's teeth, is configured to transition from a first configuration corresponding to the OTA to a second configuration corresponding to the FTA, and wherein determining the data corresponding to the FTA comprises determining whether a portion of the appliance in the first or second configuration exceeds a yield strength of a material of the appliance.

150. A method for determining an arrangement of an orthodontic device, the method comprising:
obtaining data corresponding to an original tooth arrangement (OTA) of a patient; and
determining data corresponding to a final tooth arrangement (FTA) based on the OTA and a predetermined parameter,
wherein the FTA can be used to form a fixture and/or an orthodontic appliance, the appliance being configured to move teeth of the patient from the OTA toward the FTA.

151. The method of any one of the Clauses herein, wherein the predetermined parameter is that of any one of the clauses herein.

152. A method of fabricating an orthodontic appliance, the method comprising:
obtaining position data corresponding to an original tooth arrangement (OTA) of a patient;
obtaining position data corresponding to a desired final tooth arrangement (FTA) of the patient;
fabricating an orthodontic appliance that, when installed within a mouth of the patient, is configured to urge teeth of the patient from the OTA to the FTA, wherein, when the appliance is coupled to the teeth of the patient in the FTA, the appliance exerts a non-zero force on one or more teeth of the patient, the non-zero force falling below a minimum threshold force.

153. A method of fabricating an orthodontic appliance, the method comprising:
obtaining position data corresponding to an original tooth arrangement (OTA) of a patient;
obtaining position data corresponding to a desired final tooth arrangement (FTA) of the patient;
fabricating an orthodontic appliance configured to move teeth of the patient from the OTA toward the FTA; and
shape-setting the appliance by applying the appliance to a treatment fixture such that the appliance assumes a first configuration, the fixture having a shape that deviates from the FTA such that, after the appliance is removed from the fixture, the appliance assumes a second configuration in which at least a portion of the appliance is deflected away from the first configuration.

154. A tangible, non-transitory computer-readable medium storing instructions that, when executed by one or more processors, cause the one or more processors to perform a method of any one of the Clauses herein.

155. A device comprising:
one or more processors; and
a tangible, non-transitory computer-readable medium storing instructions that, when executed by the one or more processors, cause the one or more processors to perform the method of any one of the Clauses herein.

156. An orthodontic appliance manufactured according to a method of any one of the Clauses herein.

157. A heat treatment fixture manufactured according to a method of any one of the Clauses herein.

158. A method for manufacturing an orthodontic appliance for repositioning a tooth of a patient, the orthodontic appliance having an anchor and at least one arm extending away from the anchor, the arm comprising a proximal portion at the anchor and a distal portion configured to be secured to an orthodontic bracket, the method comprising:
obtaining first position data characterizing a first position of the patient's tooth prior to repositioning of the tooth by the appliance;
obtaining second position data characterizing a second position of the patient's tooth after repositioning of the tooth by the appliance;
obtaining third position data characterizing a desired position of the patient's tooth after an anticipated movement of the tooth after repositioning of the tooth by the appliance; and
forming a three-dimensional configuration of the appliance such that the distal portion of the arm of the appliance is located at the second position,
wherein the appliance is configured to reposition the tooth from the first position to the second position such that, after the tooth moves according to the anticipated movement, the tooth is positioned at the desired position.

159. The method of Clause 158, wherein the appliance is configured to reposition the tooth from the first position to the second position along a path in a first direction.

160. The method of Clause 158 or Clause 159, wherein the anticipated movement of the tooth is along the path in a second direction opposite of the first direction.

161. A method for designing an orthodontic appliance for repositioning a tooth of a patient, the method comprising:
obtaining first position data characterizing an initial position of the patient's tooth;
obtaining second position data characterizing an intended position of the patient's tooth;
obtaining deformation data characterizing an anticipated deformation of the appliance releasing the appliance from a shape-setting fixture; and
based on the first position data, the second position, and the deformation data, obtaining appliance data characterizing a three-dimensional (3D) configuration of the appliance such that the appliance is configured to reposition the tooth from the initial position to the intended position.

162. The method of Clause 161, wherein the anticipated deformation is due to a superelastic property of the appliance.

163. The method of Clause 161 or Clause 162, wherein the orthodontic appliance has an anchor and at least one arm extending away from the anchor, the arm comprising a proximal portion at the anchor and a distal portion configured to be secured to an orthodontic bracket that is configured to be secured to the patient's tooth, and wherein a position of the distal portion of the arm in the 3D configuration is different than the intended position of the tooth.

164. The method of any one of Clauses 161 to 163, wherein resilience data characterizes an anticipated deformation of the appliance after setting a shape of the appliance while the appliance is secured to the shape-setting fixture.

165. A method for designing an orthodontic appliance for repositioning a tooth of a patient, the method comprising:
obtaining first position data characterizing an initial position of the patient's tooth;
obtaining second position data characterizing an intended position of the patient's tooth;
obtaining appliance data characterizing a pre-installation configuration of the appliance;
obtaining deformation data characterizing an anticipated deformation of the appliance from the pre-installation configuration to an installed configuration; and
based on the first position data, the second position, and the deformation data, obtaining modified appliance data characterizing a modified pre-installation configuration of the appliance.

166. The method of Clause 165, wherein the deformation data characterizes a stress and/or a strain in one or more portions of the appliance.

167. The method of Clause 165 or Clause 166, further comprising determining whether plastic deformation is expected to occur at one or more portions of the appliance due to the anticipated deformation of the appliance from the pre-installation configuration to the installed configuration.

168. The method of Clause 167, wherein determining whether plastic deformation is expected to occur comprises comparing the deformation data to at least one of a yield stress or a yield strain of a material of the appliance.

169. The method of any one of Clauses 165 to 168, wherein the modified pre-installation configuration is a first modified pre-installation configuration, the method further comprising, after obtaining the modified appliance data:
obtaining second deformation data characterizing an anticipated deformation of the appliance from the first modified pre-installation configuration to an installed configuration; and
based on the first position data, the second position, and the deformation data, obtaining second modified appliance data characterizing a second modified pre-installation configuration of the appliance.

170. A method for designing an orthodontic appliance for repositioning a tooth of a patient, the orthodontic appliance having an anchor and at least one arm extending away from the anchor, the arm comprising a proximal portion at the anchor and a distal portion configured to be received within a securing portion of an orthodontic bracket, the method comprising:
obtaining first position data characterizing an initial position of the patient's tooth prior to repositioning of the tooth by the appliance;
obtaining second position data characterizing an intended position of the patient's tooth after repositioning of the tooth by the appliance;
obtaining arm data characterizing a dimension of the distal portion of the arm of the appliance;
obtaining bracket data characterizing a dimension of the securing portion of the orthodontic bracket;
obtain play data characterizing a difference between the arm data and the bracket data;
based on the play data, obtaining force data characterizing an anticipated force to be applied to the bracket by the appliance; and
based on the force data, obtaining third position data characterizing a passive position of the distal portion of the arm of the appliance after the appliance has been shape-set, the passive position being different than the intended position of the tooth and/or the original position of the tooth.

171. The method of Clause 170, further comprising forming a three-dimensional configuration of the appliance such that the distal portion of the arm of the appliance is located at the second position.

172. The method of Clause 170 or 171, wherein obtaining the play data comprises determining an anticipated maximum angular displacement between a plane of the distal portion of the arm and a plane of the securing portion of the bracket.

173. The method of any one of Clauses 170 to 172, wherein obtaining the force data comprises determining an anticipated torque loss parameter associated with a connection between the distal portion of the arm and the securing portion of the bracket.

174. The method of any one of Clauses 170 to 173, wherein the arm data characterizes at least two of an occlusogingival dimension of the distal portion of the arm, a buccolingual dimension of the distal portion of the arm, or a mesiodistal dimension of the distal portion of the arm.

175. The method of any one of Clauses 170 to 174, wherein the bracket data characterizes at least two of an occlusogingival dimension of the securing portion of the bracket, a buccolingual dimension of the securing portion of the bracket, or a mesiodistal dimension of the securing portion of the bracket.

176. The method of any one of Clauses 170 to 175, wherein obtaining the play data comprises calculating an anticipated maximum distance between the distal portion of the arm and the securing portion of the bracket.

177. A method for manufacturing an orthodontic appliance for repositioning a tooth of a patient, the orthodontic appliance having an anchor and at least one arm extending away from the anchor, the arm comprising a proximal portion at the anchor and a distal portion configured to be secured to an orthodontic bracket that is secured to the patient's tooth, the method comprising:
   obtaining first position data characterizing an original position of the patient's tooth prior to repositioning of the tooth by the appliance;
   obtaining second position data characterizing an intended position of the patient's tooth after repositioning of the tooth by the appliance; and
   setting a shape of the appliance such that, when the distal portion of the arm is secured to the bracket that is secured to the tooth and the appliance has repositioned the tooth to its intended position, the appliance applies a force to the tooth, the force having a magnitude greater than a predetermined threshold.

178. The method of Clause 177, wherein the predetermined threshold is greater than zero.

179. The method of Clause 177 or Clause 178, wherein the predetermined threshold is between about 5 grams and about 150 grams.

180. The method of any one of Clauses 177 to 179, wherein, after setting a shape of the appliance, the distal portion of the arm is located at a passive position, the passive position being different than the intended position of the tooth and/or the original position of the tooth.

181. The method of any one of Clauses 177 to 180, wherein the predetermined threshold is unique to the tooth.

182. A method for designing an orthodontic appliance for repositioning a tooth of a patient, the method comprising:
   obtaining an appliance digital model characterizing the orthodontic appliance in an initial configuration;
   obtaining a fixture digital model characterizing a fixture for setting a shape of the appliance; and
   performing a finite element analysis (FEA) to virtually deform the appliance digital model based on the fixture digital model.

183. The method of Clause 182, wherein the fixture digital model comprises:
   a gingival portion having a shape substantially corresponding to a surface of the patient's gingiva; and
   at least one securing portion carried by the gingival portion and configured to retain a portion of the appliance.

184. The method of Clause 182 or Clause 183, wherein performing the FEA comprises causing at least one portion of the appliance digital model to substantially conform to the fixture digital model.

185. The method of any one of Clauses 182 to 184, wherein the appliance comprises an anchor and an arm extending away from the anchor, the arm comprising a proximal portion at the anchor and a distal portion configured to be secured to an orthodontic bracket, and wherein performing the FEA comprises positioning a distal portion of an arm of the appliance digital model at or within the securing portion of the fixture digital model.

186. The method of any one of Clauses 182 to 185, wherein the appliance comprises an anchor and an arm extending away from the anchor, and wherein performing the FEA comprises applying a non-zero displacement to an anchor of the appliance digital model.

187. The method of any one of Clauses 182 to 186, wherein the appliance is substantially planar in the initial configuration.

188. A method for designing an orthodontic appliance for repositioning a tooth of a patient, the method comprising:
   obtaining an appliance digital model characterizing the orthodontic appliance in a pre-installation configuration;
   obtaining an anatomy digital model characterizing a patient's teeth and gingiva in an original arrangement; and
   performing an FEA to virtually deform the appliance digital model based on the anatomy digital model.

189. The method of Clause 188, the appliance comprises an anchor and an arm extending away from the anchor, the arm comprising a proximal portion at the anchor and a distal portion configured to be secured to an orthodontic bracket, and wherein performing the FEA comprises causing the distal portion of the arm to be positioned at or adjacent to one of the patient's teeth.

190. The method of Clause 188 or Clause 189, wherein the appliance has a substantially three-dimensional (3D) shape in the pre-installation configuration.

191. The method any one of Clauses 188 to 190, further comprising evaluating the deformed appliance digital model.

192. The method of Clause 191, wherein evaluating the deformed appliance digital model comprises determining whether the deformed appliance digital model impinges on the gingiva or is spaced apart from the gingiva by greater than a predetermined threshold.

193. The method of Clause 191 or Clause 192, wherein evaluating the deformed configuration comprises determining whether any portion of the deformed appliance digital model exceeds an elastic strain limit.

194. The method of any one of Clauses 191 to 193, wherein evaluating the deformed configuration comprises determining a difference between a force and/or moment applied to the teeth by the deformed appliance and an intended force and/or moment.

195. The method of any one of Clauses 191 to 194, further comprising, based on the evaluation, modifying the appliance digital model, wherein modifying the appliance digital model comprises changing at least one of a shape of an arm of the appliance, a shape of an anchor of the appliance, or a shape of the appliance in the pre-installation configuration.

196. A method for designing an orthodontic appliance for repositioning a tooth of a patient, the method comprising:
 obtaining a preliminary appliance digital model virtually representing the appliance in a preliminary configuration;
 obtaining a heat treatment fixture digital model, the heat treatment fixture digital model characterizing a geometry of a heat treatment fixture for shape-setting an appliance, wherein the heat treatment fixture comprises a gingival surface having a shape substantially corresponding to a shape of a gingival surface of the patient and a securing portion configured to releasably retain a portion of the appliance;
 performing a first FEA to virtually deform the preliminary appliance digital model based on the heat treatment fixture digital model;
 obtaining an intended appliance digital model virtually representing the appliance in a three-dimensional configuration with a geometry based at least in part on the heat treatment fixture digital model;
 obtaining an original tooth arrangement (OTA) digital model virtually representing a patient's teeth and gingiva in an original arrangement;
 performing a second FEA to virtually deform the intended appliance digital model based on the OTA digital model; and
 obtaining a deformed intended appliance digital model and an analysis result.

197. The method of Clause 196, wherein the appliance is substantially planar in the preliminary configuration.

198. The method of Clause 196 or Clause 197, wherein performing the first FEA comprises:
 discretizing at least one of the preliminary appliance digital model and the heat treatment fixture digital model into a plurality of finite elements and a plurality of nodes;
 assigning material properties to at least one of the preliminary appliance digital model and the heat treatment fixture digital model;
 defining a contact interaction between the preliminary appliance digital model and the heat treatment fixture digital model;
 assigning boundary conditions to at least one of the preliminary appliance digital model and the heat treatment fixture digital model;
 defining an analysis parameter; and
 running the FEA until an exit condition is reached.

199. The method of Clause 198, wherein assigning the boundary conditions includes at least one of assigning a non-zero displacement a portion of the planar appliance digital model or defining a relationship between an orientation of a portion of the planar appliance digital model and a base plane of a securing portion of the heat treatment fixture.

200. The method of any one of Clauses 196 to 199, wherein performing the second FEA comprises:
 discretizing at least one of the intended appliance digital model and the OTA digital model into a plurality of finite elements and a plurality of nodes;
 assigning material properties to at least one of the intended appliance digital model and the OTA digital model;
 defining a contact interaction between the intended appliance digital model and the OTA digital model;
 assigning boundary conditions to at least one of the intended appliance digital model and the OTA digital model;
 defining an analysis parameter; and
 running the FEA until an exit condition is reached.

201. The method of Clause 200, wherein assigning the boundary conditions comprises assigning a displacement to a portion of the intended appliance digital model, the displacement based at least in part on a movement of the patient's tooth from the original arrangement to a desired final arrangement.

202. The method of any one of Clauses 196 to 201, wherein the analysis result comprises at least one of a strain in the deformed intended appliance digital model or a distance between the deformed intended appliance digital model and the gingival surface of the patient.

203. The method of any one of Clauses 196 to 202 wherein the orthodontic appliance comprises an anchor and at least one arm extending away from the anchor, the arm comprising a proximal portion at the anchor and a distal portion configured to be secured to an orthodontic bracket.

204. The method of Clause 203, wherein performing the first FEA causes the anchor of the appliance to be positioned at or adjacent to the gingival surface of the heat treatment fixture digital model.

205. The method of Clause 203 or Clause 204, wherein performing the second FEA causes the distal portion of the arm of the appliance to be positioned at or adjacent to one of the patient's teeth.

206. A method for designing an orthodontic appliance for repositioning a tooth of a patient, the method comprising:
 obtaining an OTA digital model of a patient's teeth and gingiva in an original arrangement, the OTA digital model comprising original position data of a tooth to be repositioned by the orthodontic appliance when installed in the patient's mouth;
 obtaining an FTA digital model characterizing the patient's teeth and gingiva in a desired final arrangement, the FTA digital model comprising final position data of the tooth;
 determining displacement data characterizing a displacement between the original position data of the tooth and the final position data of the tooth;
 obtaining a heat treatment fixture digital model based on at least one of the OTA digital model or the FTA digital model;
 obtaining a 3D template digital model based on the heat treatment fixture digital model;
 obtaining a planar template digital model, wherein the planar template digital model is a substantially planar configuration of the 3D template digital model;
 obtaining a planar appliance digital model based on the planar template digital model; obtaining an intended appliance digital model, wherein the intended appliance digital model characterizes the orthodontic appliance in 3D configuration based on the heat treatment fixture digital model;
 performing an FEA on the OTA and intended appliance digital models to deform the intended appliance digital model based on the displacement data; and evaluating an analysis result of the virtual deformation.

207. The method of Clause 206, wherein the displacement data comprises three translations and three rotations.

208. The method of Clause 206 or Clause 207, further comprising modifying the heat treatment fixture digital model based on the intended appliance digital model.

209. The method of Clause 208, wherein modifying the heat treatment fixture digital model comprises defining a tangent relationship between a gingival surface of the heat treatment fixture digital model and a gingival-facing surface of the intended appliance digital model.

210. The method of any one of Clauses 206 to 209, further comprising manufacturing at least one of the planar template digital model, the heat treatment fixture digital model, or the intended appliance digital model.

211. The method of any one of Clauses 206 to 210, wherein the orthodontic appliance comprises an anchor and an arm extending away from the anchor, the arm comprising a proximal portion at the anchor and a distal portion configured to be secured to an orthodontic bracket.

212. A device for holding a planar configuration of an orthodontic appliance in a three-dimensional configuration while a heat treatment is applied to the orthodontic appliance, the orthodontic appliance comprising an attachment portion configured to be secured to an orthodontic bracket coupled to a tooth of a patient, the attachment portion comprising a first region and a second region extending at an angle from the first region, the first region being occlusal to the second region, the device comprising:
  a body portion comprising a surface having a shape corresponding at least in part to a gingiva of a patient; and
  a securing portion carried by the body portion and configured to retain the attachment portion in a desired position during the heat treatment, wherein the securing portion comprises a first engagement surface, a second engagement surface, and a gap between the first and second engagement surfaces, wherein the gap is configured to receive the attachment portion such that a first region of the attachment portion is positioned adjacent the first engagement surface and a second region of the attachment portion is positioned adjacent the second engagement surface.

213. The device of Clause 212, wherein the securing portion is configured to limit motion of the attachment portion with respect to the securing portion along a first and second dimension of the securing portion.

214. The device of Clause 213, wherein the first engagement surface is configured to limit motion of the attachment portion along the first dimension.

215. The device of Clause 213 or Clause 214, the second engagement surface is configured to limit motion of the attachment portion along the second dimension.

216. The device of any one of Clauses 213 to 215, wherein the securing portion comprises a third engagement surface configured to limit motion of the attachment portion along the first and/or second dimension.

217. The device of any one of Clauses 212 to 216, wherein, when the attachment is retained by the securing portion at the desired position, the securing portion engages the attachment portion at two or more locations.

218. The device of any one of Clauses 212 to 217, wherein, when the attachment portion is retained by the securing portion at the desired position, two or more edges of the attachment portion are free.

219. The device of any one of Clauses 212 to 218, wherein the securing portion is configured to retain an attachment portion having a width within 0.1 mm and −0.1 mm of a nominal width of the attachment portion.

220. The device of any one of Clauses 212 to 219, wherein at least one of the engagement surfaces comprises a raised region of the securing portion.

221. The device of any one of Clauses 212 to 220, wherein the attachment portion is configured to be releasably secured to the securing portion such that motion of the attachment portion along a third dimension is limited.

222. The device of Clause 221, wherein the attachment portion is configured to be releasably secured to the securing portion of the device by wrapping an elongated member around the attachment portion and the securing portion.

223. The device of Clause 222, wherein the elongated member is wrapped along a generally diagonal path with respect to the first and/or second dimensions.

224. The device of Clause 222 or Clause 223, wherein the securing portion includes a recess configured to receive at least a portion of the elongated member.

225. The device of any one of Clauses 212 to 224, wherein the desired position of the attachment portion is based at least in part on a desired position of a tooth of the patient.

226. The device of any one of Clauses 212 to 225, wherein, when the attachment portion is retained by the securing portion, one or more portions of the appliance substantially conforms to the body portion of the device.

227. The device of any one of Clauses 213 to 226, wherein the attachment portion of the appliance has a first projection extending along a first direction and a second projection extending along a second direction disposed at an angle to the first direction, and wherein, when the attachment portion is retained by the securing portion at the desired position, the first projection engages the first engagement surface and the second projection engages the second engagement surface.

228. The device of Clause 227, wherein the first engagement surface is substantially parallel to the first direction.

229. The device of Clause 227 or Clause 228, wherein the second engagement surface is substantially parallel to the second direction.

230. The device of any one of Clauses 227 to 229, wherein the first and second directions are substantially orthogonal.

231. The device of any one of Clauses 227 to 230, wherein, when the attachment portion is retained by the securing portion at the desired position, a first surface of the first projection engages the first engagement surface and a second surface of the first projection is free and a first surface of the second projection engages the second engagement surface and a second surface of the second projection is free.

232. A method of manufacturing an orthodontic appliance, the method comprising:
  obtaining an orthodontic appliance in a substantially planar configuration, the appliance comprising an attachment portion including a first projection extending along a first direction and a second projection extending along a second direction disposed at an angle to the first direction;
  obtaining a fixture comprising any of the devices of Clauses 212 to 231;
  positioning the attachment portion at the desired position such that the first projection engages the first engagement surface and the second projection engages the second engagement surface;
securing the appliance to the fixture such that the attachment portion is retained by the securing portion at the desired position; and
forming a three-dimensional configuration of the appliance while the appliance is secured to the fixture.

233. The method of Clause 232, wherein securing the appliance to the fixture comprises wrapping an elongated member about the securing member and the attachment portion.

234. The method of Clause 233, wherein wrapping the elongated member about the securing member and the attachment portion comprises wrapping the elongated member along a third direction that is disposed at an angle to the first and second directions.

235. The method of Clause 234, wherein the angle is about 45 degrees.

236. The method of any of Clauses 232 to 235, wherein forming the three-dimensional configuration comprises heat-treating the appliance and fixture.

237. A device for forming a three-dimensional configuration of an orthodontic appliance comprising an attachment portion configured to be secured to an orthodontic bracket coupled to a tooth of a patient, the attachment portion comprising first and second regions extending along a first direction and third and fourth regions extending along a second direction disposed at an angle to the first direction, wherein, when the appliance is installed in a mouth of a patient, the first region is closer to the patient's gingiva than the second, third, and fourth regions and the third and fourth regions are closer to the patient's gingiva than the second region, the device comprising:
a body portion comprising a surface corresponding at least in part to a gingival surface of a patient; and
a securing portion carried by the body portion and configured to retain the attachment portion of the orthodontic appliance at an intended position, the securing portion comprising first and second engagement surfaces that are substantially parallel to the first direction and a third engagement surface that is substantially parallel to the second direction,
wherein, when the attachment portion is retained by the securing portion at the intended position, the first region engages the first engagement surface, the second region engages the second engagement surface, and at least one of the third region or the fourth region engages the third engagement surface.

238. The device of Clause 237, wherein, when the attachment portion is retained by the securing portion at the intended position, a first surface of the first region engages the first engagement surface, a first surface of the second region engages the second engagement surface, and a first surface of at least one of the third region or the fourth region engages the third engagement surface.

239. The device of Clause 238, wherein, when the attachment portion is retained by the securing portion at the intended position, a second surface of the first region opposite the first surface along a width of the first region does not engage the securing portion.

240. The device of Clause 238 or Clause 239, wherein, when the attachment portion is retained by the securing portion at the intended position, a second surface of the second region opposite the first surface along a width of the second region does not engage the securing portion.

241. The device of any one of Clauses 238 to 240, wherein, when the attachment portion is retained by the securing portion at the intended position, a second surface of the third region opposite the first surface along a width of the third region does not engage the securing portion.

242. The device of any one of Clauses 238 to 241, wherein, when the attachment portion is retained by the securing portion at the intended position, a second surface of the fourth region opposite the first surface along a width of the fourth region does not engage the securing portion.

243. The device of any one of Clauses 237 to 242, wherein the third engagement surface is spaced apart from the first engagement surface along the second direction.

244. The device of any one of Clauses 237 to 243, wherein the third engagement surface is spaced apart from the second engagement surface along the second direction.

245. The device of any one of Clauses 237 to 244, wherein the first engagement surface is spaced apart from the second engagement surface along the second direction.

246. The device of any one of Clauses 237 to 245, wherein the first and second directions are substantially orthogonal.

247. The device of any one of Clauses 237 to 246, wherein the intended position corresponds to or is derived from a desired position of a tooth of the patient to be moved by the appliance.

248. The device of any one of Clauses 237 to 247, wherein when the attachment portion is retained by the securing portion, one or more portions of the appliance substantially conforms to the body portion of the device.

249. A method of manufacturing an orthodontic appliance, the method comprising:
obtaining an orthodontic appliance in a substantially planar configuration, the appliance an attachment portion configured to be secured to an orthodontic bracket coupled to a tooth of a patient, the attachment portion comprising first and second regions extending along a first direction and third and fourth regions extending along a second direction disposed at an angle to the first direction, wherein, when the appliance is installed in a mouth of a patient, the first region is closer to the patient's gingiva than the second, third, and fourth regions and the third and fourth regions are closer to the patient's gingiva than the second region;
obtaining a fixture comprising any of the devices of Clauses 237 to 248;
positioning the attachment portion at the intended position such that the first region engages the first engagement surface, the second region engages the second engagement surface, and at least one of the third region or the fourth region engages the third engagement surface;
securing the appliance to the fixture such that the attachment portion is retained by the securing portion at the intended position; and
forming a three-dimensional configuration of the appliance while the appliance is secured to the fixture.

250. The method of Clause 249, wherein, when the attachment portion is positioned at the intended position, the third region or the fourth region does not engage the first engagement surface, the second engagement surface, or the third engagement surface.

251. The method of Clause 249 or Clause 250, wherein forming the three-dimensional configuration of the appliance while the appliance is secured to the fixture comprises subjecting the appliance and the fixture to heat.

252. The method of Clause 251, wherein subjecting the appliance and the heat treatment fixture to heat comprises heating to at least 200 degrees centigrade.

253. The method of Clause 252, further comprising, after heating, cooling the appliance and the heat treatment fixture via liquid quench or air cooling.

254. The method of any one of Clauses 249 to 253, further comprising removing the appliance from the fixture.

255. The method of Clause 254, wherein after removing the appliance from the fixture, the appliance maintains the three-dimensional configuration such that the attachment portion is at the intended position.

256. A device for forming a three-dimensional configuration of an orthodontic appliance comprising an attachment portion having a first projection extending along a first direction and a second projection extending along a second direction disposed at an angle to the first direction, the device comprising:
  a body portion comprising a surface corresponding at least in part to a gingival surface of a patient; and
  a securing portion carried by the body portion and configured to retain the attachment portion of the arm of the orthodontic appliance at an intended position, the securing portion comprising a first channel extending along the first direction, a second channel extending along the second direction,
  wherein, when the attachment portion is retained by the securing portion at the intended position, the first projection is positioned within the first channel and the second projection is positioned within the second channel such that a surface of the first projection is substantially in contact with the first channel and a surface of the second projection is substantially in contact with the second channel.

257. The device of Clause 256, further comprising a third channel extending along a third direction disposed at an angle to the first and second directions, wherein the third channel is configured to receive an elongated member therein such that the elongated member releasably secures the attachment portion of the arm to the securing portion of the device.

258. The device of Clause 256 or Clause 257, wherein the channel extends partially into a thickness of the securing portion.

259. A method of manufacturing an orthodontic appliance, the method comprising:
  obtaining an orthodontic appliance in a substantially planar configuration, the appliance comprising an attachment portion having a first projection extending along a first direction and a second projection extending along a second direction disposed at an angle to the first direction;
  obtaining a fixture comprising any of the devices of Clauses 256 to 258;
  positioning the attachment portion at the intended position such that the first projection is positioned within the first channel and the surface of the first projection is substantially in contact with the first channel and such that the second projection is positioned within the second channel and the surface of the second projection is substantially in contact with the second channel;
  securing the appliance to the fixture such that the attachment portion is retained by the securing portion at the intended position; and
  forming a three-dimensional configuration of the appliance while the appliance is secured to the fixture.

260. The method of Clause 259, wherein, when the attachment portion is positioned at the intended position, another surface of the first projection and another surface of the second projection do not substantially contact the fixture.

261. A device for forming a three-dimensional configuration of an orthodontic appliance comprising an attachment portion configured to be secured to an orthodontic bracket coupled to a tooth of a patient, the device comprising:
  a body portion comprising a surface corresponding at least in part to a gingival surface of a patient; and
  a securing portion carried by the body portion and configured to position the attachment portion of the orthodontic appliance at an intended position, the securing portion comprising an appliance-facing surface including one or more protrusions extending from the appliance-facing surface away from the securing member, wherein the one or more protrusions define at least two engagement surfaces,
  wherein, when the attachment portion is retained by the securing portion at the intended position, the attachment portion contacts the at least two engagement surfaces.

262. The device of Clause 261, wherein, when the attachment portion is retained by the securing portion at the intended position, at least one region of the attachment portion does not contact the at least two engagement surfaces.

263. The device of Clause 261 or Clause 262, wherein the one or more protrusions comprise three protrusions.

264. The device of any one of Clauses 261 to 263, wherein the one or more protrusions define three engagement surfaces.

265. The device of any one of the preceding Clauses, wherein the device comprises a metal.

266. The device of any one of the preceding Clauses, wherein the device is formed by additive manufacturing.

267. The device of any one of the preceding Clauses, wherein the device is formed by investment casting.

268. The device of any one of the preceding Clauses, wherein the body portion is monolithic with the securing portion.

269. The device of any one of the preceding Clauses, further comprising an opening extending therethrough, wherein the opening is configured to receive a fastener therein.

270. The device of any one of the preceding Clauses, wherein the elongated member is a ligature wire.

271. The device of any one of the preceding Clauses, wherein the appliance comprises an anchor configured be positioned adjacent to and extend along the patient's teeth.

272. The device of any one of the preceding Clauses, wherein the appliance comprises an arm extending from a first end positioned at an anchor to a free second end, wherein the free second end includes the attachment portion.

273. The device of any one of the preceding Clauses, wherein the surface of the body corresponds at least in part to a gingival surface of a patient when the patient's teeth are in an original arrangement.

274. The device of any one of the preceding Clauses, wherein the surface of the body corresponds at least in part to a gingival surface of a patient when the patient's teeth are in a final arrangement.

275. The device of any one of the preceding Clauses, wherein, when the attachment portion is retained by the securing portion at the intended position, the anchor substantially conforms to the body portion.

276. A method for determining an orthodontic treatment plan for moving a plurality of teeth disposed in one of a patient's jaws, the method comprising:
  obtaining first data characterizing original positions of the teeth;

obtaining second data characterizing final positions of the teeth;

for each tooth, determining a displacement between the corresponding original position and the corresponding final position based on the first and second data; and for each displacement,
determining a first portion of the displacement unique to the tooth associated with the displacement, and
determining a second portion of the displacement shared by all of the displacements.

277. The method of any one of the preceding Clauses, wherein the treatment plan includes the use of a first orthodontic appliance and a second orthodontic appliance, and wherein a) each of the first portions of the displacements represent a movement of the corresponding tooth caused by a first orthodontic appliance, and b) each of the second portions of the displacements represent a movement of the corresponding tooth caused by a second orthodontic appliance.

278. The method of any one of the preceding Clauses, further comprising obtaining third data characterizing intermediate positions of the teeth, wherein the intermediate positions correspond to positions of the teeth after the teeth have been moved from their original positions according to the first portions of the displacements.

279. The method of any one of the preceding Clauses, further comprising obtaining third data characterizing intermediate positions of the teeth, wherein the intermediate positions correspond to a rigid transformation of the teeth in the final positions.

280. The method of any one of the preceding Clauses, wherein a first error parameter characterizing a difference between the second data and the first data is greater than a second error parameter characterizing a difference between the third data and the first data.

281. The method of any one of the preceding Clauses, wherein each of the first and second error parameters comprises a sum of a plurality of distance parameters, each distance parameter being associated with one of the patient's teeth.

282. The method of any one of the preceding Clauses, wherein each distance parameter comprises a distance between a reference point on the patient's tooth in one of the positions and a corresponding reference point on the tooth in another one of the positions.

283. The method of any one of the preceding Clauses, wherein the distance comprises a Euclidian distance.

284. The method of any one of the preceding Clauses, wherein determining the first and second portions of the displacements comprises registering the second data to the first data.

285. The method of any one of the preceding Clauses, wherein the second portions of the displacements are identical in six directions of movement, the six directions of movement comprising three translational directions of movement and three rotational directions of movement.

286. A tangible, non-transitory, computer-readable medium storing instructions that, when executed by one or more processors of a computing device, cause the one or more processors to perform operations, the operations comprising:

obtaining first data characterizing original positions of the teeth;

obtaining second data characterizing final positions of the teeth;

for each tooth, determining a displacement between the corresponding original position and the corresponding final position based on the first and second data; and for each displacement,
determining a first portion of the displacement unique to the tooth associated with the displacement, and
determining a second portion of the displacement shared by all of the displacements.

287. The tangible, non-transitory, computer-readable medium of any one of the preceding Clauses, further comprising obtaining third data characterizing intermediate positions of the teeth, wherein the intermediate positions correspond positions of the teeth after the teeth have been moved from their original positions according to the first portions of the displacements.

288. The tangible, non-transitory, computer-readable medium of any one of the preceding Clauses, wherein determining the second portions of the displacements comprises determining a rigid transformation that aligns the second data with the first data.

289. The tangible, non-transitory, computer-readable medium of any one of the preceding Clauses, wherein determining the first portions of the displacements comprises aligning the second data with the first data according to the rigid transformation and determining a distance between a first reference point of each of the teeth as characterized by the first data and a second corresponding reference point of each of the teeth as characterized by the aligned second data.

290. The tangible, non-transitory, computer-readable medium of any one of the preceding Clauses, wherein each displacement, each first portion of the displacement, and each second portion of the displacement comprises a 4×4 transformation matrix.

291. The tangible, non-transitory, computer-readable medium of any one of the preceding Clauses, wherein the second portions of the displacements are identical in six directions of movement, the six directions of movement comprising three translational directions of movement and three rotational directions of movement.

292. A method comprising:

obtaining first data characterizing a first movement of a first tooth of a patient from an original position to a desired final position;

obtaining second data characterizing a second movement of a second tooth of the patient from an original position to a desired final position, wherein the second tooth is within the same jaw of the patient as the first tooth; and determining a first portion of the first movement that is identical to a first portion of the second movement and a second portion of the first movement that is unique from a second portion of the second movement.

293. The method of any one of the preceding Clauses, further comprising obtaining position data characterizing intermediate positions of the first tooth and the second tooth, wherein the intermediate position of the first tooth corresponds to a position of the first tooth after the first tooth is moved according to the first portion of the first movement and the intermediate position of the second tooth corresponds to a position of the second tooth after the second tooth is moved according to the first portion of the second movement.

294. The method of any one of the preceding Clauses, wherein the first portions of the first and second movements are achievable by a first orthodontic intervention and the second portions of the first and second movements are achievable by a second orthodontic intervention different from the first orthodontic intervention.

295. The method of any one of the preceding Clauses, wherein the first movement comprises a sum of the first and second portions of the first movement.

296. The method of any one of the preceding Clauses, wherein the first portions of the first and second movements each comprise a rigid transformation defining translations along three axes and rotations about the three axes.

297. The method of any one of the preceding Clauses, wherein the second portions of the first and second movements each comprise a unique transformation.

298. A tangible, non-transitory, computer-readable medium storing instructions that, when executed by one or more processors of a computing device, cause the one or more processors to perform operations, the operations comprising:
obtaining first data characterizing a first movement of a first tooth of a patient from an original position to a desired final position;
obtaining second data characterizing a second movement of a second tooth of the patient from an original position to a desired final position, wherein the second tooth is within the same jaw of the patient as the first tooth; and
determining a first portion of the first movement that is identical to a first portion of the second movement and a second portion of the first movement that is unique from a second portion of the second movement.

299. The tangible, non-transitory, computer-readable medium of any one of the preceding Clauses, the operations further comprising obtaining position data characterizing intermediate positions of the first tooth and the second tooth, wherein the intermediate position of the first tooth corresponds to a position of the first tooth after the first tooth is moved according to the first portion of the first movement and the intermediate position of the second tooth corresponds to a position of the second tooth after the second tooth is moved according to the first portion of the second movement.

300. The tangible, non-transitory, computer-readable medium of any one of the preceding Clauses, wherein the first portions of the first and second movements are achievable by a first orthodontic intervention and the second portions of the first and second movements are achievable by a second orthodontic intervention different from the first orthodontic intervention.

301. The tangible, non-transitory, computer-readable medium of any one of the preceding Clauses, wherein the first portions of the first and second movements each comprise a rigid transformation defining translations along three axes and rotations about the three axes.

302. A method for evaluating an orthodontic treatment plan for moving a plurality of teeth disposed in one of a patient's jaws, the method comprising:
obtaining first data characterizing original positions of the teeth;
obtaining second data characterizing desired final positions of the teeth; and
obtaining third data characterizing intermediate positions of the teeth, the intermediate positions corresponding to a rigid transformation of the teeth in the final positions.

303. A method of obtaining an orthodontic treatment plan comprising:
obtaining first data characterizing original positions of teeth of a patient;
obtaining second data characterizing final positions of the patient's teeth;
based on the first and second data, determining movement data characterizing a movement of each of the patient's teeth from the original position to the final position; and
decomposing the movement data into first movement data and second movement data,
wherein the first movement data characterizes a first component of the movement achievable by a first orthodontic intervention, and
wherein the second movement data characterizes a second component of the movement achievable by a second orthodontic intervention different than the first orthodontic intervention.

304. The method of any one of the preceding Clauses, wherein at least one of the first component of the movement or the second component of the movement comprises a movement of one of the patient's teeth in a first dental arch of the patient relative to others of the patient's teeth in the first dental arch.

305. The method of any one of the preceding Clauses, wherein at least one of the first component of the movement or the second component of the movement comprises a movement of all of the patient's teeth in a first dental arch of the patient relative to all of the patient's teeth in a second dental arch of the patient.

306. The method of any one of the preceding Clauses, wherein at least one of the first component of the movement or the second component of the movement comprises a movement of all of the patient's teeth relative to a skull of the patient.

307. The method of any one of the preceding Clauses, wherein at least one of the first orthodontic intervention or the second orthodontic intervention comprises an orthodontic device.

308. The method of any one of the preceding Clauses, wherein the orthodontic device comprises an orthodontic appliance configured to be secured to the patient's teeth and, once secured, apply forces to the teeth to move the teeth from the original positions.

309. The method of any one of the preceding Clauses, wherein the orthodontic device comprises an orthodontic elastic, a temporary anchorage device, or a platform.

310. The method of any one of the preceding Clauses, wherein at least one of the first orthodontic intervention or the second orthodontic intervention comprises orthognathic surgery.

311. A method for obtaining a desired final arrangement of all of a patient's teeth disposed in both of the patient's jaws, the method comprising, the method comprising:
obtaining an OTA digital model characterizing an original arrangement of the patient's teeth;
obtaining an FTA digital model characterizing a final arrangement of the patient's teeth;
rigidly transforming the FTA digital model to align the FTA digital model with the OTA digital model, thereby generating a modified FTA digital model characterizing a modified final arrangement of the patient's teeth; and
selecting the modified final arrangement as the desired final arrangement.

312. The method of any one of the preceding Clauses, wherein a first error parameter characterizing a distance between corresponding teeth in the final arrangement and the original arrangement is greater than a second error parameter characterizing a distance between corresponding teeth in the modified final arrangement and the original arrangement.

313. A method for obtaining desired final positions of both of a patient's dental arches, the method comprising:
- obtaining first data characterizing original positions of the arches;
- obtaining second data characterizing final positions of the arches;
- for each arch, determining a displacement between the corresponding original position and the corresponding final position based on the first and second data;
- for each displacement,
  - determining a first portion of the displacement unique to the arch associated with the displacement, and
  - determining a second portion of the displacement shared by all of the displacements; and
- obtaining third data characterizing modified final positions of the arches corresponding to positions of the arches after being moved from the original positions according to the first portions of the displacements.

314. The method of any one of the preceding Clauses, further comprising selecting the modified final positions of the arches as the desired final positions of the arches.

315. A method of evaluating an orthodontic treatment, the method comprising:
- obtaining first data characterizing original positions of a patient's teeth;
- obtaining second data characterizing planned positions of the teeth;
- for each tooth in one jaw of a patient, determining a planned displacement between the corresponding original position and the corresponding planned position based on the first and second data;
- for each planned displacement,
  - determining a first portion of the planned displacement unique to the tooth associated with the planned displacement, and
  - determining a second portion of the planned displacement shared by all of the planned displacements;
- obtaining third data characterizing actual positions of the teeth after the teeth have been at least partially repositioned by the orthodontic treatment;
- for each tooth in the one jaw of the patient, determining a residual displacement between the corresponding actual position and the corresponding planned position based on the second and third data;
- for each residual displacement,
  - determining a first portion of the residual displacement unique to the tooth associated with the residual displacement, and
  - determining a second portion of the residual displacement shared by all of the residual displacements;
- comparing the first portion of the residual displacement to the first portion of the planned displacement and comparing the second portion of the residual displacement to the second portion of the planned displacement; and
- based at least in part on the comparison, indicating if further orthodontic treatment is recommended.

316. The method of any one of the preceding Clauses, wherein the indication includes one or more suggested orthodontic interventions to accomplish one or more portions of the residual displacements.

317. The method of any one of the preceding Clauses, wherein comparing a corresponding portion of the planned and residual displacements comprises determining a remaining percentage of the corresponding portion of the planned displacement.

318. The method of any one of the preceding Clauses, wherein further orthodontic treatment is recommended if the percentage remaining of the planned displacement for one of the teeth is greater than a predetermined threshold.

319. The method of any one of the preceding Clauses, wherein further orthodontic treatment is recommended if a magnitude of the residual displacement for one of the teeth is greater than a predetermined threshold.

320. The method of any one of the preceding Clauses, further comprising, before determining the residual displacements, registering the third data to the second data.

321. The method of any one of the preceding Clauses, wherein registering the third data to the second data comprises identifying a rigid transformation that, when applied to the third data, reduces an error parameter characterizing a difference between the third data and the second data.

322. The method of any one of the preceding Clauses, further comprising:
- for each tooth in the one jaw of the patient, determining an actual displacement between the corresponding original position and the corresponding actual position based on the first and third data;
- for each actual displacement,
  - determining a first portion of the actual displacement unique to the tooth associated with the actual displacement, and
  - determining a second portion of the actual displacement shared by all of the actual displacements.

323. A tangible, non-transitory, computer-readable medium storing instructions that, when executed by one or more processors of a computing device, cause the one or more processors to perform operations, the operations comprising:
- obtaining first data characterizing original positions of a patient's teeth;
- obtaining second data characterizing planned positions of the teeth;
- for each tooth in one jaw of a patient, determining a planned displacement between the corresponding original position and the corresponding planned position based on the first and second data;
- for each planned displacement,
  - determining a first portion of the planned displacement unique to the tooth associated with the planned displacement, and
  - determining a second portion of the planned displacement shared by all of the planned displacements;
- obtaining third data characterizing actual positions of the teeth after the teeth have been at least partially repositioned by the orthodontic treatment;
- for each tooth in the one jaw of the patient, determining a residual displacement between the corresponding actual position and the corresponding planned position based on the second and third data;
- for each residual displacement,
  - determining a first portion of the residual displacement unique to the tooth associated with the residual displacement, and
  - determining a second portion of the residual displacement shared by all of the residual displacements;
- comparing the first portion of the residual displacement to the first portion of the planned displacement and comparing the second portion of the residual displacement to the second portion of the planned displacement; and
- based at least in part on the comparison, indicating if further orthodontic treatment is recommended.

324. The tangible, non-transitory, computer-readable medium of any one of the preceding Clauses, wherein the indication includes a suggested orthodontic intervention to accomplish the residual displacements.

325. The tangible, non-transitory, computer-readable medium of any one of the preceding Clauses, wherein comparing a corresponding portion of the planned and residual displacements comprises determining a remaining percentage of the corresponding portion of the planned displacement.

326. The tangible, non-transitory, computer-readable medium of any one of the preceding Clauses, wherein further orthodontic treatment is recommended if a magnitude of one or more portions of the residual displacement is greater than a predetermined threshold.

327. The tangible, non-transitory, computer-readable medium of any one of the preceding Clauses, the operations further comprising, before determining the residual displacements, registering the third data to the second data.

328. A method of evaluating an orthodontic treatment, the method comprising:
  obtaining first characterizing original positions of teeth of a patient;
  obtaining second data characterizing final positions of the patient's teeth;
  based on the first and second data, determining planned movement data characterizing a planned movement of each of the patient's teeth from the original position to the final position;
  decomposing the planned movement data into first planned movement data and second planned movement data, wherein the first planned movement data characterizes a first component of the planned movement achievable by a first orthodontic intervention, and wherein the second planned movement data characterizes a second component of the planned movement achievable by a second orthodontic intervention;
  obtaining third characterizing actual positions of the patient's teeth after at least one of the first orthodontic intervention or the second orthodontic intervention has been at least partially implemented;
  based on first and third data, determining actual movement data characterizing an actual movement of each of the patient's teeth from the original position to the actual position;
  decomposing the actual movement data into first actual movement data and second actual movement data, wherein the first actual movement data characterizes a first component of the actual movement achieved by the first orthodontic intervention, and wherein the second actual movement data characterizes a second component of the actual movement achieved by the second orthodontic intervention;
  comparing the first actual movement data to the first planned movement data and comparing the second actual movement data to the second planned movement data; and
  based at least in part on the comparison, indicating whether further orthodontic treatment is recommended.

329. The method of any one of the preceding Clauses, wherein comparing the first actual movement data to the first planned movement data comprises determining a percentage of the first portion of the planned movement that has been achieved by the first orthodontic intervention.

330. The method of any one of the preceding Clauses, wherein comparing the second actual movement data to the second planned movement data comprises determining a percentage of the second portion of the planned movement that has been achieved by the second orthodontic intervention.

331. The method of any one of the preceding Clauses, further comprising, based on the comparison, indicating a first orthodontic intervention to accomplish the first component of the residual movement and indicating a second orthodontic intervention to accomplish the second component of the residual movement data.

332. The method of any one of the preceding Clauses, wherein the first orthodontic intervention is different from the second orthodontic intervention.

333. The method of any one of the preceding Clauses, wherein obtaining the third data comprises obtaining image data characterizing the patient's teeth after at least one of the first orthodontic intervention or the second orthodontic intervention has been at least partially implemented.

334. A method of evaluating an orthodontic treatment, the method comprising:
  obtaining an original tooth arrangement (OTA) digital model characterizing original positions of a patient's teeth;
  obtaining a final tooth arrangement (FTA) digital model characterizing desired, final positions of the patient's teeth;
  based on the OTA and FTA digital models, determining planned displacement data characterizing a planned movement of each of the patient's teeth from the original position to the final position, wherein each planned movement has a first portion unique to the tooth associated with the planned movement and a second portion shared by all of the planned movements;
  obtaining an actual tooth arrangement (ATA) digital model characterizing actual positions of the patient's teeth;
  registering the ATA digital model to the FTA digital model;
  based on the registered ATA digital model and the FTA digital model, determining residual movement data characterizing a residual movement of each of the patient's teeth from the actual position to the final position, wherein each residual movement has a first portion unique to the tooth associated with the residual movement and a second portion shared by all of the residual movements;
  comparing the first portions of the planned and residual movements and comparing the second portions of the planned and residual movements; and
  based on the comparison, indicating whether further orthodontic treatment is recommended.

335. The method of any one of the preceding Clauses, wherein at least one of the OTA digital model, the FTA digital model, or the ATA digital model is segmented and comprises a plurality of distinct tooth models.

336. The method of any one of the preceding Clauses, wherein obtaining the ATA digital model comprises, for each of the teeth in the ATA digital model, positioning a corresponding one of the distinct tooth models from the OTA digital model or the FTA digital model at the corresponding actual position of the tooth as characterized by the ATA digital model.

BRIEF DESCRIPTION OF THE DRAWINGS

Many aspects of the present disclosure can be better understood with reference to the following drawings. The components in the drawings are not necessarily to scale.

Instead, emphasis is placed on illustrating clearly the principles of the present disclosure.

FIGS. 23A-23D are schematic diagrams of example orthodontic tooth movements in accordance with the present technology.

FIGS. 28A-28C schematically illustrate a one-dimensional example of performing an arch registration in accordance with the present technology.

FIGS. 29A-29C schematically illustrate a one-dimensional example of performing an arch registration in accordance with the present technology.

FIGS. 33B and 33C are front and side views, respectively, of a securing portion of the heat treatment fixture shown in FIG. 33A in accordance with the present technology.

FIG. 45A is a perspective view of a securing member, FIG. 45B is a perspective view of a portion of an arm of an orthodontic appliance coupled to the securing member shown in FIG. 45A, and FIG. 45C is an enlarged side view of the securing member and appliance shown in FIG. 45B, in accordance with embodiments of the present technology.

DETAILED DESCRIPTION

The present technology relates to orthodontic treatment and associated devices, systems, and methods. Some embodiments of the present technology, for example, are directed to a method of obtaining planned movements of a patient's teeth from original positions in which the teeth are maloccluded, misaligned, or otherwise in need of orthodontic correction to desired positions in which the teeth are functionally and aesthetically improved. Various embodiments are directed to a method of obtaining an orthodontic treatment plan in which orthodontic interventions to accomplish the tooth movements are indicated. Some embodiments of the present technology are directed to orthodontic appliances and associated methods of manufacturing. A method of the present technology can comprise evaluating an orthodontic treatment during and/or after implementation of the treatment and, based on the evaluation, determining planned movements Specific details of several embodiments of the technology are described below with reference to FIGS. 1A-58.

I. Definitions

Figure 1A:
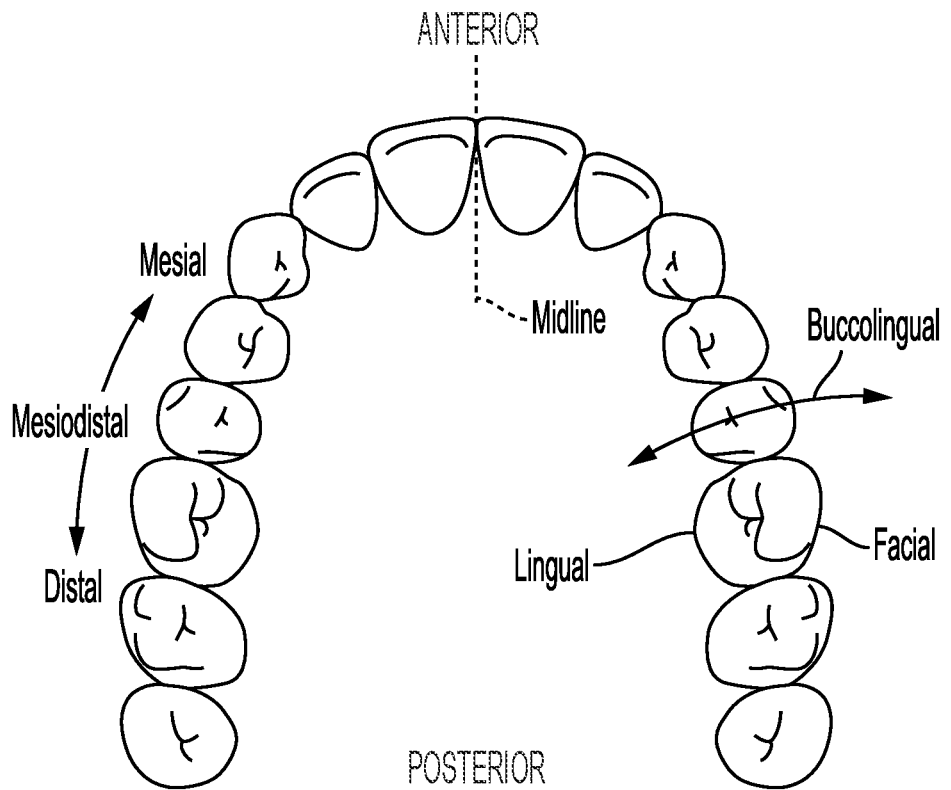
FIGS. 1A and 1B schematically illustrate directional references relative to a patient's dentition.
Figure 1B:
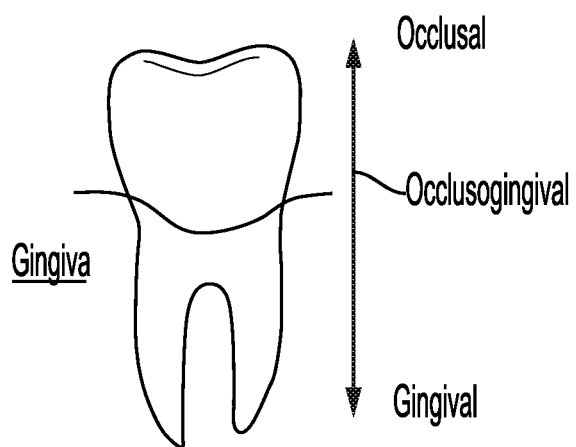

FIGS. 1A and 1B schematically depict several directional terms related to a patient's dentition. Terms used herein to provide anatomical direction or orientation are intended to encompass different orientations of the appliance as installed in the patient's mouth, regardless of whether the structure being described is shown installed in a mouth in the drawings. As illustrated in FIGS. 1A and 1B: "mesial" means in a direction toward the midline of the patient's face along the patient's curved dental arch; "distal" means in a direction away from the midline of the patient's face along the patient's curved dental arch; "occlusal" means in a direction toward the chewing surfaces of the patient's teeth; "gingival" means in a direction toward the patient's gums or gingiva; "facial" means in a direction toward the patient's lips or cheeks (used interchangeably herein with "buccal" and "labial"); "lingual" means in a direction toward the patient's tongue; "anterior" means in a direction toward a front of the patient's body; and "posterior" means in a direction toward a back of the patient's body.

As used herein, the terms "proximal" and "distal" refer to a position that is closer and farther, respectively, from a given reference point. In many cases, the reference point is a certain connector, such as an anchor, and "proximal" and "distal" refer to a position that is closer and farther, respectively, from the reference connector along a line passing through the centroid of the cross-section of the portion of the appliance branching from the reference connector.

As used herein, the terms "generally," "substantially," "about," and similar terms are used as terms of approximation and not as terms of degree, and are intended to account for the inherent variations in measured or calculated values that would be recognized by those of ordinary skill in the art.

As used herein, the term "operator" refers to a clinician, practitioner, technician or any person or machine that designs and/or manufactures an orthodontic appliance or portion thereof, and/or facilitates the design and/or manufacture of the appliance or portion thereof, and/or any person or machine associated with installing the appliance in the patient's mouth and/or any subsequent treatment of the patient associated with the appliance.

As used herein, the term "force" refers to the magnitude and/or direction of a force, a torque, or a combination thereof.

II. Overview of Orthodontic Appliances of the Present Technology

Figure 2A:
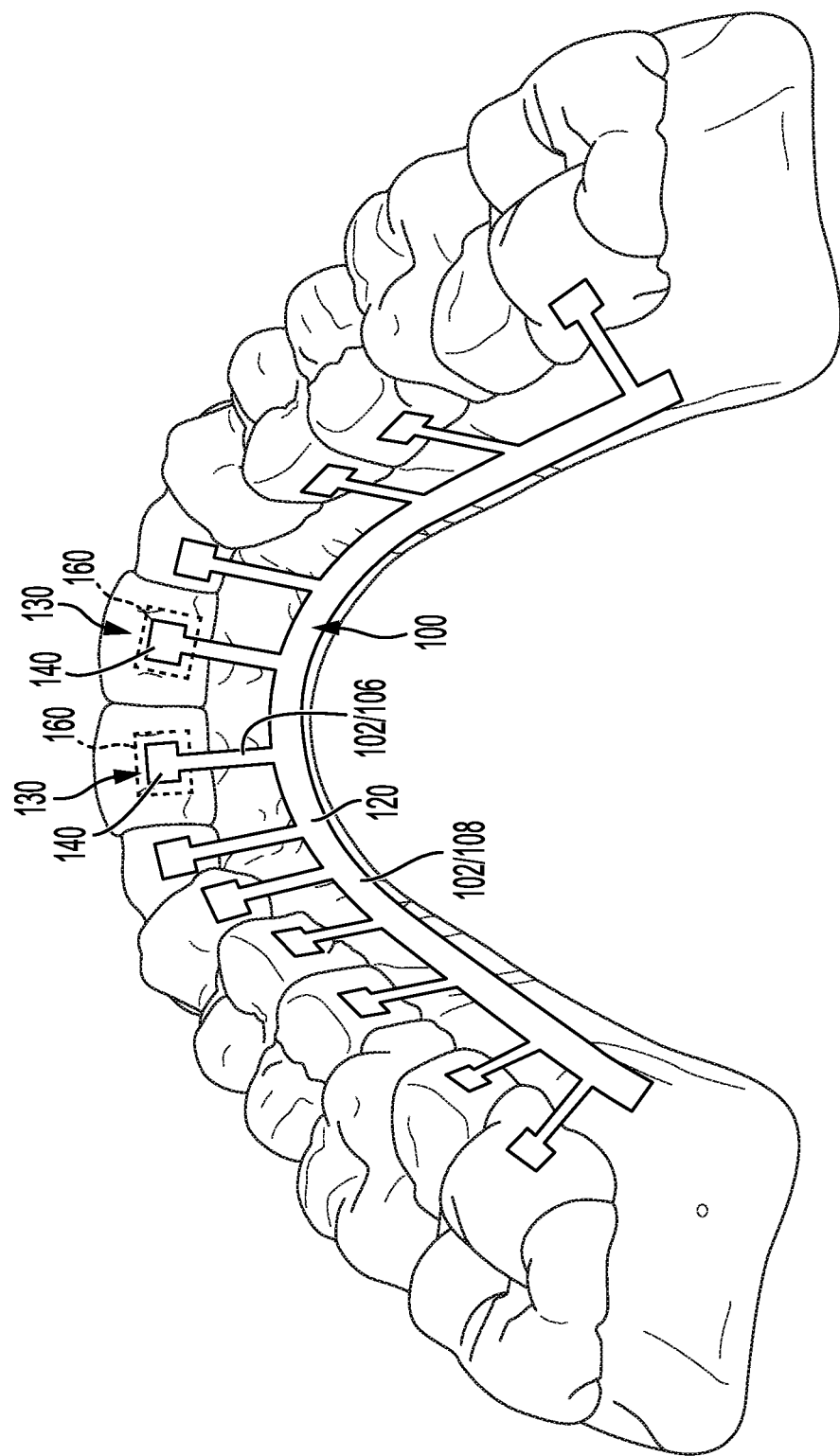
FIG. 2A shows the schematic representation of an orthodontic appliance configured in accordance with the present technology installed in a patient's mouth adjacent the patient's dentition.
Figure 2B:
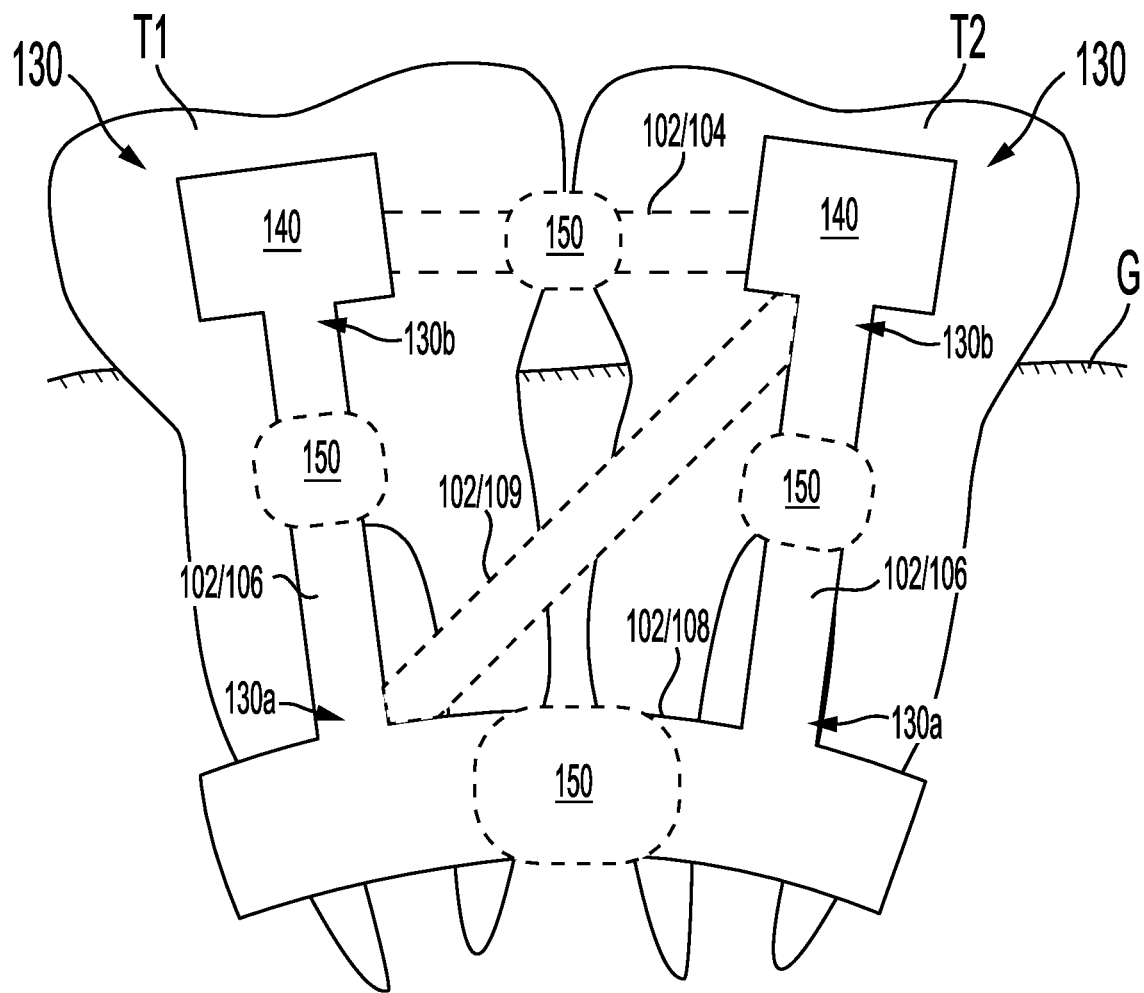
FIG. 2B is a schematic depiction of connection configuration options configured in accordance with embodiments of the present technology.

FIG. 2A is a schematic representation of an orthodontic appliance 100 (or "appliance 100") configured in accordance with embodiments of the present technology, shown positioned in a patient's mouth adjacent the patient's teeth. FIG. 2B is an enlarged view of a portion of the appliance 100. The appliance 100 is configured to be installed within a patient's mouth to impart forces on one or more of the teeth to reposition all or some of the teeth. In some cases, the appliance 100 may additionally or alternatively be configured to maintain a position of one or more teeth. As shown schematically in FIGS. 2A and 2B, the appliance 100 can comprise a deformable member that includes one or more attachment portions 140 (each represented schematically by a box), each configured to be secured to a tooth surface directly or indirectly via a securing member 160. The appliance 100 may further comprise one or more connectors 102 (also depicted schematically), each extending directly between attachment portions 140 ("first connectors 104"), between an attachment portion 140 and one or more other connectors 102 ("second connectors 106"), or between two or more other connectors 102 ("third connectors 108"). Only two attachment portions 140 and two connectors 102 are labeled in FIG. 2A for ease of illustration. As discussed herein, the number, configuration, and location of the connectors 102 and attachment portions 140 may be selected to provide a desired force on one or more of the teeth when the appliance 100 is installed.

The attachment portions 140 may be configured to be detachably coupled to a securing member 160 that is bonded, adhered, or otherwise secured to a surface of one of the teeth to be moved. In some embodiments, one or more of the attachment portions 140 may be directly bonded, adhered, or otherwise secured to a corresponding tooth without a securing member or other connection interface at the tooth. The attachment portions 140 may also be referred to as "bracket connectors" or "male connector elements" herein. The different attachment portions 140 of a given appliance 100 may have the same or different shape, same or different size, and/or same or different configuration. The attachment portions 140 may comprise any of the attachment portions, bracket connectors, and/or male connector elements disclosed in U.S. patent application Ser. No. 15/370,704 (Publ. No. 2017/0156823) filed Dec. 6, 2016, U.S. patent application Ser. No. 15/929,443 (Publ. No. 2021/0007830) filed May 2, 2020, and U.S. patent application Ser. No. 15/929,444 (Publ. No. 2020/0390524) filed May 2, 2020, which are incorporated by reference herein in their entirety.

The appliance 100 may include any number of attachment portions 140 suitable for securely attaching the appliance 100 to the patient's tooth or teeth in order to achieve a desired movement. In some examples, multiple attachment portions 140 may be attached to a single tooth. The appliance 100 may include an attachment portion for every tooth, fewer attachment portions than teeth, or more attachment portions 140 than teeth. In these and other embodiments, the appliance 100 one or more of the attachment portions 140 may be configured to be coupled to one, two, three, four, five or more connectors 102.

As previously mentioned, the connectors 102 may comprise one or more first connectors 104 that extend directly between attachment portions 140. The one or more first connectors 104 may extend along a generally mesiodistal dimension when the appliance 100 is installed in the patient's mouth. In these and other embodiments, the appliance 100 may include one or more first connectors 104 that extend along a generally occlusogingival and/or buccolingual dimension when the appliance 100 is installed in the patient's mouth. In some embodiments, the appliance 100 does not include any first connectors 104.

Additionally or alternatively, the connectors 102 may comprise one or more second connectors 106 that extend between one or more attachment portions 140 and one or more connectors 102. The one or more second connectors 106 can extend along a generally occlusogingival dimension when the appliance 100 is installed in the patient's mouth. In these and other embodiments, the appliance 100 may include one or more second connectors 106 that extend along a generally mesiodistal and/or buccolingual dimension when the appliance 100 is installed in the patient's mouth. In some embodiments, the appliance 100 does not include any second connectors 106. In such embodiments, the appliance 100 would only include first connectors 104 extending between attachment portions 140. A second connector 106 and the attachment portion 140 to which it is attached may comprise an "arm," as used herein (such as arm 130 in FIGS. 2A and 2B). In some embodiments, multiple second connectors 106 may extend from the same location along the appliance 100 to the same attachment portion 140. In such cases, the multiple second connectors 106 and the attachment portion 140 together comprise an "arm," as used herein. The use of two or more connectors to connect two points on the appliance 100 enables application of a greater force (relative to a single connector connecting the same points) without increasing the strain on the individual connectors. Such a configuration is especially beneficial given the spatial constraints of the fixed displacement treatments herein.

Additionally or alternatively, the connectors 102 may comprise one or more third connectors 108 that extend between two or more other connectors 102. The one or more third connectors 108 may extend along a generally mesiodistal dimension when the appliance 100 is installed in the patient's mouth. In these and other embodiments, the appliance 100 may include one or more third connectors 108 that extend along a generally occlusogingival and/or buccolingual dimension when the appliance 100 is installed in the patient's mouth. In some embodiments, the appliance 100 does not include any third connectors 108. One, some, or all of the third connectors 108 may be positioned gingival to one, some, or all of the first connectors 104. In some embodiments, the appliance 100 includes a single third connector 108 that extends along at least two adjacent teeth and provides a common attachment for two or more second connectors 106. In several embodiments, the appliance 100 includes multiple non-contiguous third connectors 108, each extending along at least two adjacent teeth.

As shown in FIG. 2A, in some embodiments the appliance 100 may be configured such that all or a portion of one, some, or all of the connectors 102 are disposed proximate the patient's gingiva when the appliance 100 is installed within the patient's mouth. For example, one or more third connectors 108 may be configured such that all or a portion of the one or more third connectors 108 is positioned below the patient's gum line and adjacent to but spaced apart from the gingiva. In many cases it may be beneficial to provide a small gap (e.g., 0.5 mm or less) between the third connector(s) 108 and the patient's gingiva, as contact between the third connector(s) 108 (or any portion of the appliance 100) and the gingiva can cause irritation and patient discomfort. In some embodiments, all or a portion of the third connector(s) 108 is configured to be in direct contact with the gingiva when the appliance 100 is disposed in the patient's mouth. Additionally or alternatively, all or a portion of one or more first connectors 104 and/or second connectors 106 may be configured to be disposed proximate the gingiva.

According to some embodiments, one or more connectors 102 may extend between an attachment portion 140 or connector 102 and a joint comprising (a) two or more connectors 102, (b) two or more attachment portions 140, or (c) at least one attachment portion 140 and at least one connector 102. According to some embodiments, one or more connectors 102 may extend between a first joint comprising (a) two or more connectors 102, (b) two or more attachment portions 140, or (c) at least one attachment member and at least one connector 102, and a second joint comprising (a) two or more connectors 102, (b) two or more attachment portions 140, or (c) at least one attachment portion 140 and at least one connector 102. An example of a connector 102 extending between (a) a joint between a second and third connector 106, 108, and (b) a joint between a second connector 106 and an attachment portion 140 is depicted schematically and labeled 109 in FIG. 2B.

Each of the connectors 102 may be designed to have a desired stiffness so that an individual connector 102 or combination of connectors 102 imparts a desired force on one or more of the teeth. In many cases, the force applied by a given connector 102 may be governed by Hooke's Law, or $F=kx$, where F is the restoring force exerted by the connector 102, k is the stiffness coefficient of the connector 102, and x is the displacement. In the most basic example, if a connector 102 does not exist between two points on the appliance 100, then the stiffness coefficient along that path is zero and no forces are applied. In the present case, the individual connectors 102 of the present technology may have varying non-zero stiffness coefficients. For example, one or more of the connectors 102 may be rigid (i.e., the stiffness coefficient is infinite) such that the connector 102 will not flex or bend between its two end points. In some embodiments, one or more of the connectors 102 may be "flexible" (i.e., the stiffness coefficient is non-zero and positive) such that the connector 102 can deform to impart (or absorb) a force on the associated tooth or teeth or other connector 102.

In some embodiments it may be beneficial to include one or more rigid connectors between two or more teeth. A rigid connector 102 is sometimes referred to herein as a "rigid bar" or an "anchor." Each rigid connector 102 may have sufficient rigidity to hold and maintain its shape and resist bending. The rigidity of the connector 102 can be achieved by selecting a particular shape, width, length, thickness, and/or material. Connectors 102 configured to be relatively rigid may be employed, for example, when the tooth to be connected to the connector 102 or arm is not to be moved (or moved by a limited amount) and can be used for anchorage. Molar teeth, for example, can provide good anchorage as molar teeth have larger roots than most teeth and thus require greater forces to be moved. Moreover, anchoring one or more portions of the appliance 100 to multiple teeth is more secure than anchoring to a single tooth. As another example, a rigid connection may be desired when moving a group of teeth relative to one or more other teeth. Consider, for instance, a case in which the patient has five teeth separated from a single tooth by a gap, and the treatment plan is to close the gap. The best course of treatment is typically to move the one tooth towards the five teeth, and not vice versa. In this case, it may be beneficial to provide one or more rigid connectors between the five teeth. For all of the foregoing reasons and many others, the appliance 100 may include one or more rigid first connectors 104, one or more rigid second connectors 106, and/or one or more rigid third connectors 108.

In these and other embodiments, the appliance 100 may include one or more flexible first connectors 104, one or more flexible second connectors 106, and/or one or more flexible third connectors 108. Each flexible connector 102 may have a particular shape, width, thickness, length, material, and/or other parameters to provide a desired degree of flexibility. According to some embodiments of the present technology, the stiffness of a given connector 102 may be tuned via incorporation of a one or more resiliently flexible biasing portions 150. As shown schematically in FIG. 2B, one, some, or all of the connectors 102 may include one or more biasing portion 150, such as springs, each configured to apply a customized force specific to the tooth to which it is attached.

Figure 2C:
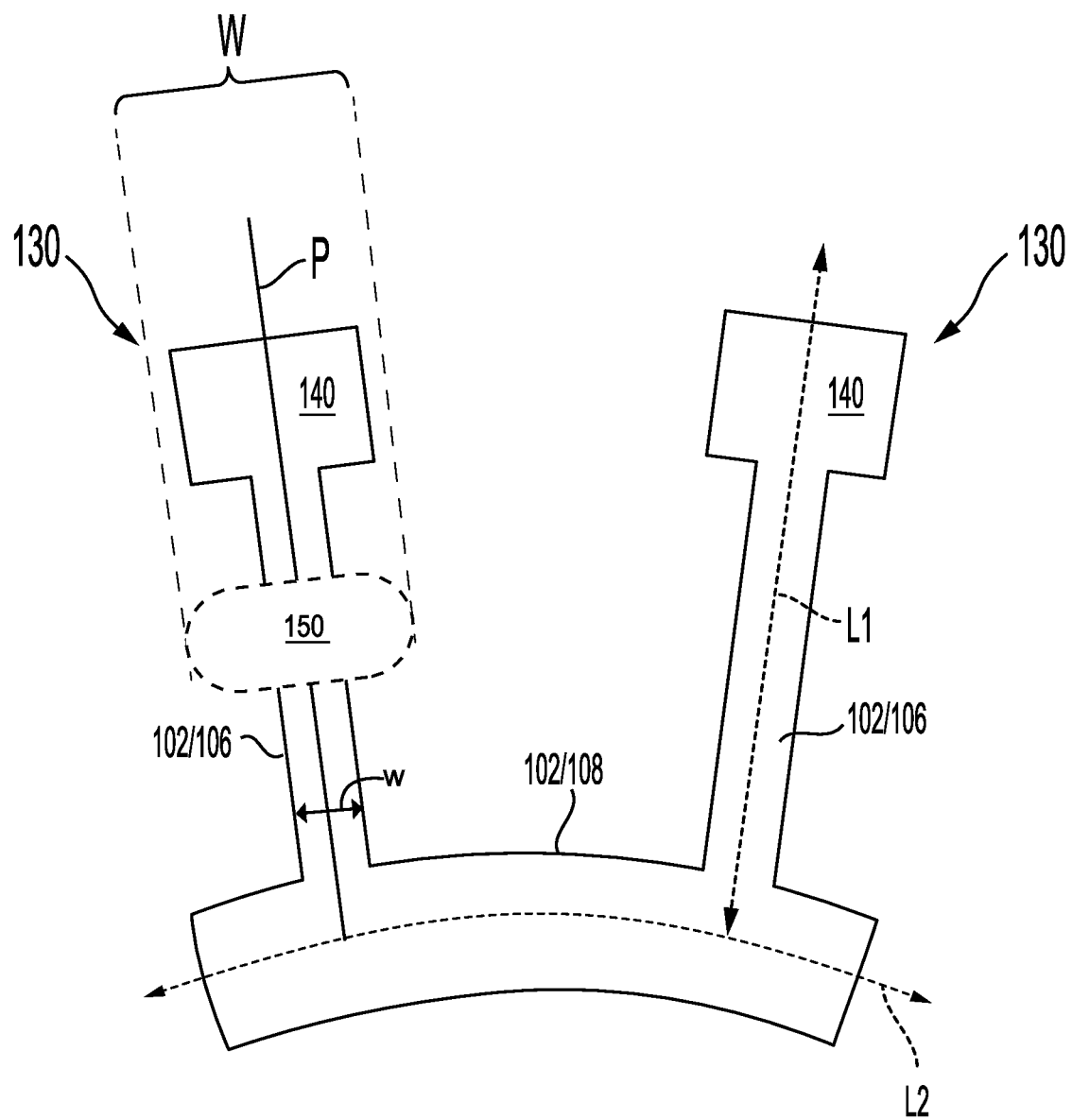
FIG. 2C is a schematic depiction of a portion of an appliance configured in accordance with embodiments of the present technology.

As depicted in the schematic shown in FIG. 2C, the biasing portion(s) 150 may extend along all or a portion of the longitudinal axis L1 of the respective connector 102 (only the longitudinal axis L1 for second connector 106 and the longitudinal axis L2 for third connector 108 is labeled in FIG. 2C). The direction and magnitude of the force and torque applied on a tooth by a biasing portion 150 depends, at least in part, on the shape, width, thickness, length, material, shape set conditions, and other parameters of the biasing portion 150. As such, one or more aspects of the biasing portion 150 (including the aforementioned parameters) may be varied so that the corresponding arm 130, connector 102, and/or biasing portion 150 produces a desired tooth movement when the appliance 100 is installed in the patient's mouth. Each arm 130 and/or biasing portion 150 may be designed to move one or more teeth in one, two, or all three translational directions (i.e., mesiodistal, buccolingual, and occlusogingival) and/or in one, two, or all three rotational directions (i.e., buccolingual root torque, mesiodistal angulation and mesial out-in rotation).

The biasing portions 150 of the present technology can have any length, width, shape, and/or size sufficient to move the respective tooth towards a desired position. In some embodiments, one, some, or all of the connectors 102 may have one or more inflection points along a respective biasing portion 150. The connectors 102 and/or biasing portions 150 may have a serpentine configuration such that the connector 102 and/or biasing portion 150 doubles back on itself at least one or more times before extending towards the attachment portion 140. For example, in some embodiments the second connectors 106 double back on themselves two times along the biasing portion 150, thereby forming first and second concave regions facing in generally different directions relative to one another (as an example, see FIG. 3B). The open loops or overlapping portions of the connector 102 corresponding to the biasing portion 150 may be disposed on either side of a plane P (FIG. 2C) bisecting an overall width W (FIG. 2C) of the arm 130 and/or connector 102 such that the extra length of the arm 130 and/or connector 102 is accommodated by the space medial and/or distal to the arm 130 and/or connector 102. This allows the arm 130 and/or connector 102 to have a longer length (as compared to a linear arm) to accommodate greater tooth movement, despite the limited space in the occlusal-gingival or vertical dimension between any associated third connector 108 and the location at which the arm 130 attaches to the tooth.

It will be appreciated that the biasing portion 150 may have other shapes or configurations. For example, in some embodiments the connector 102 and/or biasing portion 150 may include one or more linear regions that zig-zag towards the attachment portion 140. One, some, or all of the connectors 102 and/or biasing portions 150 may have only linear segments or regions, or may have a combination of curved and linear regions. In some embodiments, one, some, or all of the connectors 102 and/or biasing portions 150 do not include any curved portions.

According to some examples, a single connector 102 may have multiple biasing portions 150 in series along the longitudinal axis of the respective connector 102. In some embodiments, multiple connectors 102 may extend between two points along the same or different paths. In such embodiments, the different connectors 102 may have the same stiffness or different stiffnesses.

In those embodiments where the appliance 100 has two or more connectors 102 with biasing portions 150, some, none, or all of the connectors 102 may have the same or different lengths, the same or different widths, the same or different thicknesses, the same or different shapes, and/or may be made of the same or different materials, amongst other properties. In some embodiments, less than all of the connectors 102 have biasing portions 150. Connectors 102 without biasing portions 150 may, for example, comprise one or more rigid connections between a rigid third connector 108 and the attachment portion 140. In some embodiments, none of the connectors 102 of the appliance 100 have a biasing portion 150.

According to some embodiments, for example as depicted schematically in FIG. 2A, the appliance 100 may include a single, continuous, substantially rigid third connector (referred to as "anchor 120") and a plurality of flexible arms 130 extending away from the anchor 120. When the appliance 100 is installed in the patient's mouth, each of the arms 130 may connect to a different one of the teeth to be moved and exerts a specific force on its respective tooth, thereby allowing an operator to move each tooth independently.

Such a configuration provides a notable improvement over traditional braces in which all of the teeth are connected by a single archwire, such that movement of one tooth can cause unintentional movement of one or more nearby teeth. The independent and customized tooth movement enabled by the appliances of the present technology allows the operator to move the teeth from an original tooth arrangement ("OTA") to a final tooth arrangement ("FTA") more efficiently, thereby obviating periodic adjustments, reducing the number of office visits, and reducing or eliminating patient discomfort, and reducing the overall treatment time (i.e., the length of time the appliance is installed in the patient's mouth) by at least 50% relative to the overall treatment time for traditional braces.

The anchor 120 may comprise any structure of any shape and size configured to comfortably fit within the patient's mouth and provide a common support for one or more of the arms 130. In many embodiments, the anchor 120 is disposed proximate the patient's gingiva when the appliance 100 is installed within the patient's mouth, for example as shown in FIG. 2B. For instance, the appliance may be designed such that, when installed in the patient's mouth, all or a portion of the anchor 120 is positioned below the patient's gum line and adjacent but spaced apart from the gingiva. In many cases it may be beneficial to provide a small gap (e.g., 0.5 mm or less) between the anchor 120 (or any portion of the appliance 100) and the patient's gingiva as contact between the anchor 120 and the gingiva can cause irritation and patient discomfort. In some embodiments, all or a portion of the anchor 120 is configured to be in contact with the gingiva when the appliance 100 is disposed in the patient's mouth.

The anchor 120 may be significantly more rigid than the arms 130 such that the equal and opposite forces experienced by each of the arms 130 when exerting a force on its respective tooth are countered by the rigidity of the anchor 120 and the forces applied by the other arms 130, and do not meaningfully affect the forces on other teeth. As such, the anchor 120 effectively isolates the forces experienced by each arm 130 from the rest of the arms 130, thereby enabling independent tooth movement.

According to some embodiments, for example as shown schematically in FIGS. 2A and 2B, the anchor 120 comprises an elongated member having a longitudinal axis L2 (see FIG. 2C) and forming an arched shape configured to extend along a patient's jaw when the appliance 100 is installed. In these and other embodiments, the anchor 120 may be shaped and sized to span two or more of the patient's teeth when positioned in the patient's mouth. In some examples, the anchor 120 includes a rigid, linear bar, or may comprise a structure having both linear and curved segments. In these and other embodiments, the anchor 120 may extend laterally across all or a portion of the patient's mouth (e.g., across all or a portion of the palate, across all or a portion of the lower jaw, etc.) and/or in a generally anterior-posterior direction. Moreover, the appliance 100 may comprise a single anchor or multiple anchors. For example, the appliance 100 may comprise multiple, discrete, spaced apart anchors, each having two or more arms 130 extending therefrom. In these and other embodiments, the appliance 100 may include one or more other connectors extending between adjacent arms 130.

Any and all of the features discussed above with respect to anchor 120 applies to any of the third connectors 108 disclosed herein.

As shown in FIG. 2B, each of the arms 130 may extend between a proximal or first end portion 130a and a distal or second end portion 130b, and may have a longitudinal axis L extending between the first end portion 130a and the second end portion 130b. The first end portion 130a of one, some, or all of the arms 130 may be disposed at the anchor 120. In some embodiments, one, some, or all of the arms 130 are integral with the anchor 120 such that the first end portion 130a of such arms are continuous with the anchor 120. The arms 130 may extend from the anchor 120 at spaced intervals along the longitudinal axis L2 of the, as shown in FIG. 2A. In some embodiments, the arms 130 may be spaced at even intervals relative to each other, or at uneven intervals relative to each other, along the longitudinal axis L2 of the anchor 120.

One, some, or all of the arms 130 may include an attachment portion 140 at or near the second end portion 130b. In some embodiments, for example as shown in FIGS. 2A-2C, one or more of the arms 130 is cantilevered from the anchor 120 such that the second end portion 130b of the cantilevered arm(s) 130 has a free distal end portion 130b. In these and other embodiments, a distal terminus of the attachment portion 140 may coincide with a distal terminus of the arm 130. The attachment portion 140 may be configured to detachably couple the respective arm 130 to a securing member (e.g., a bracket) that is bonded, adhered, or otherwise secured to a surface of one of the teeth to be moved. In some embodiments, the attachment portion 140 may be directly bonded, adhered, or otherwise secured to a corresponding tooth without a securing member or other connection interface at the tooth.

Referring to still to FIGS. 2A and 2B, one, some, or all of the arms 130 may include one or more resiliently flexible biasing portions 150, such as springs, each configured to apply a customized force, torque or combination of force and torque specific to the tooth to which it is attached. The biasing portion(s) 150 may extend along all or a portion of the longitudinal axis L1 of the respective arm 130 between the anchor 120 and the attachment portion 140. The direction and magnitude of the force and torque applied on a tooth by a biasing portion 150 depends, at least in part, on the shape, width, thickness, length, material, shape set conditions, and other parameters of the biasing portion 150. As such, one or more aspects of the arm 130 and/or biasing portion 150 (including the aforementioned parameters) may be varied so that the arm 130 and/or biasing portion 150 produce a desired tooth movement when the appliance 100 is installed in the patient's mouth. Each arm 130 and/or biasing portion 150 may be designed to move one or more teeth in one, two, or all three translational directions (i.e., mesiodistal, buccolingual, and occlusogingival) and/or in one, two, or all three rotational directions (i.e., buccolingual root torque, mesiodistal angulation and mesial out-in rotation).

The biasing portions 150 of the present technology can have any length, width, shape, and/or size sufficient to move the respective tooth towards a desired FTA. In some embodiments, one, some, or all of the arms 130 may have one or more inflection points along a respective biasing portion 150. The arms 130 and/or biasing portions 150 may have a serpentine configuration such that the arm 130 and/or biasing portion 150 doubles back on itself at least one or more times before extending towards the attachment portion 140. In FIG. 2B, the arm 130 doubles back on itself two times along the biasing portion 150, thereby forming first and second concave regions facing in generally different directions relative to one another. The open loops or overlapping portions of the arm 130 corresponding to the biasing portion 150 may be disposed on either side of a plane P bisecting an overall width W of the arm 130 such that the extra length of the arm 130 is accommodated by the space medial and/or distal to the arm 130. This allows the arm 130 to have a longer length (as compared to a linear arm) to accommodate greater tooth movement, despite the limited space in the occlusal-gingival or vertical dimension between the anchor 120 and the location at which the arm 130 attaches to the tooth.

It will be appreciated that the biasing portion 150 may have other shapes or configurations. For example, in some embodiments the arm 130 and/or biasing portion 150 may include one or more linear regions that zig-zag towards the attachment portion 140. One, some, or all of the arms 130 and/or biasing portions 150 may have only linear segments or regions, or may have a combination of curved and linear regions. In some embodiments, one, some, or all of the arms 130 and/or biasing portions 150 do not include any curved portions.

According to some examples, a single arm 130 may have multiple biasing portions 150. The multiple biasing portions 150 may be in series along the longitudinal axis L1 of the respective arm 120. In some embodiments, multiple arms 130 may extend in parallel between two points along the same path or along different paths. In such embodiments, the different arms 130 may have the same stiffness or different stiffnesses.

In those embodiments where the appliance 100 has two or more arms 130 with biasing portions 150, some, none, or all of the arms 130 may have the same or different lengths, the same or different widths, the same or different thicknesses, the same or different shapes, and/or may be made of the same or different materials, amongst other properties. In some embodiments, less than all of the arms 130 have biasing portions 150. Arms 130 without biasing portions 150 may, for example, comprise one or more rigid connections between the anchor 120 and the attachment portion 140. In some embodiments, none of the arms 130 of the appliance 100 have a biasing portion 150.

The appliances of the present technology may include any number of arms 130 suitable for repositioning the patient's teeth while taking into account the patient's comfort. Unless explicitly limited to a certain number of arms in the specification, the appliances of the present technology may comprise a single arm, two arms, three arms, five arms, ten arms, sixteen arms, etc. In some examples, one, some, or all of the arms 130 of the appliance may be configured to individually connect to more than one tooth (i.e., a single arm 130 may be configured to couple to two teeth at the same time). In these and other embodiments, the appliance 100 may include two or more arms 130 configured to connect to the same tooth at the same time.

Any portion of the appliances of the present technology may include a biasing portion 150. For example, in some embodiments, portions thereof (e.g., the anchor(s), the arm(s), the biasing portion(s), the attachment portion(s), the link(s), etc.) may comprise one or more superelastic materials.

Additional details related to the individual directional force(s) applied via the biasing portion 150 or, more generally the arm 130, are described in U.S. application Ser. No. 15/370,704, now U.S. Pat. No. 10,383,707, issued Aug. 20, 2019, the disclosure of which is incorporated by reference herein in its entirety.

The appliances disclosed herein and/or any portion thereof (e.g., the anchor(s), the arm(s), the biasing portion(s), the attachment portion(s), the link(s), etc.) may comprise one or more superelastic materials. The appliances disclosed herein and/or any portion thereof (e.g., the anchor(s), the arm(s), the biasing portion(s), the attachment portion(s), the link(s), etc.) may comprise Nitinol, stainless steel, beta-titanium, cobalt chrome, MP35N, 35N LT, one or more metal alloys, one or more polymers, one or more ceramics, and/or combinations thereof.

Figure 3B:
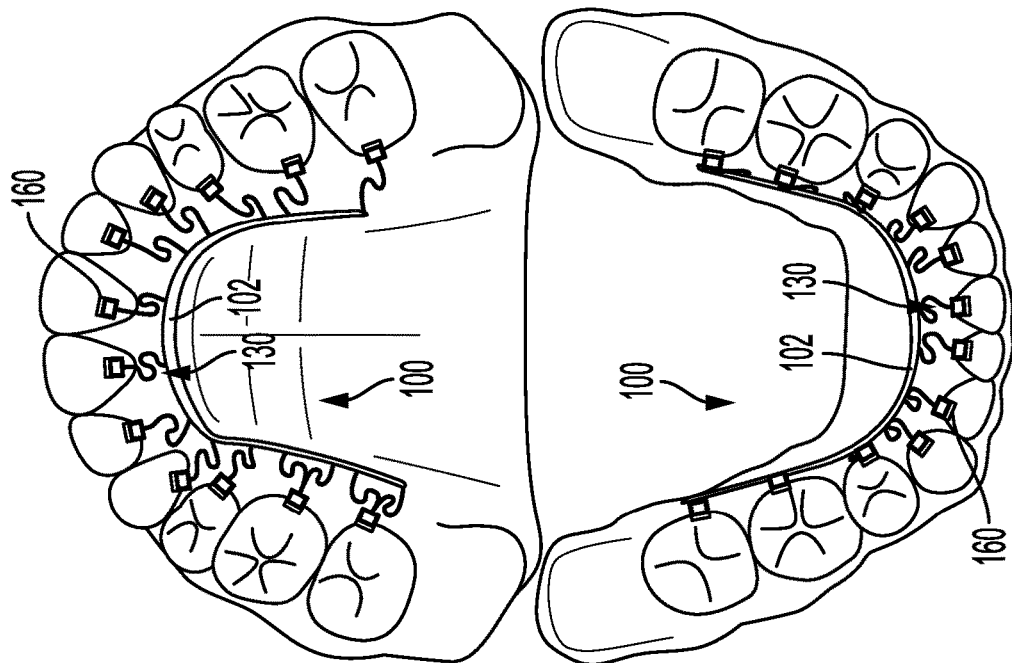
FIGS. 3A and 3B are elevation views of an appliance configured in accordance with several embodiments of the present technology installed in an upper and lower jaw of a patient's mouth with the patient's teeth in an original tooth arrangement and a final tooth arrangement, respectively.
Figure 3A:
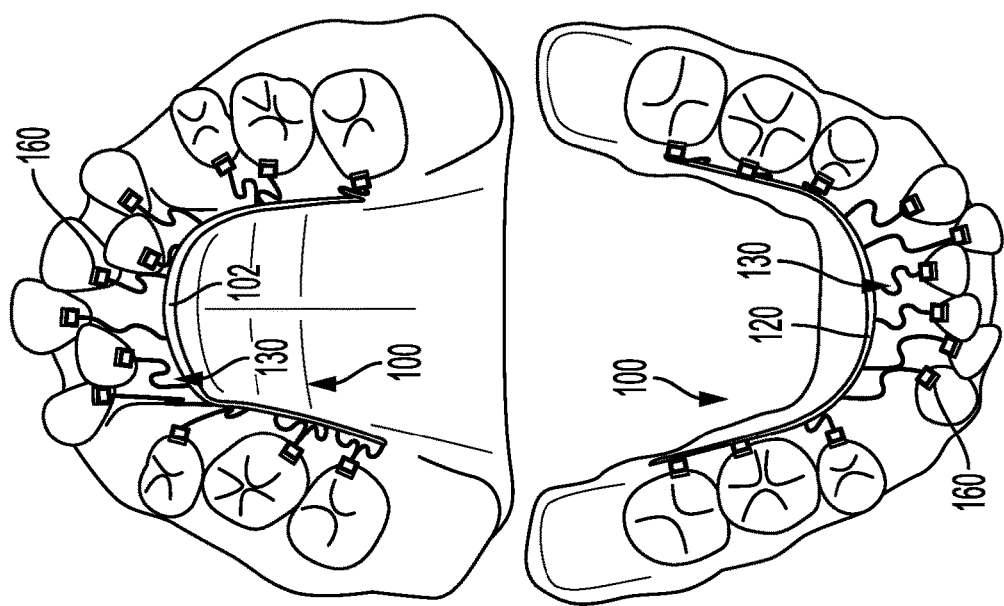

FIGS. 3A and 3B are elevation views of the appliance 100 installed on both the upper and lower arches of a patient's mouth with the arms 130 coupled to securing members 160 attached to the lingual surfaces of the teeth. It will be appreciated that the appliance 100 of one or both of the upper and lower arches may be positioned proximate a buccal side of a patient's teeth, and that the securing members 160 and/or arms 130 may alternatively be coupled to the buccal surface of the teeth.

FIG. 3A shows the teeth in an OTA with the arms 130 in a deformed or loaded state, and FIG. 3B shows the teeth in the FTA with the arms 130 in a substantially unloaded state. When the arms 130 are initially secured to the securing members 160 when the teeth are in the OTA, the arms 130 are forced to take a shape or path different than their "as designed" configurations. Because of the inherent memory of the resilient biasing portions 150, the arms 130 impart a continuous, corrective force on the teeth to move the teeth towards the FTA, which is where the biasing portions 150 are in their as-designed or unloaded configurations. As such, tooth repositioning using the appliances of the present technology can be accomplished in a single step, using a single appliance. In addition to enabling fewer office visits and a shorter treatment time, the appliances of the present technology greatly reduce or eliminate the pain experienced by the patient as the result of the teeth moving as compared to braces. With traditional braces, every time the orthodontist makes an adjustment (such as installing a new archwire, bending the existing archwire, repositioning a bracket, etc.), the affected teeth experience a high force which is very painful for the patient. Over time, the applied force weakens until eventually a new wire is required. The appliances of the present technology, however, apply a movement-generating force on the teeth continuously while the appliance is installed, which allows the teeth to move at a slower rate that is much less painful (if painful at all) for the patient. Even though the appliances disclosed herein apply a lower and less painful force to the teeth, because the forces being applied are continuous and the teeth can move independently (and thus more efficiently), the appliances of the present technology arrive at the FTA faster than traditional braces or aligners, as both alternatives require intermediate adjustments.

Figure 3C:
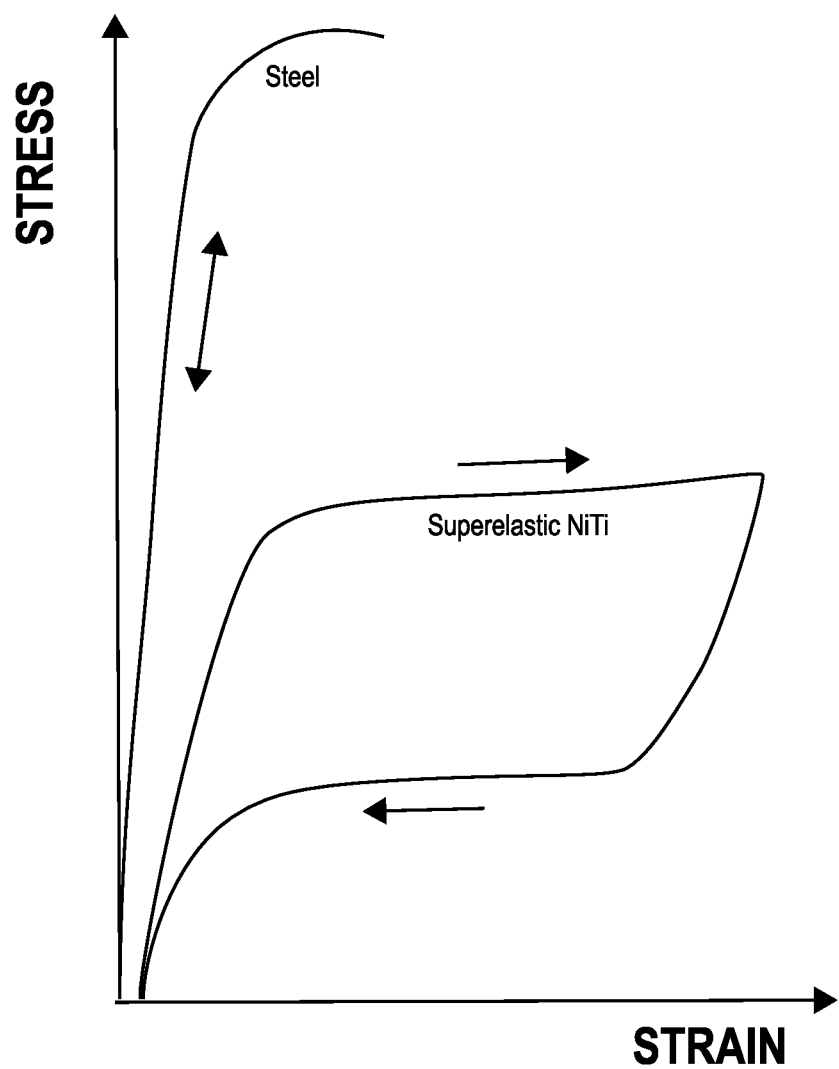
FIG. 3C depicts example stress-strain curves of nitinol and steel.

In many embodiments, the movement-generating force is lower than that applied by traditional braces. In those embodiments in which the appliance comprises a superelastic material (such as nitinol), the superelastic material behaves like a constant force spring for certain ranges of strain, and thus the force applied does not drop appreciably as the tooth moves. For example, as shown in the stress-strain curves of nitinol and steel in FIG. 3C, the curve for nitinol is relatively flat compared to that of steel. Thus, the superelastic connectors, biasing portions, and/or arms of the present technology apply essentially the same stress for many different levels of strain (e.g., deflection). As a result, the force applied to a given tooth stays constant as the teeth move during treatment, at least up until the teeth are very close or in the final arrangement. The appliances of the present technology are configured to apply a force just below the pain threshold, such that the appliance applies the maximum non-painful force to the tooth (or teeth) at all times during tooth movement. This results in the most efficient (i.e., fastest) tooth movement without pain.

Embodiments involving multiple steps (or multiple appliances, or both) may include one or more intermediate tooth arrangements (ITAs) between an original tooth arrangement (OTA) and a desired final tooth arrangement (FTA). Likewise, the appliances disclosed herein may be designed to be installed after a first or subsequently used appliance had moved the teeth from an OTA to an ITA (or from one ITA to another ITA) and was subsequently removed. Thus, the appliances of the present technology may be designed to move the teeth from an ITA to an FTA (or to another ITA). Additionally or alternatively, the appliances may be designed to move the teeth from an OTA to an ITA, or from an OTA to an FTA without changing appliances at an ITA.

In some embodiments, the appliances disclosed herein may be configured such that, once installed on the patient's teeth, the appliance cannot be removed by the patient. In some embodiments, the appliance may be removable by the patient.

Any of the example appliances or appliance portions described herein may be made of any suitable material or materials, such as, but not limited to Nitinol (NiTi), stainless steel, beta-titanium, cobalt chrome or other metal alloy, polymers, or ceramics, and may be made as a single, unitarily-formed structure or, alternatively, in multiple separately-formed components connected together in single structure. However, in particular examples, the rigid bars, bracket connectors and loop or curved features of an appliance (or portion of an appliance) described in those examples are made by cutting a two dimensional (2D) form of the appliance from a 2D sheet of material and bending the 2D form into a desired 3D shape of the appliance, according to processes as described in U.S. Pat. No. 10,383,707, U.S. patent application Ser. No. 15/929,442 (Publ. No. 2020/0345455), filed May 2, 2020, or other suitable processes.

III. Selected Methods for Manufacturing Orthodontic Appliances and Fixtures

Several of the methods disclosed herein can be performed using one or more aspects of a manufacturing system. The system can include an imaging device configured to be communicatively coupled to a computing device. The imaging device can include any suitable device or collection of devices configured to obtain image data or other digital representation of a patient's teeth, gingiva, and other dental anatomy. For example, the imaging device can include an optical scanning device (e.g., as commercially sold by ITERO, 3 SHAPE, and others), a cone-beam computed tomography scanner, or any other suitable imaging device.

The computing device can be any suitable combination of software and hardware. For example, the computing device can include a special purpose computer or data processor that is specifically programmed, configured, or constructed to perform one or more of the computer-executable instructions explained in detail herein. Additionally or alternatively, the computing device can include a distributed computing environment in which tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

The system can also include one or more input devices (e.g., touch screen, keyboard, mouse, microphone, camera, etc.) and one or more output devices (e.g., display, speaker, etc.) configured to be communicatively coupled to the computing device. In operation, a user can provide instructions to the computing device and receive output from the computing device via the input and output devices.

The computing device may be configured to be communicatively connected to one or more fabricating systems (including fabricating machines) for fabricating appliances, shape setting fixtures, and any other components thereof and associated tools, as described herein. The computing device can be connected to the fabricating system(s) by any suitable communication connection including, but not limited to a direct electronic connection, network connection, or the like. Alternatively, or in addition, the connection may be provided by delivery to the fabricating system of a physical, non-transient storage medium on which data from the computing device has been stored.

Methods of Designing Orthodontic Appliances and Fixtures

Figure 4:
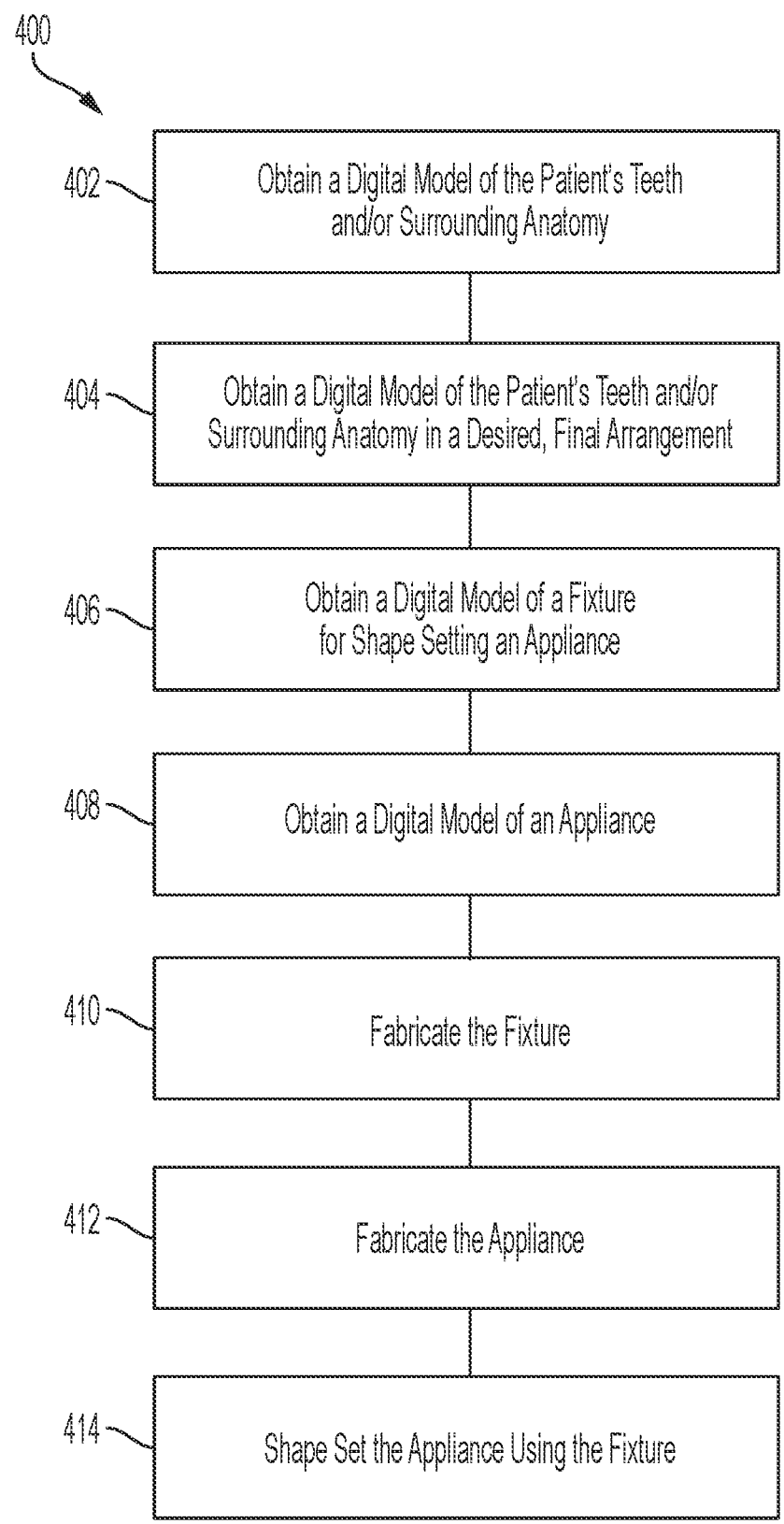
FIG. 4 is a schematic block diagram of a system for manufacturing an orthodontic appliance in accordance with the present technology.

FIG. 4 is a flow diagram of a process 400 for making an orthodontic appliance. The process 400 begins at block 402 with obtaining a digital model of the patient's teeth and/or surrounding anatomy (such as the gingiva) in the OTA. The process 400 continues at block 404 with obtaining a digital model of the patient's teeth and/or surrounding anatomy in the FTA. Next the process 400 comprises obtaining a digital model (block 406) of a fixture for shape setting the appliance. The process 400 further includes obtaining an appliance digital model (block 408). As shown at blocks 410 and 412, the process 400 continues with fabricating the fixture and fabricating the appliance. Finally, the process 400 includes shape setting the appliance using the fixture (block 414). While the foregoing steps are presented in a particular order, it will be appreciated they need not be executed in the presented order. For example, in some embodiments obtaining the appliance digital model occurs prior to and/or at the same time as obtaining the fixture digital model. In other embodiments, obtaining the appliance digital model occurs after and/or at the same time as obtaining the fixture digital model.

Figure 5:
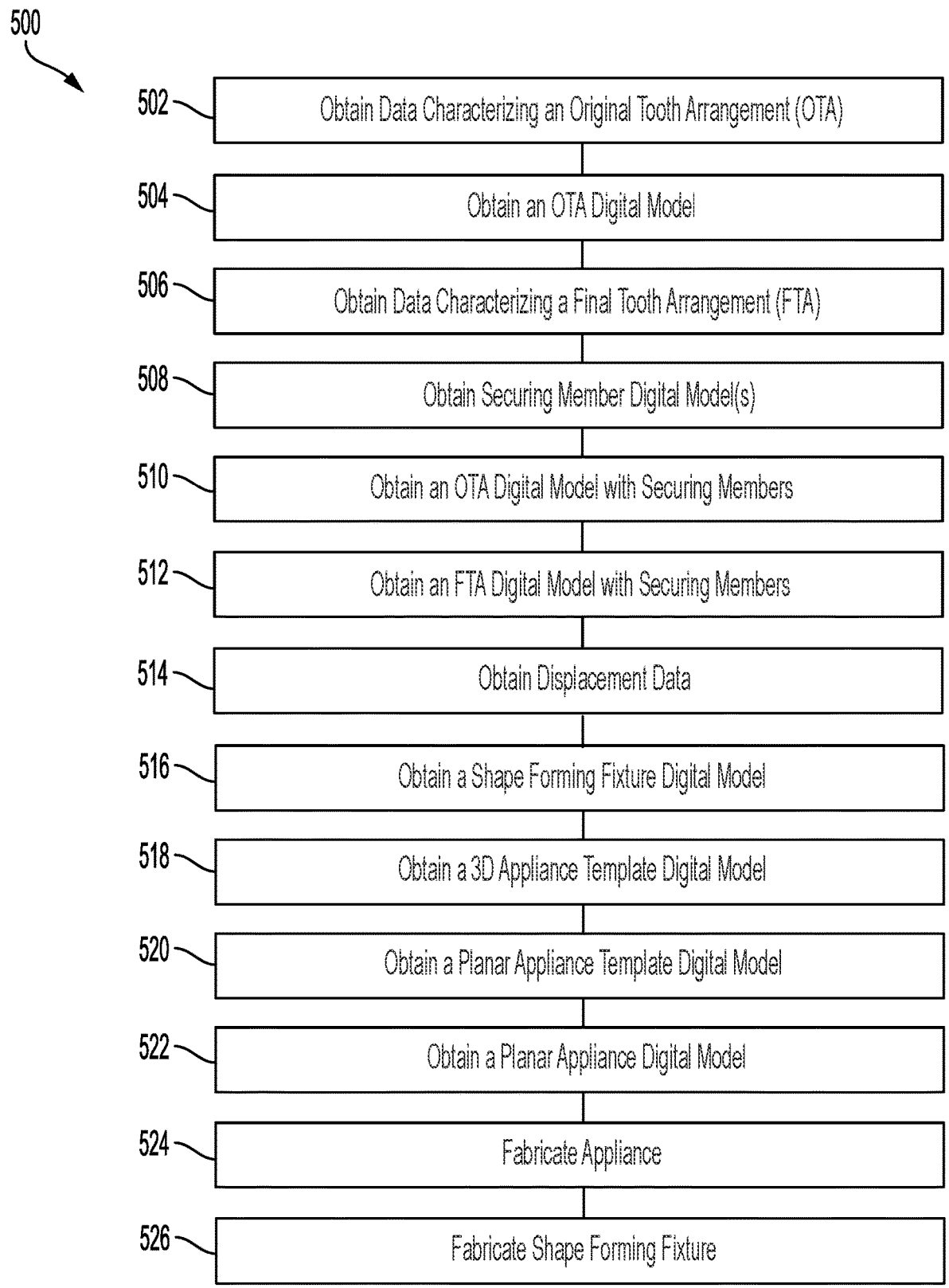
FIG. 5 is a flow diagram of a process for designing an orthodontic appliance in accordance with the present technology.
Figure 6:
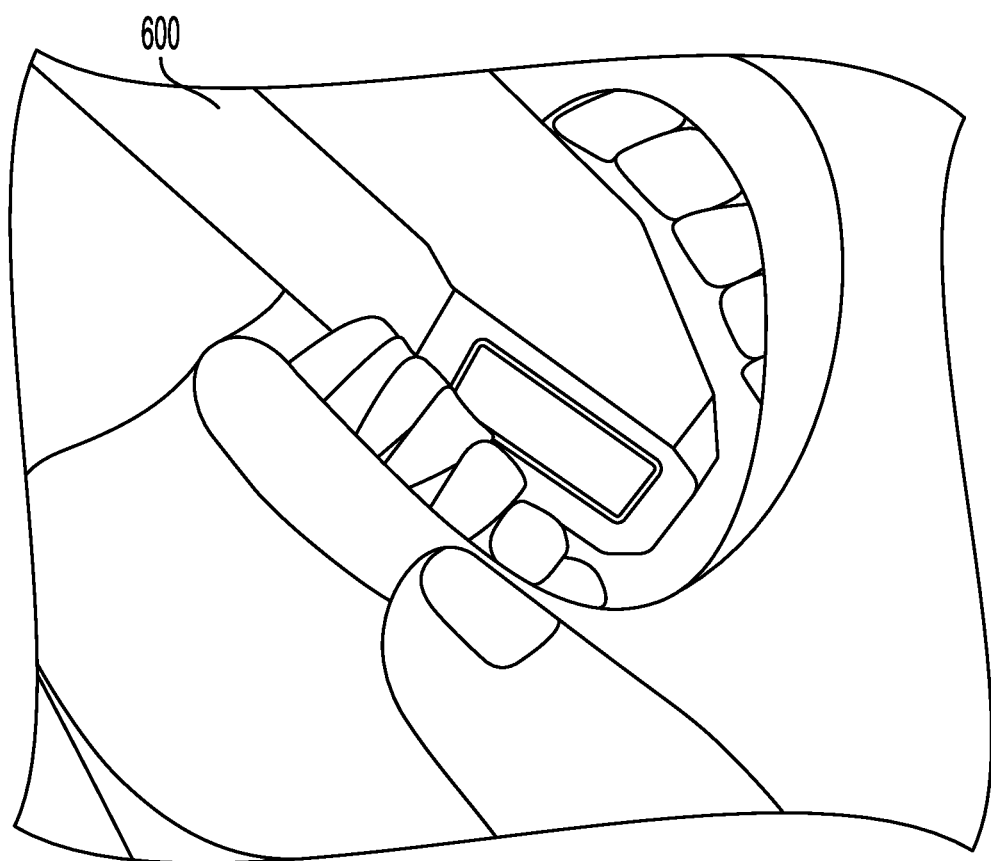
FIG. 6 illustrates scanning a patient's teeth to obtain original tooth arrangement data.

FIG. 5 is a flow diagram of an example process 500 for making an orthodontic appliance of the present technology. The process 500 begins at block 502 with obtaining data characterizing an OTA. For example, as shown in FIG. 6, the OTA data can be obtained by scanning the patient's teeth using an intraoral optical scanner 600. Such a scanner 600 can be used to scan the patient's oral anatomy to obtain data characterizing a property (e.g., a shape, a color, a material property, etc.) of the anatomy. For example, the scanner 600 can be used to scan the patient's upper dental arch, the patient's lower dental arch, one or more of the patient's teeth, the patient's oral tissues (such as gingival tissue), and/or the patient's oral or facial bones. The scanning can be performed using any suitable technique, for example using a dental cone beam CT scanner, a magnetic resonance imaging (MRI) device, or a similar device or technique. In some examples, the OTA data can be obtained using an impression made of the patient's upper and lower jaws (e.g., using polyvinyl siloxane or any other suitable impression material). The impression can then be scanned to create 3D data, which can include the relationship between the upper and lower jaw (e.g., to record the patient's bite). In examples in which impressions are used, the relationship between the teeth in the upper and lower arches (inter-arch relationship) can be obtained by taking a wax bite of the patient in the centric position. In various embodiments, the OTA data can be obtained directly (e.g., by imaging the patient's mouth using an appropriate imaging device) or indirectly (e.g., by receiving pre-existing OTA data from an operator or another source).

The OTA data can include data characterizing the roots of the teeth as well as the exposed portions (e.g., the crowns), which may be advantageous in designing an appropriate orthodontic appliance. Additionally or alternatively, the OTA data can include data characterizing the patient's oral tissues such as the gingiva, palate, tongue, etc.

In some embodiments, the OTA data comprises a point cloud including a plurality of points and coordinates associated with each point. According to various embodiments, the OTA data can comprise image data. For example, the OTA data can comprise one or more 2D images obtained, for example, via mobile phone imaging, CT scanning, MRI, etc.

Figure 7:
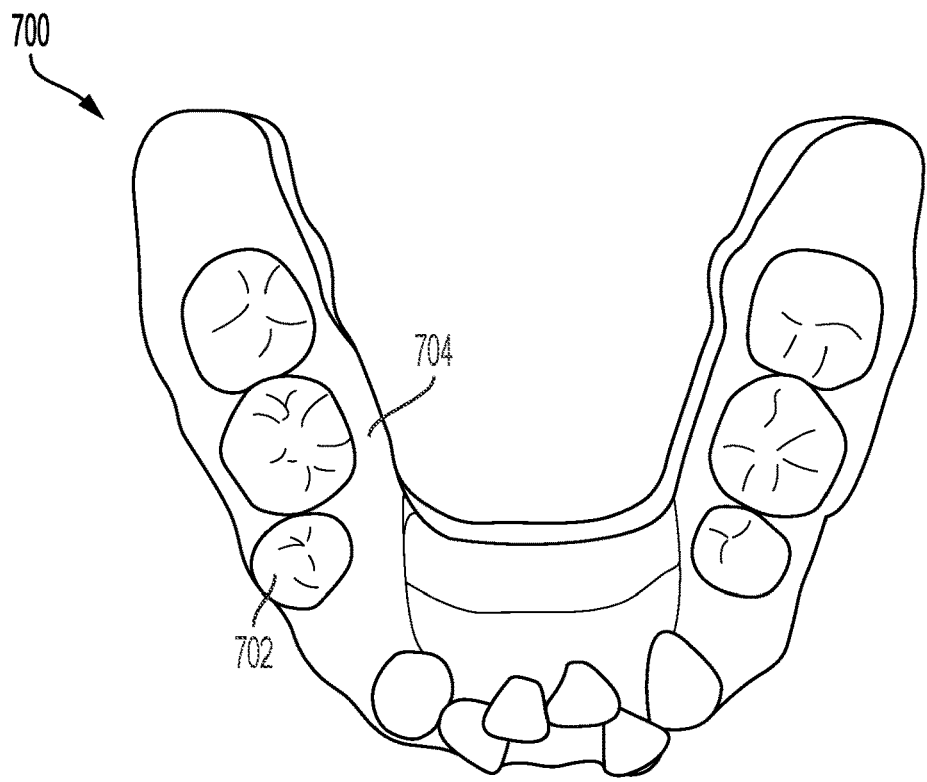
FIG. 7 illustrates an example of a digital model of a patient's teeth and gingiva in an original tooth arrangement.

Returning to FIG. 5, the process 500 continues with obtaining an OTA digital model at block 504. FIG. 7 is a graphical representation of an example of an OTA digital model 700. The digital model 700 can virtually represent or characterize the arrangement of the patient's teeth and gingiva in the original tooth arrangement. As seen in FIG. 7, the teeth in the OTA may be maloccluded, mis-aligned, crowded, or otherwise in need of orthodontic correction. In some embodiments, one or more teeth present in the OTA may be designated for extraction prior to use of the orthodontic appliance. The OTA digital model 700 can include a teeth portion 702 comprising one, some, or all of the patient's teeth and a gingiva portion 704.

In some embodiments, the OTA digital model comprises a mesh model (e.g., a triangle mesh model, a polygon mesh model, a volumetric mesh model, etc.), a surface model (e.g., a non-uniform rational basis spline (NURBS) surface model, a T-Spline surface model, etc.), a parametric CAD model, or another suitable type of model. The OTA digital model can be based, at least in part, on the OTA data. For example, if the OTA data comprises a point cloud, obtaining the OTA digital model can comprise converting the point cloud to a 3D surface model via surface reconstruction methods. Such surface reconstruction methods can include, for example, Delaunay triangulation, alpha shapes, ball pivoting, or other suitable methods. In some embodiments, a 3D OTA digital model can be obtained from two or more 2D images. For example, OTA data comprising a plurality of 2D images obtained via CT scanning can be segmented to identify portions of the images that correspond to one or more specific anatomical feature (e.g., bone, soft tissue, a specific tooth or teeth, the mandible, the maxilla, the skull, etc.) and a 3D model can be generated from the segmented image data.

Figure 8:
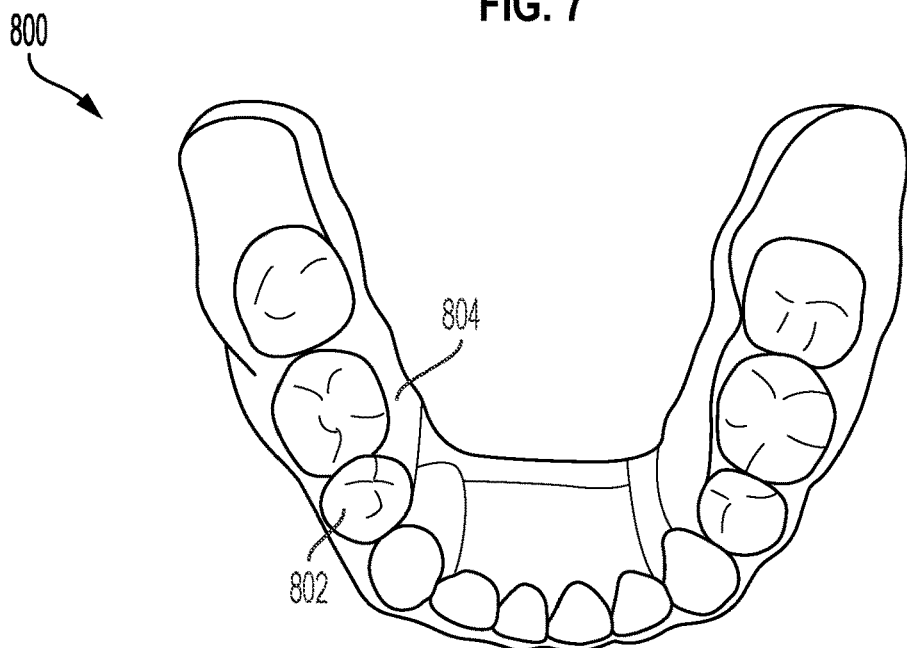
FIG. 8 illustrates an example of a digital model of a patient's teeth and gingiva in a final tooth arrangement.

In some embodiments, obtaining the OTA digital model corresponding to the OTA data can include first obtaining a single complex 3D database of the patient's jaw, which is then segmented to separate the patient's teeth into separate 3D bodies (e.g., individual teeth or blocks of multiple teeth) that can then be manipulated virtually by an operator. In embodiments in which the OTA digital model comprises a mesh model, a single, continuous mesh model of the patient's jaw can be segmented to obtain two or more mesh models each characterizing one of the patient's teeth or gingiva. For example, one digital model in an STL file format can be segmented into two or more individual STL files. Such segmentation can be performed using any suitable techniques or software. Following segmentation, the resulting 3D databases of upper and lower teeth can include a model of the gingiva and an independent model of each tooth. As a result, the OTA data can be manipulated by an operator to virtually move teeth relative to the gingiva. For example, at process portion 506, the teeth can be manipulated from the OTA towards a final tooth arrangement (FTA) to obtain FTA data. FIG. 8 illustrates an example digital model 800 of an FTA. Similar to the OTA digital model 700, the FTA digital model 800 includes a teeth portion 802 and a gingiva portion 804. The FTA digital model 800 can be based at least in part on data characterizing the teeth in the FTA. Such FTA data can include a digital representation of the desired final positions and orientations of the patient's teeth relative to one another and to the gingiva. The FTA data can be obtained directly (e.g., generated by the operator) or may be received from an external source (e.g., the FTA data may be generated by a third party and provided to an operator for design of an appropriate orthodontic appliance). In some cases, virtual movement of the teeth relative to the OTA also results in movement of the virtual gingiva (relative to the virtual gingiva in the OTA) in order to maintain the natural look of the gingiva and more accurately reflect the orientation and position of the gingiva when the teeth are at the FTA. This movement of the gingiva can be achieved using gingiva morphing or other suitable techniques. Accordingly, in some embodiments, the gingiva portion 804 in the FTA digital model 800 is different than the gingiva portion 704 in the OTA digital model 700. In some embodiments the gingival surface is not affected by the movement of the teeth and the gingiva portions 804, 704 of the FTA and OTA digital models 800, 700 are substantially the same.

As seen in FIG. 8, the teeth in the FTA digital model may be more aligned, less mal-occluded, and otherwise aesthetically and functionally improved relative to the OTA digital model 700. In some embodiments, the FTA can have desired or favorable inter-arch and intra-arch arrangements, for example, based on an operator's prescription. For example, one or more (or all) teeth from the upper or lower jaws (or both) are moved until their cusps have a good interdigitation and fit.

According to various embodiments, obtaining the OTA digital model and/or obtaining the FTA digital model can comprise obtaining a local coordinate system for one or more portions of the model. For example, in embodiments in which the OTA digital model comprises a plurality of individual models representing individual teeth of a patient, a local coordinate system can be obtained for one or more of the teeth. In some embodiments, the local coordinate system comprises three orthogonal axes. One or more of the three axes can substantially correspond to an occlusogingival dimension of the tooth, a buccolingual dimension of the tooth, and/or a mesiodistal dimension of the tooth. Additionally or alternatively, the axes can comprise other standard anatomical axes (e.g., anteroposterior, mediolateral, longitudinal, etc.) or other suitable axes. An origin of a local coordinate system of a tooth can be located at a center of mass of the tooth, a center of mass of the crown of the tooth, a surface of the tooth, or another suitable location. The location of the origin of the local coordinate system can be selected to facilitate moving and/or aligning the individual tooth models in a digital environment. The local coordinate system for each individual tooth model in the OTA or FTA digital model can be unique to the specific tooth. In some embodiments, the local coordinate systems for two or more individual tooth models can be the same. According to various embodiments, a local coordinate system can be defined for any number or combination of portions of a digital model of the present technology (e.g., an OTA digital model, an FTA digital model, etc.). For example, a local coordinate system can be defined for each of the teeth in one of the patient's dental arches, each of the teeth in one of the patient's dental arches and the surrounding bone of the corresponding jaw (e.g., the mandible or the maxilla), each of the teeth in both of the patient's dental arches, combinations thereof, and/or others.

In some embodiments, individual models of a patient's teeth in an OTA digital model can be virtually moved with reference to the local coordinate system of the tooth to generate an FTA digital model. In various embodiments, a human operator can view and/or interact with the digital models disclosed herein in a digital environment, e.g., via a user interface. The operator can specify a desired movement of one or more of the individual tooth models along and/or about the axes of the local coordinate system of the tooth model. For example, the operator can select (e.g., via an input device such as a mouse) a graphical representation of an axis of a local coordinate system (or a portion thereof) of a tooth model to move the tooth. In some embodiments, selecting the graphical representation of the axis changes the position of the tooth model in the digital environment by a predetermined translation along the axis and/or rotation about the axis. In some embodiments, the operator can select a graphical representation of an allowable movement of an individual tooth model (e.g., a rotation about an axis of a local coordinate system, a translation along an axis of a local coordinate system, etc.) to move the tooth model in the direction of the allowable movement. In some embodiments, selection of the graphical representation of the allowable movement moves the tooth model by a predetermined distance. Additionally or alternatively, an operator can select and drag the graphical representation of the local coordinate system (or a portion thereof) and/or the graphical representation of one or more allowable movements to move the tooth model. A magnitude of the virtual movement of the tooth model can be based, at least in part, on the duration and/or distance of the drag. In some examples, the operator can select the tooth model directly to move the tooth model by a predetermined amount and/or the operator can select and drag the tooth model directly to move the tooth model by an amount is based on the drag duration and/or distance. In various embodiments, the digital environment can include an input field into which an operator can enter a numerical value for a desired movement of the tooth. For example, the digital environment can comprise input fields for translations along the axes of the tooth local coordinate system and/or rotations about the axes of the tooth local coordinate system. According to various embodiments, movement of the teeth in the digital environment can be performed automatically. For example, processors of a computing device can be configured to move the teeth to accomplish an objective such as reducing a contact between adjacent teeth, reducing excessive spacing between the teeth, etc.

Figure 9:
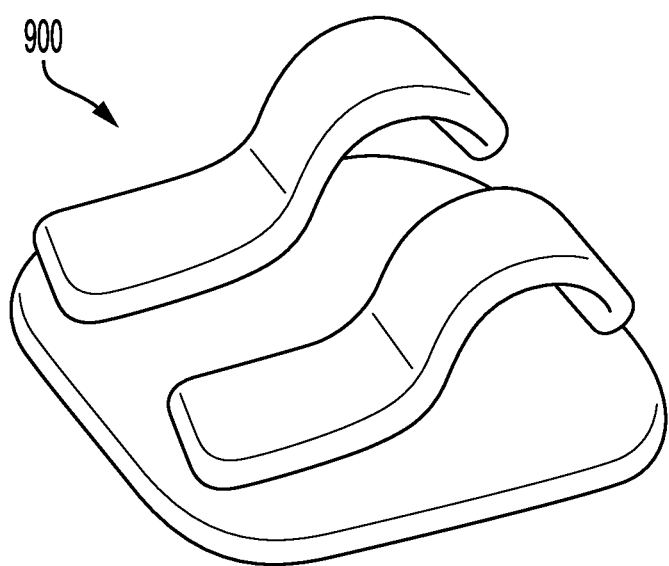
FIG. 9 illustrates an example of a digital model of a securing member.

Referring back to FIG. 5, the process 500 continues in block 508 with obtaining securing member digital model(s). As discussed previously, securing members (e.g., securing members 160, brackets, etc.) can be coupled to the patient's teeth to allow for an orthodontic appliance (e.g., appliance 100) to be mated thereto. The securing member digital models can include a virtual representation of the geometry and/or other structural characteristics of the securing member(s). The securing member digital model(s) can comprise a mesh model, a parametric CAD model, or any other suitable type of digital model. In various embodiments, the securing member digital models can be identical for each securing member, or may vary among the securing members. For example, different securing members may be used for molars than for incisors. FIG. 9 illustrates an example securing member digital model 900.

Figure 10:
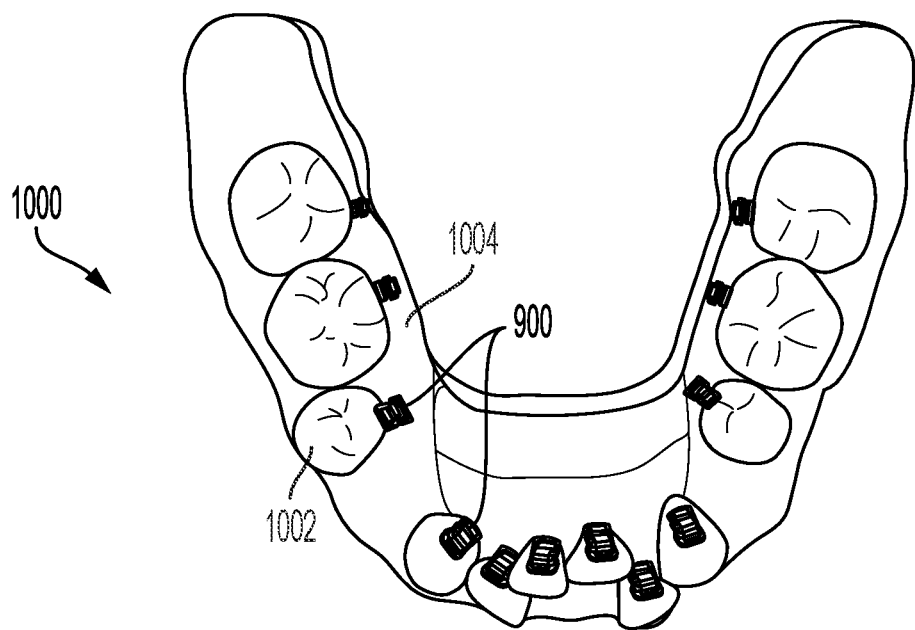
FIG. 10 illustrates an example of a digital model of a patient's teeth and gingiva and a plurality of securing members in an original tooth arrangement.

With continued reference to FIG. 5, the process 500 continues in block 510 with obtaining an OTA digital model with securing members positioned on the teeth. For example, a securing member digital model 900 (FIG. 9) can be applied to appropriate locations on the patient's teeth within the OTA digital model 700 (FIG. 7). The resulting digital model 1000 is shown in FIG. 10, in which a plurality of digital models of securing members 900 are disposed at the lingual surfaces of the patient's teeth. In some embodiments, the securing members 900 are disposed at the buccal surfaces of the patient's teeth. The securing member can be positioned on one, some, or all of the teeth of the OTA digital model 700. In some embodiments the process 500 does not include obtaining an OTA digital model with securing members.

In some examples, the digital models 900 of the securing members can be virtually positioned on the teeth in the OTA using appropriate software. In some embodiments, virtually positioning the securing members can include selecting virtual models of particular securing members from a library of available securing members, and then virtually positioning the selected securing members on one or more teeth. In some embodiments, the bracket positioning can be assigned automatically (e.g., by automatically positioning the bracket in a central or the predefined portion of the tooth) or manually (e.g., by an operator selecting and/or manipulating the attachment location for each securing member). In some embodiments, the position of each securing member can be refined by the operator as desired. For example, it may be desirable to position the securing members as close to the gingiva as possible so as to avoid interference with securing members on the other jaw or interference with the teeth from the other jaw when the mouth is closed. In various embodiments, the desired position of a securing member on one tooth may be different than the desired position of a securing member on another tooth. For example, it may be advantageous to position securing members on the anterior teeth gingivally to prevent or limit collision of securing members on the upper and lower jaws during chewing, while it may be advantageous to position securing members on the posterior teeth at mesial portions and/or distal portions of the posterior teeth to prevent or limit undesired rotation of the posterior teeth during closing of a space resulting from extraction of one or more of the patient's teeth.

In some embodiments, the OTA digital model with securing members 1000 can be used to determine a configuration of a bonding tray, which may then be used to physically attach securing members to the patient's teeth by an operator. For example, the bonding tray can be configured to fit over the patient's teeth similar to an aligner, and can include recesses on a side of each tooth that are sized and configured to receive an appropriate securing member (e.g., bracket) therein. In various embodiments, such recesses can be positioned on the lingual, buccal, mesial/distal, occlusal, root, or any suitable surface of a tooth to which a corresponding bracket is intended to be bonded. In operation, an appropriate securing member can be placed in each recess of the bonding tray and then an adhesive (e.g., an adhesive that cures when illuminated by ultraviolet light) can be applied to the bonding surface of each securing member. The tray can then be placed over the patient's teeth and the adhesive cured to bond all the securing members to the appropriate location on each tooth.

To generate such a bonding tray, the OTA digital model with securing members 1000 can be manipulated, for example, to remove excess virtual gingiva to limit the size of the tray to only what is necessary to hold the securing members in position against the patient's teeth.

The trimmed digital model can then be used to generate a physical 3D model of the patient's teeth with the securing members disposed thereon, for example using 3D printing in a polymer resin or other suitable technique. In some embodiments, a suitable material (e.g., a clear polymer resin) can then be formed over (e.g., thermoformed over) the physical model of the patient's teeth with securing members in the OTA. This can create the aligner-like tray with recesses shaped and configured to receive securing members therein. The securing members can then be placed into corresponding recesses of the tray, and the tray can be applied to the patient's teeth with a curable adhesive to attach the securing members to the patient's teeth in the OTA. The tray may then be removed, leaving the securing members in place.

In some embodiments, the bonding tray can be 3D printed directly, without the need for a physical model of the patient's teeth and without the use of thermoforming. For example, a digital model of a bonding tray can be derived from the digital model 1000 characterizing the teeth in the OTA with securing members attached. In some embodiments, a negative of the digital model 1000 can be generated then trimmed to provide a general tray-like structure with a surface corresponding to the teeth and securing members in the digital model 1000. This resulting model can be manipulated to provide features for retaining brackets in the corresponding recesses. Finally, the bonding tray can be 3D printed based on this digital model, for example using 3D printable polymer resins or other suitable materials or deposition techniques.

Alternatively, the operator may attach securing members to the patient's teeth directly, without the assistance of a tray.

Figure 11:
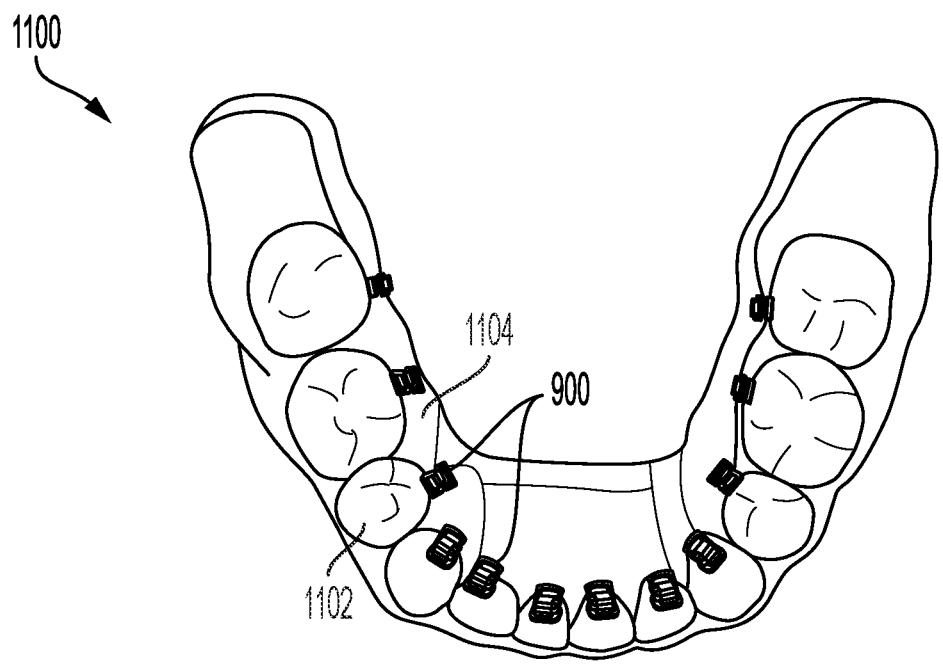
FIG. 11 illustrates an example of a digital model of a patient's teeth and gingiva and a plurality of securing members in a final tooth arrangement.

Referring back to FIG. 5, the process 500 continues at block 512 with obtaining an FTA digital model. In some embodiments, the FTA digital model is generated using the OTA digital model without the securing members (as shown in FIGS. 7 and 8) and the securing members can later be added to the FTA digital model. In some embodiments, the FTA digital model is generated using the OTA digital model with the securing members. In either case, the process 500 includes obtaining an FTA digital model with securing members, an example of which is shown in FIG. 11. As depicted, the FTA digital model 1100 with securing members 900 comprises a teeth portion 1102 and a gingiva portion 1104. The FTA digital model with securing members 1100 can be based at least in part on data characterizing the teeth in the FTA. Such FTA data can include a digital representation of the desired final positions and orientations of the patient's teeth relative to one another and to the gingiva. The FTA data can be obtained directly (e.g., generated by the operator) or may be received from an external source (e.g., the FTA data may be generated by a third party and provided to an operator for design of an appropriate orthodontic appliance).

As previously mentioned, in some embodiments the FTA data can be obtained by manipulating the OTA data to virtually move the patient's teeth. Suitable software can be used by an operator to move the teeth to a desired FTA. For example, a tooth of the OTA digital model can be moved based on translations and/or rotations of the tooth relative to a local coordinate system. In some cases, virtual movement of the teeth relative to the OTA also results in movement of the virtual gingiva (relative to the virtual gingiva in the OTA) in order to maintain the natural look of the gingiva and more accurately reflect the orientation and position of the gingiva when the teeth are at the FTA. This movement of the gingiva can be achieved using gingiva morphing or other suitable techniques. The gingiva portion 1104 of the FTA digital model with securing members may be the same as or different than the gingiva portion 704 of the OTA digital model.

In some embodiments, the FTA can reflect changes to the patient's teeth that may occur as part of the treatment process. For example, an operator may extract one or more teeth of the patient as part of the treatment (for example because of lack of space for all of the teeth to fit in the arch or other reasons). In that event, the extracted teeth can be excluded from the FTA data. If the operator decides that the teeth need to become smaller due to a lack of space, then interproximal reduction (IPR) may be performed on the patient. In this case, stripping and reducing the size of the teeth in the FTA can be performed so as to match the IPR done by the operator.

In some embodiments, a proposed FTA can be developed by an operator (e.g., independently or based in whole or in part on input from a treating orthodontist) and then sent to a treating orthodontist for review and comment. If the treating orthodontist has comments, she can provide input to the operator (e.g., written notes, proposed manipulation of one or more teeth or securing members, etc.) that can be transmitted electronically or otherwise. The operator may then revise the FTA and send a revised proposed FTA back to the treating orthodontist for further review and comment. This iterative process may repeat until the treating orthodontist approves the proposed FTA, and the resulting digital model 1100.

Referring still to FIG. 5, the process 500 continues at block 514 with determining the displacements of individual teeth or groups or teeth between the OTA and the FTA. For example, the displacement of each tooth between the OTA and FTA can be described using six degrees of freedom (e.g., translation along X, Y, and Z axes, and rotation around the same three axes; or alternatively translation along mesiodistal, buccolingual, and/or occlusogingival directions, and rotation in the form of buccolingual root torque, mesiodistal angulation, and/or mesial out-in rotation). In some embodiments, these values can be determined by calculating the difference between the location of each tooth in the FTA data and the OTA data. This can be performed for each tooth in each jaw to generate a dataset that includes the required displacement along six degrees of freedom for each tooth.

In some embodiments, the process 500 can include evaluating proposed displacements of the patient's teeth and, based on the evaluation, modifying the proposed displacements and/or final positions of the patient's teeth. For example, the process 500 can include decomposing an overall displacement of one or more of the patient's teeth into component displacements. A component displacement can comprise a common displacement of all of the patient's teeth, a common displacement of all of the teeth in one of the patient's dental arches, a displacement that is unique to an individual tooth, or another displacement of one or more teeth. Additional details relating to evaluating and modifying proposed final positions and/or planned displacements are described with respect to FIGS. 19-32E.

Figure 12:
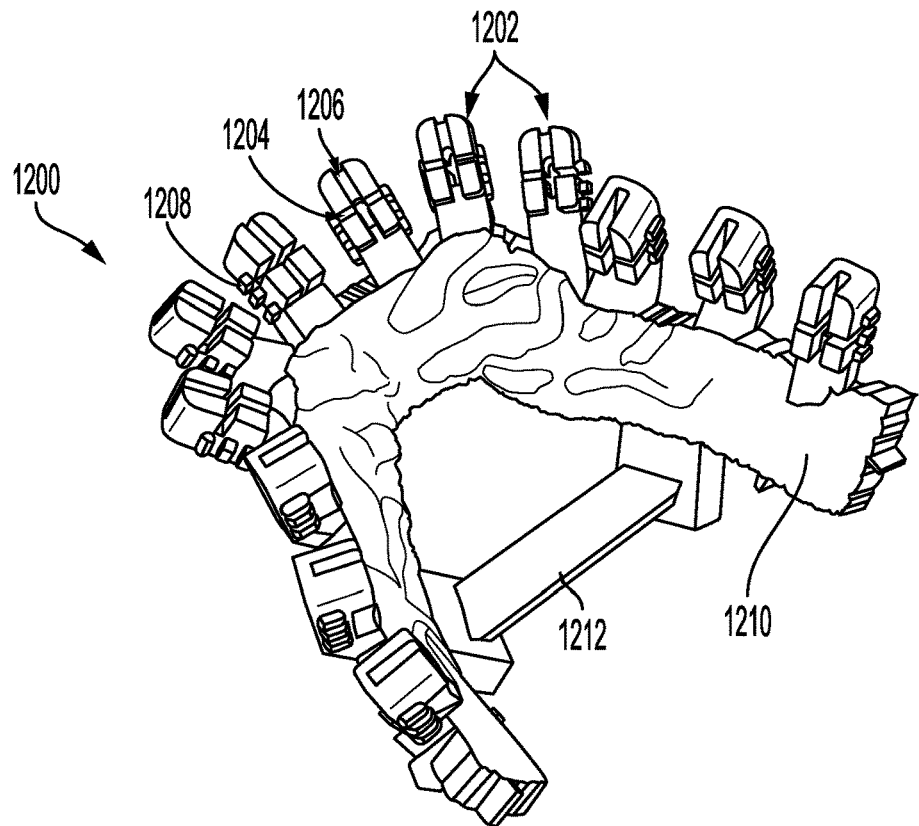
FIG. 12 illustrates an example of a digital model of a shape forming fixture.

The process 500 continues at block 516 with obtaining a digital model of a fixture that, in its physical form, is used to shape set the appliance. FIG. 12 illustrates an example fixture digital model 1200, which can be generated by manipulating the digital model of the OTA, the digital model of the FTA, the digital model of the OTA with securing members attached, and/or the digital model of the FTA with securing members attached. The digital model(s) 700, 800, 1000, 1100 can be manipulated in a number of ways to generate suitable fixture data.

As shown in FIG. 12, the fixture digital model 1200 can comprise one or more securing portions 1202 and a gingiva portion 1210. In their physical form, the securing portions 1202 can be configured to releasably retain one or more portions of an appliance at a specific location relative to other portions of the appliance. For example, the securing portions 1202 can be configured to retain attachment portions (e.g., attachment portions 140, etc.) of an appliance during a shape setting procedure in positions corresponding to intended positions of corresponding securing members when the appliance is later installed in the patient's mouth and the securing members are secured to the patient's teeth (for example, when the teeth, and thus securing members, are in an OTA or FTA). In some embodiments, the securing portions 1202 are positioned relative to one another and to the gingiva portion 1210 to reflect the positions of the teeth in the FTA. In other embodiments, the securing portions 1202 are positioned to reflect the teeth in the OTA or an ITA.

The fixture model can be generated based on one, some, or all of the OTA and FTA digital models (with and/or without the securing members). In some embodiments, the fixture digital model 1200 can be generated by using one of the FTA digital models to position the securing portions 1202 of the fixture digital model 1200 at desired locations and merging the digital model of the securing portions 1202 with a digital model of the patient's gingiva obtained from one of the OTA digital models. For example, generating the fixture digital model 1200 can include obtaining the "FTA with securing members" digital model and one-by-one replacing individual securing members with individual securing portions such that the securing portions are located at positions corresponding to positions of the securing members in the "FTA with securing members" digital model. In some embodiments, positioning a digital model of a securing portion (e.g., securing portion 1202, etc.) at a position corresponding to a position of a securing member in the "FTA with securing members" digital model comprises aligning a local coordinate system of the securing portion digital model with a local coordinate system of the securing member digital model, which can comprise positioning an origin of the local coordinate system of the securing portion digital model at a position of an origin of the local coordinate system of the securing member digital model. In some cases, axes of the local coordinate system of the securing portion digital model can be aligned with axes of the local coordinate system of the securing member digital model. Additionally or alternatively, the securing portion digital model can be transformed to align the axes of the local coordinate systems.

Once the securing portions 1202 are positioned at their intended locations, the portions of the FTA with securing members digital model corresponding to the securing members, the teeth, and/or the gingiva can be deleted. Additionally or alternatively, the securing members can be replaced with the securing portions in a single step. The resulting digital model can be saved as the fixture digital model 1200 or a component digital model thereof. In some embodiments, obtaining the fixture digital model 1200 comprises merging two or more digital models. For example, obtaining the fixture digital model 1200 can comprise merging the individual digital models of the securing portions 1202 at their intended positions with an individual digital model of the gingiva portion 1210 of the fixture. According to various embodiments, such individual digital model of the gingiva portion 1210 can be obtained from one of the OTA digital models.

In some embodiments, merging the individual models of the securing portions 1202 at their intended positions with an individual digital model of the gingiva portion 1210 can comprise extruding a surface of one or more of the models of the securing portions 1202 to meet the model of the gingiva portion 1210, or vice versa. Such extrusion may be useful or necessary because a securing member, and therefore a corresponding securing portion, will often be positioned occlusally of the patient's gingiva. In such examples, it can be advantageous to extend the securing portion and/or the gingiva to meet one another such that the securing portions and gingiva comprise a single, continuous structure. Extruding a surface of a securing portion to meet the gingiva can comprise obtaining one or more references (e.g., points, lines, surfaces, and/or other features) of the digital model of the securing portion 1202, obtaining one or more corresponding references (e.g., points, lines, surfaces, and/or other features) of the digital model of the gingiva portion 1210, and/or obtaining an extrusion path based on the references of the securing portion and/or the gingiva portion. As but one example, a unique identifier can be assigned to certain distinctive reference points on the securing portion digital model. Such identifiers can comprise a label or a property (e.g., a color, an opacity, etc.). Additionally or alternatively, such reference points can comprise vertices defining a boundary of a surface of the securing portion digital model. An operator or a processor can identify the reference points and/or distinguish the reference points from the rest of the digital model based on the unique identifiers of the reference points. In some embodiments, identifying the reference points comprises identifying 3D coordinates of the reference points. In these embodiments, and in others, obtaining corresponding references of the gingiva portion digital model can comprise identifying points, lines, features, etc. of the gingiva portion digital model that are the closest and/or most similar to the references of the securing portion digital model.

In some embodiments, to obtain the fixture digital model 1200, the digital model(s) 700, 800 without securing members and/or the digital model(s) 1000, 1100 with securing members can be manipulated to remove the teeth or other structural elements not needed for shape setting the appliance, and/or to add structural features to reinforce the fixture for sufficient rigidity during the heat treatment process. For example, as shown in FIG. 12, the fixture model 1200 does not include any teeth, but retains at least a portion of the gingiva portion 1210. Additionally, the fixture model 1200 includes a stabilizing crossbar 1212 that can enhance the rigidity of the resulting fixture. Various other modifications to the digital model(s) 700, 800, 1000, 1100 can be made to achieve the desired fixture model 1200.

The securing portions 1202 can have a geometry configured to facilitate positioning and/or retaining corresponding attachment portions at the intended positions. For example, as shown in FIG. 12, the securing portions 1202 can define first channels 1204 and second channels 1206 angled with respect to the first channels 1204. The first and second channels 1204, 1206 are configured to receive attachment portions of an appliance at least partially therein to locate the attachment portions at their intended positions. The securing portions 1202 can comprise protrusions (e.g., protrusions 1208) extending away from the corresponding securing portion 1202 and defining channels. In some embodiments, the protrusions 1208 define the first and second channels 1204, 1206 and/or the protrusions 1208 can define third channels configured to receive a fastener at least partially therein. For example, an elongate member such as a ligature wire can be wound about one of the securing portions 1202 and an attachment portion of an appliance such that the ligature wire is positioned within channels defined by the protrusions 1208 and secures the attachment portion to the securing portion 1202. The securing portions 1202 can be configured to receive and/or coupled with other fasteners, such as ties, sutures, bands, clasps, and others. In various embodiments, the securing portions 1202 can define one or more through-channels, apertures, or other openings to facilitate securing of an attachment portion to the securing portion 1202 via a fastener. For example, such openings can allow a pushing tool to be inserted from the back of the securing portion 1202 (e.g., through the buccal surface of the fixture model 1200) to push an attachment portion 140 away from the securing portion 1202 after the heat treatment has been completed and the ligature wire or other fastener has been removed.

The gingiva portion 1210 of the fixture model 1200 can be a virtual representation of gingival tissue and, in its physical form, provides a surface on which a portion of the appliance is conformed during a shape setting procedure. The gingiva portion 1210 may be substantially identical to the gingiva portion from any of the OTA or FTA digital models (e.g., 700, 800, 1000, 1100). For example, it can be desirable to use the gingiva portion 704 from the OTA digital model 700 for the gingiva portion 1210 of the fixture model 1200 to prevent or limit impingement of the patient's gingiva by an appliance having a shape based on the fixture model 1200 when the appliance is installed. In some cases, the securing portions 1202 can be positioned to reflect the teeth in the FTA while the gingiva portion 1210 reflects the gingiva in the OTA.

In some embodiments, the gingiva portion 1210 of the fixture model 1200 is a modified version of the gingiva portions from any of the OTA or FTA digital models (e.g., 700, 800, 1000, 1100). When an appliance is installed, a patient may experience considerable discomfort if any portion of the appliance impinges on the gingiva. On the other hand, it is desirable to have the appliance as close to the gingiva as possible to reduce irritation of the tongue (if a lingual device) or lips (if a buccal device). Accordingly, it can be desirable to design the appliance and/or fixture so that the appliance rests as close to the patient's gingiva as possible without impinging. To achieve this balance, in some embodiments the fixture model has a gingiva portion 1210 with a modified shape and/or size relative to the shape and/or size of the gingiva of the OTA digital model, the FTA digital model, the OTA digital model with securing members, or the FTA digital model with securing members. The modifications could affect the curvature of the gingiva and/or the topography. For example, the gingiva portion 1210 of the FTA digital model 1200 can be an enlarged version of the gingiva portion in one of the OTA or FTA digital model(s) 700, 800, 1000, 1100. In such embodiments, a thickness of the gingiva portion 1210 can be modified to adjust a position of one or more surfaces of the gingiva portion 1210 relative to the securing portions 1202. The gingiva can be enlarged by about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, at least about 1.5 mm, at least about 1.4 mm, at least about 1.3 mm, at least about 1.2 mm, at least about 1.1 mm, at least about 1.0 mm, at least about 0.9 mm, at least about 0.8 mm, at least about 0.7 mm, at least about 0.6 mm, at least about 0.5 mm, at least about 0.4 mess, at least about 0.3 mm, at least about 0.2 mm, or at least about 0.1 mm.

While the gingiva portion 1210 can reflect the actual curvature and topography of a patient's gingiva as defined in the OTA or FTA, in other embodiments the gingiva portion 1210 can more crudely represent the gingiva. For example, in some embodiments the gingiva portion 1210 can have the general curvature but not the surface topography of the gingiva from the OTA or FTA digital models. In certain embodiments, the gingiva portion 1210 is not derived from the gingiva portion of any of the models and instead is a generic structure that connects and holds the relative positions of the securing portions 1202. The gingiva portion can also be referred to as a "body portion" herein.

Figure 13:
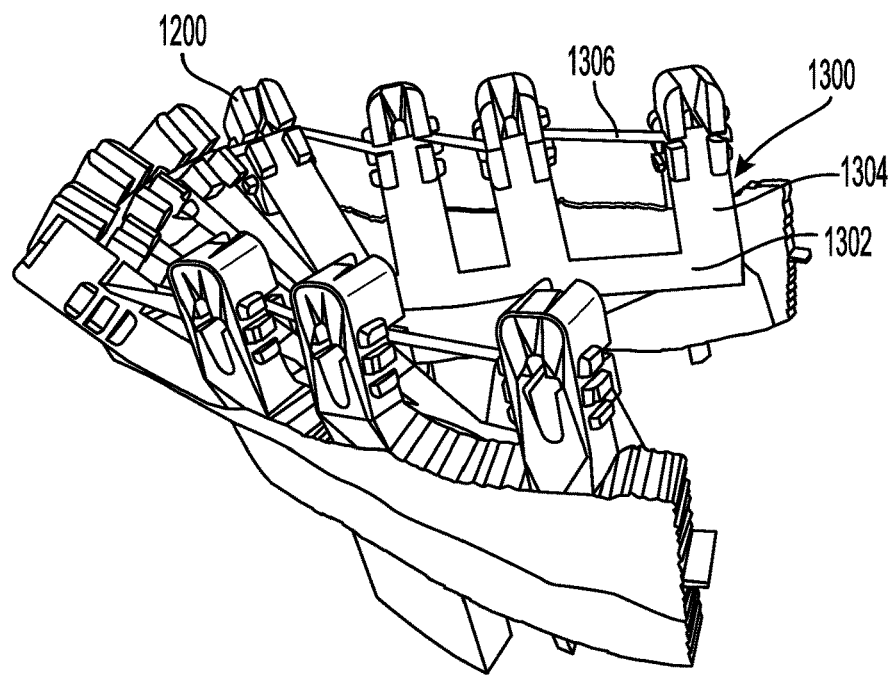
FIG. 13 illustrates an example of a digital model of a three-dimensional appliance template that is based on the heat treatment fixture model.

Referring back to FIG. 5, the process 500 continues at block 518 with obtaining an appliance template digital model. FIG. 13 illustrates an example of an appliance template digital model 1300, shown here in a configuration in which the appliance template digital model 1300 is secured to the fixture digital model 1200. In some embodiments, the template model 1300 can comprise an anchor portion 1302, arm portions 1304, and an attachment bar portion 1306. These components can take the form of a genericized template for an appliance that is later customized for a particular patient (as described in more detail below with respect to FIG. 15). For example, the anchor portion 1302 can correspond to the anchor 120 of the completed appliance, and the arm portions 1304 can serve as placeholders for the arms 130 of the completed appliance. The attachment bar portion 1306 takes the form of a continuous strip connecting each of the arms 130. As shown in FIG. 13, the attachment bar portion 1304 can be configured to be received within the channels 1204 of the securing portions 1202 of the fixture model 1200. The attachment bar 1306 can correspond in part to portions of the attachment portions 140 of the arms 130 of the completed appliance.

In various embodiments, the appliance template digital model 1300 can be generated using surface data of the fixture model 1200. For example, the appliance template digital model 1300 can be configured to substantially conform to the surface of the fixture model 1200. The anchor portion 1302 can correspond to a curvature and/or topography of the gingiva portion 1210 of the fixture model 1200, for example. The treatment fixture model 1200 can be modified with respect to the OTA and/or FTA models (with or without securing members) by, among other things, enlarging the gingiva. As such, when the anchor portion 1302 contacts the gingiva portion 1210 of the fixture model 1200, the anchor portion 1302 may be positioned so as to be slightly spaced apart from the actual gingiva as characterized in the OTA digital model 700. In some embodiments, the appliance template model 1300 can have little to no thickness dimension, instead corresponding to a three-dimensional surface following a contour of the fixture model 1200. In some embodiments, the appliance template model 1300 can have at least some thickness.

Figure 14:
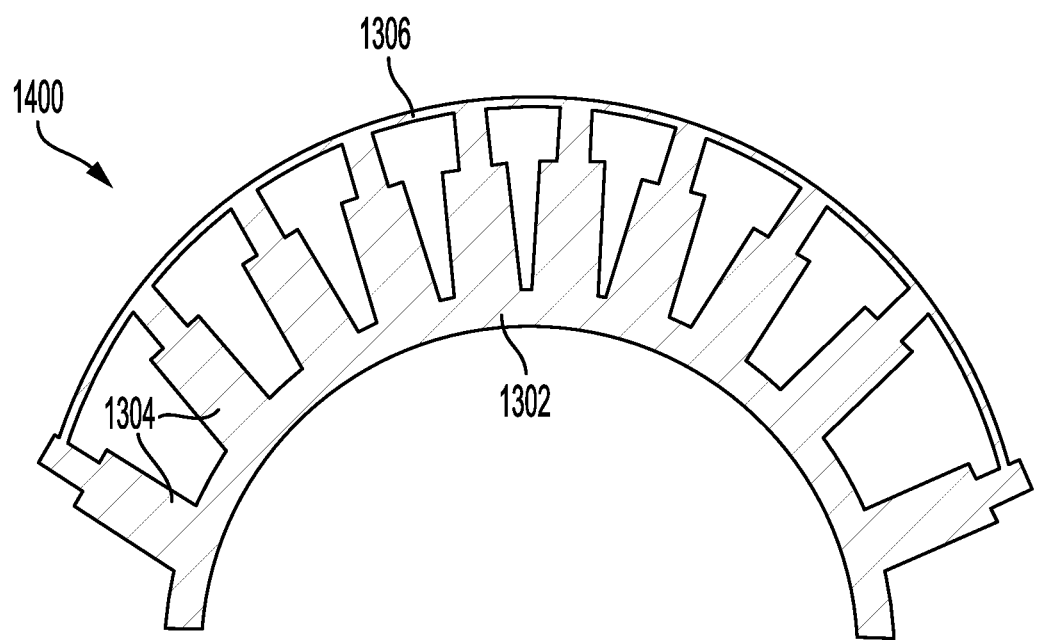
FIG. 14 illustrates an example of a digital model of a substantially planar appliance template.

In block 520, the appliance template digital model 1300 can be flattened or otherwise manipulated to generate a planar appliance template model 1400 (FIG. 14). The planar template model 1400 can characterize the appliance template in a 2D or substantially planar data configuration. In some embodiments, the planar appliance template digital model 1400 corresponds to or is at least derived from the contoured appliance template model 1300. For example, the appliance template digital model 1300 (FIG. 13) can be converted into the planar appliance template model 1400 (FIG. 14) by flattening, planarizing, or otherwise converting the digital model 1300 to generate the planar appliance template model 1400. Such conversion may be carried out using a processor system and appropriate software such as, but not limited to ExactFlat®, Solidworks®, Autodesk® Inventor, Creo®, or other suitable software.

Figure 15:
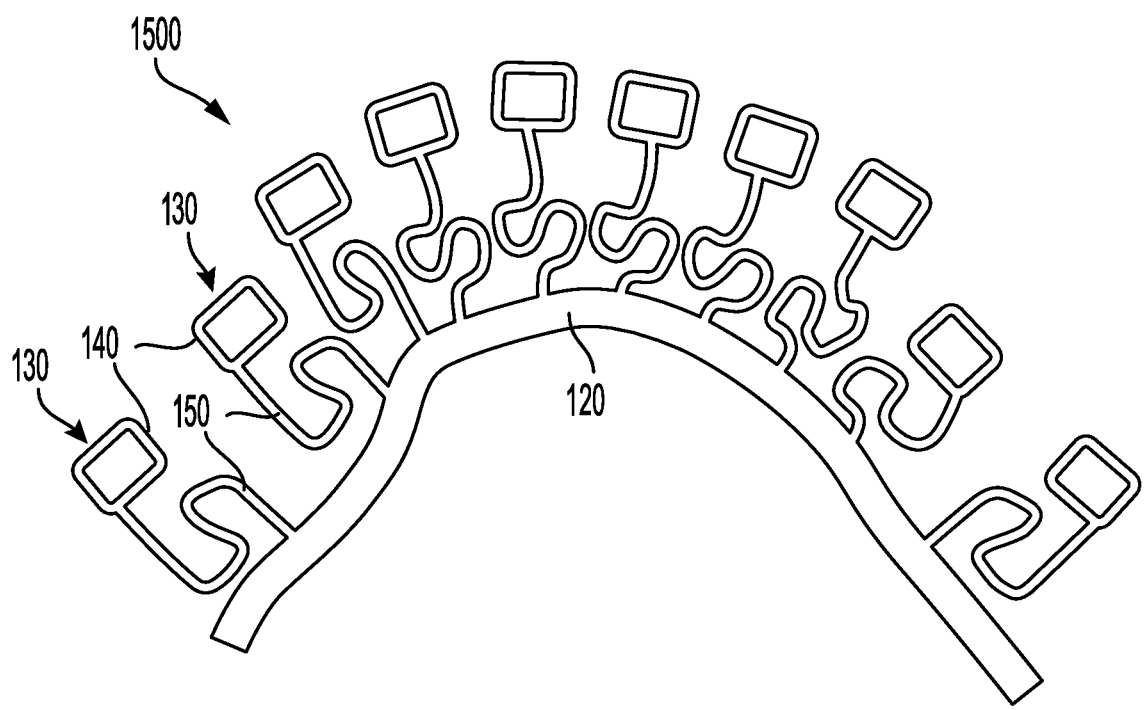
FIG. 15 illustrates an example of a digital model of a substantially planar appliance with unique arm geometry based on determined displacement of each tooth.

At block 522, the planar appliance digital model is obtained. An example of a planar appliance model 1500 is shown in FIG. 15. In this stage, the particular shape and configuration of the arms of the appliance can be determined, such as by modifying or substituting portions or components of the planar template model 1400 (FIG. 14). For example, the particular dimensions, geometry, and material properties of arms of the appliance can be selected so as to apply the necessary force and/or torque to achieve the desired displacement determined at block 512. In some embodiments, a pre-populated library of arm designs can be used to select an appropriate design and configuration to achieve the desired displacement. In some embodiments, the arm designs in the pre-populated library can be analyzed using finite element analysis (FEA) or other techniques to determine the spring force such arms would apply when deflected by particular amounts (e.g., the amount of deflection between the FTA (when the arm is at rest) and the OTA). In some embodiments, fully or partially automated selection of particular arm designs can be reviewed and/or modified by an operator based on relevant criteria. For example, if the proposed arm designs include overlapping or otherwise interfering arms, the operator may manually adjust the shape and/or configuration of the arms.

Based on the determined displacement, the required forces and/or torques required to move each tooth from the OTA to the FTA can be determined. The forces required to move teeth are generally in the range of centiNewtons, and distances moved are typically in the range of millimeters. The amount of moment (Newton-millimeter) acting to rotate a tooth can be found by multiplying the magnitude of the applied force by the force arm. In general, the displacement can be a 3D tooth movement that combines both translational and rotational motion.

The forces and/or torques required to achieve the FTA may depend on the patient's anatomy, for example the size of the particular tooth being moved, the anatomy of the root, etc. The forces and/or torques may also depend on other physiological parameters (e.g., bone density, biological determinants, sex, ethnicity, jaw (maxilla or mandible), mechanical properties of surrounding tissues (lips, tongue, gingiva, and bone) around the moving tooth, etc.). The particular force and/or torque applied to a given tooth will also depend on the particular positioning of the securing member (e.g., bracket). For example, a securing member positioned further off a center-of-resistance of a tooth will generate more torque under a given applied force than a securing member that is positioned nearer to a center-of-resistance of the tooth. Based on the desired displacement (e.g., along six degrees of freedom), the patient's anatomy, and the location of the securing member, a particular arm configuration can be selected to generate the desired force and/or torque on the subject tooth, so as to move the tooth from the OTA to the FTA. By determining appropriate thickness, widths, shapes, and configurations of the arms and other components of the orthodontic appliance, an appliance configuration that applies forces and torques to the appropriate teeth to move the teeth to the FTA is determined.

In particular examples, the design of the appliance may be performed by an operator, with the processor system and appropriate design software such as, but not limited to CAD software such as, but not limited to Solidworks®, Autodesk® Inventor, Creo®, or the like. FEA software such as, but not limited to Abaqus, Ansys, etc. may be employed to design the springs and arms in order to apply the desired or optimal force to the teeth. For example, such software and processing systems may be employed to design and alter the thickness, cut width, length, as well as the overall design of each arm based at least in part on the movement of the tooth to which the arm is connected.

In some examples, if a tooth needs to be displaced by a longer distance or the tooth is smaller (e.g. lower incisors), the arm 130 may be designed such that it is more flexible. In some embodiments, the selection or design of the arms 130 can account for variation in the rate of teeth movement based on direction. It is known that the rate of tooth movement when a given force is applied to the tooth is different depending on the direction of movement. For example, extrusion is the fastest movement for a given force, intrusion is the slowest, and mesiodistal and buccolingual movements are somewhere in between these two extremes. In one example, if a tooth moves 2 mm per month occlusally and 1 mm per month distally under the same applied force, the tooth will not move in a straight line as the occlusal movement will be more rapid than the distal movement. The occlusal movement will finish first, and then the tooth will move in a straight line from there in the distal direction until that motion is complete. It may be desired to move the tooth in a particular trajectory, and so the force applied distally can be different from the force applied occlusally. For example, it may be desired to move the tooth in a straight line, and so the distal force would have to be greater than the occlusal force in order to result in a straight trajectory from OTA to FTA.

In some embodiments, the arms 130 can be designed to impart less force on some or all of the teeth because of periodontal problems such as bone resorption, root resorption or attachment loss. The ability to customize the force or torque (or both) applied to each tooth can provide significant advantages over traditional orthodontics. In particular examples, the computer-aided procedure employs an algorithm for selecting or configuring an arm or other feature of an appliance, for example, from one or more predefined sets of options or one or more ranges of options. Thus, for example, a set of options or a range of options may be predefined for one or more parameters associated with an arm or other feature.

The one or more parameters associated with an arm 130 may include, but are not limited to, the overall length of the arm, the shape or configuration of the biasing portion 150, the shape or configuration of the attachment portion 140, the width dimension of one or more sections of the arm 130, the thickness dimension of one or more sections of the arm 130, or the like.

Obtaining the planar appliance digital model 1500 can also include determining the shape and configuration of the anchor 120. For example, the anchor 120 can be selected so as to substantially conform to the patient's gingiva without impinging thereon. The thickness, depth, or other properties of the anchor 120 can also be selected to provide sufficient rigidity against the forces generated by the arms. In some embodiments, the anchor 120 design can be automatically generated (e.g., by being automatically generated to substantially conform to the patient's gingiva or other location in the FTA model (e.g., model 1100) or the OTA model (e.g., model 700 or 1000). In some embodiments, an operator may manually select or revise the design and configuration of the anchor as desired.

Although in the illustrated embodiment, the specific features of the arms 130 are selected while the appliance model is in a substantially planar or 2D form, in other embodiments the appliance features can be selected and configured based on a digital model that is contoured to correspond to a patient's anatomy. For example, the 3D appliance template model 1300 (FIG. 13) can be modified to select particular arms 130, anchor 120, or any aspects thereof to achieve the desired appliance. In some embodiments, the template is omitted altogether, and a customized appliance model is generated based on the OTA model and/or the FTA model without the use of an intervening template model.

In some embodiments, the planar appliance model 1500 can be 2D, such that the model defines no thickness of the appliance. Such a model can be used, for example, to cut an appliance out of a sheet of material. In such cases, the thickness can be determined by selecting the sheet of material and by polishing, etching, grinding, deposition, or other techniques used to modify a final thickness of the appliance. In some embodiments, the planar appliance model 1500 can define a thickness dimension while remaining substantially planar or flat. For example, the planar appliance model 1500 can define a thickness of the appliance which may be uniform or may vary across some or all of the anchor 120 and arms 130.

In some embodiments, a 3D or contoured appliance model can be generated, for example by manipulating the planar appliance model 1500 into a curved or contoured configuration. In some embodiments, the 3D appliance model can correspond to the appliance mounted to the teeth in the OTA (e.g., by manipulating the planar appliance model 1500 using position data of the securing members 900 in the OTA model 1000 (FIG. 10), or by manipulating the planar appliance model 1500 using position data of the securing members 900 in the FTA model 1100 (FIG. 11)).

With reference to blocks 516, 518 and 520 together, in some examples a computer-aided procedure can be used to select or determine the shape and configuration of the arms, anchor, and/or any other features of an appliance. The procedure may be configured to select one (or more than one) arm, securing member, anchor, or parameter thereof, or any other aspect of the appliance based on one or more input data. For example, input data may include, but is not limited to, a type of a tooth (e.g., molar, canine, incisor, etc.) or a size of a tooth. A larger tooth (such as a molar) may require larger arms or larger, wider or thicker loop or curved features for providing a greater force, than for a smaller tooth (such as an incisor). Additionally or alternatively, input data may include the size of the periodontal ligament (PDL) of one or more teeth. The size of the PDL may be obtained by any suitable process including, but not limited to, CBCT scan or other imaging technique. Other input data may include, but is not limited to, the number or direction of forces to be applied to a tooth or teeth in a three-dimensional space. For example, a desired tooth movement direction may require one or more shapes or configurations of arms that differ from the shapes or configurations required for a different tooth movement direction. Other input data may include but is not limited to, the number or direction of rotational forces (or torque) to be applied to a tooth or teeth. For example, a desired tooth movement in a rotational direction may require one or more shapes or configurations of arms that differ from the shapes or configurations required for a different tooth movement direction. Additionally, in some embodiments two or more arms can be attached to a single tooth, either with each arm coupled to a separate securing member, or with two arms coupled to the same securing member. In such instances, the input data can include a number of arms and/or securing members coupled to each tooth, or alternatively the number of arms and/or securing members can be generated as output data.

In some embodiments, this computer-aided procedure can include an algorithm that includes, as input, (but is not limited to) one or more values representing one or more of: (a) up to three translational and up to three rotational movements from an OTA to an ITA or FTA, or from an ITA to another ITA or FTA; (b) the surface of periodontal ligament (PDL) or the area of the root of a or each tooth; (c) bone density of the patient; (d) biological determinants for example, obtained from saliva, gingival fluid (GCF), blood, urine, mucosa, or other sources; (e) gender of the patient; (f) ethnicity of the patient; (g) the jaw (maxilla or mandible) for which the appliance is to be installed; (i) the number of teeth on which the appliance is to be installed; and (j) mechanical properties of the tissue (lips, tongue, gingiva) and bone around the teeth to be moved. In various embodiments, one or more of such inputs can affect the forces (e.g., magnitude, direction, point of contact) required to move each tooth from the OTA to or toward the FTA.

In other examples, other suitable input data may be employed. The computer-aided process employs a computer programed or configured with suitable non-transient software, hardware, firmware, or combinations thereof, to generate an output (such as one or more selected arm configurations, anchor configurations, or securing member configurations), based on the one or more input data.

An output generated by the computer-aided procedure, based on such input, can include, but is not limited to one or more of: (a) a design of an arm; (b) a width or cut-width of one or more of such arms; (c) a thickness dimension of any portion of the appliance of the entire appliance; (d) mechanical properties of such arms including but not limited to amount of flexibility, or a magnitude of bias force or resilience; (e) a design of an anchor; (f) a width or thickness of the anchor; (g) connection locations between the arms and the anchor; and/or (h) transformational temperature of the nitinol (or other material) in one or more (or each) section of the appliance. As noted previously, in some embodiments the output can include particular configurations selected from among a pre-populated library of anchors and/or arms. For example, based on the inputs, a desired force (e.g., magnitude and direction) can be determined for each tooth. Based on the desired force, an appropriate anchor member and/or arm configuration can be selected that provides the desired force or a suitable approximation thereof. In some embodiments, the configuration of the appliance (including any of the outputs listed above) can be generated independently of any pre-populated library. In some embodiments, generating the output can include analyzing provisional selections or designs using finite element analysis (FEA) or other techniques to determine performance parameters, for example, the spring force such arms would apply when deflected by particular amounts (e.g., the amount of deflection between the FTA (when the arm is at rest) and the OTA).

In particular examples, computer-aided processes can be employed to make customized appliances, for each given patient. In other examples, appliances may be made in a plurality of predefined sizes, shapes, configurations, or the like, based on a population group. Accordingly, a different semi-customized size, shape or configuration would be configured to fit each different selected portion of the population group. In that manner, a more limited number of different appliance sizes, shapes and configurations may be made to accommodate a relatively large portion of the population.

Based on the determined shape and configuration of the arms and the anchor, the full appliance shape data can be generated. In some embodiments, the appliance shape data can take the form of 3D data (e.g., the appliance in its shape-set form following heat treatment or other suitable setting technique) or planar or substantially 2D data (e.g., the appliance in its laid-flat form, for example as cut out from a sheet of material).

At block 524, an appliance can be fabricated (e.g., based on the planar appliance digital model 1500 (block 520). And at block 526, a fixture can be fabricated (e.g., based on the fixture digital model 1200 (block 516). Fabrication of the fixture and the appliance are described in more detail below.

Methods of Fabricating Orthodontic Appliances

Figure 16:
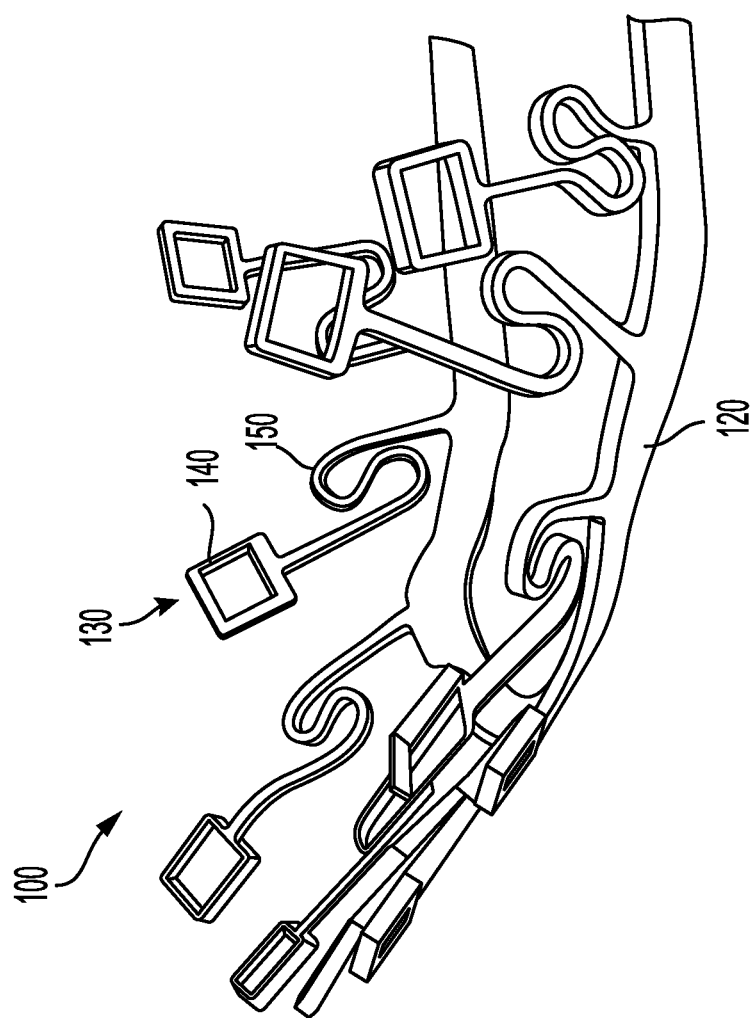
FIG. 16 illustrates a perspective view of an orthodontic appliance in accordance with embodiments of the present technology.

As noted above, one or more digital models can be generated that characterize or define an appliance (e.g., the planar appliance digital model 1500, or a contoured appliance digital model). In various embodiments, one or more such digital models can be used to fabricate an appliance for use in a patient. FIG. 16 illustrates an example of an appliance 100 fabricated using one or more of the digital models described herein. Certain example fabrication processes are described below. However, one of skill in the art will appreciate that any suitable fabrication process may be used to manufacture appliances (or components thereof) as disclosed herein.

In some embodiments, an orthodontic appliance 100 can be fabricated using a planar digital appliance model (e.g., the planar appliance digital model 1500). For example, the planar appliance digital model can include planar or substantially 2D shape data. The planar shape data can be provided to a suitable fabrication device (such as, but not limited to one or more machines that perform cutting, laser cutting, milling, chemical etching, wire electrical discharge machining (EDM), water jetting, punching (stamping), etc.) for cutting a flat sheet of material into a member having a shape corresponding to the planar appliance digital model 1500. The member may be cut from a flat sheet of any suitable material, such as, but not limited to Nitinol, stainless steel, cobalt chrome, or another type of metal, a polymer, a superelastic material, etc. The sheet of material can have a thickness selected to achieve the desired material properties of the resulting member. In various embodiments, the thickness of the sheet of material can be uniform or can vary (e.g., along a gradient, being thinned at particular regions using etching, grinding, etc., or thickened at particular regions using deposition, etc.). In some examples, the sheet can have a thickness of between about 0.1 mm and about 1.0 mm, between about 0.2 mm and about 0.9 mm, between about 0.3 mm and about 0.8 mm, between about 0.4 mm and about 0.7 mm, or about 0.5 mm. In some embodiments, the sheet can have a thickness of less than about 1.5 mm, less than about 1.4 mm, less than about 1.3 mm, less than about 1.2 mm, less than about 1.1 mm, less than about 1.0 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm.

Next, the cut member can be bent from its substantially planar form into a contoured arrangement. FIG. 16 illustrates an example of a completed appliance 100 resulting from such bending of a planar member. As illustrated, and as described elsewhere herein, the appliance 100 can include an anchor 120 and a plurality of arms 130 extending away from the anchor 120. Each arm 130 can include an attachment portion 140 configured to mate with a securing member adhered to a patient's tooth, and a biasing portion 150 disposed between the attachment portion 140 and the anchor 120. When the appliance 100 is installed in the patient's mouth, each of the arms 130 can connect to a different one of the teeth to be moved and exerts a specific force on its respective tooth, thereby allowing an operator to move each tooth independently.

In some embodiments, the planar member, after being cut from a sheet or otherwise formed, may be bent or otherwise manipulated into a shape or contour corresponding or substantially corresponding to the FTA configuration. For example, the member can be a shape cut from a flat sheet of Nitinol or other suitable material and assume a generally planar configuration. The member can be bent into a desired 3D or contoured configuration, for example corresponding to the contoured appliance digital model 1600. In certain examples, one or more fixtures are configured for use in bending the planar member into the desired 3D shape. In such examples, after cutting the planar member, the planar member can be fixed on or between one or more fixtures and bent or otherwise manipulated to form a desired 3D shape. In some embodiments, either before or after cutting the member from the sheet, the thickness of the member can be modified at least in some portions to achieve desired material properties. For example, the thickness of the member can be reduced in at least some regions using grinding, chemical etching, photoetching, electrical discharge machining, or any other suitable material removal process. The thickness of the member can be increased in at least some regions using thin film deposition, electroplating, or any other suitable additive technique. In some embodiments, the planar member can be formed using 3D printing or other technique instead of or in addition to cutting the planar member from a sheet of material. 3D printing may provide certain advantages, for example ease of controlling the thickness of different portions of the appliance. In some embodiments, the planar member can be formed by 3D printing metal, a polymer, or any other suitable material amendable to additive manufacturing by 3D printing.

In some embodiments, the appliance can be shape set into the desired contoured or 3D configuration (e.g., corresponding to the OTA, the FTA, the fixture, etc.). One or more shape setting procedures, such as, but not limited to heat treatment, may be applied to the appliance while held in the desired 3D shape, during or after the bending operation, to set the desired 3D shape. A shape setting procedure involving a heat treatment may include rapid cooling, following heating of the member during or after bending. Additional details regarding example heat treatment and associated fixtures are described below.

By employing a cut planar member, instead of a traditional single-diameter wire, a greater variety of resulting 3D shapes may be made, as compared to shapes made by bending single-diameter wire. The cut planar member may have designed or varying widths and lengths that, when bent into a desired shape, can result in portions of the 3D appliance having variances in thickness, width and length dimensions. In this manner, the planar member can be cut into a shape that provides a desired thickness, width and length of biasing portions, arms, or other components of the appliance. A larger variety of shapes may be provided by bending a custom cut planar member, as compared to bending a single-diameter wire.

In some examples, the entire appliance (including arms and anchor) is fabricated by bending the cut planar member into the desired 3D shaped member. In other examples, additional components may be attached to the 3D shape, for example, after bending. Such additional components may include, but are not limited to attachment portions 40, biasing portions 150, arms 130, etc. Such additional components may be attached to the 3D shaped member by any suitable attachment mechanism including, but not limited to, adhesive material, welding, friction fitting, etc.

In some embodiments, the appliance can be 3D printed directly into the desired contoured or 3D shaped configuration. In some embodiments, the 3D shaped member can be 3D printed, for example using any suitable material. In cases in which the appliance is 3D printed using Nitinol, there may be no need for a shape-setting process (e.g., heat treatment). Additionally, 3D printing may allow the use of different geometries (e.g., a cross-sectional shape of the anchor member may be oval, rather than rectangular, which may increase patient comfort on both the gingival-facing and lingual-facing sides of the anchor).

Methods of Shape-Setting Orthodontic Appliances

In various embodiments of the present technology, a physical fixture for use in manufacturing of an orthodontic appliance can be fabricated based on a fixture digital model (such as fixture digital model 1200). The fixture can be used to shape-set the appliance. For example, the appliance can be manufactured in a planar configuration (e.g., cut from a sheet of material, 3D printed, etc.). The appliance can then be manipulated into a desired 3D configuration by securing and/or conforming the appliance to the fixture. The appliance and fixture can undergo a shape setting process while the appliance is retained in the desired 3D configuration by the fixture such that, when the appliance is separated from the fixture, the appliance retains the desired 3D configuration. In some embodiments, the appliance can be manufactured in a non-planar, first 3D configuration and manipulated into a desired second 3D configuration (different than the first 3D configuration) by securing and/or conforming the appliance to the fixture.

Figure 17:
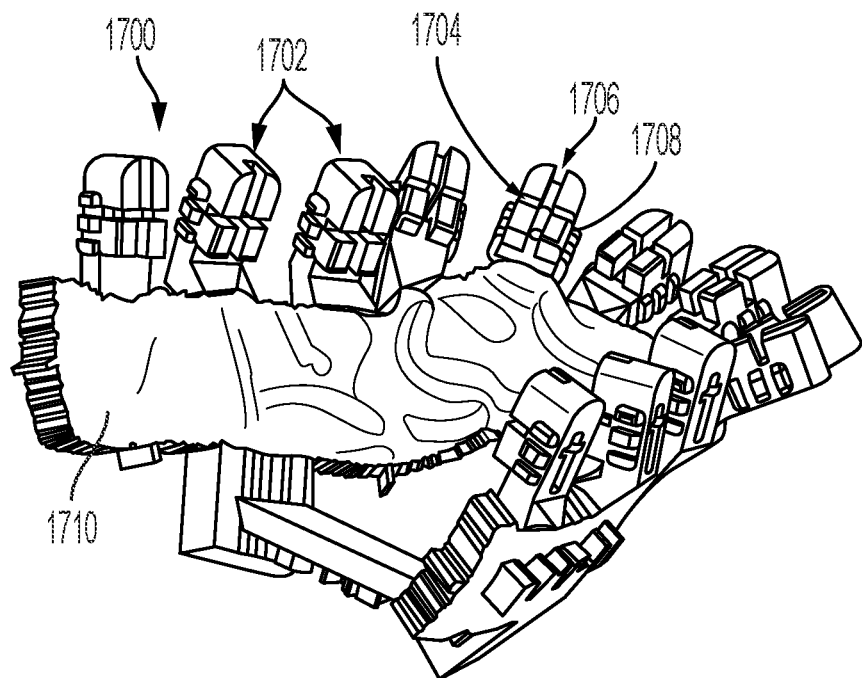
FIG. 17 illustrates a perspective view of a shape forming fixture for an appliance in accordance with the present technology.

FIG. 17 illustrates an example of a fixture 1700 configured to retain a pre-installation version of the appliance in a desired configuration during a shape setting procedure. The fixture 1700 can be configured to hold a pre-installation version of the appliance in a configuration corresponding to an intended configuration of the appliance when the teeth are in the FTA. When the appliance is removed from the fixture after the shape setting procedure, the appliance is biased to maintain its shape corresponding to the FTA. When the appliance is installed in the patient's mouth in the OTA, the appliance is deformed. Because the appliance is biases to maintain its shape corresponding to the FTA, it will tend to return from a deformed configuration to its intended configuration, and thus will urge the teeth toward their desired, final positions.

The fixture 1700 can be manufactured based on the fixture digital model (e.g., the fixture digital model 1200 (FIG. 12)). For example, the fixture digital model or associated data can be provided to a fabricating system to produce a physical fixture based on the fixture digital model. In one example, the fixture data can be used to 3D print a model of the fixture in wax. The wax model may then be used to investment cast the fixture in brass or other suitable material. In some embodiments, the fixture can be 3D printed directly in brass or other suitable material (e.g., stainless steel, bronze, a ceramic or other material that tolerates high temperatures required for heat treatment).

As shown in FIG. 17, the fixture 1700 can comprise one or more securing portions 1702 and a gingiva portion 1710. The securing portions 1702 can extend away from the gingiva portion 1710. The securing portions 1702 can be configured to releasably retain one or more portions of an appliance at a specific location relative to other portions of the appliance. For example, the securing portions 1702 can be configured to retain attachment portions (e.g., attachment portions 140, etc.) of an appliance during a shape setting procedure in positions corresponding to intended positions of corresponding securing members when the appliance is later installed in the patient's mouth and the securing members are secured to the patient's teeth (for example, when the teeth, and thus securing members, are in an OTA or FTA). In some embodiments, the securing portions 1702 are positioned relative to one another and to the gingiva portion 1710 to reflect the positions of the teeth in the FTA. In other embodiments, the securing portions 1702 are positioned to reflect the teeth in the OTA or an ITA.

The securing portions 1702 can have a geometry configured to facilitate positioning and/or retaining corresponding attachment portions at the intended positions. For example, as shown in FIG. 17, the securing portions 1702 can define first channels 1704 and second channels 1706 angled with respect to the first channels 1704. The first and second channels 1704, 1706 are configured to receive attachment portions of an appliance at least partially therein to locate the attachment portions at their intended positions. The securing portions 1702 can comprise protrusions (e.g., protrusions 1708) extending away from the corresponding securing portion 1702 and defining channels. In some embodiments, the protrusions 1708 define the first and second channels 1704, 1706 and/or the protrusions 1708 can define third channels configured to receive a fastener at least partially therein. For example, an elongate member such as a ligature wire can be wound about one of the securing portions 1702 and an attachment portion of an appliance such that the ligature wire is positioned within channels defined by the protrusions 1708 and secures the attachment portion to the securing portion 1702. The securing portions 1702 can be configured to receive and/or coupled with other fasteners, such as ties, sutures, bands, clasps, and others. In various embodiments, the securing portions 1702 can define one or more through-channels, apertures, or other openings to facilitate securing of an attachment portion to the securing portion 1702 via a fastener. For example, such openings can allow a pushing tool to be inserted from the back of the securing portion 1702 (e.g., through the buccal surface of the fixture 1700) to push an attachment portion away from the securing portion 1702 after the heat treatment has been completed and the ligature wire or other fastener has been removed.

The gingiva portion 1710 of the fixture 1700 comprises the shape of gingival tissue and provides a surface on which a portion of the appliance is conformed during a shape setting procedure. Because the fixture 1700 is based on the fixture digital model 1200, the gingiva portion 1710 may be substantially identical to the gingiva portion 1210 of the fixture model 1200, which may be substantially identical to the gingiva portion from any of the OTA or FTA digital models (e.g., 700, 800, 1000, 1100). For example, it can be desirable to use the gingiva portion 704 from the OTA digital model 700 for the gingiva portion 1210 of the fixture model 1200 to prevent or limit impingement of the patient's gingiva by an appliance installed in the patient's mouth and having a shape corresponding to a shape of the fixture 1700. In some cases, the securing portions 1202 can be positioned to reflect the teeth in the FTA while the gingiva portion 1210 reflects the gingiva in the OTA.

Additional details regarding fixtures and components thereof are discussed below with reference to FIGS. 33A-34B, for example.

Figure 18:
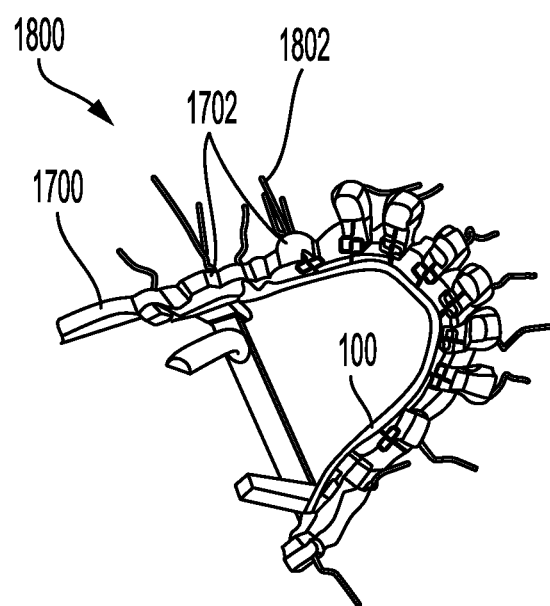
FIG. 18 is a perspective view of an orthodontic appliance fastened to a heat treatment fixture in accordance with the present technology.

As shown in FIG. 18, a pre-installation version of the appliance can be positioned on and secured to the fixture 1700. The combined assembly 1800 thus includes an appliance 100 that has been bent or otherwise manipulated into shape against a surface of the fixture 1700. The appliance 100 can be secured to the fixture 1700 by placing attachment portions into the securing portions 1702 of the fixture. Fasteners 1802 (e.g., ties, ligature wires, sutures, bands, wraps, etc.) can be wrapped around the appliance 100 at a plurality of positions to secure the appliance 100 with respect to the fixture 1700. Next, the shape setting procedure is performed shape set the appliance 100, after which the appliance 100 can be removed from the fixture 1700.

Some examples of a shape setting procedure can include heating the appliance 100 to a selected temperature (such as, but not limited to 525 degrees centigrade) for a selected period of time (such as, but not limited to 20 minutes), followed by rapid cooling. The rapid cooling can be achieved by any suitable cooling procedure such as, but not limited to water quench or air-cooling. In other examples, the time and temperature for heat treatment can be different than those discussed above, for example, based upon the specific treatment plan. For example, heat treatment temperatures can be within a range from 200 degrees centigrade to 700 degrees centigrade and the time of heat treatment can be a time in the range up to about one hundred and twenty minutes. In particular examples, the heat treatment procedure may be carried out in an air or vacuum furnace, salt bath, fluidized sand bed or other suitable system. After completing the heat treatment, the appliance has a desired 3D shape and configuration (e.g., corresponding substantially to the fixture and/or to the desired FTA). In other examples, other suitable heat-treating procedures may be employed including, but not limited to resistive heating or heating by running a current though the metal of the appliance structure. In some embodiments, the shape setting procedure does not rely on heat.

One or more additional post processing operations may be provided on the 3D shaped article, including, but not limited to abrasive grit blasting, shot peening, polishing, chemical etching, electropolishing, electroplating, coating, ultrasonic cleansing, sterilizing or other cleaning or decontamination procedures.

In examples in which the appliance is made of multiple components, some (or each) of the components of the appliance may be made according to methods described above, and then connected together to form the desired 3D appliance configuration. In these or other examples, the appliance (or some or each component of the appliance) may be made in other suitable methods including, but not limited to: directly printing of metal, first printing of a wax member and then investment casting the wax member into a metal or other material, printing of elastomeric material or other polymer, cutting or machining out of solid material, or cutting the components out of a sheet of metal and shape setting into the desired 3D configuration.

As discussed herein, one or more fixtures may be configured for use in bending a cut planar member into a desired 3D shape configuration. In particular examples, one or more fixtures are provided (such as, but not limited to, custom made) for each jaw of a patient. For example, the fixtures may be customized in shape and configuration for each patient and can be made in any suitable manner, including molding, machining, direct metal printing of stainless steel or other suitable metals, 3D printing of a suitable material, such as, but not limited to stainless steel via powder bed fusion, or a steel/copper mix via binder jetting, as well as first printing the configuration in wax and then investment casting the wax into various metals. In various examples described herein, the fixtures may be configured of material that is sufficiently resistant to the temperature of the heat treatment. In particular examples, one or more robots may be employed with or without the one or more fixtures, for bending the cut planar member into a desired 3D shape configuration.

In some embodiments, a single shape-setting step may be completed to deform the member from its planar configuration to its desired 3D configuration. However, in certain embodiments the shape setting may include two or more shape-setting steps (e.g., two or more heat treatment processes, potentially using two or more different fixtures). In such cases, the amount of deformation imparted to the appliance within each shape-setting step may be limited, with each subsequent shape-setting step moving the appliance further toward the desired 3D configuration.

The completed appliances can then be sent (optionally along with bonding trays and/or securing members) to the treating clinician. To install the appliances, the orthodontist can clean the lingual side of the patient's teeth to prepare them for bonding (e.g., with pumice powder). The surface of the teeth can then be sandblasted (e.g., with 50-micron aluminum oxide). The securing members can then be attached using a bonding tray as described elsewhere herein.

After the appliances are fabricated and the securing members are attached to the teeth, each arm can be coupled to its corresponding securing member element to install the appliance. Once installed, the appliance imparts forces and torques on the teeth, to move the teeth to the desired FTA. After treatment is completed (e.g., OTA to FTA, OTA to ITA, ITA to ITA, or ITA to FTA) the arms may sit passively in the securing members and force will no longer be applied to the teeth. Alternatively, any remaining force applied by the arms may fall below a threshold for causing further displacement of the teeth.

The patient can return for a check-up appointment (e.g., at approximately 2-3 months), and if the treatment is advancing as planned, nothing is done until the patient returns at a planned time for appliance removal. At this stage the securing members may be removed. If treatment is not progressing as planned, the appliance may be removed, the patient's mouth rescanned, and a new appliance can be device designed and installed based on a modified treatment plan.

IV. Selected Embodiments of Methods of Orthodontic Treatment

Figure 19:
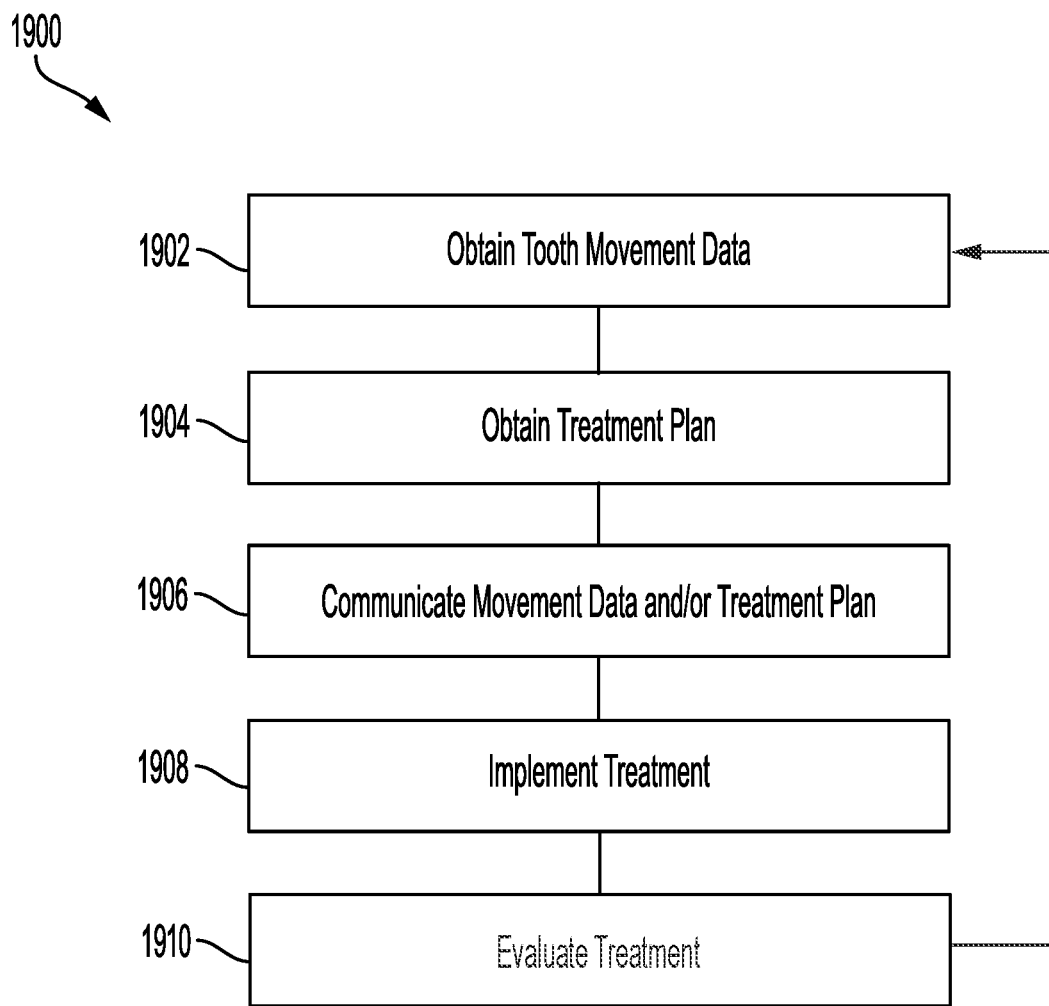
FIG. 19 is a flow diagram of an example process for orthodontically treating a patient in accordance with the present technology.

FIG. 19 is a flow diagram of an example process 1900 of orthodontically treating a patient in accordance with several embodiments of the present technology. As shown in FIG. 19 and described in greater detail herein, the process 1900 can include obtaining tooth movement data characterizing movements of the patient's teeth to be accomplished during the orthodontic treatment (process portion 1902). The tooth movement data can characterize a movement (or lack thereof) of each of the patient's teeth from an original position of the tooth to a desired, final position of the tooth. In some embodiments, obtaining the tooth movement data comprises identifying, evaluating, and/or modifying one or more of the tooth movements. The process 1900 can also include obtaining a treatment plan (process portion 1904), which may include an indication and/or a suggestion of one or more orthodontic interventions to be employed to accomplish the tooth movements, a design of an appliance or other intervention configured to accomplish the tooth movements, and/or other useful information regarding the planned treatment (e.g., an estimated duration of the treatment, a complexity of the treatment, etc.). At process portion 1906, the treatment plan and/or the tooth movement data can be communicated to any one stakeholder or combination of stakeholders involved in the orthodontic treatment. Such stakeholders may include, but are not limited to, a technician designing an orthodontic appliance, an orthodontist, a patient, and/or others. The treatment can be implemented at process portion 1908 according to the treatment plan. In some embodiments, the treatment is evaluated (process portion 1910) during and/or after implementation of the orthodontic treatment, which can comprise comparing actual positions and/or movements of the patient's teeth to planned positions and/or movements of the teeth. The evaluation can be used in assessing treatment outcomes, determining if further treatment is necessary, selecting and designing orthodontic interventions to accomplish further treatment, etc. As shown in FIG. 19, the process 1900 can repeat based on the evaluation. For example, if a first treatment is evaluated at the end of the first treatment and it is determined that further treatment is necessary, process portion 1902 can be repeated to obtain new movement data characterizing movements of the patient's teeth from the actual positions to the desired, final positions, process portion 1904 can be repeated to obtain a new treatment plan, etc.

All or a portion of the process 1900 can be iterative. For example, the process 1900 can include evaluating and/or modifying the output at any given stage, such as the tooth movement data and/or the treatment plan. Evaluation of the movement data and the treatment plan can be qualitative or quantitative. In any of the examples herein and others, evaluating and/or modifying the movement data and/or the treatment plan can be performed manually (e.g., by a human operator) and/or automatically (e.g., by suitable software).

The following discussion expands on several aspects of the process 1900.

A. Obtaining Tooth Movement Data

Figure 20:
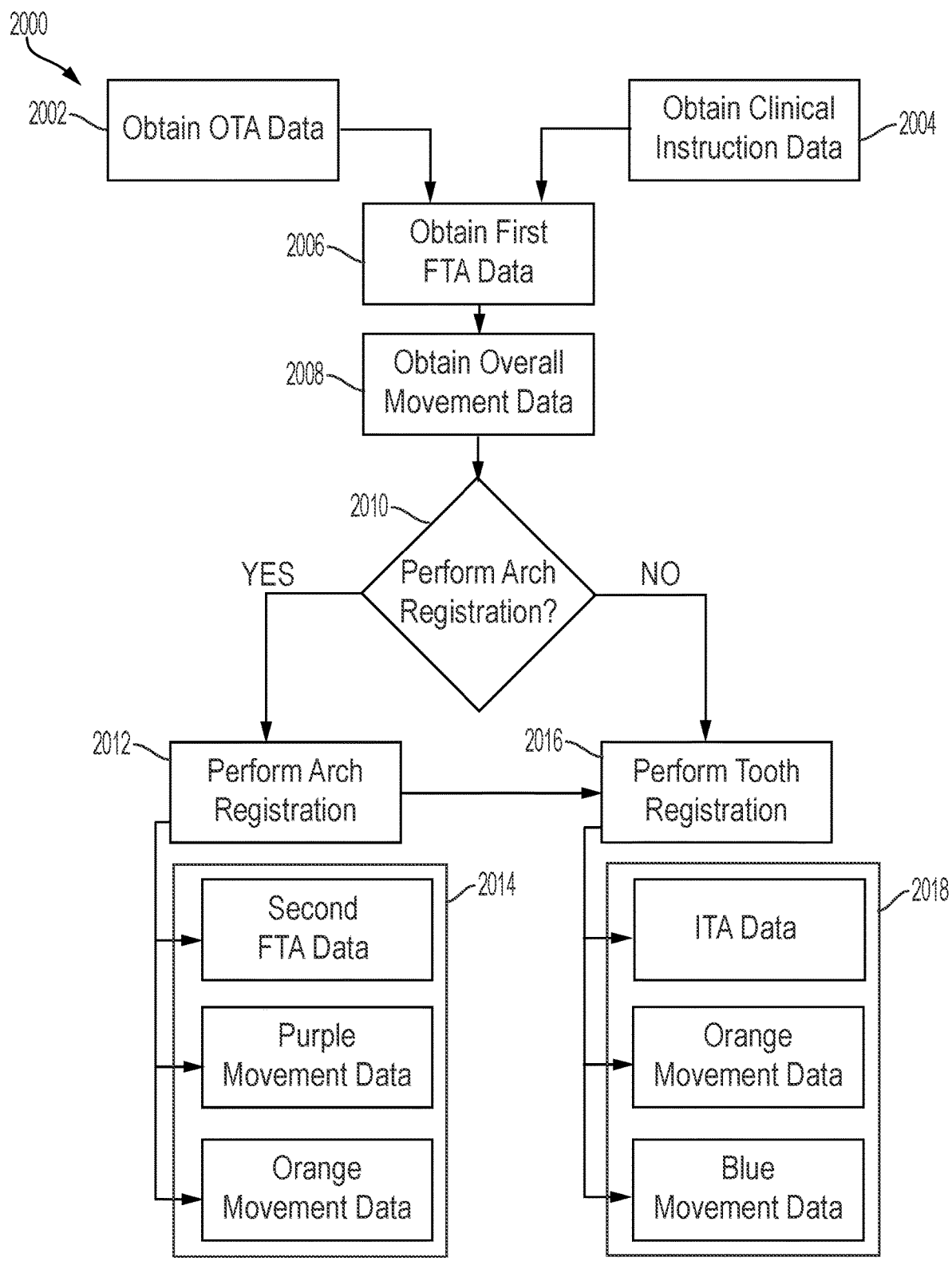
FIG. 20 is a flow diagram of an example process for obtaining tooth movements in accordance with the present technology.

The process 1900 of orthodontically treating a patient includes obtaining tooth movement data characterizing desired movements of the patient's teeth (process portion 1902). FIG. 20 is a flow diagram of an example process 2000 for obtaining such tooth movement data. The process 2000 can include obtaining OTA data characterizing original positions of the patient's teeth (process portion 2002). In some embodiments, the process 2000 includes obtaining clinical instructions (process portion 2004). As described in greater detail below, the clinical instructions can provide useful information regarding the orthodontic treatment such as the types of interventions to be used, clinical objectives and/or priorities for the treatment, etc. From the OTA data and/or the clinical instructions, the process 2000 can include obtaining first FTA data characterizing final positions of the patient's teeth (process portion 2006). From the OTA data and the first FTA data, the process 2000 can include obtaining overall movement data characterizing overall movements of the patient's teeth from the original positions to the final positions (process portion 2008). An overall movement of one of a patient's teeth can comprise zero, one, two, or three translational displacements and zero, one, two, or three rotational displacements. The overall movement comprises a transformation that, when applied to a tooth, would move the tooth from its original position to its final position.

As shown in FIG. 20, the process 2000 can include determining whether to perform an arch registration (process portion 2010). In its simplest form, an arch registration process compares both of the patient's dental arches as a single unit in the OTA to both arches as a single unit in the FTA and identifies a common movement of both arches. In some embodiments, the arch registration process also eliminates the common movement.

The arch registration can be beneficial for identifying, evaluating, and/or modifying the positions of the patient's dental arches in the first FTA to facilitate coordination of the orthodontic treatment, ensure that the movements of the arches are achievable, reduce the treatment time, etc. For example, a temporary anchorage device (TAD) or surgery can be employed to move all of the patient's teeth in both of the patient's dental arches in the same direction according to the same transformation. Conversely, such movements may not be possible with other interventions such as appliances, elastics, or others. Accordingly, if the clinical instructions indicate that surgery or TADs are not an option, it might not be appropriate for tooth movements to indicate that both dental arches should be moved in the same direction according to the same transformation. In these and other embodiments, an arch registration can be performed (process portion 2012) to modify the positions of the dental arches in the first FTA. However, if the clinical instructions indicate that TADs or surgery are an option, movement of both arches may be appropriate and the result of the decision at process portion 2010 is that an arch registration should not be performed. In some embodiments, the arch registration is performed regardless of the clinical instructions.

If the result of the decision at process portion 2010 is that an arch registration should be performed, the process 2000 can proceed to performing the arch registration at process portion 2012. Performing the arch registration can include registering the first FTA data to the OTA data to obtain first outputs 2014, which include second FTA data, "purple movement" data, and/or "orange movement" data. As used herein, "purple movements" refer to a movement of all of a patient's teeth in both of the patient's dental arches according to the same transformation. Also as used herein, "orange movements" refer to a movement of all of a patient's teeth in one of the patient's dental arches according to the same transformation.

After performing the arch registration at process portion 2012, the process 2000 proceeds to performing a tooth registration (process portion 2016). Alternatively, the process 2000 can proceed to performing a tooth registration (process portion 2016) directly after process portion 2010 if the result of the decision is that an arch registration should not be performed. If an arch registration was performed, performing the tooth registration can comprise registering the second FTA data to the OTA data. If an arch registration was not performed, performing the tooth registration can comprise registering the first FTA data to the OTA data. The tooth registration can be performed to obtain second outputs (process portion 2018) including ITA data, orange movement data, and/or blue movement data. As used herein, "blue movements" refer to a movement of at least one tooth in one dental arch of a patient relative to other teeth in the same dental arch. The ITA data can characterize positions of the teeth in one of the patient's dental arches after the teeth have been moved from their original positions according to the blue movement data. If there are no orange movements, then the ITA data corresponds to the FTA data (e.g., the first FTA data if no arch registration was performed, the second FTA data if an arch registration was performed, etc.).

1. Obtaining OTA Data

Obtaining OTA data characterizing original positions of a patient's teeth (process portion 2002) can be performed as described elsewhere herein. The OTA data can comprise one-dimensional coordinates, two-dimensional coordinates, three-dimensional coordinates, or higher-dimensional coordinates. In some embodiments, the OTA data characterizes one original position of each tooth. Additionally or alternatively, the OTA data can characterize multiple original positions of each tooth. For example, the OTA data can characterize the original positions of multiple locations on each tooth. In some embodiments, the OTA data characterizes original positions of only some of the patient's teeth.

The OTA data can be obtained prior to suggesting and/or implementing an orthodontic intervention. In some embodiments, the OTA data can be obtained when the teeth are maloccluded, mis-aligned, crowded, or otherwise in need of orthodontic correction. For example, the OTA data can be obtained when the teeth are in an original arrangement. The OTA data can be obtained by scanning the patient's teeth. For example, as shown in FIG. 6, the OTA data can be obtained by scanning the patient's teeth using an intraoral optical scanner. The scanning can be performed using any suitable technique, for example dental cone beam CT scanning, magnetic resonance imaging (MRI), or similar device or technique. In various examples, the OTA data can include data associated with the roots of the teeth as well as the exposed portions. In some examples, the OTA data can be obtained using an impression made of the patient's upper and/or lower jaws (e.g., using polyvinyl siloxane or any other suitable impression material). The impression can then be scanned to create 3D data, which can include the relationship between the upper and lower jaw (e.g., to record the patient's bite). In examples in which impressions are used, the relationship between the teeth in the upper and lower arches (inter-arch relationship) can be obtained by taking a wax bite of the patient in the centric position. In various embodiments, the OTA data can be obtained directly (e.g., by imaging the patient's mouth using an appropriate imaging device) or indirectly (e.g., by receiving pre-existing OTA data from an operator or another source).

In some embodiments, the process 2000 can comprise obtaining a digital model of the patient's teeth and/or other oral tissues. For example, as detailed herein, a digital model of the patient's teeth can be obtained that characterizes the teeth in an original arrangement in which the teeth are maloccluded, mis-aligned, crowded, or otherwise in need of orthodontic correction. An example digital model 700 is depicted in FIG. 7. In some embodiments, one or more teeth present in the original arrangement may be designated for extraction prior to use of the orthodontic appliance.

In various embodiments, obtaining the digital model corresponding to the OTA data can include first obtaining a single complex 3D database of the patient's jaw, which is then segmented to separate the patient's teeth into separate 3D bodies (e.g., individual teeth or blocks of multiple teeth) that can then be manipulated virtually by an operator. Such segmentation can be performed using any suitable techniques or software, for example using iROK Digital Dentistry Studio or other suitable software. Following segmentation, the resulting 3D databases of the upper and lower teeth can include a model of the gingiva and independent models of each tooth. As a result, the OTA data can be manipulated by an operator to virtually move teeth relative to the gingiva and/or each other.

In some embodiments, obtaining the OTA data can be iterative. For example, obtaining the OTA data can comprise obtaining preliminary OTA data from an intraoral scan of a patient's teeth and evaluating the preliminary OTA data. The evaluation can assess whether the preliminary OTA data sufficiently characterizes the patient's teeth and oral tissue, a quality of the data, etc. For example, an operator and/or suitable software can review a digital model of the patient's teeth in the original arrangement and identify portions (if any) with poor resolution, gaps in the model, etc. If the preliminary OTA data is acceptable and/or preferred, the preliminary OTA data can be selected as the OTA data. If the preliminary OTA data is not acceptable and/or preferred, the preliminary OTA data can be modified and/or new preliminary OTA data can be obtained (e.g., via an additional scan of the patient's teeth) and the process 2000 can repeat.

2. Obtaining Clinical Instructions

The clinical instructions obtained at process portion 2004 can be generated by a human operator (e.g., an orthodontist, an oral surgeon, a technician, etc.). The instructions can include information regarding the orthodontic treatment such as orthodontic issues to be addressed (e.g., malocclusions, misalignments, etc.), desired final positions of the teeth, desirable or undesirable movements of the teeth, orthodontic interventions available for the treatment, requested timing of the orthodontic interventions, and/or other useful information. For example, the instructions might include that the patient will not consent to orthognathic surgery, and that the tooth movements should be able to be accomplished by other orthodontic interventions. As examples, the instructions might include phrases such as, but not limited to, "rotate the central incisor," "address class II malocclusion," "extrude lateral incisor by 1 mm," and/or "fix torque for lateral incisor." The instructions can be provided verbally, in writing, electronically, or via any other suitable form of communication. In some embodiments, the instructions can be entered into suitable software on a computing device by a human operator. The instructions can be obtained before or after obtaining the OTA data. In some embodiments, the instructions are obtained prior to obtaining the first FTA data, as the instructions may facilitate generation of the first FTA data.

3. Obtaining First FTA Data

The first FTA data obtained at process portion 2006 can be performed as described elsewhere herein. The first FTA data can comprise one-dimensional coordinates, two-dimensional coordinates, three-dimensional coordinates, or higher-dimensional coordinates. In some embodiments, the first FTA data characterizes one final position per tooth. Additionally or alternatively, the first FTA data can characterize multiple final positions per tooth. For example, the first FTA data can characterize the final positions of multiple locations on each tooth. In some embodiments, the first FTA data characterizes final positions of only some of the patient's teeth. In some embodiments, the final positions of the teeth correspond to positions of the teeth in an optimal or preferred arrangement (e.g., after complete orthodontic treatment) or in an intermediate arrangement (e.g., after partial orthodontic treatment).

As previously noted, in some embodiments the first FTA data can be obtained by manipulating the teeth from the original positions towards the final positions. In some cases, the process 2000 includes obtaining a digital model of the patient's teeth in the final positions. FIG. 8 shows an example FTA digital model. Obtaining the digital model can include manipulating the OTA data and/or a digital model of the patient's teeth in the original positions to virtually move teeth relative to one another, the patient's gingiva, the patient's skull, etc. When the teeth are in their final positions, they may be more aligned, less maloccluded, and otherwise aesthetically and functionally improved relative to the teeth in the original positions. In some embodiments, obtaining the first FTA data comprises manipulating the teeth from the original positions towards the final positions according to the clinical instructions. In some cases, for example when orthognathic surgery is to be performed, obtaining the first FTA data can comprise manipulating one or more of the patient's jaws, and thereby the teeth carried by one or more jaws.

In some embodiments, obtaining the first FTA data can be iterative. In some embodiments, obtaining the first FTA data includes evaluating preliminary final positions of the patient's teeth and determining whether the preliminary final positions are acceptable and/or preferred. If the teeth are still maloccluded, misaligned, and/or otherwise in need of further orthodontic correction in the preliminary final positions, obtaining the first FTA data can comprise further manipulating the teeth from the preliminary final positions towards modified final positions. As previously described with reference to obtaining the OTA data, the process can repeat until acceptable and/or preferred first FTA data is obtained.

In some embodiments, the first FTA data can be modified based on an occlusive contact force between the upper and lower dental arches when the teeth are in the final positions. If a first tooth in a maxilla of a patient contacts a second tooth in a mandible of the patient when the teeth are in an original arrangement and a human operator extrudes the second tooth when obtaining the first FTA, there may be undesirable and excessive contact force between the first and second teeth. The excessive contact force may cause the patient's mandible to rotate about its condyloid processes. Rotation of the mandible about the condyloid processes can be predicted by an operator and/or suitable software and/or communicated as feedback to the operator and/or software generating the first FTA. For example, obtaining the rotation can include performing an algorithm to determine the rotation based on the contact between the patient's teeth and anatomy of the patient. An axis of rotation for obtaining the rotation can be based, at least in part, on a distance between the condyloid processes of the mandible, a distance between the coronoid processes of the mandible, and/or another suitable anatomical distance. The axis of rotation can be obtained from a scan of the patient's jaws (e.g., via cone beam computed tomography, computed tomography, magnetic resonance imaging, etc.) or from a database of anthropometric measurements. For example, an average distance between condyloid processes for people of similar age, gender, ethnicity, etc. as the patient can be used in obtaining the axis of rotation.

Feedback regarding the first FTA data, such as feedback regarding occlusive contact force described above, can be communicated to a human operator and/or suitable software involved in obtaining the first FTA data. The first FTA data can then be modified by the operator and/or software. For example, the angular displacement between the patient's mandible and maxilla can be visually communicated as an animation in which a software platform displays the mandible moving according to the rotation. In some embodiments, the angular displacement can be communicated as a number, a color map, and/or another suitable type of indicia visually or audibly displayed by the software. Based on the feedback, the first FTA data can be modified and/or specific orthodontic interventions can be suggested. For example, a bite block could be implemented if large occlusive contact force and rotation of the mandible are predicted. As but one example, a bite block could be suggested to reduce the likelihood of debonding of a bracket if a collision is predicted between the bracket and a structure of an opposing dental arch (e.g., a tooth, another bracket, etc.).

In some embodiments, the first FTA can be obtained based on one or more clinical considerations. For example, if the patient has mandibular anterior facial gingival recession, it may be advantageous to minimize or limit anterior movement of the mandibular incisors during orthodontic treatment to prevent worsening of the gingival recession. Other clinical considerations can include, but are not limited to, a duration of the treatment, a comfort of the patient, a cost of the treatment, a facial structure of the patient, etc. Such clinical considerations and others may be included in the clinical instructions.

Figure 21:
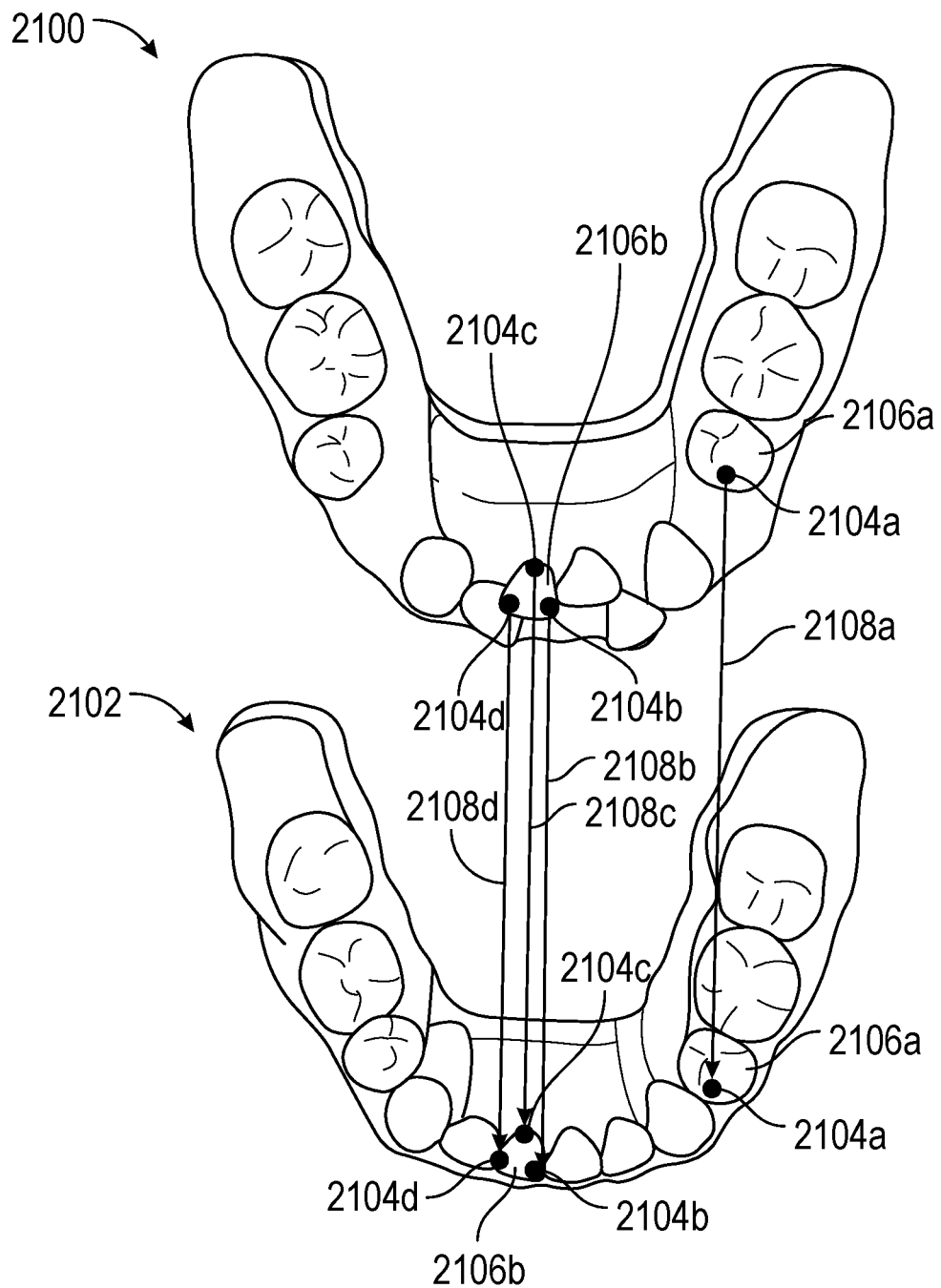
FIG. 21 illustrates movement data characterizing movements of a patient's teeth from original positions in an original arrangement to final positions in a final arrangement in accordance with the present technology.

FIG. 21 depicts an example of a patient's teeth in an original arrangement 2100 and a final arrangement 2102. As shown in FIG. 21, the OTA data and the first FTA data can be obtained at one location per tooth (e.g., location 2104a at tooth 2106a) and/or multiple locations per tooth (e.g., locations 2104b-d at tooth 2106b).

4. Obtaining Overall Movement Data

Overall movement data characterizing a movement of one or more of the patient's teeth from an original position to a final position can be obtained at process portion 2008 using the OTA data and/or the first FTA data. Since an overall movement of a patient's tooth from an original position to a final position can comprise one or more component movements, such as a blue movement, an orange movement, and/or a purple movement, the overall movement data can comprise blue movement data, orange movement data, and/or purple movement data. FIGS. 22A-22F are provided to help explain the different components.

Figure 22A:
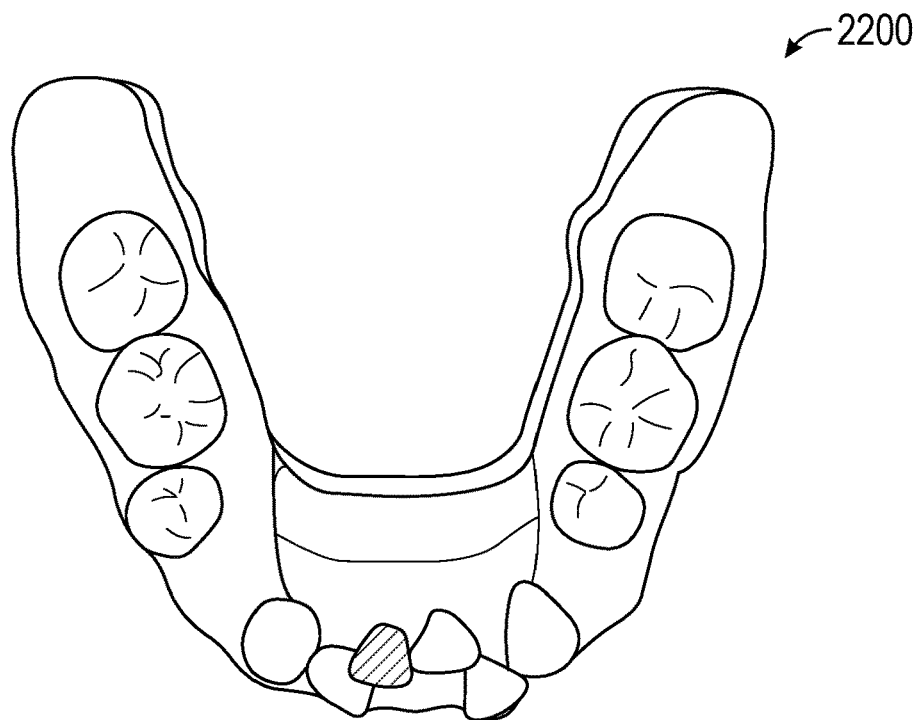
FIG. 22A illustrates a patient's teeth of one of a patient's dental arches in an original arrangement.
Figure 22B:
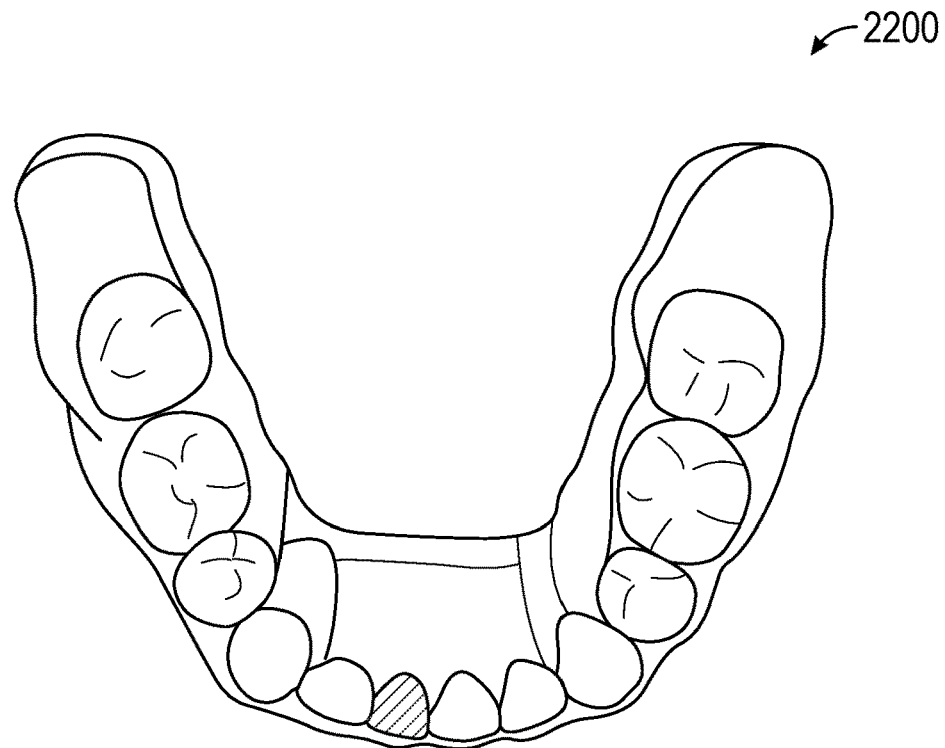
FIG. 22B illustrates the teeth of FIG. 22A in a final arrangement after the teeth have been moved relative to one another in accordance with the present technology.

In some embodiments, the overall movement data includes blue movement data that represents a movement (or non-movement) of each of the teeth relative to the other teeth in the same dental arch (e.g., individual tooth movements). To illustrate, FIG. 22A shows one of a patient's dental arches 2200 in an original arrangement and FIG. 22B shows the same arch in an intended final arrangement. Moving the teeth in one of the patient's dental arches relative to the other teeth in the same dental arch can improve an alignment of the teeth in the arch. In some embodiments, such movements can change a shape of the dental arch.

Figure 22C:
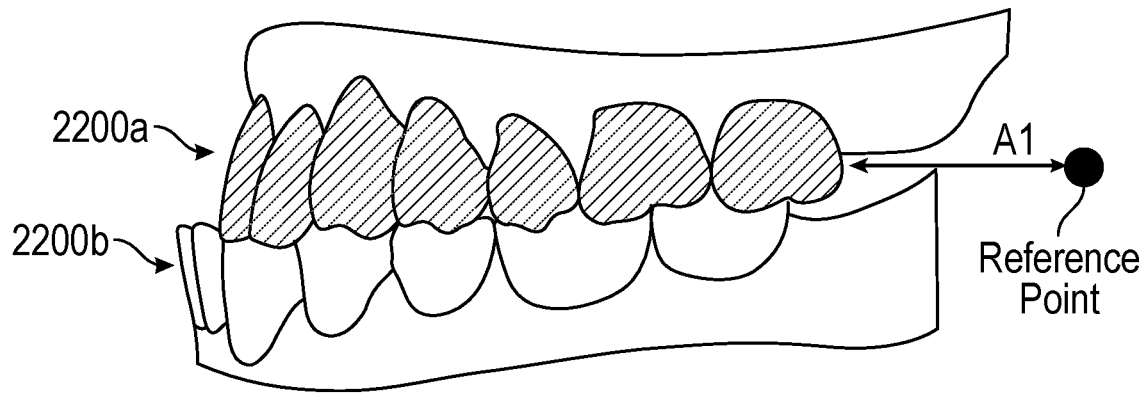
FIG. 22C illustrates a patient's dental arches in an original arrangement.
Figure 22D:
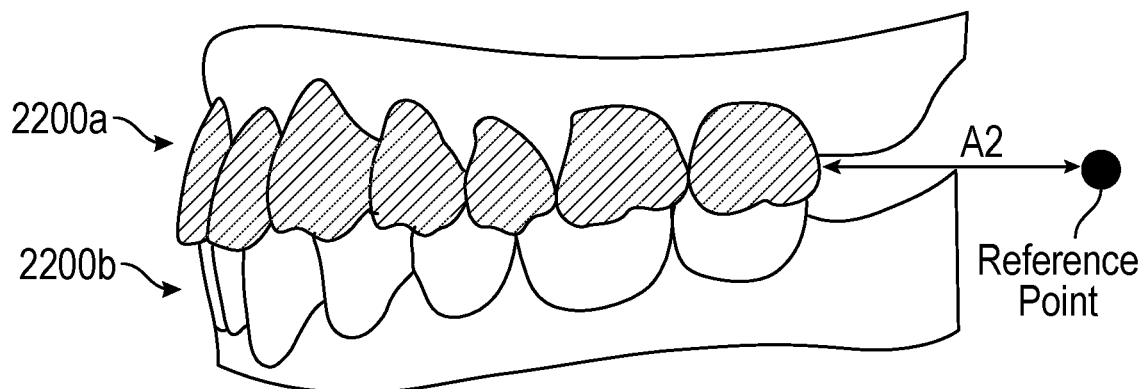
FIG. 22D illustrates the dental arches of FIG. 22C in a final arrangement after the arches have been moved relative to one another in accordance with the present technology.

In some embodiments, the overall movement data includes orange movement data that represents a common movement of all of the teeth in one of the patient's dental arches relative to a reference point. The common movement can comprise a transformation that is applied to all teeth in the dental arch. In some embodiments, the transformation is rigid, e.g., such that the collective structure of all of the teeth maintains its shape and size after being transformed (e.g., distances between points defining the digital models of the teeth do not change after being transformed). The reference point can comprise a point on the patient's anatomy away from the arch being analyzed, such as a skull of a patient, a point on the other dental arch of the patient, etc. FIG. 22C, for example, illustrates teeth of an upper dental arch 2200a and a lower dental arch 2200b in an original arrangement and FIG. 22D illustrates the teeth after all of the teeth in the patient's upper dental arch 2200a have been moved according to an orange movement. In this particular example, the orange movement is a forward movement of all of the teeth in the upper dental arch 2200a relative to the lower dental arch 2200b. Moving one or more of the patient's dental arches 2200a, 2200b according to an orange movement can improve a patient's occlusion (e.g., bite). For example, the patient shown in FIG. 22C has a class II malocclusion in which the upper dental arch 2200a is positioned substantially anterior of the lower dental arch 2200b. In FIG. 22D, the patient's upper dental arch 2200a and lower dental arch 2200b are aligned such that the class II malocclusion has been treated.

Figure 22E:
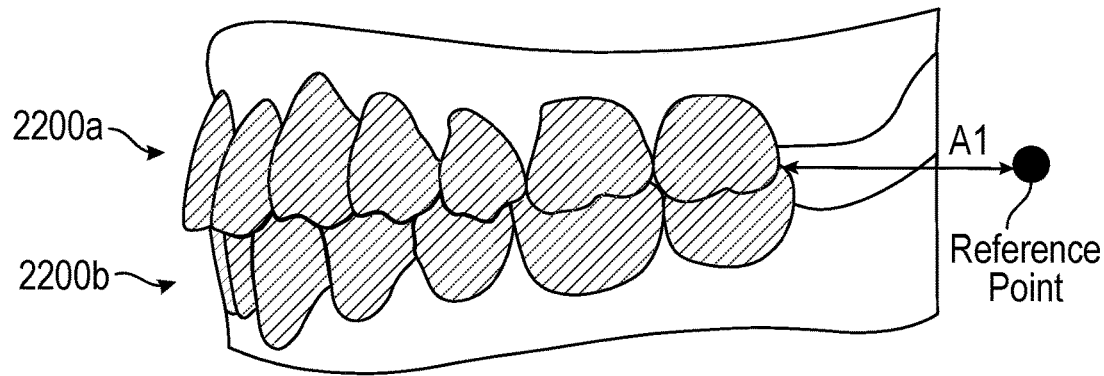
FIG. 22E illustrates a patient's dental arches.
Figure 22F:
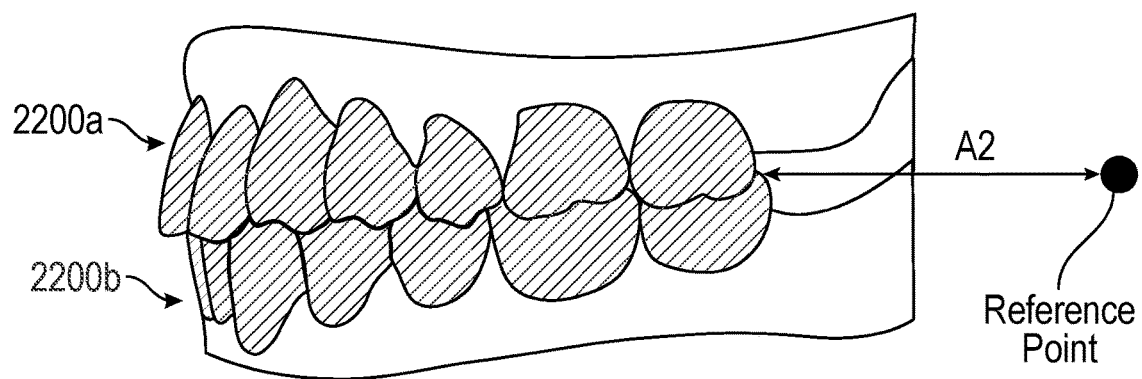
FIG. 22F illustrates the dental arches of FIG. 22E after both of the arches have been moved relative to a reference point in accordance with the present technology.

In some embodiments, the overall movement data includes purple movement data that represents a common movement of all of the teeth (i.e., the teeth in both of a patient's dental arches) relative to a reference point according to a common movement. The common movement can comprise a transformation that is applied to all teeth in the dental arches. In some embodiments, the transformation is rigid. The reference point can comprise a point on the patient's anatomy away from the dental arches being analyzed, such as the patient's skull or another suitable reference point. In such embodiments, neither the patient's tooth alignment nor occlusion are modified. Rather, the teeth in both arches are moved according to the same transformation. For example, if the patient's occlusion does not need modification but the patient experiences lip drooping due to posteriorly positioned dental arches, the orthodontic treatment may include moving both of the patient's arches anteriorly to improve the patient's facial structure. FIG. 22E illustrates an example of a patient's upper and lower dental arches 2200a, 2200b in an original arrangement in which the upper and lower dental arches 2200a, 2200b are positioned at a first distance A1 relative to a reference point, and FIG. 22F illustrates the patient's upper and lower dental arches 2200a, 2200b after they have been moved away from the reference point by the purple movement such that the upper and lower dental arches 2200a, 2200b are positioned at a second distance A2 relative to the reference point.

The overall movement data can be obtained for one, some, or all of the patient's teeth. The overall movement data can comprise one or more translational displacements and/or one or more rotational displacements per tooth. For example, the overall movement data can comprise zero, one, two, or three translational displacements and zero, one, two, or three rotational displacements per tooth. Additionally or alternatively, the overall movement data can be obtained for each location at which the OTA data and/or the first FTA data was obtained.

To further illustrate the possible different component movements of the overall movement data, FIGS. 23A-25C schematically depict a patient's teeth in one of the patient's dental arches subject to a variety of arrangements and movements. FIGS. 23A and 23B, for example, depict movements 2308 of teeth in one of the patient's dental arches according to blue movements (e.g., individual tooth movements). As shown in FIG. 23A, moving the teeth in a dental arch relative to one another can comprise translating one or more of the teeth 2300 from the original arrangement 2304 (teeth 2300 depicted as white boxes with dashed edges) to the final arrangement 2306 (teeth 2300 depicted as shaded boxes with solid edges) according to movements 2308. In some embodiments, for example as shown in FIG. 23D, moving the teeth in a dental arch relative to one another can comprise rotating one or more of the teeth 2300 from the original arrangement 2304 to the final arrangement 2306 according to movements 2308. While translation and rotation are depicted in different schematics, it will be appreciated that the blue movements can have a translational and/or rotational component.

Figure 23C:
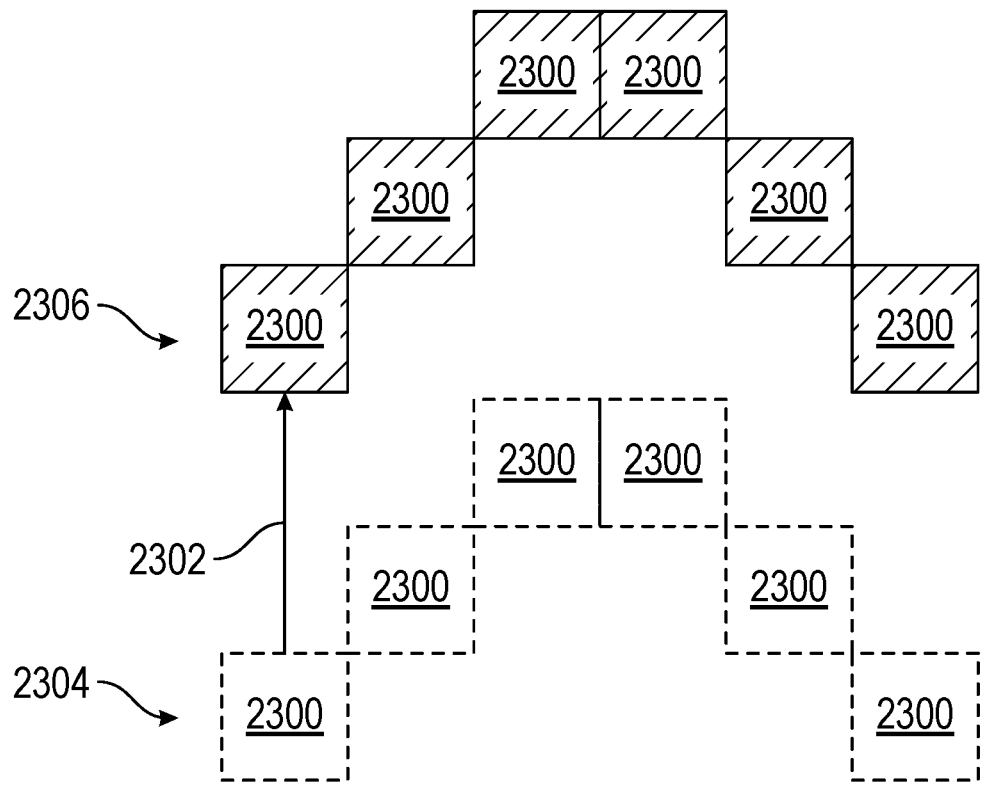
Figure 23D:
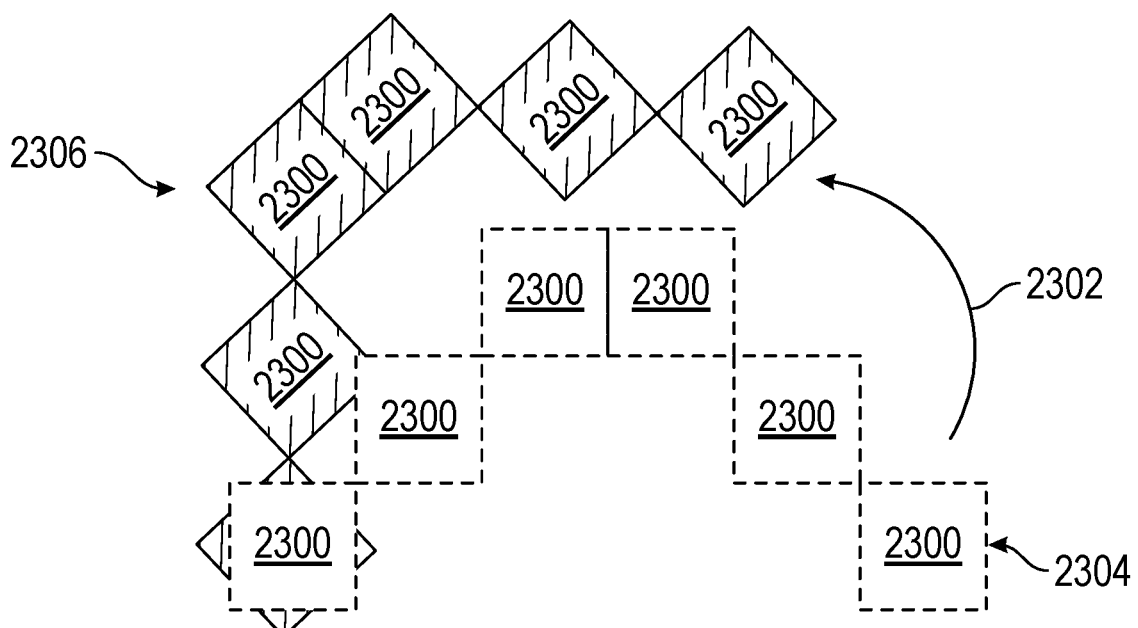

FIGS. 23C and 23D depict movement of all teeth 2300 in one of a patient's dental arches according to an orange movement. Moving a patient's teeth 2300 according to a common movement can comprise transforming each of the teeth 2300 in one of the patient's dental arches according to the same transformation. As shown in FIGS. 23C and 23D, moving all of the teeth in a dental arch from an original arrangement 2304 (teeth 2300 depicted as white boxes with dashed edges) to a final arrangement 2306 (teeth 2300 depicted as shaded boxes with solid edges) can comprise moving each of the teeth 2300 according to a translational movement 2302 (see FIG. 23C) and/or moving the teeth 2300 according to a rotational movement 2302 (see FIG. 23D). Such movements 2302 can comprise a transformation, which can be rigid and/or affine. While translation and rotation are depicted in different schematics, it will be appreciated that the orange movement can have a translational and/or rotational component.

Figure 24A:
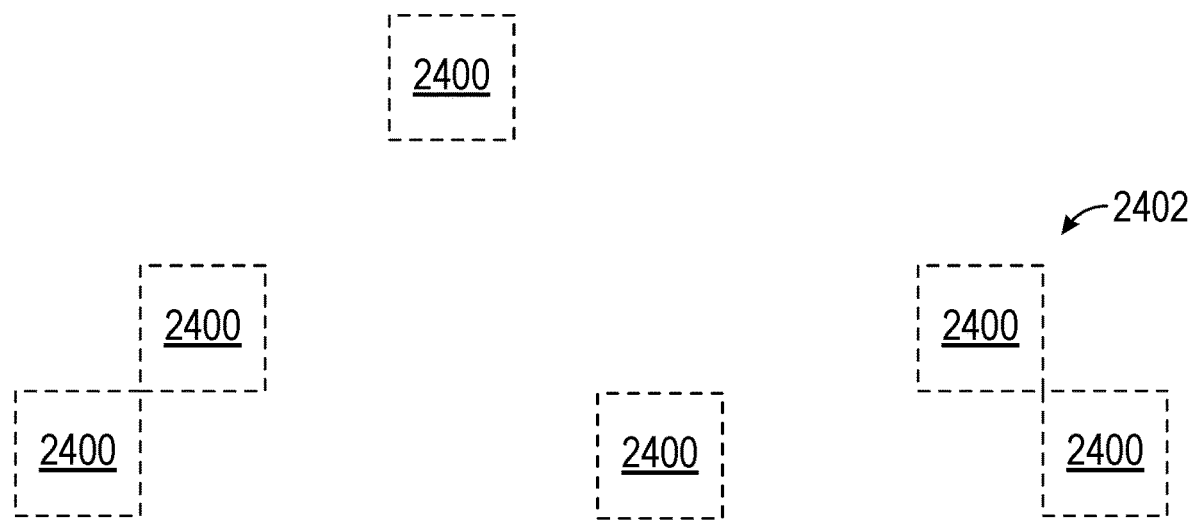
FIGS. 24A-24C are schematic diagrams of teeth of a patient in an original arrangement, an intermediate arrangement, and a final arrangement, respectively.
Figure 24B:
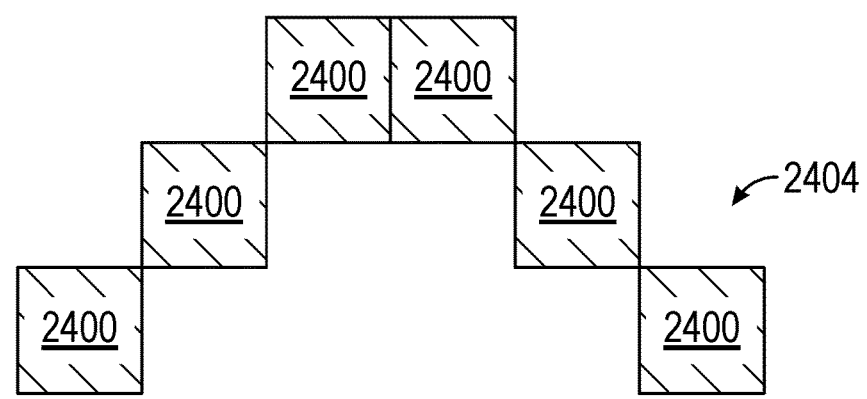
Figure 24C:
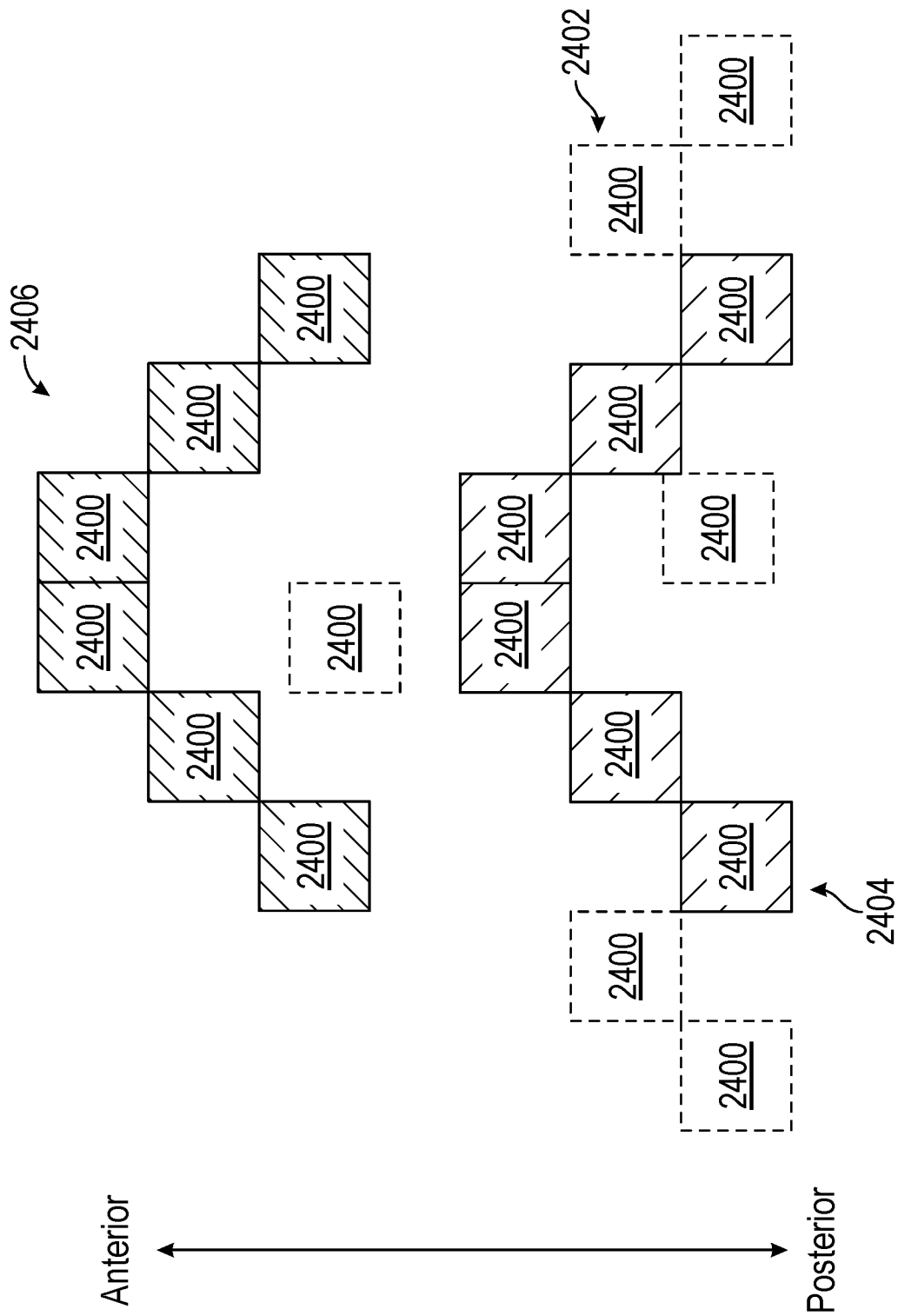

FIGS. 24A-24C schematically depict an example overall movement comprising a combination of blue and orange movements. FIG. 24A depicts a patient's teeth in an original arrangement 2402 in which each of the teeth 2400 is located at an original position. In some embodiments, the original positions of the teeth 2400 can correspond to positions of the patient's teeth 2400 prior to any orthodontic treatment, after previous orthodontic treatment but prior to additional orthodontic treatment, during orthodontic treatment, etc. In the original arrangement 2402, the teeth 2400 may be poorly aligned such that there is excessive spacing between the teeth 2400, crowding of the teeth 2400, excessive rotation of one or more of the teeth 2400, and/or other alignment issues.

In some cases, the alignment of the teeth 2400 can be improved by moving the teeth 2400 from their original positions to positions in which the teeth are better aligned (whether an ITA or an FTA) via a first orthodontic intervention. The first orthodontic intervention can be, for example, installation of any of the orthodontic appliances disclosed herein, such as orthodontic appliance 100. The first orthodontic intervention can move the teeth 2400 from their original positions to intermediate positions in an intermediate arrangement 2404 (as shown in FIG. 24B). The intermediate positions of the teeth 2400 can correspond to positions of the teeth 2400 after partial or complete orthodontic treatment. In some embodiments, the first movement comprises blue movements (e.g., movement of the teeth in one dental arch relative to one another). Movement of the teeth 2400 from the original arrangement 2402 to the intermediate arrangement 2404 can address one or more alignment issues within the dental arch. However, blue movement of the teeth 2400 from the original arrangement 2402 to the intermediate arrangement 2404 may not substantially modify a patient's occlusion (e.g., the relationship between the upper and lower dental arches).

To improve a patient's occlusion and move the patient's teeth into a final arrangement 2406 (if not already achieved by the blue movements), a second orthodontic intervention can be employed to achieve a second movement of the teeth. For example, in some embodiments, the second orthodontic intervention comprises an orthodontic elastic, a TAD, a platform, surgery, or other intervention configured to move all of the teeth in a patient's arch relative to all of the teeth in the patient's other arch. FIG. 24C shows the teeth 2400 in an original arrangement 2402, after a first movement in the intermediate arrangement 2404, and after a second movement in a final arrangement 2406. The second movement can be a common movement shared by all of the teeth that moves the teeth from the original arrangement 2402 and/or the intermediate arrangement 2404 into the final arrangement 2406. In the example shown in FIG. 24C, the second movement comprises an anterior shift of all of the teeth in the intermediate arrangement 2404 into the final arrangement 2406.

In some embodiments, the second orthodontic intervention can be the same type of intervention as the first orthodontic intervention. For example, the first and second orthodontic interventions can comprise installation of an orthodontic appliance of the present technology. Moreover, the second movement can be the same type of movement (e.g., individual tooth movement, common movement, etc.) as the first movement, or the second movement can be a different type of movement from the first movement.

Figure 25A:
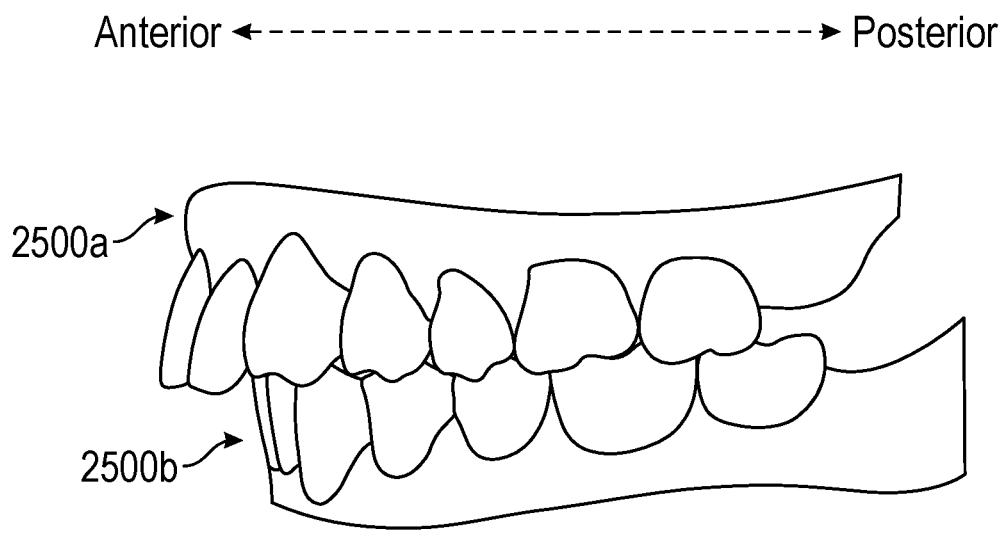
FIG. 25A depicts teeth of a patient who has a class II malocclusion.
Figure 25B:
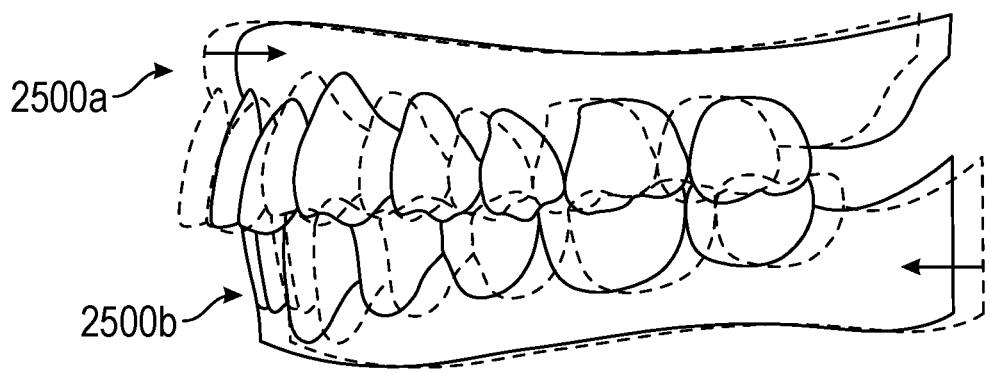
FIGS. 25B and 25C illustrate example movements of teeth of the patient of FIG. 25A in accordance with the present technology.
Figure 25C:
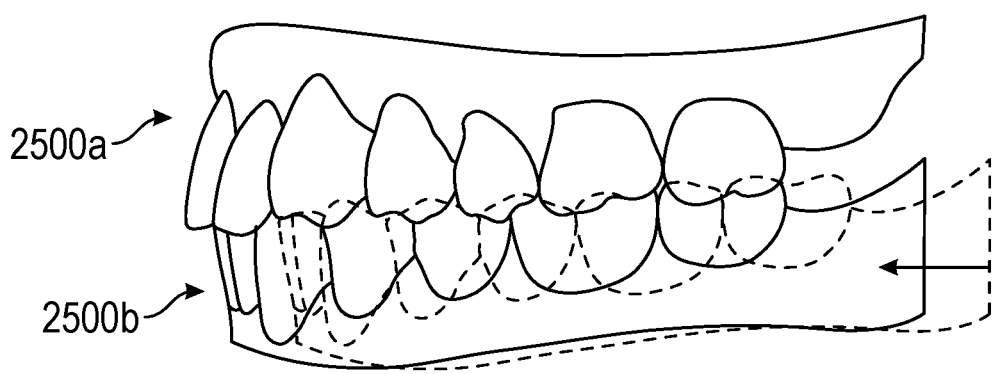

FIG. 25A illustrates teeth of a patient who has a class II malocclusion and FIGS. 25B and 25C illustrate two distinct approaches to improving the patient's occlusion in accordance with the present technology. In FIGS. 25B and 25C, the original positions of a patient's dental arches are depicted in a dashed line and the final positions of the arches are depicted in a solid line. As shown in FIG. 25A, an upper dental arch 2500a is positioned more anteriorly than the lower dental arch 2500b such that the patient has an overjet. During orthodontic treatment, the upper dental arch 2500a and/or the lower dental arch 2500b can be moved to improve the patient's occlusion. In the approach depicted in FIG. 25B, all of the teeth of the patient's upper arch 2500a are moved posteriorly according to the same transformation (e.g., via a common movement), and all of the teeth of the patient's lower arch 2500b are moved anteriorly according to the same movement (e.g., via a common movement). In these and other embodiments, the upper and lower arches 2500a, 2500b can be moved the same distance. In embodiments in which the upper and lower arches 2500a, 2500b are moved similar distances and toward one another, elastics can be used to accomplish the movements of the arches.

Additionally or alternatively, the upper and lower arches 2500a, 2500b could be moved by different distances. For example, the upper arch 2500a can be moved by a greater distance than the lower arch 2500b, or vice versa. FIG. 25C depicts a method of improving the patient's occlusion by moving all of the teeth of the patient's lower arch 2500b anteriorly (e.g., via a common movement) without moving the upper arch 2500a of the patient.

The movements of the upper and lower arches 2500a, 2500b relative to one another can be based, at least in part, on desired movements of the arches specified in the clinical instructions. For example, if the patient is older and their facial tissues are less elastic, it may be preferable to limit motion of the patient's upper arch 2500a to prevent or limit lip drooping as a result of loss of lip support that can occur with movement of the patient's upper arch 2500a. Movement of a patient's upper and lower arches 2500a, 2500b by different distances may not be achievable with an appliance and/or elastics, and may require TADs and/or surgery.

5. Determining Whether to Perform Arch Registration

In some cases it may be beneficial to identify, evaluate, and/or modify the planned common movements of all of the teeth in both of the patient's dental arches (e.g., the purple movements) to facilitate generation of an orthodontic treatment plan that is realistic, achievable, fast, and/or will lead to a more comfortable patient experience. Several aspects of the present technology comprise identifying the purple movements and evaluating whether the purple movements are feasible based on the available orthodontic interventions, as certain movements of both dental arches may only be achievable with certain orthodontic interventions. For example, moving both dental arches in the same direction or moving the dental arches apart from one another are generally not feasible with an appliance or elastics, and instead requires the use of TADs or surgical intervention. Identification of purple movements as part of the overall movement data can thus better inform the treatment plan. The present technology also comprises evaluating a position of the dental arches in the first FTA relative to the OTA to determine if an error has been made when creating the first FTA. As noted above, in some embodiments, a human operator can create the first FTA by manipulating the teeth from the OTA until the alignment of the teeth is improved. It is possible that one or more of the dental arches may be unintentionally shifted while generating the first FTA, which may change the facial structure of the patient, increase the treatment time, and/or be otherwise undesirable or unattainable. Thus, it can be advantageous to identify, evaluate, and/or modify the positions of the dental arches in the first FTA relative to the positions of the dental arches in the OTA.

If the final positions and/or the movements of the arches are unfeasible, excessive, or otherwise undesirable, the process 2000 can determine that an arch registration should be performed (process portion 2010). Performing the arch registration can include modifying the positions of the arches in the first FTA relative to the positions of the arches in the OTA. However, it is not always necessary to modify the positions of the arches in the first FTA. For example, if the positions of the arches in the first FTA are intentional and/or desirable, the positions of the arches in the first FTA should not be modified. In such cases, the process 2000 can include evaluating whether the purple movements of the arches from the OTA to the first FTA can be accomplished with the suggested, desired, available, or required interventions. If the movements are achievable, the process 2000 can determine that an arch registration does not need to be performed (process portion 2010). However, if the purple movements are not achievable with the orthodontic interventions that can be used during treatment, the process 2000 can provide such feedback to an operator and/or suitable software. The operator and/or software can determine if another orthodontic intervention can be used to accomplish the purple movements. If another orthodontic intervention cannot be used, the process 2000 can indicate that an arch registration should be performed to modify the positions of the arches and the purple movements. The decision regarding whether to perform an arch registration can be made automatically or manually.

In some embodiments it may be preferable to only move one of the patient's dental arches during the orthodontic treatment. For example, a patient's upper dental arch can remain in substantially the same position from OTA to FTA, while the patient's lower dental arch is moved anteriorly. Such relative movement (or lack thereof) of the arches may be desirable if the patient is older and their facial tissues are less elastic, for example. In such cases, moving the upper arch posteriorly to improve the patient's occlusion may result in undesirable loss of lip support and lip drooping. Thus, it may be advantageous to move only the bottom arch to improve the patient's occlusion. However, as previously noted, movement of only one dental arch, movement of both dental arches according to the same transformation, or movement of both dental arches in opposite directions may require specific orthodontic interventions.

6. Performing an Arch Registration

As previously noted, it may be beneficial to modify a position of one or more of the patient's dental arches after the first FTA data and/or the overall movement data have been obtained. For example, the dental arches may be unintentionally shifted during generation of the first FTA data, which may be undesirable. As another example, simultaneous intrusion of the patient's upper arch and extrusion of the patient's lower arch may be unfeasible with appliances alone and may require additional orthodontic interventions (e.g., TADs, surgery). Thus, if the arches were shifted unintentionally and there is no functional or aesthetic reason for shifting the arches in such a manner, it may be preferable to modify the first FTA data to eliminate and/or reduce such movement of the arches.

Figure 26:
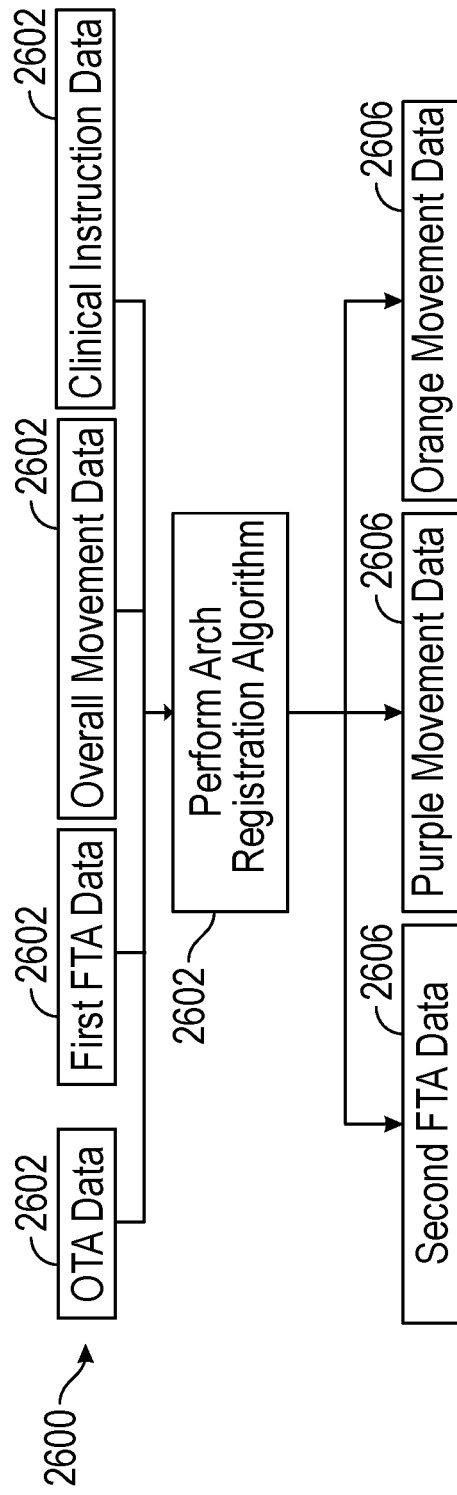
FIG. 26 is a flow diagram of an example process for performing an arch registration in accordance with the present technology.
Figure 27:
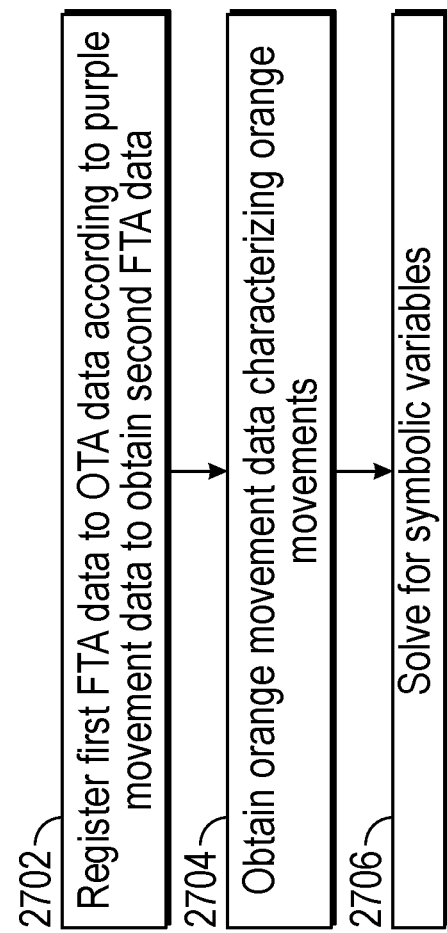
FIG. 27 is a flow diagram of an example process for performing an arch registration algorithm in accordance with the present technology.

FIG. 26 is a flow diagram of an example process 2600 for performing an arch registration, and FIG. 27 is an example process 2700 for performing an arch registration algorithm. However, before the extended discussion of the processes embodied by FIGS. 26 and 27, the schematic diagrams shown in FIGS. 28A-29C will be described. FIGS. 28A-29C are intended as visual aids to facilitate the discussion of processes 2600 and 2700. FIGS. 28A-29C show upper and lower dental arches (collectively "arches") in different arrangements to illustrate various stages of the processes 2800 and 2900. For ease of explanation, the movements of the arches depicted in FIGS. 28A-29C are limited to translational displacements, and only in one dimension (along an anterior-posterior direction). However, as discussed herein, processes 2800 and 2900 can be performed for arch movements involving displacements having one, two, or three translational components and/or one, two, or three rotational components. Although each of the arches is represented as a single box in FIGS. 28A-29C, the arches can comprise multiple teeth. Because FIGS. 28A-29C depict common movements in which of all of the teeth in both of the arches are moved (e.g., purple movements) and all of the teeth in one of the arches are moved (e.g., orange movements), the individual teeth of the arches are not depicted in FIGS. 28A-29C.

Turning now to FIG. 26, the process 2600 can comprise obtaining input data (process portion 2602), which can include OTA data, first FTA data, and/or overall movement data. Optionally, the input data can include clinical instructions, as described herein. As an example, FIGS. 28A-28C each show the upper and lower dental arches in original positions (schematically depicted as white boxes with dashed edges and labeled "OTA") characterized by the OTA data. FIGS. 28A-28C also each show the arches in preliminary final positions (schematically depicted as boxes with diagonal lines and dashed edges and labeled "FTA1") characterized by the first FTA data. FIG. 28A includes arrows depicting the movements of the arches characterized by the overall movement data (e.g., movements of the arches from their original positions to their preliminary final positions). In some embodiments, a movement of a dental arch can comprise an orange movement (e.g., a movement of all of the teeth in the dental arch according to the same transformation).

Referring to FIG. 27, the process 2700 of performing the arch registration algorithm can include registering (e.g., aligning) the first FTA data to the OTA data (process portion 2702). In some embodiments, for example as shown in FIG. 28B, registering the first FTA data to the OTA data can comprise obtaining second FTA data characterizing modified final positions of the arches (schematically depicted as boxes with diagonal lines and solid edges and labeled "FTA2"). The second FTA data can be obtained by modifying the first FTA data according to purple movement data characterizing a purple movement (depicted as arrows in FIG. 28B). As previously noted, a purple movement can comprise a common movement of all of the teeth in both of the arches. The purple movement can comprise a transformation that is applied to all of the teeth in both of the arches, and in some embodiments, the transformation is rigid. Reducing a distance between the final positions and the original positions of the arches can be beneficial for one or more reasons including, but not limited to, improving feasibility of the treatment, reducing treatment time, increasing patient comfort, reducing the number and invasiveness of additional orthodontic interventions, maintaining the patient's facial structure, etc.

As shown in FIG. 28A, a patient's occlusion (e.g., the positional relationship between the upper and lower arch) when the arches are at the preliminary final positions may be different than the patient's occlusion when the arches are at the original positions. If the second FTA data is obtained by rigidly transforming the first FTA data, there may be one or more residual distances (depicted as arrows in FIG. 28C) between the modified final positions and the original positions of the arches. Such residuals can correspond to orange movements of the dental arches (e.g., movements of all of the teeth in one of the patient's dental arches according to a common movement). Thus, the process 2700 can include obtaining orange movement data characterizing orange movements of the patient's dental arches (process portion 2704). The orange movements can be based on the overall movements and the purple movements. For example, the orange movement of each arch can be equal to the overall movement of the arch minus the purple movement of the arch.

In various embodiments, the purple movement data, the orange movement data, and/or the second FTA data may comprise symbolic data. For example, the orange movement data can be equivalent to the overall movement data minus the purple movement data and/or the second FTA data can be equivalent to the first FTA data minus the purple movement data. If the overall movement data is numeric but the purple movement data is symbolic, the orange movement data and the second FTA data will also be symbolic.

Thus, the process 2700 can include solving for the unknown symbolic variables (process portion 2706). To solve for the unknown symbolic variables, an analysis such as a regression analysis, a matrix decomposition analysis, or another suitable analysis can be performed. The analysis can be linear or nonlinear. For example, the matrix decomposition analysis can comprise a singular value decomposition, LU decomposition, rank factorization, Cholesky decomposition, QR decomposition, RRQR factorization, interpolative decomposition, eigen decomposition, Jordan decomposition, Schur decomposition, QZ decomposition, Takagi's factorization, scale-invariant decomposition, polar decomposition, Mostow's decomposition, Sinkhorn normal form, sectoral decomposition, Williamson's normal form, combinations thereof, or any other suitable matrix decomposition or factorization. The regression analysis can include an ordinary least squares regression, a nonlinear least squares regression, a weighted least squares regression, a robust regression, combinations thereof, or any other suitable regression method. Solving for the symbolic variables can include finding the numeric values of the symbolic variables that minimize the orange movements (e.g., the distances between the original and modified final positions of each arch). The numeric values for the symbolic variables can then be entered into the purple movement data, the orange movement data, and the second FTA data, which can be obtained as outputs of processes 2000 and 2600.

As previously noted, the process of registering the first FTA data to the OTA data to obtain the second FTA data can comprise determining the purple and/or orange movements that minimize the distances between the modified final positions of the arches and the original positions of the arches while maintaining a desired occlusion between the arches. The registration can be subject to one or more constraints and/or weightings that influence the manner in which the distances between the modified final and original positions of the arches are minimized, and thereby the modified final positions of the arches. The constraints and/or weightings can be based, at least in part, on the clinical instructions, biological factors (e.g., relative speeds of certain types of movements, age of the patient, etc.), and/or other relevant information. For example, as discussed with reference to FIGS. 25A-25C, in some cases it may be preferable to equally minimize movement of both arches, whereas in other cases it may be preferable to minimize movement of one arch.

FIGS. 28A-28C depict an example in which the magnitudes of the orange movements of the upper and lower arches are substantially equivalent, but the directions of the orange movements of the upper and lower arches are opposite. In this example, as the arches are moved from their original positions to their modified final positions according to the orange movements, the arches will move equal distances towards one another. Such movements of the arches can be accomplished with elastics, and so may be desirable for a patient who is not amenable to using TADs or receiving surgery.

However, as previously noted, in some cases it may be desirable to move the arches by different amounts. For example, in some cases it may be desirable to move only one of the patient's arches (see FIG. 25C). FIGS. 29A-29C depict an example of performing an arch registration such that the upper arch does not substantially move from its original position to its modified final position, while maintaining the occlusion characterized by the first FTA data. Such a registration could be performed, for example, when the clinical instructions indicate that the lower arch alone should be moved with TADs and/or surgery. Similar to FIGS. 28A-28C, FIGS. 29A-29C schematically depict a patient's dental arches in original positions, preliminary final positions, and modified final positions. As previously described, the purple movement (and thereby the orange movements and the second FTA data) can initially be symbolic. An analysis such as the analyses described above can be performed to determine the numerical values of the symbolic variables such that the orange movements are minimized. However, in the embodiment depicted in FIGS. 29A-29C, the upper arch can be weighted in the minimization analysis to a much greater extent than the lower arch. As a result, the analysis will obtain numerical values of the symbolic variables that reduce the magnitude of the orange movement of the upper arch to a greater extent than the magnitude of the orange movement of the lower arch. In some embodiments, the upper arch and lower arch can be weighted such that the analysis obtains an orange movement of the upper arch with a negligible magnitude (e.g., the modified final position of the upper arch is substantially equivalent to the original position). In such embodiments, a magnitude of the orange movement of the lower arch can correspond to a magnitude of the purple movement, which can correspond to a distance between the preliminary final position and the original position of the upper arch.

In the previously described embodiment, the arch registration algorithm for minimizing the movement of one arch can be substantially similar to the arch registration algorithm for minimizing the movements of both arches, except for the weighting of the arches in the minimization analysis. However, in some embodiments a different arch registration algorithm for minimizing the movement of one arch can be employed. Such algorithm can comprise determining a purple movement (depicted as arrows in FIG. 29B) having a magnitude substantially equivalent to a distance between the original position and the preliminary final position of the upper arch such that the modified final position of the upper arch is substantially equivalent to the original position of the upper arch. Accordingly, the residual distances (depicted as arrows in FIG. 29C) characterizing the orange movements of the arches can have different magnitudes. A magnitude of the orange movement of the upper arch can be negligible whereas a magnitude of the orange movement of the lower arch can be substantially equivalent to a magnitude of the purple movement.

7. Performing a Tooth Registration

Figure 30:
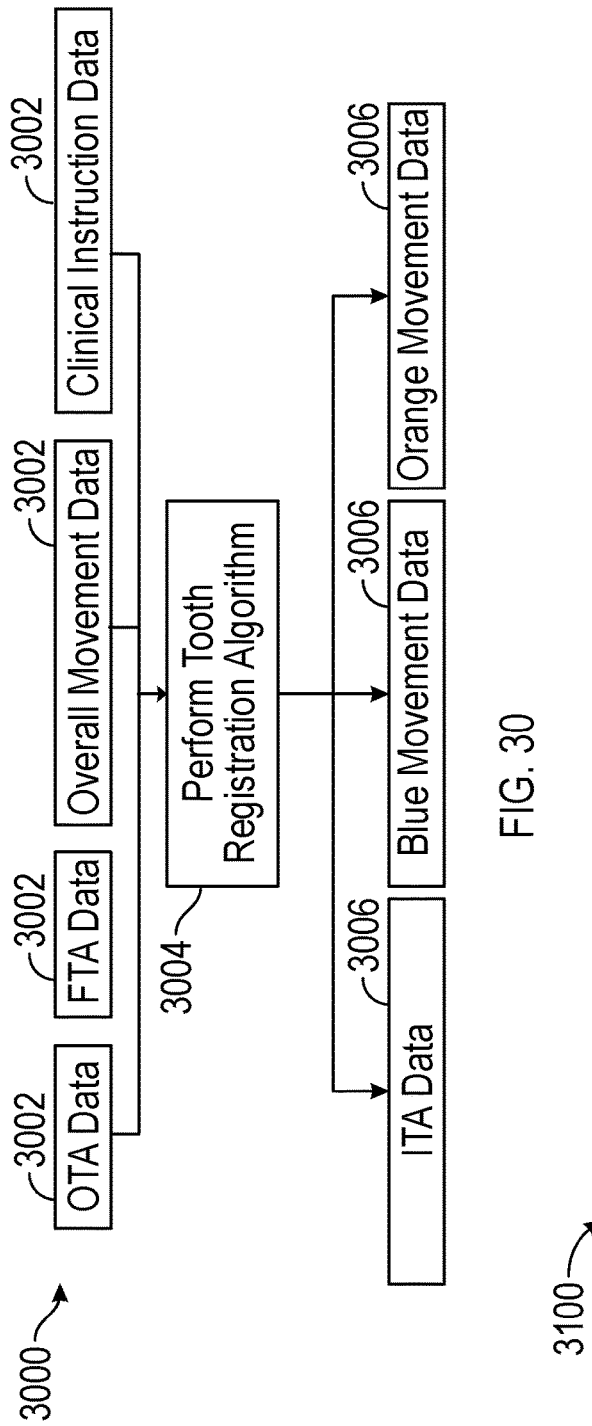
FIG. 30 is a flow diagram of an example process for performing a tooth registration in accordance with the present technology.
Figure 31:
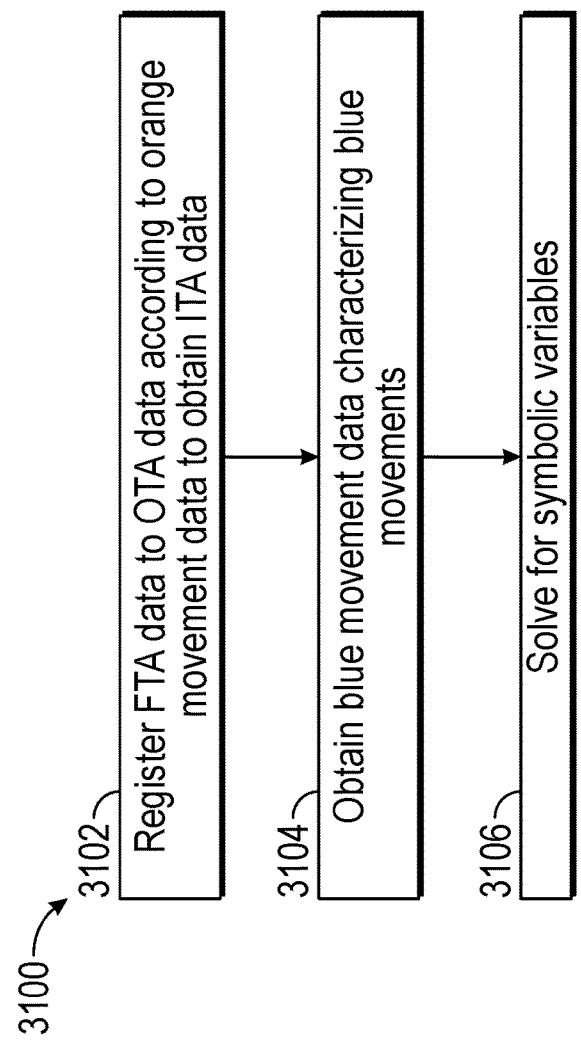
FIG. 31 is a flow diagram of an example process for performing a tooth registration algorithm in accordance with the present technology.

Referring back to FIG. 20, the process 2000 can include performing a tooth registration (process portion 2016). As shown in FIG. 20, the tooth registration can occur either directly after the process 2000 determines that an arch registration should not be performed or after the process 2000 performs an arch registration. A tooth registration can differ from an arch registration in that the tooth registration can be performed to obtain movements of the teeth in a single dental arch relative to one another (e.g., blue movement) and movements of all of the teeth in a single dental arch according to a common movement (e.g., orange movements). FIG. 30 is a flow diagram of an example process 3000 for performing a tooth registration and FIG. 31 is a flow diagram of an example process 3100 for performing a tooth registration algorithm. FIGS. 32A-32E are schematic diagrams provided as visual aids to facilitate the discussion of processes 3000 and 3100. In particular, FIGS. 32A-32E show first, second, third, and fourth teeth 3200a, 3200b, 3200c, and 3200d (collectively "teeth 3200") in different arrangements to illustrate various stages of the processes 3000 and 3100. For ease of explanation, the movements of the teeth 3200 depicted in FIGS. 32A-32E are limited to translational displacements, and only in two dimensions (x and y). However, as discussed herein, processes 3000 and 3100 can be performed for displacements having one, two, or three translational components and/or one, two, or three rotational components. Moreover, although four teeth 3200a-d are shown in FIGS. 32A-32E, one or both of the processes 3000 and 3100 can be performed for fewer than four teeth (e.g., one tooth, two teeth, three teeth) or more than four teeth (e.g., five teeth, six teeth, seven teeth, eight teeth, nine teeth, 14 teeth, 28 teeth, 32 teeth, etc.). In some embodiments, one or both of the processes 3000 and 3100 are performed for all of the teeth in one or both of the patient's jaws.

Figure 32A:
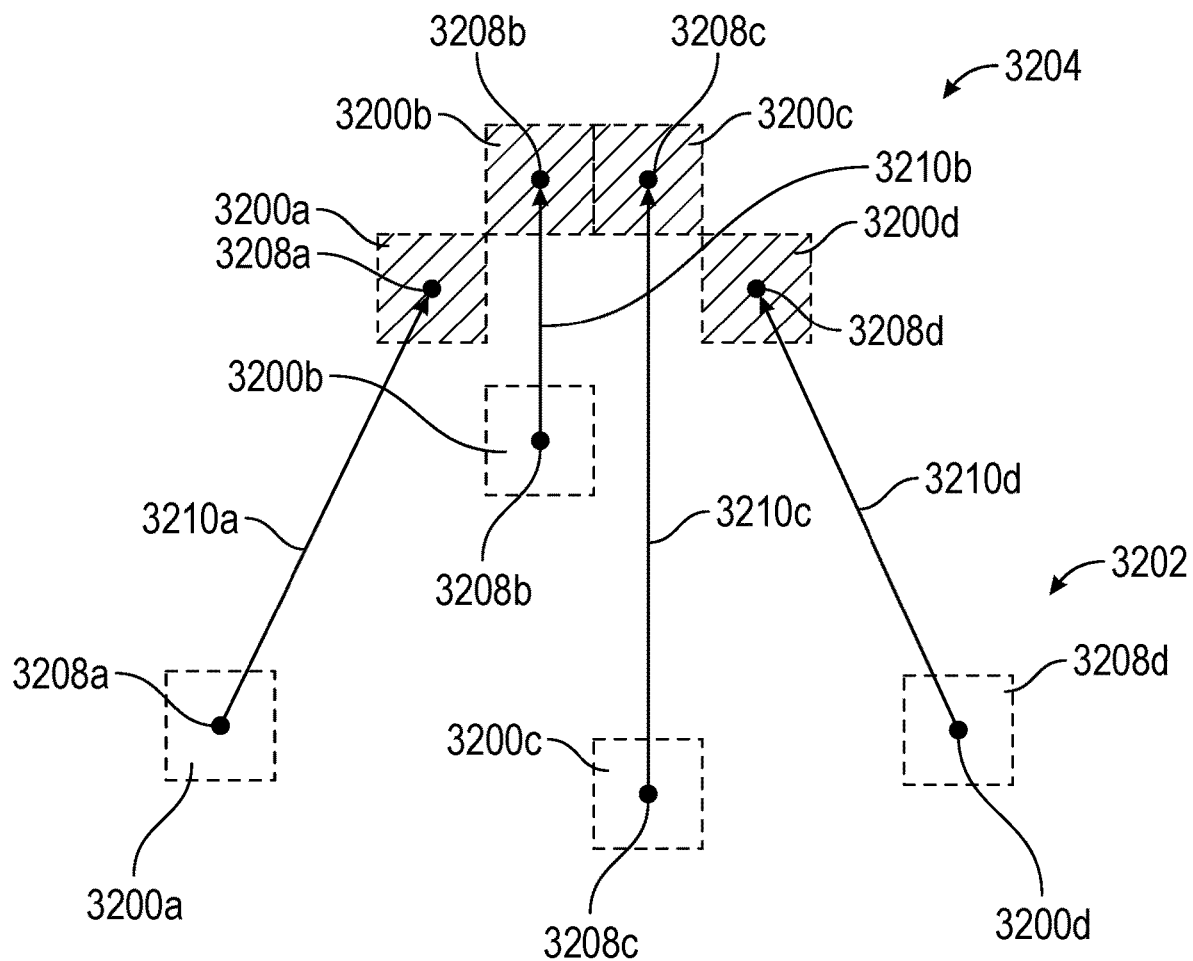
FIGS. 32A-32E schematically illustrate a two-dimensional example of performing a tooth registration in accordance with the present technology.

With reference to FIG. 30, the process 3000 includes obtaining input data 3002. The input data 3002 can include OTA data characterizing original positions of the teeth and either first FTA data if an arch registration has not been performed or second FTA data if an arch registration has been performed. The input data 3002 can also include movement data characterizing an overall movement of each tooth from its original position to its final position and/or clinical instructions. As an example, FIG. 32A shows first-fourth teeth 3200 in an original arrangement 3202 (schematically depicted as white boxes with dashed edges) and in a final arrangement 3204 (schematically depicted as boxes with diagonal lines and dashed edges), with arrows representing the overall movements 3210a-d of the teeth 3200 from the original arrangement 3202 to the final arrangement 3204. The overall movement data can comprise one or more displacements of each tooth defined from one or more locations on the teeth in the original arrangement to the corresponding locations on the teeth in the final arrangement. FIG. 32A, for example, shows the displacements 3210a-d defined from a single location 3208a-d on each of the first-fourth teeth 3200a-d in the original arrangement 3202 to the corresponding locations 3208a-d on the first-fourth teeth 3200a-d in the final arrangement 3204. In some embodiments a single location on each tooth can be used to define a movement of the tooth (as in FIGS. 32A-32E), and in some embodiments multiple locations on each tooth can be used to define the movement (see, for example, FIG. 21).

The process 3000 can continue with performing a tooth registration algorithm (process portion 3004) with the input data obtained at process portion 3102 to determine output data (process portion 3006). The output data can include, for example, orange movement data characterizing orange movements of the teeth in which all of the teeth in the dental arch (e.g., first-fourth teeth 3200a-d) are moved according to a common movement. As previously noted, the common movement can comprise a transformation that is applied to all of the teeth in the arch. Additionally or alternatively, the output data can include blue movement data characterizing blue movements of the teeth. As previously noted, a blue movement can comprise a movement of one of the teeth in the patient's dental arch relative to other teeth in the same dental arch. In some embodiments, the blue movement is unique and/or individual to the tooth to which it is applied. The output data can also comprise ITA data characterizing intermediate positions of the teeth in the dental arch after the teeth have been moved according to the blue movements. As discussed herein, such output data can be useful for selecting a particular orthodontic intervention to accomplish the movements, for determining one or more design features of an orthodontic appliance for use during the treatment, etc. As but one example, if the treatment plan includes orange movements, it may be advantageous to position hooks of a heat treatment fixture for setting a shape of an appliance at the intermediate positions (instead of the final positions), as the appliance might only accomplish the blue movements.

Figure 32B:
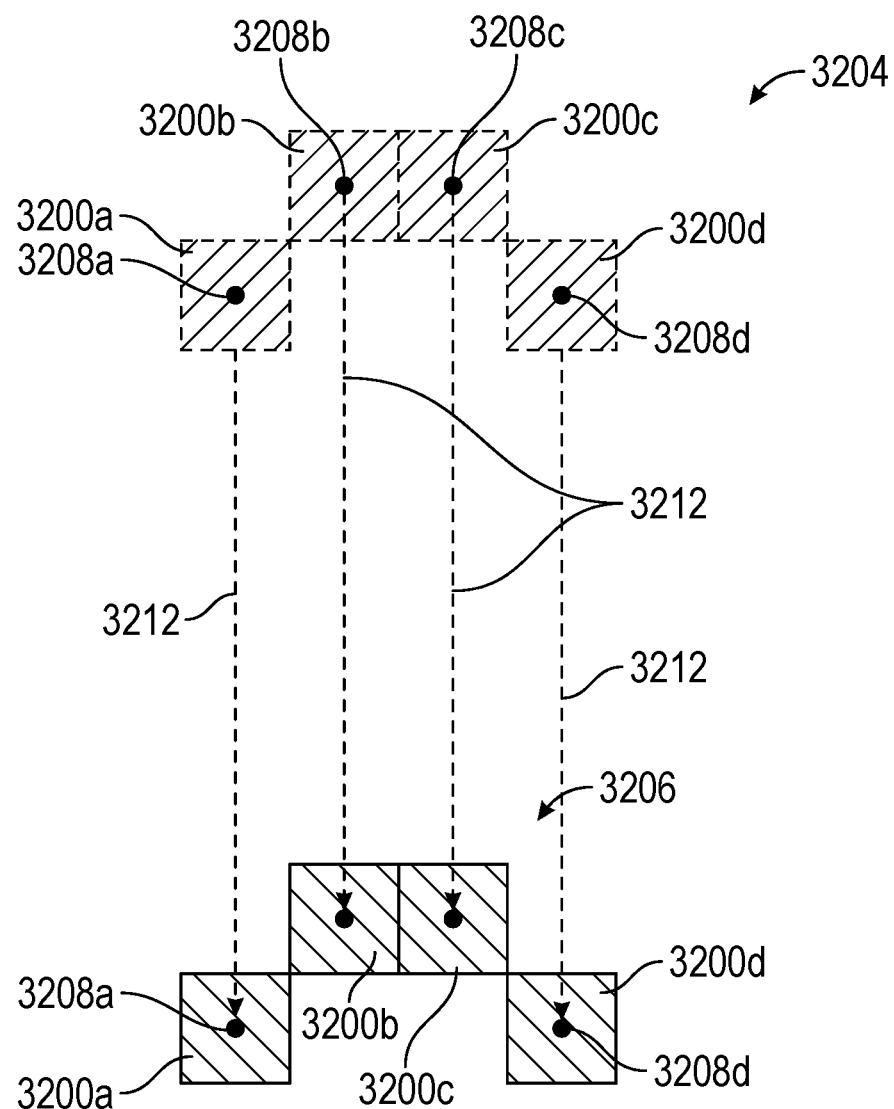
Figure 32C:
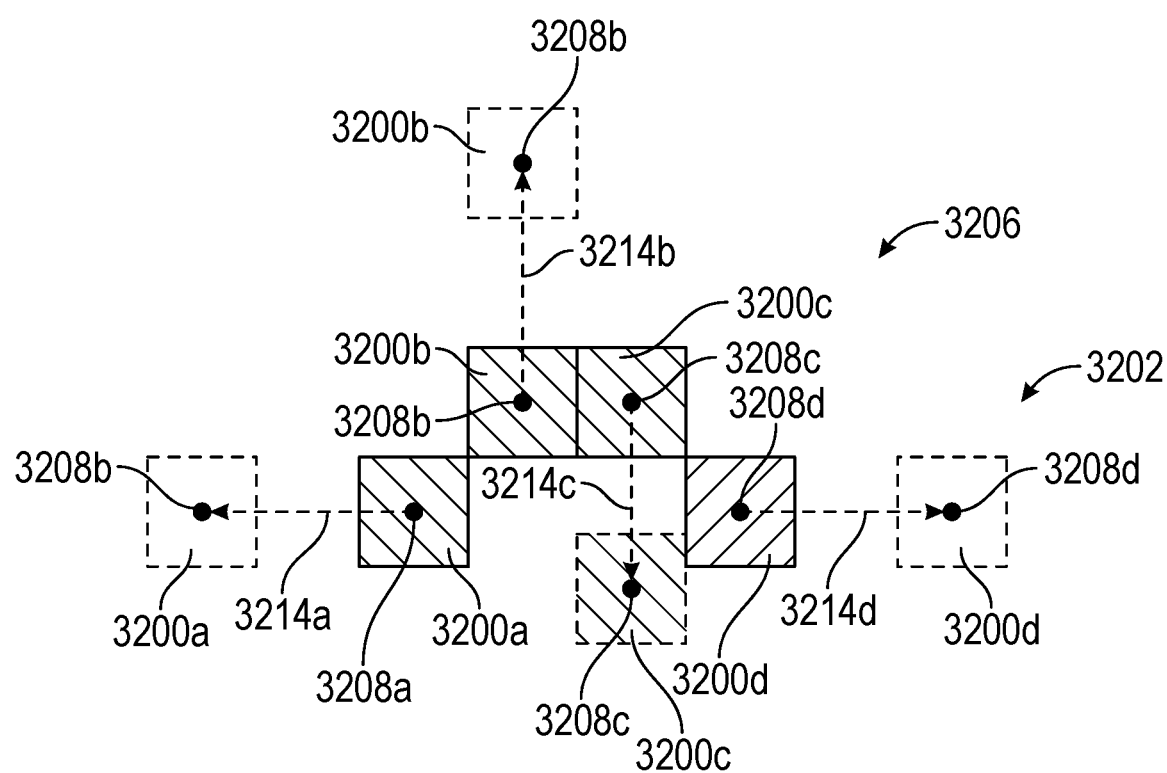
Figure 32D:
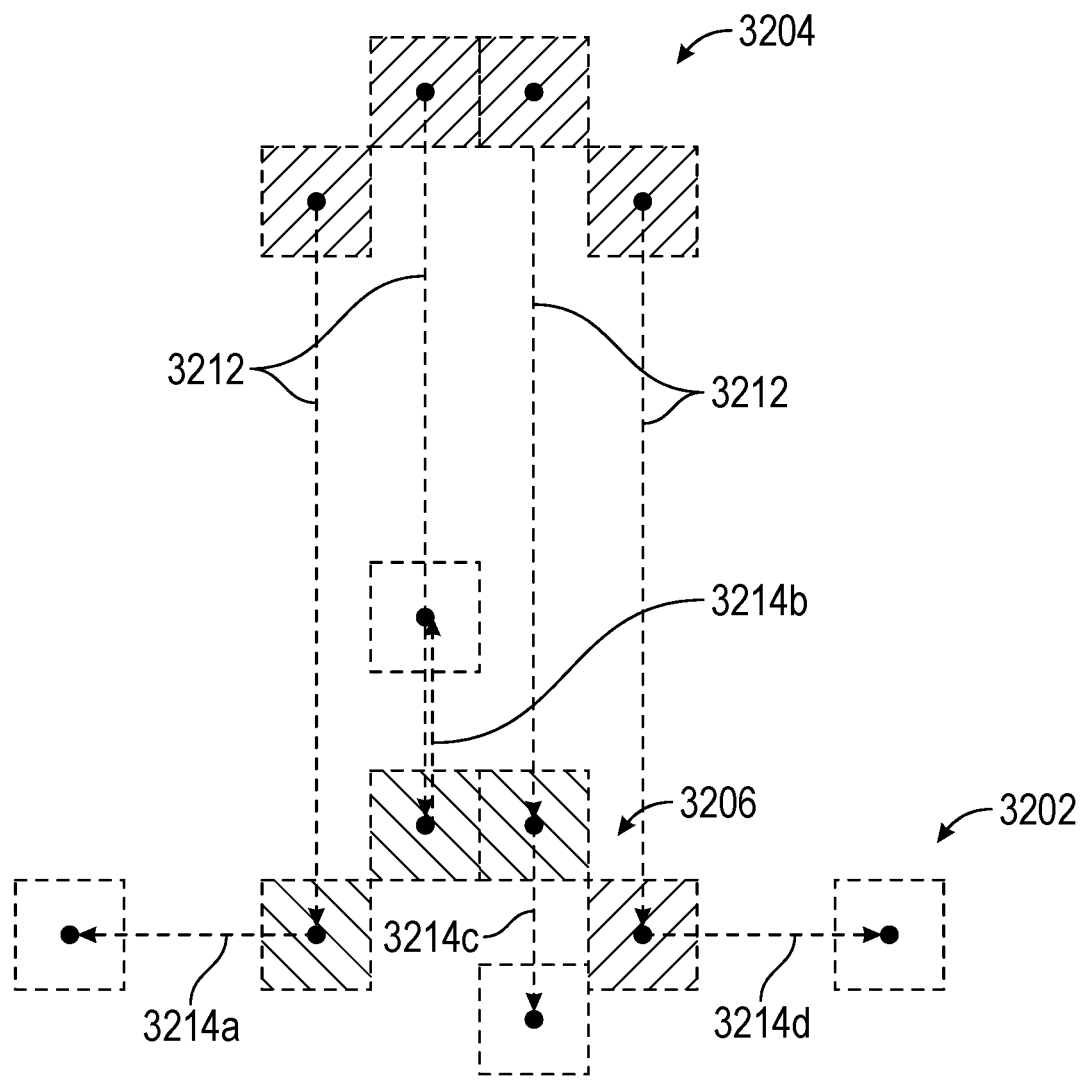

FIG. 31 is a flow diagram showing an example tooth registration algorithm 3104 configured to decompose input movements into sub-components, thereby identifying the contribution of different forces to the resulting overall movement. As depicted at process portion 3102, performing the decomposition algorithm can include registering the FTA data to the OTA data to obtain the ITA data. Registering the FTA data to the OTA data can comprise applying a transformation to the FTA data. The transformation 3212, for example, can be a rigid transformation. The transformation 3212 can be applied to a single location on each of the teeth or the transformation 3212 can be applied to multiple locations on each of the teeth. As an example, FIG. 32B shows first-fourth teeth 3200a-d in the final arrangement 3204 and an intermediate arrangement 3206 (schematically depicted as boxes with diagonal lines and solid edges). In FIG. 32B, the transformation 3212 has been applied to a single location 3208a-d on each of the teeth 3200a-d.

According to several aspects of the technology, the transformation 3212 substantially corresponds to an orange movement in which all of the teeth in one of the patient's dental arches are moved according to the same translations and rotations. In the example depicted in FIG. 32B, the first-fourth teeth 3200a-d in the final arrangement 3204 have been translated in the same direction and with the same magnitude with respect to the final arrangement 3204. In various embodiments, the rigid transformation 3212 may be a symbolic transformation. For example, in FIG. 32B the teeth 3200a-d may have been translated from the final arrangement 3204 to the intermediate arrangement 3206 in a single direction by a variable 'y' amount. As will be described in greater detail below, the algorithm can be configured to solve for the symbolic variables in the transformation 3212.

Performing the tooth registration algorithm can further include obtaining blue movement data (process portion 3104) characterizing blue movements of the teeth between the intermediate arrangement and the original arrangement. In some embodiments, obtaining the blue movement data can comprise minimizing the distances between a position of each tooth in the original arrangement 3202 and a position of the tooth in the intermediate arrangement 3206. In some embodiments, obtaining the blue movement data comprises determining the displacements 3214a-d between the selected locations 3208a-d of each of the teeth 3200a-d in the intermediate arrangement and the original arrangement. The displacements 3214a-d, which correspond to blue movements of the teeth, can also be considered residuals or errors between the intermediate positions of the teeth 3200a-d and the original positions of the teeth 3200a-d. The displacements 3214a-d can be found in terms of symbolic variables. For example, consider a scenario in which the first tooth 3200a has an original position of (x1,y1) at location 3208a and a final position of (x2,y2) at location 3208a in the second arrangement 3204. In process portion 3102, a first tooth 3200a can undergo a rigid transformation 3212 such that the first tooth 3200a is translated by −y amount along a first dimension. In such a scenario, the first tooth 3200a has an intermediate position of (x2,(y2−y)). In such embodiments, the variable 'y' is symbolic, and the values 'x2' and 'y2' are known, numerical values that were obtained when obtaining the FTA data characterizing the final position of the first tooth 3200a (e.g., by moving the tooth from its original position according to clinical instructions). In some embodiments, 'x2' and 'y2' can be determined by transforming the teeth from the original arrangement to the final arrangement according to a known transformation.

To solve for the unknown symbolic variables (e.g., at process portion 3106), an analysis such as a regression analysis, a matrix decomposition analysis, or another suitable analysis can be performed. The analysis can be linear or nonlinear. For example, the matrix decomposition analysis can comprise a singular value decomposition, LU decomposition, rank factorization, Cholesky decomposition, QR decomposition, RRQR factorization, interpolative decomposition, eigen decomposition, Jordan decomposition, Schur decomposition, QZ decomposition, Takagi's factorization, scale-invariant decomposition, polar decomposition, Mostow's decomposition, Sinkhorn normal form, sectoral decomposition, Williamson's normal form, combinations thereof, or any other suitable matrix decomposition or factorization. The regression analysis can include an ordinary least squares regression, a nonlinear least squares regression, a weighted least squares regression, a robust regression, combinations thereof, or any other suitable regression method. As previously noted, the algorithm can include solving for the symbolic variables that minimize the distances (e.g., errors) between the teeth in the original and intermediate arrangements 3202, 3206. In some embodiments, the distances between the teeth can be minimized equally. In some embodiments, and as discussed herein, minimizing the distances between the teeth may be subject to one or more constraints and/or be weighted such that the distances between the teeth are not minimized equally.

Figure 32E:
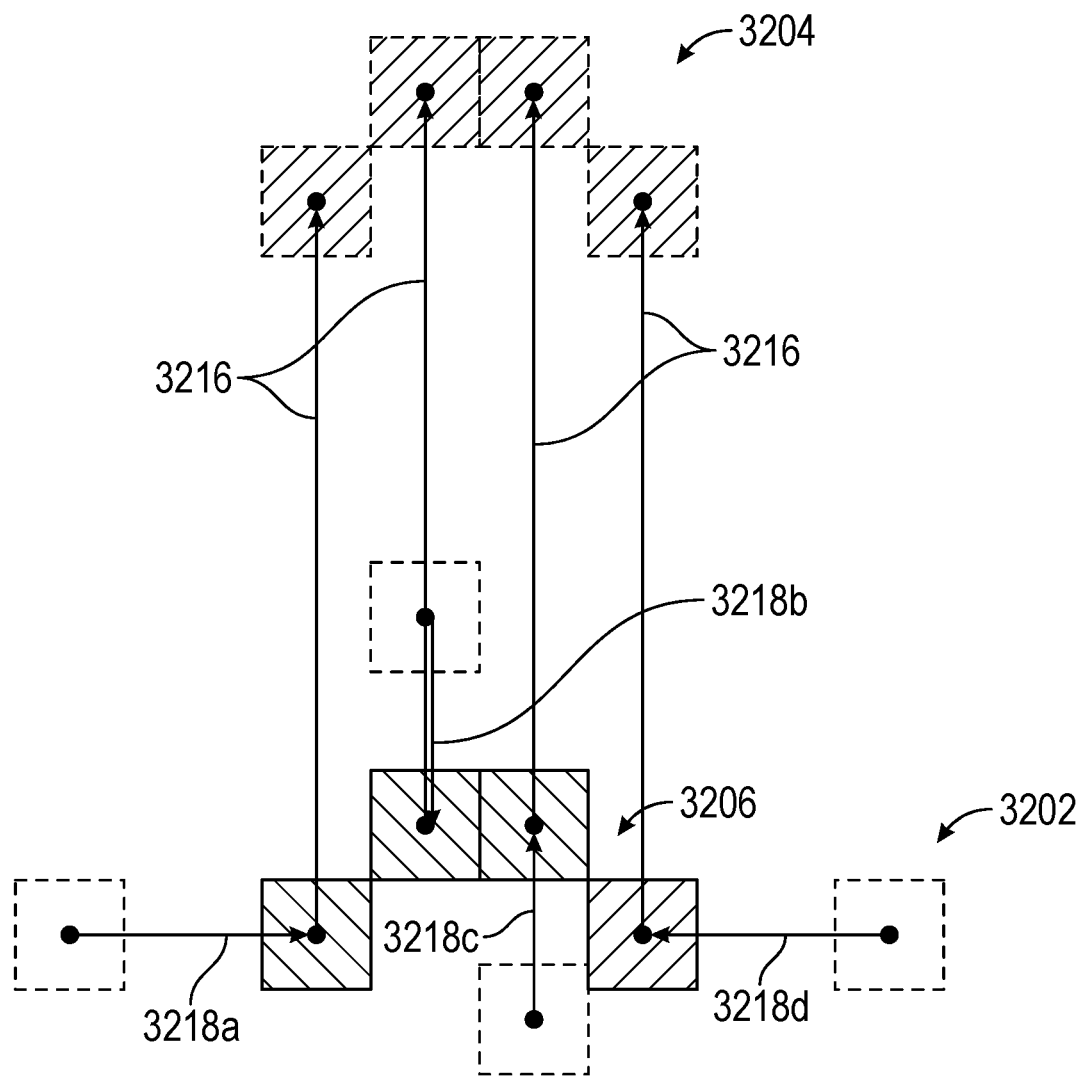

In some embodiments, an analysis including the method of least squares or a similar method can be conducted in which the displacements 3214a-d are squared and summed. The symbolic function can be minimized (e.g., by setting a derivative of the function equal to zero), and the symbolic variables solved for. The numeric values for the symbolic variables can then be entered into ITA data to solve for numeric values of the intermediate positions. Additionally or alternatively, the numeric values for the symbolic variables can be plugged into the orange movement data and/or blue movement data to solve for the orange and/or blue movements. In some embodiments, the transformation 3212 corresponds to orange movements of the teeth 3200a-d and/or the displacements 3214a-d correspond to blue movements of the teeth 3200a-d. The orange movements can have the same magnitude as transformation 3212 and/or the blue movements 3218a-d can have the same magnitude as the displacements 3214a-d. In some embodiments, for example as shown in FIG. 32E, the orange movements have an opposite direction as transformation 3212 and/or the blue movements have opposite directions as the corresponding displacements 3214a-d.

When computing the displacement between an intermediate position and an original position of a tooth, one or more locations on the tooth may be selected for evaluation. Use of fewer locations is associated with a lower computational cost; however, using fewer locations may also compromise fidelity of the algorithm. For example, consider a tooth that is to undergo rotation but no translation. Based, on the original position and the prescribed final position of the tooth, the movement data may indicate that the tooth should be rotated 90 degrees from the original position to the final position. If the tooth is only rotated 50 degrees via the orange movements, the algorithm should compute a non-zero angular displacement between the intermediate position of the tooth and the original position of the tooth. However, if the location that is evaluated is positioned at the center of rotation of the tooth (see FIGS. 32A-32E), the algorithm will compute an angular displacement of zero between the intermediate and original positions. Accordingly, it may be advantageous to evaluate the displacements between multiple locations on each tooth.

In its simplest form, a least squares analysis solves for the symbolic variables associated with the movements of the tooth by reducing the displacements between the original positions and the intermediate positions for each tooth by an even amount, thereby simulating the teeth moving at the same rate. However, as noted above with respect to the arch registration, it may be advantageous to reduce the displacements by an uneven amount. Orthodontic tooth movement is a complex biological process, and certain teeth move at a slower rate than others. Moreover, certain types of tooth movements occur at a slower rate than others. To improve fidelity of the algorithm, weighting can be applied to displacements corresponding to specific teeth and/or specific locations on the teeth to simulate various rates and extents of movement more accurately. A larger weight can be assigned to teeth and/or locations that move more slowly and/or are harder to move in reality. For example, bone formation occurs at a faster rate than bone resorption. Thus, locations on a tooth that are on a compression side of the tooth (i.e., the side at which bone resorption is occurring) can be assigned a larger weight than locations on a tension side of the tooth (i.e., the side at which bone formation is occurring). In some embodiments, certain teeth are weighted more heavily in the analysis by evaluating more points on the teeth. For example, the number of points evaluated for each tooth can be proportional to the surface area of a root of the tooth to simulate the slower movement of a tooth with a larger root (and vice versa) more accurately.

B. Obtaining an Orthodontic Treatment Plan

Referring back to FIG. 19, the orthodontic treatment process 1900 can include obtaining an orthodontic treatment plan (process portion 1904). As previously noted, orthodontic treatment can involve moving a patient's teeth according to specific movements such that the teeth are moved to desired, final locations. The orthodontic treatment can include one or more specific types of movements, such as a movement of all of the teeth in one of the patient's dental arches according to the same transformation, a movement of one of the teeth in one of the patient's dental arches, and/or others. Moreover, different types of tooth movements can be accomplished by different types of orthodontic interventions. For example, a movement of all of the teeth in one of the patient's dental arches can be accomplished by surgery, growth of the patient, TADs, elastics, platforms, etc., whereas a movement of only some of the patient's teeth in one of the patient's dental arches can be accomplished by an appliance such as the appliances disclosed herein. Thus in various embodiments, an orthodontic treatment plan can include one or more suggested orthodontic interventions to accomplish one or more types of tooth movements.

In some embodiments, the orthodontic treatment plan can include one or more suggested parameters of the orthodontic interventions. For example, as detailed below, the orthodontic treatment plan can include a design of an orthodontic appliance, which may include a stiffness of one or more portions of the appliance, a preset shape of one or more portions of the appliance, and/or others. In some embodiments, the orthodontic treatment plan can suggest an attachment location for an elastic, a location of a TAD in the patient's jaw, a type of surgery, etc.

In some embodiments, the orthodontic treatment plan includes suggestions with regards to coordination of the component movement(s) and/or the orthodontic intervention(s). For example, the orthodontic treatment plan can indicate that a patient's teeth should be moved sequentially from a first arrangement (e.g., the first arrangement 502) to a second arrangement (e.g., the second arrangement 504) to a third arrangement (e.g., the third arrangement 506) or from the first arrangement to the third arrangement to the second arrangement. In various embodiments, an orthodontic treatment plan can indicate that the teeth should be moved from the first arrangement to the second and third arrangements at least partially simultaneously. Still, in some embodiments an orthodontic treatment plan can be silent as to a suggested order of the component movements.

In some embodiments, obtaining the treatment plan can comprise modifying the treatment approach (e.g., by separating the movements into multiple stages, by modifying the selection of orthodontic intervention to accomplish the movements, etc.). For example, if the movements include simultaneously extruding a patient's lower dental arch and intruding the upper arch, TADs may be required to accomplish the movements. Accordingly, the method may include modifying the suggested orthodontic intervention to include TADs. As previously described, the process can repeat until an acceptable and/or preferred treatment plan is obtained.

1. Obtaining a Design of an Orthodontic Intervention

In some embodiments, an orthodontic treatment plan can include data characterizing a design of an orthodontic intervention. For example, the treatment plan can include data characterizing an appliance (e.g., a shape or a material property of an appliance, a digital model of an appliance, etc.). A 3D configuration of an appliance disclosed herein can be based, at least in part, on a shape of a fixture to which the appliance is conformed during manufacturing of the appliance. Thus, in some embodiments a treatment plan includes a design of a heat treatment fixture or other auxiliary device used to manufacture an appliance or other intervention.

In various embodiments, an orthodontic treatment can involve moving a patient's teeth according to multiple types of movements (e.g., blue movements, orange movements, purple movements, etc.). In some embodiments, each type of movement can be accomplished by one orthodontic intervention. For example, appliances of the present technology may be configured to move teeth in one of a patient's dental arches relative to other teeth in the same dental arch (e.g., according to blue movements), but are not configured to accomplish common movements of all of the patient's teeth in one or both arches (e.g., orange movements to be accomplished by elastics, purple movements to be accomplished by surgery, etc.). In these and other embodiments, it may be advantageous to locate the attachment portions of the appliance at positions substantially corresponding to positions of the teeth after they have been moved from their original positions according to the blue movements (e.g., at intermediate positions rather than final positions). Positioning the attachment portions at intermediate positions (e.g., at positions after the teeth have been moved from OTA according to blue movements) instead of final positions can prevent or limit impingement of the patient's gingiva by the appliance when the appliance is installed. In some embodiments, the positions of the attachment portions can be based, at least in part, on the blue movements of the teeth, the orange movements of the teeth, and/or the purple movements of the teeth. For example, if an orthodontic treatment plan includes moving each of a patient's dental arches with an appliance secured to one or more TADs in each of the patient's jaws, the appliance can be configured to accomplish blue movements, orange movements, and/or purple movements. Accordingly, the positions of the securing portions can be based on the desired positions of the teeth after some or all of the blue, orange, and/or purple movements have been accomplished.

Appliances of the present technology can be configured to impart forces on a patient's teeth to move the teeth from original positions to desired, final positions. In some embodiments, an appliance is configured to apply a specific force to one or more teeth based on a 3D configuration of the appliance. For example, an appliance can have attachment portions located at positions based on desired positions of the patient's teeth. The 3D configuration can be formed by manipulating the appliance from a planar configuration into the 3D configuration (e.g., by securing the appliance to a fixture) and setting a shape of the appliance (e.g., via heat treatment, cold working, plastic deformation, etc.). When the appliance is in the 3D configuration, an attachment portion of the appliance is located at an intended position with respect to other attachment portions of the appliance and/or an anchor of the appliance. The intended position of the attachment portion can correspond to or be derived from a desired position of the tooth to which the attachment portion is configured to be secured. In operation, the appliance can move the tooth toward its desired position by moving the attachment portion toward its intended position.

Accurately locating attachment portions of an appliance at their intended positions while forming a 3D configuration of the appliance is essential to the efficacy of moving a patient's teeth to their desired, final positions. If an attachment portion is located at an incorrect position when the appliance is in the 3D configuration, the tooth may not reach its desired position when the attachment portion returns to its pre-set position. Such errors in locating the attachment portions in their intended positions can result in a need for additional appliances to complete the treatment, increased cost and time of treatment, and/or patient dissatisfaction with the treatment.

Errors in forming the 3D configuration of the appliance can occur while manipulating the appliance from the planar configuration into the 3D configuration, including while securing the appliance to the fixture and/or setting a shape of the appliance. For example, when securing the appliance to the fixture, the attachment portion can be secured at a position deviating from the intended position if there is excessive play between the attachment portion and a securing portion of the fixture configured to retain the attachment portion. In some cases, a securing portion of a fixture must be designed to accommodate attachment portions of a range of sizes due to manufacturing tolerances and errors, which can result in play between certain attachment portions and the securing portion.

Various embodiments of the present technology comprise methods of manufacturing an orthodontic appliance with high accuracy and precision. In some embodiments, the present technology comprises a fixture configured to releasably retain the appliance in the 3D configuration such that attachment portions of the appliance are located in intended positions corresponding to or derived from desired positions of the teeth to be treated. The fixture can comprise a body portion and one or more securing portions. In some embodiments, each of the securing portions is configured to retain a corresponding attachment portion of the appliance at an intended position.

Figure 33A:
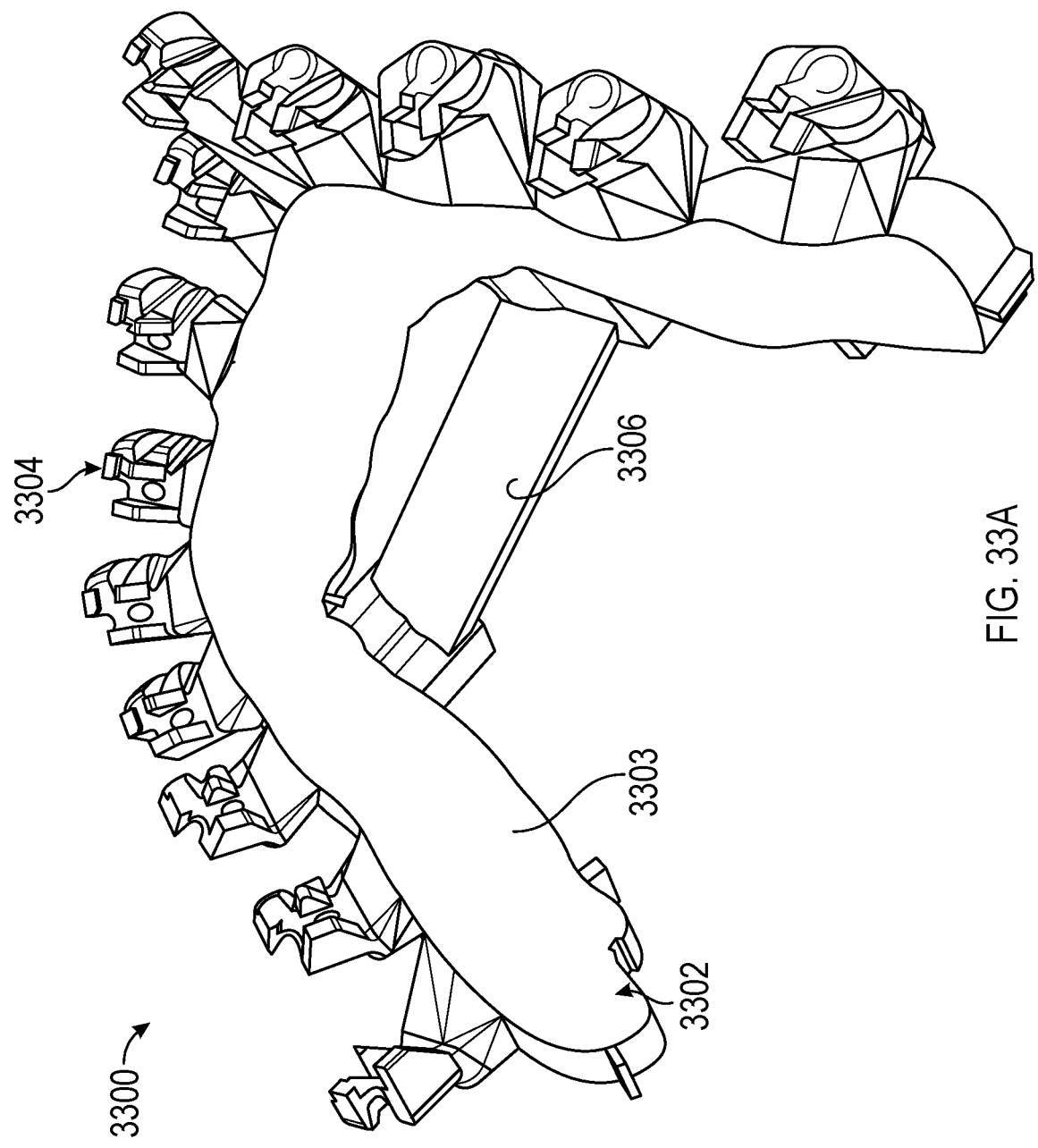
FIG. 33A is a perspective view of a heat treatment fixture in accordance with the present technology.

FIG. 33A depicts a fixture 3300 configured in accordance with several embodiments of the present technology. The fixture 3300 can be similar to fixture 1700, except as described below. The fixture 3300 can comprise a body portion 3302 and one or more securing portions 3304 carried by the body portion 3302. The body portion 3302 and the securing portions 3304 can be monolithic or the securing portions 3304 can be separate pieces that are coupled to the body portion 3302. In some embodiments, the fixture 3300 includes one or more structural components that generally do not directly engage the appliance and rather stabilize the body portion and/or securing portions. The fixture in FIG. 33A, for example, includes a stabilizer 3306 that extends between opposite sides of the body portion 3302.

The fixture 3300 is configured to be releasably secured to an appliance and retain the appliance in a desired 3D configuration. In some embodiments, the appliance is releasably secured to the fixture 3300 such that an anchor of the appliance substantially conforms to the body portion 3302 of the fixture 3300. Additionally or alternatively, attachment portions of the appliance may be releasably secured to the securing portions 3304 of the fixture 3300.

As shown in FIG. 33A, the body portion 3302 of the fixture 3300 can have a first surface 3303 at a lingual side of the fixture 3300 and a second surface (not visible) at the buccal side of the fixture 3300 and opposite the first surface 3303 along a thickness of the body portion 3302. The first surface 3303 and/or the second surface can have a shape substantially corresponding to a shape of the patient's gingiva in the OTA, the FTA, and/or one or more ITAs. In some embodiments, the body portion 3302 can be a modified version of the gingiva portion of the OTA digital model, the FTA digital model, and/or another suitable digital model. For example, the body portion 3302 can be enlarged or thickened with respect to the gingiva portion of the OTA digital model and/or the FTA digital model to prevent or limit impingement of the patient's gingiva by the appliance once installed. In some embodiments, the appliance is releasably secured to the fixture 3300 such that one or more portions (e.g., an anchor, an arm, etc.) of the appliance substantially conform to the first surface 3303.

The securing portions 3304 of the fixture 3300 can be configured to releasably secure the appliance to the fixture 3300 such that the appliance is manipulated into the desired 3D configuration. For example, each of the securing portions 3304 can be configured to releasably retain an attachment portion of the appliance at an intended position with respect to the anchor, other attachment portions, etc. Accordingly, the appliance can be shape set (e.g., heat treated, etc.) while secured to the fixture 3300 such that the attachment portion remains located at the intended position once the appliance is removed from the fixture 3300. The intended position at which the securing portion 3304 is configured to retain the attachment portion can substantially correspond to and/or be derived from a desired position of the tooth to be treated. In operation, the arm can move the attachment portion to the intended position, thereby moving the tooth to the desired position via the attachment portion.

Figure 33D:
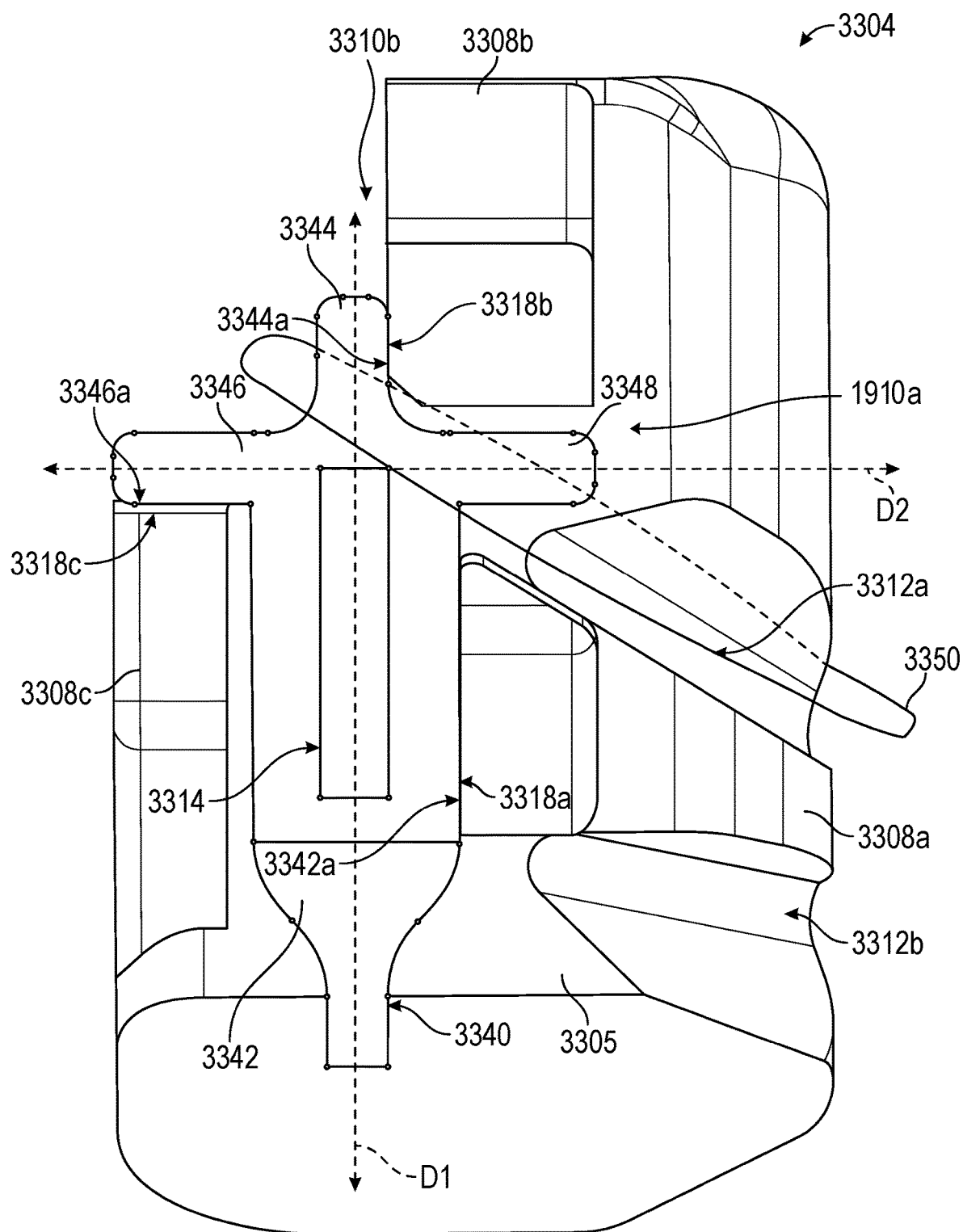
FIG. 33D depicts an attachment portion of an orthodontic appliance secured to the securing portion of the heat treatment fixture shown in FIGS. 33A-33C in accordance with the present technology.

FIGS. 33B and 33C are front and side views, respectively, of one of the securing portions 3304 shown isolated from the fixture 3300. FIG. 33D is a front view of the securing portion 3304 shown in FIGS. 33A-33C releasably secured to an attachment portion 3340 of an appliance. As shown in FIGS. 33B and 33C, the securing portion 3304 can comprise a surface 3305 configured to be positioned adjacent to and/or in contact with an attachment portion 3340. The securing portion 3304 can include one or more protrusions 3308 configured to locate the attachment portion 3340 of the appliance at the intended position. For example, the securing portion 3304 depicted in FIGS. 33A-33D includes a first protrusion 3308*a*, a second protrusion 3308*b*, and a third protrusion 3308*c* (collectively referred to as "protrusions 3308") extending away from the surface 3305. The protrusions 3308 define channels therebetween that receive the attachment portion 3340. The channels can comprise a first channel 3310*a* and a second channel 3310*b* (referred to collectively as "channels 3310"). The securing portion 3304 can further include first and second grooves 3312*a* and 3312*b* (referred to collectively as "grooves 3312") configured to receive a fastener at least partially therein. As shown in FIG. 33D, the attachment portion 3340 can be positioned against the surface 3305 between the protrusions 3308.

Although the channels 3310 in FIGS. 33A-33D are defined by protrusions 3308 extending away from the surface 3305, in some embodiments the securing portion 3304 includes channels 3310 formed by recesses in the surface 3305. The channels 3310 would thus extend into the thickness of the securing portion 3304. In these and other embodiments, the securing portion 3304 may not include protrusions 3308 or channels 3310. Instead, the securing portion 3304 can comprise printed markings, for example, on the securing portion 3304 that are configured to indicate the intended position of the attachment portion 3340.

As described in greater detail below, the securing portion 3304 can include one or more recesses 3312 and/or openings 3314 configured to receive ligature wire or another fastener at least partially therein. In various embodiments, the securing portion 3304 comprises one or more structural components (see structural component 3316 in FIG. 33C) configured to increase rigidity of the securing portion 3304.

According to some embodiments, for example as shown in FIG. 33D, the attachment portion 3340 can be positioned in, at, or adjacent to the securing portion 3304 such that the attachment portion 3340 is located at its intended position. In some embodiments, the attachment portion 3340 is positioned substantially parallel with and/or in contact with the surface 3305 of the securing portion 3304. In some embodiments, the securing portion 3304 and/or protrusions 3308 include one or more engagement surfaces 3318 configured to facilitate alignment of the attachment portion 3340 with the intended position. For example, the securing portion 3304 shown in FIGS. 33A-33D includes a first engagement surface 3318a, a second engagement surface 3318b, and a third engagement surface 3318c. The first engagement surface 3318a can be a surface of the first protrusion 3308a, the second engagement surface 3318b can be a surface of the second protrusion 3308b, and the third engagement surface 3318c can be a surface of third protrusion 3308c.

As shown in FIG. 33D, in some embodiments the attachment portion 3340 of the appliance is generally T-shaped. The attachment portion 3340 can comprise a first projection 3342 extending along a first direction D1, a second projection 3344 extending along the first direction D1, a third projection 3346 extending along a second direction D2, and/or a fourth projection 3348 extending along the second direction D2 (collectively "projections 3342-3348" and "directions D"). In some embodiments, for example as shown in FIG. 33D, the first direction D1 is generally orthogonal to the second direction D2. Although FIG. 33D depicts the attachment portion 3340 with four projections 3342-3348, other numbers of projections are possible. Moreover, the projections 3342-3348 may extend along different directions D than the two generally orthogonal directions D1, D2 depicted in FIG. 33D. For example, each of the projections 3342-3348 can extend along a unique direction.

To locate the attachment portion 3340 at the intended position, the attachment portion 3340 can be positioned in, at, or adjacent to the securing portion 3304 of the fixture 3300 such that the attachment portion 3340 engages the engagement surfaces 3318. For example, as shown in FIG. 33D, the first projection 3342 of the attachment portion 3340 can engage the first engagement surface 3318a, the second projection 3344 can engage the second engagement surface 3318b, and the third projection 3346 can engage the third engagement surface 3318c. In some embodiments, a first vertical surface 3342a of the first projection 3342 can be configured to contact the first engagement surface 3318a, a first vertical surface 3344a of the second projection 3344 can be configured to contact the second engagement surface 3318b, and a first horizontal surface 3346a of the third projection 3346 can be configured to contact the third engagement surface 3318c. Accordingly, a second vertical surface of the first projection 3342, a second vertical surface of the second projection 3344, a second horizontal surface of the third projection 3346, and all surfaces of the fourth projection 3348 are not constrained by the securing portion 3304. This design of the securing portion 3304 allows the attachment portion 3340 to be constrained in two degrees of freedom, e.g., along the first and second directions D1, D2. Moreover, in some cases a distance between the first and second vertical surfaces of the first projection 3342, the first and second vertical surfaces of the second projection 3344, the first and second horizontal surfaces of the third projection 3346, etc. may be different than an intended distance between the respective surfaces due to tolerance stacking and/or manufacturing errors. The securing portions disclosed herein address these limitations by allowing attachment portions of various widths to be aligned at the intended position.

Although FIGS. 33A-33D depict a securing portion 3304 including three engagement surfaces 3318, other configurations are possible. The securing portion 3304 can include two or more engagement surfaces 3318 configured to engage two or more surfaces of the attachment portion 3340. In various embodiments, the securing portion 3304 includes three or more engagement surfaces 3318 configured to engage three or more surfaces of the attachment portion 3340. In various embodiments, for example, a securing portion can include a first protrusion including (i) a first engagement surface configured to engage the second vertical surface of the first projection of the attachment portion and (ii) a second engagement surface configured to engage the first horizontal surface of the third projection of the attachment portion and a second protrusion including a third engagement surface configured to engage the first vertical surface or the second vertical surface of the second projection. In some embodiments, the securing portion includes a first engagement surface configured engage the first horizontal surface of the third projection, a second engagement surface configured to engage the first horizontal surface of the fourth projection, and the first or second vertical surface of the first or second projections.

The first engagement surface 3318a, the second engagement surface 3318b, and/or the third engagement surface 3318c can have a shape corresponding to and/or derived from a shape of a corresponding projection (e.g., the first projection 3342, the second projection 3344, the third projection 3346, etc.). For example, as shown in FIG. 33D, each of the first, second, and third engagement surfaces 3318a, 3318b, 3318c can be substantially flat to engage a substantially flat surface of the first, second, and third projections 3342, 3344, 3346 of the attachment portion 3340, respectively. As shown in FIGS. 33B-33D, the first and second engagement surfaces 3318a, 3318b can be substantially parallel to each other and/or the third engagement surface 3318c can be substantially orthogonal to the first engagement surface 3318a and/or the second engagement surface 3318b. In some embodiments, the first engagement surface 3318a is spaced apart from the second engagement surface 3318b and/or the third engagement surface 3318c along the second direction D2. The first engagement surface 3318a and/or the third engagement surface 3318c can be spaced apart from the second engagement surface 3318b along the first direction D1.

Prior to setting a shape of the appliance, the appliance can be releasably secured to the fixture 3300. In various embodiments, the attachment portion 3340 is releasably secured to the securing portion 3304 of the fixture 3300. For example, as shown in FIG. 33D, one or more elongated members 3350 (e.g., a ligature wire, a cord, a braid, a coil, etc.) can be wrapped around the attachment portion 3340 and the securing portion 3304. A first elongated member 3350a can be wrapped around the attachment portion 3340 and the securing portion 3304 such that the first elongated member 3350a is positioned within a first recess 3312a in the securing portion 3304 and extends across the attachment portion 3340 along a diagonal path between a first corner between the first and fourth projections 3342, 3348 and a second corner between the second and third projections 3344, 3346. Such a diagonal path can reduce or eliminate play between the attachment portion 3340 and the securing portion 3304 in two dimensions. For example, the diagonal path can reduce or eliminate (i) any vertical play between the first vertical surface 3342a of the first projection 3342 of the attachment portion 3340 and the first engagement surface 3318a and (ii) any horizontal play between the first horizontal surface 3346a of the third projection 3346 of the attachment portion 3340 and the third engagement surface 3318c. The first elongated member 3350a extends along a direction that is disposed at an angle of about 10 degrees to about 80 degrees with respect to the first direction D1 and/or the second direction D2. In some embodiments, the first elongated member 3350a extends along a direction that is disposed at approximately 45 degrees with respect to the first direction D1 and/or the second direction D2. Moreover, wrapping the first elongated member 3350a around the attachment portion 3340 and the securing portion 3304 can reduce or eliminate any play between the attachment portion 3340 and the first surface 3304a of the securing portion 3304. The first recess 3312a can extend through the securing portion 3304 along a direction that is generally parallel to the diagonal path across which the first elongated member 3350a extends such that the first recess 3312a guides the first elongated member 3350a along the desired diagonal path. In some embodiments, a second elongated member (not depicted) is wrapped around the securing portion 3304 and the attachment portion 3340 such that the second elongated member is positioned within a second recess 3312b in the securing portion 3304 and extends across the attachment portion 3340, through an opening in the attachment portion 3340, and through the opening 3314 in the securing portion 3304.

In some embodiments, securing the attachment portions 3340 of the appliance to the securing portions 3304 of the fixture 3300 can cause the anchor of the appliance to substantially conform to the body portion 3302 of the fixture 3300. Additionally or alternatively, fasteners (e.g., ligature wires, clamps, etc.) may be used to cause the anchor of the appliance to substantially conform to the body portion 3302 of the fixture 3300. Moreover, fasteners other than ligature wire may be used to manipulate the appliance into the 3D configuration and/or secure the appliance to the fixture 3300. For example, a clip, a clamp, a positive mold, a pin, a screw, and/or other fasteners can be used.

The fixture 3300 can be manufactured based on a heat treatment fixture digital model. For example, the digital model or associated data can be provided to a fabricating system to produce a physical model based on the digital model. In one example, the digital model and/or data can be used to 3D print a model of the fixture 3300 in wax. The wax model may then be used to investment cast the fixture 3300 in brass or other suitable material. In some embodiments, the fixture 3300 can be 3D printed directly in brass or other suitable material (e.g., stainless steel, bronze, a ceramic or other material that tolerates high temperatures required for heat treatment). In such embodiments, the fixture 3300, including the body portion 3302, the securing portion 3304, the protrusions 3308, the channels 3310, the recesses 3312, etc. can be designed to prevent or reduce the support material required on critical surfaces of the fixture 3300 (e.g., the first surface 3302a of the body portion 3302, the first surface 3304a of the securing portion 3304, etc.) to print the fixture 3300.

Figure 34A:
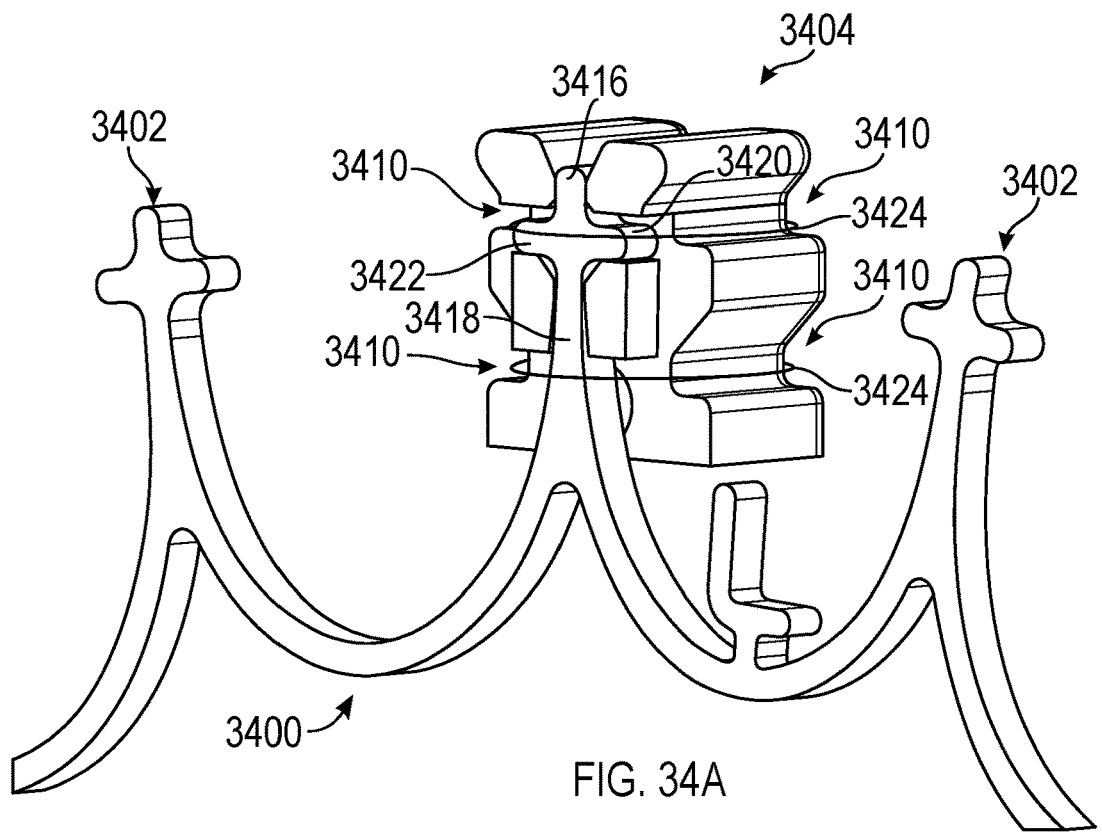
FIG. 34A depicts an attachment portion of an orthodontic appliance secured to a securing portion of a shape forming fixture in accordance with the present technology.

FIG. 34A depicts an appliance 3400 comprising attachment portions 3402, one of which is engaged with a securing portion 3404 of a fixture configured in accordance with several embodiments of the present technology. For ease of understanding, only one securing portion 3404 of the fixture is shown in FIG. 34A. However, the fixture can comprise multiple securing portions 3404 and/or a body portion (e.g., such as body portion 3302, etc.). The securing portion 3404 can be configured to releasably secure an attachment portion 3402, which can facilitate manipulating the appliance 3400 into a desired 3D configuration. The appliance 3400 can be shape set (e.g., heat treated, etc.) while secured to the fixture such that the attachment portion remains located at the intended position once the appliance is removed from the fixture. The intended position at which the securing portion 3404 is configured to retain the attachment portion 3402 can substantially correspond to and/or be derived from a desired position of the tooth to be treated. In operation, an arm and/or a connector of the appliance 3400 can move the attachment portion 3402 to the intended position, thereby moving the tooth to the desired position via the attachment portion 3402.

Figure 34B:
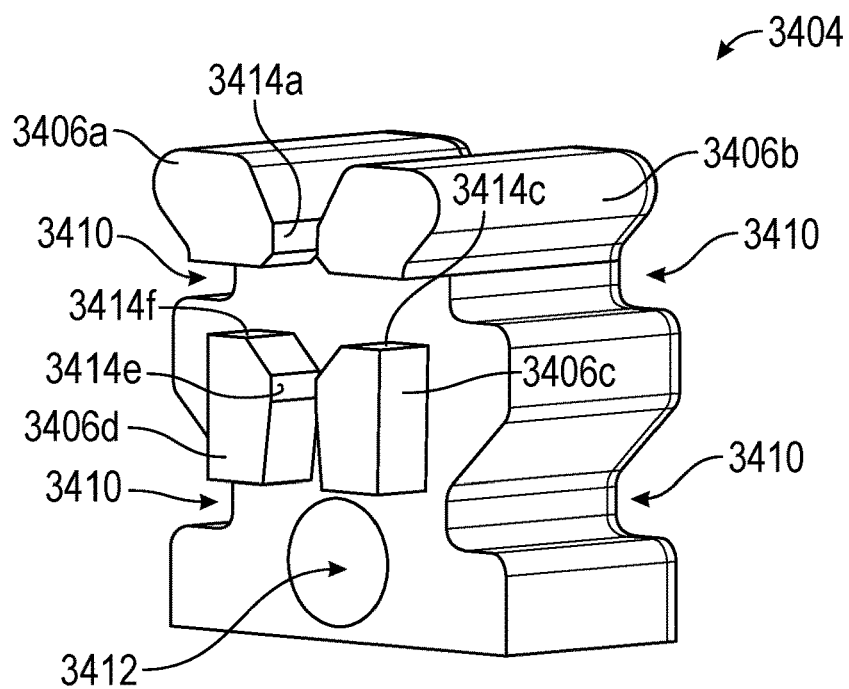
FIG. 34B is a perspective view of the securing portion of FIG. 34A in accordance with the present technology.

FIG. 34B is an isolated view of the securing portion 3404 of FIG. 34A. The securing portion 3404 can comprise a surface 3405 configured to be positioned adjacent to and/or in contact with an attachment portion 3402. The securing portion 3404 can include one or more protrusions 3406 configured to locate the attachment portion 3402 of the appliance 3400 at the intended position. For example, the securing portion 3404 depicted in FIGS. 34A and 34B includes a first protrusion 3406a, a second protrusion 3406b, a third protrusion 3406c, and a fourth protrusion 3406d (collectively referred to as "protrusions 3406") extending away from the surface 3405. The protrusions 3406 define channels therebetween that receive the attachment portion 3402. The channels can comprise a first channel 3408a and a second channel 3408b (referred to collectively as "channels 3408"). As shown in FIG. 34A, the attachment portion 3402 can be positioned against the surface 3405 between the protrusions 3406. The securing portion 3404 can further include one or more grooves 3410 and/or openings 3412 configured to receive a fastener at least partially therein. For example, as shown in FIG. 34A, one or more ligature wires 3424 can be positioned within the grooves 3410 and wrapped around the attachment portion 3402 and the securing portion 3404 to secure the attachment portion 3402 to the securing portion 3404.

Although the channels 3408 in FIGS. 34A and 34B are defined by protrusions 3406 extending away from the surface 3405, in some embodiments the securing portion 3404 includes channels 3408 formed by recesses in the surface 3405. The channels 3408 would thus extend into the thickness of the securing portion 3404. In some embodiments, the securing portion 3404 does not include protrusions 3406 or channels 3408. Instead, the securing portion 3404 can comprise printed markings, for example, on the securing portion 3404 that are configured to indicate the intended position of the attachment portion 3400.

According to some embodiments, for example as shown in FIG. 34A, the attachment portion 3402 can be positioned in, at, or adjacent to the securing portion 3404 such that the attachment portion 3402 is located at its intended position. In some embodiments, the attachment portion 3402 is positioned substantially parallel with and/or in contact with the surface 3405 of the securing portion 3404. In some embodiments, the securing portion 3404 and/or protrusions 3406 include one or more engagement surfaces 3414 configured to facilitate alignment of the attachment portion 3402 with the intended position. For example, the securing portion 3404 shown in FIGS. 34A and 34B includes a first engagement surface 3414a, a second engagement surface (not visible), a third engagement surface 3414c, a fourth engagement surface (not visible), a fifth engagement surface 3414e, and/or a sixth engagement surface 3414f. The first engagement surface 3414a can be a surface of the first protrusion 3406a, the second engagement surface can be a surface of the second protrusion 3406b, the third engagement surface 3414c and the fourth engagement surface can be surfaces of third protrusion 3406c, and the fifth and sixth engagement surfaces 3414e, 3414f can be surfaces of the fourth protrusion 3406d.

As shown in FIG. 34A, in some embodiments the attachment portion 3402 of the appliance 3400 is generally T-shaped. The attachment portion 3400 can comprise a first projection 3416 extending along a first direction D1, a second projection 3418 extending along the first direction D1, a third projection 3420 extending along a second direction D2, and/or a fourth projection 3422 extending along the second direction D2 (collectively "projections 3416-3422" and "directions D"). In some embodiments, the first direction D1 is generally orthogonal to the second direction D2. Although FIG. 34A depicts the attachment portion 3402 with four projections 3416-3422, other numbers of projections are possible. Moreover, the projections 3416-3422 may extend along different directions D than the two generally orthogonal directions D1, D2 depicted in FIG. 34A. For example, each of the projections 3416-3422 can extend along a unique direction.

To locate the attachment portion 3402 at the intended position, the attachment portion 3402 can be positioned in, at, or adjacent to the securing portion 3404 of the fixture such that the attachment portion 3402 engages the engagement surfaces 3414. For example, as shown in FIG. 34A, the first projection 3416 of the attachment portion 3402 can engage the first and second engagement surfaces, the second projection 3418 can engage the third and fifth engagement surfaces, the third projection 3420 can engage the fourth engagement surface, and the fourth projection 3422 can engage the sixth engagement surface. This design of the securing portion 3404 allows the attachment portion 3402 to be constrained in two degrees of freedom, e.g., along the first and second directions D1, D2. The securing portions disclosed herein address these limitations by allowing attachment portions of various widths to be aligned at the intended position.

V. Use of Finite Element Analysis for Design of Orthodontic Appliances and Treatment Fixtures As noted previously, in some embodiments, designing and/or fabricating an orthodontic appliance (or components thereof) or a shape forming fixture (or components thereof) can include using computer-aided or computer-automated analyses. In some embodiments, such computer-aided analysis can include obtaining one or more digital models and performing a finite element analysis (FEA) using such models. For example, digital models can be obtained that characterize or represent the patient's teeth, gingiva, maxilla, mandible, skull, and/or other anatomical structures of the oral cavity (e.g., whether in the OTA, ITA, or FTA), an orthodontic appliance (e.g., in planar form, in desired, 3D pre-installation form, in a deformed configuration, etc.), and/or a shape forming fixture. As described in more detail below, FEA can be used to evaluate the design and configuration of an orthodontic appliance and/or a shape forming fixture prior to fabricating the appliance and/or shape forming fixture. As such, the designs may be corrected, improved, or otherwise modified based on the evaluation before proceeding to fabrication, thereby reducing costly errors and improving device designs.

Orthodontic appliances of the present technology may have a planar form corresponding to a flattened or substantially two-dimensional (2D) configuration, a desired, pre-installation form corresponding to a substantially three-dimensional (3D) configuration of the appliance after manufacturing (e.g., after shape forming the appliance), and/or an installed form corresponding to a substantially 3D configuration of the appliance at the start of treatment once installed in the patient's mouth (e.g., with the appliance coupled to the patient's teeth in an OTA or ITA). According to some embodiments, the pre-installation form of an appliance can be created by coupling an appliance in a planar form (or other intermediate form) to a shape forming fixture setting a shape of the appliance while the appliance is coupled to the fixture (e.g., by heat treating the appliance and fixture to form a 3D, contoured shape of the appliance). A pre-installation form of the appliance can be created by any suitable process including, for example, 3D printing an appliance, mechanically deforming an appliance, etc. In some embodiments, a pre-installation form of the appliance can be based on an arrangement of the patient's teeth and/or gingiva in the OTA, the FTA, and/or an ITA. Additionally or alternatively, the pre-installation form of the appliance can have a shape based on a shape of the shape forming fixture. In some embodiments, when the appliance is coupled to the shape forming fixture, one or more portions of the appliance (e.g., the anchor, the arms, etc.) substantially conforms to a gingival surface of the shape forming fixture while certain portions of the appliance (e.g., attachment portions, etc.) are secured to securing portions of the shape forming fixture. The gingival surface of the shape forming fixture can be derived from and/or substantially correspond to the patient's gingiva as represented in the OTA digital model, in the FTA digital model, etc. Each form of the appliance may be virtually represented as a unique digital model. For example, the appliance in the planar form may be virtually represented as a planar appliance digital model.

In some cases, it may be beneficial to evaluate an intended appliance design and/or configuration prior to fabricating a physical appliance based on the intended appliance design and/or configuration to assess how the physical appliance would perform during treatment. For example, because the pre-installation form of the appliance can be based at least in part on a desired FTA, the position of one or more portions of the appliance may shift relative to the gingiva once the physical appliance is deformed to be installed in the patient's mouth (e.g., with the patient's teeth in the OTA or an ITA). As a result, one or more shifted positions of the physical appliance may engage the patient's oral tissues and cause pain for the patient that may reduce treatment compliance and/or satisfaction. The anchor of the appliance, for example, may be intended to sit adjacent to and slightly spaced apart from the patient's gingiva throughout treatment. In the installed form, the anchor may sit too far away from the gingiva and irritate the tongue (with a lingual appliance), or the anchor member may sit too close to the gingiva and apply painful pressure to the gingiva (e.g., impinge the gingiva). Thus, one or more systems and methods of the present technology may evaluate the position of the appliance relative to a patient's local anatomy once installed in the patient's mouth, such as the position of the anchor relative to the gingiva. Based on the evaluation, one or more parameters of the shape forming fixture or the appliance can be modified.

Additionally, when the physical appliance is installed in the patient's mouth, the appliance is deformed from the pre-installation form to the installed form and large strain may develop in certain portions of the appliance (e.g., the arms). If strain in the appliance exceeds an elastic limit of the appliance material, plastic deformation may occur, which can alter the forces the appliance is able to apply to the teeth. Thus, one or more systems and methods of the present technology may predict and/or evaluate potential plastic deformation of the appliance and, based on the prediction and/or evaluation, modify one or more parameters of the appliance (e.g., geometry of the arms, the geometry of the 3D pre-installation form, and/or the locations of the securing members on the teeth, etc.) to reduce or eliminate the predicted plastic deformation.

Orthodontic appliances of the present invention can be configured apply a force and/or moment to a patient's tooth to move the tooth from an original position (e.g., OTA or ITA) to a planned position (e.g., ITA or FTA). Various parameters of an orthodontic appliance design such as arm geometry, anchor geometry, material properties, etc. can be selected and adjusted based on an intended force and/or moment to be applied to a tooth. In some cases, it may be beneficial to evaluate the forces and/or moments that an intended appliance design will apply to a patient's teeth before physically manufacturing the appliance to determine whether a physical appliance based on the intended appliance design will perform as desired. Thus, one or more systems and methods of the present technology may evaluate forces and/or moments applied to the patient's teeth by an appliance with an intended appliance design and, based on the evaluation, modify one or more parameters of the appliance and/or shape forming fixture.

To address the foregoing challenges, prior to fabricating the physical appliance and installing the physical appliance in the patient's mouth, one or more processes may be performed to evaluate an intended appliance design by virtually deforming a digital model of the appliance in one form to produce a digital model of the appliance in another form. For example, a digital model of the appliance in a pre-installation form may be deformed to obtain a digital model of the appliance in an installed form. An output of the virtual deformation can be evaluated to assess whether the physical appliance will function as intended, and based on the evaluation of the output, the intended appliance design can be modified, or a final appliance design can be obtained.

Some or all of the analyses described herein can be performed using suitable computing devices (e.g., computing device described previously). The processes can be performed on one computing device or cluster of computing devices working in concert, or various processes can be performed by remote or distributed computing devices, with different steps being performed by different entities and/or different computing devices. For example, some or all of the analysis processes described herein can be performed in a distributed computing environment in which tasks or modules are performed by remote processing devices, which are linked through a communication network (e.g., a wireless communication network, a wired communication network, a cellular communication network, the Internet, a short-range radio network (e.g., via Bluetooth)). In various embodiments, some or all of the processes described herein can be performed automatically. According to some embodiments, some of the processes described herein may rely at least in part on one or more inputs from a human operator, such as a clinician or technician.

Figure 35:
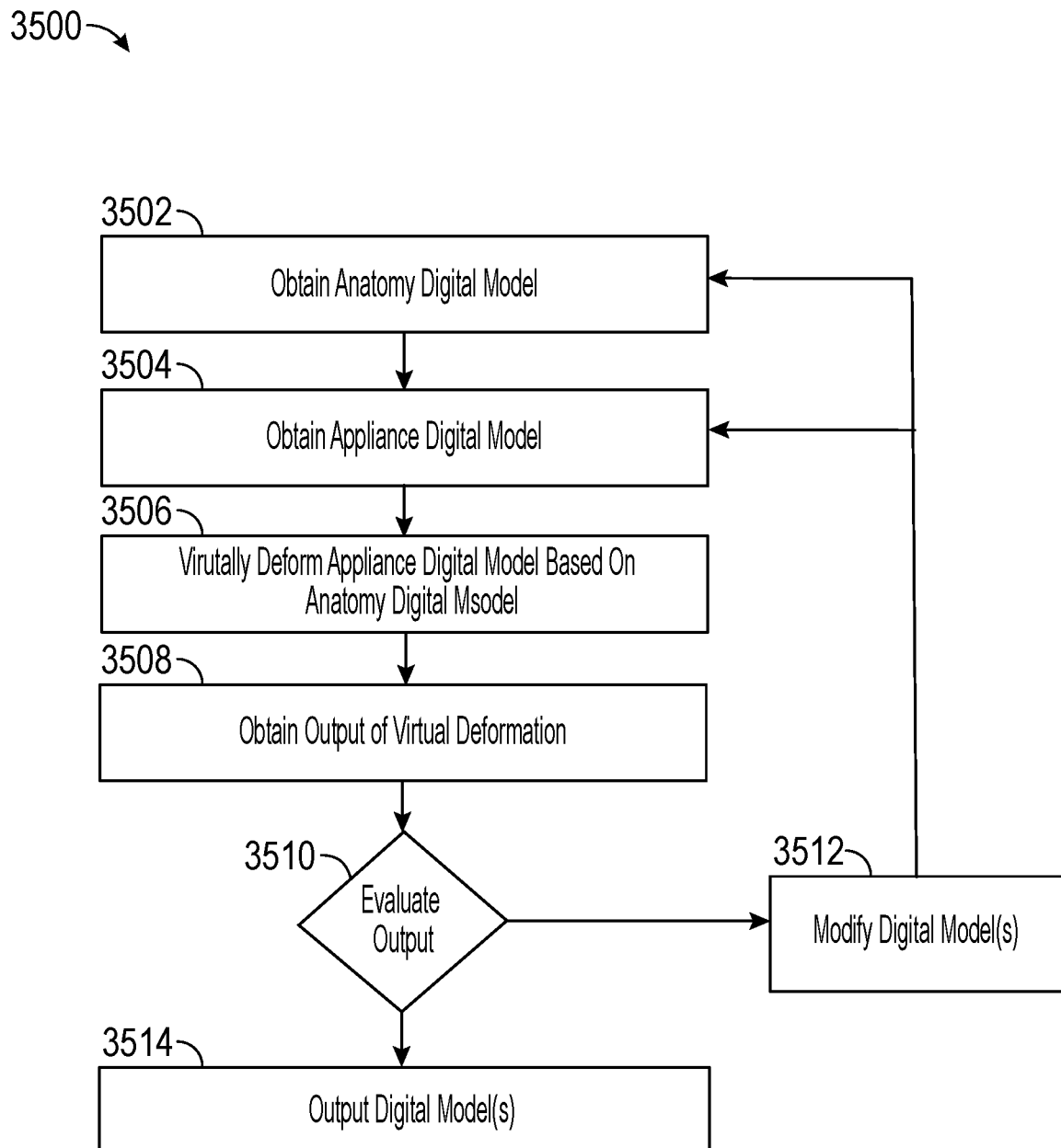
FIG. 35 is a flow diagram of an example process for determining a design of an orthodontic appliance.

FIG. 35 is a flow diagram of a process 3500 for obtaining a design of an orthodontic appliance. In some embodiments, the process 3500 may include obtaining an anatomy digital model (e.g., at process portion 3502) representing or characterizing the geometry of one or more anatomical structures of the patient (e.g., the teeth, the gingiva, the jaw, the skull, etc.) in an arrangement. The arrangement may be an original tooth arrangement (OTA), an intermediate tooth arrangement (ITA), or a final tooth arrangement (FTA). In some embodiments the anatomy digital model may be a modified representation of the patient's teeth and/or gingiva. For example, the anatomy digital model may represent a shape forming fixture based on an OTA and/or a desired FTA. Such shape forming fixture can include securing portions at positions based at least in part on positions of the patient's teeth in a desired FTA and a gingiva portion having a curvature and/or topography based on a gingiva portion of an OTA digital model or an FTA digital model, for example. The process 3500 may include obtaining an appliance digital model (process portion 3504) representing the orthodontic appliance in a specific form. For example, the appliance digital model may be a planar appliance digital model that represents the orthodontic appliance in a substantially flattened or 2D configuration. In some embodiments, the appliance digital model represents the appliance in an intermediate configuration (e.g., prior to shape forming, etc.).

The process 3500 may continue at process portion 3506 with virtually deforming the appliance digital model based on the anatomy digital model. The process 3500 may perform the virtual deformation at process portion 3506 by finite element analysis (FEA), finite difference methodology, finite volume methodology, or any other suitable numerical methodology. For example, virtually deforming the appliance digital model may include performing an FEA with the appliance digital model and the anatomy digital model to deform the appliance digital model based on a difference in position between a portion of the appliance digital model and a portion of the anatomy digital model. The process 3500 may obtain an output of the virtual deformation at process portion 3508 and may evaluate the output in process portion 3510. The output may comprise the virtually deformed appliance digital model, the anatomy digital model, and/or data produced by the virtual deformation such as displacement, force, strain, stress, and/or relative position. Evaluating the output may comprise performing a quantitative comparison of the output to a predetermined threshold or parameter. In some embodiments, evaluation of the output may be qualitative. For example, a human operator can visually inspect the output. Based on the evaluation of the output performed at process portion 3510, the process 3500 may continue with modifying one or more of the previously obtained digital models (process portion 3512). For example, the process 3500 may determine that a strain in the appliance digital model exceeds a predetermined threshold and can therefore modify the geometry of one or more portions of the appliance digital model to reduce the strain that occurs in the appliance when the appliance is deformed. Based on the evaluation of the output 3510, the process 3500 may continue to process portion 3514 and output one or more previously obtained digital models. The digital model(s) output by process portion 3514 may be used to fabricate a physical appliance and/or fixture, as previously described.

Figure 36:
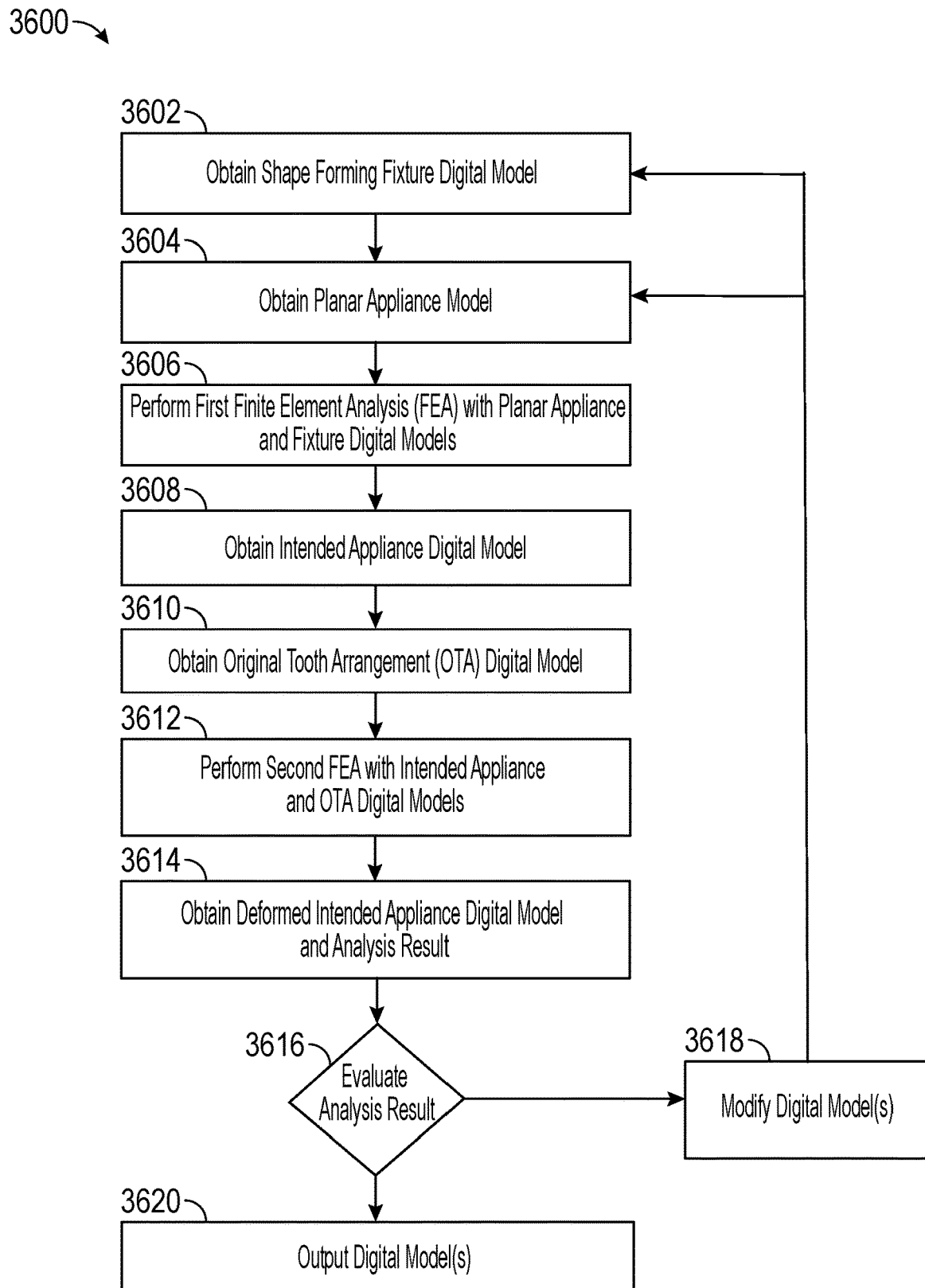
FIG. 36 is a flow diagram of an example process for determining a design of an orthodontic appliance.

FIG. 36 illustrates an example process 3600 for evaluating an orthodontic appliance design. In some embodiments, each of the process portions of the process 3600 can be executed automatically or manually, by human operator, for example. The process 3600 may begin at process portion 3602 with obtaining a shape forming fixture digital model. An example of a shape forming fixture model 1200 is shown in FIG. 12, described above. The shape forming fixture digital model may correspond to and/or be derived from an OTA digital model and/or a desired FTA digital model. In some embodiments, the shape forming fixture digital model can have with certain modifications relative to an anatomy digital model (e.g., enlarging the gingiva, replacing securing members with securing portions, etc.). At process portion 3604, a planar appliance digital model may be obtained. An example of a planar appliance digital model 1500 is shown in FIG. 15, described above. The planar appliance digital model may have a substantially flattened or 2D configuration and may virtually represent the appliance design comprising an anchor, a plurality of arms, a plurality of attachment portions, etc. In some embodiments, the planar appliance digital model can include a thickness dimension, which can be uniform over the appliance or may vary over different portions of the appliance. The process 3600 may continue at process portion 3606 with performing a first FEA with the planar appliance digital model based on the shape forming fixture digital model. For example, an output of the first FEA can comprise an intended appliance digital model, in which the planar appliance digital model has been substantially conformed to the fixture digital model. The intended appliance digital model can comprise a contoured, 3D appliance having a shape based on a shape of the fixture digital model. In some examples, performing the first FEA can comprise deforming the planar appliance digital model based on a feature (e.g., securing portions, gingiva portion, etc.) of the fixture model. For example, attachment portions of the planar appliance digital model can be virtually mated to corresponding securing portions of the fixture digital model. In some embodiments, the process 3600 may perform the first FEA at process portion 3606 using suitable commercial FEA software (e.g., Abaqus, Ansys, etc.) and/or suitable proprietary FEA software.

Although some embodiments describe using the shape forming fixture digital model to generate a contoured, 3D configuration of the appliance digital model, in some embodiments an FTA digital model (e.g., FTA models 800 or 1100 described above) can be used. For example, a planar appliance digital model can be deformed to conform to a surface of an FTA digital model, without the need for the shape forming fixture digital model. Additionally or alternatively, other anatomy digital models or boundary conditions can be used to deform a digital model of an appliance an intermediate form to obtain a digital model of the appliance in the intended form. In some embodiments process portions 3602-3606 can be omitted from the process 3600 and an intended appliance digital model can be obtained (process portion 3608) without performing the first FEA.

In some embodiments, performing the first FEA at process portion 3606 may include meshing one or more of the digital models, wherein meshing comprises discretizing a digital model into a plurality of finite elements and a plurality of nodes. Meshing may be performed manually, such as by human operator providing inputs to suitable software, and/or automatically using suitable software. Suitable software may include commercial meshing software (e.g., Hypermesh®), commercial FEA software with meshing capabilities (e.g., Abaqus, Ansys, etc.), and/or proprietary meshing software. The finite elements may have a dimensionality based on a geometry of the digital model, including, but not limited to, 2D (e.g., triangular, quadrilateral, etc.) or 3D (e.g., tetrahedral, quadrilateral, etc.) elements. For example, the finite elements for the planar appliance digital model may comprise hexahedral 3D elements. Element parameters (e.g., element type, element order, number of integration points, hourglass control, etc.) may be selected to control and/or modify the accuracy and stability of the FEA. In some embodiments, performing the FEA may include meshfree techniques such as element-free Galerkin process, generalized-strain mesh-free formulation, isogeometric analysis, or the process of external approximations.

Performing the first FEA at process portion 3606 may include assigning material properties (e.g., Young's modulus, Poisson's ratio, density, etc.) to the planar appliance digital model and the shape forming fixture digital model. For example, material properties for nitinol may be assigned to the planar appliance digital model, such as a Young's modulus between about 28 GPa and 83 GPa. In some embodiments, the shape forming fixture model may be represented as a deformable component with material properties for brass, such as a Young's modulus between about 100 GPa and 130 GPa. In some embodiments, the shape forming fixture digital model may be represented as a rigid component such that the shape forming fixture digital model does not deform during the first FEA. The shape forming fixture digital model may be represented as a rigid component by assigning an artificially large Young's modulus to the shape forming fixture digital model. The process 3600 may obtain the material properties from a database and/or the material properties may be entered manually.

In some embodiments, performing the first FEA (process portion 3606) may include defining a contact interaction between at least one portion of the appliance digital model and at least one portion of the shape forming fixture digital model. Defining the contact interaction may include creating a first contact surface by selecting digital nodes, elements, and/or surfaces of the planar appliance digital model. Another contact surface may be created by selecting digital nodes, elements, and/or surfaces of the shape forming fixture digital model. Defining the contact interaction may further comprise defining a contact formulation to govern the contact interaction between the contact surfaces. The type of contact formulation (e.g., bonded, frictional, frictionless, etc.) may be selected from a database of contact formulations and/or or the contact formulation may be entered manually. The process may further comprise entering relevant parameters of the contact formulation including, but not limited to, a coefficient of friction, a penalty contact stiffness, and/or a nodal search distance. For example, in some embodiments a bonded contact interaction can be defined between an attachment portion of the appliance digital model and a channel, a surface, and/or a protrusion of a securing portion of the shape forming fixture digital model. In some embodiments, a sliding contact interaction can be defined between an attachment portion of the appliance digital model and a securing portion of the shape forming fixture digital model. For example, a sliding contact interaction can be defined to simulate interplay between an attachment portion and a securing member.

Performing the FEA in process portion 3606 may include assigning boundary conditions to at least one of the digital models. In some embodiments, the boundary conditions may include a constraint to prevent translation and/or rotation of one or more portions of one or more digital models. For example, the boundary conditions may include a constraint of the shape forming fixture digital model and one or more attachment portions of the planar appliance digital model. In addition or alternatively, the boundary conditions may include a non-zero force, moment, displacement, and/or rotation. For example, to virtually deform the planar appliance digital model into a contoured or 3D digital model representing the pre-installation form of the appliance, a non-zero displacement may be applied to a portion of the anchor of the planar appliance digital model. The non-zero displacement can correspond to a distance between the anchor member and a distal region of the gingiva portion of the fixture digital model when the attachment portions of the planar appliance digital model are within the securing portions of the shape forming fixture digital model. In some embodiments, the planar appliance digital model can be virtually deformed into a contoured or 3D digital model representing the pre-installation form of the appliance by applying a non-zero displacement to an attachment portion of the planar appliance digital model such that the attachment portion is positioned within a corresponding securing portion 1202 of the shape forming fixture digital model. In addition, or alternatively, a non-zero displacement can be applied to an attachment portion and/or arm of the planar appliance digital model such that the attachment portion and/or arm is tangent to a base plane (e.g., the broad surface, etc.) of a corresponding securing portion of the shape forming fixture digital model.

In some embodiments, performing the FEA in process portion 3606 may include defining one or more analysis parameters such as analysis type (e.g., static or dynamic), geometric linearity, integration scheme (e.g., implicit, explicit), simulation duration, incrementation size, and/or incrementation control. Performing the FEA may include running the FEA until an exit condition is reached. For example, running the FEA may include applying a non-zero displacement to the planar appliance digital model, wherein the exit condition is reached once the entire magnitude of the non-zero displacement has been applied.

Figure 37:
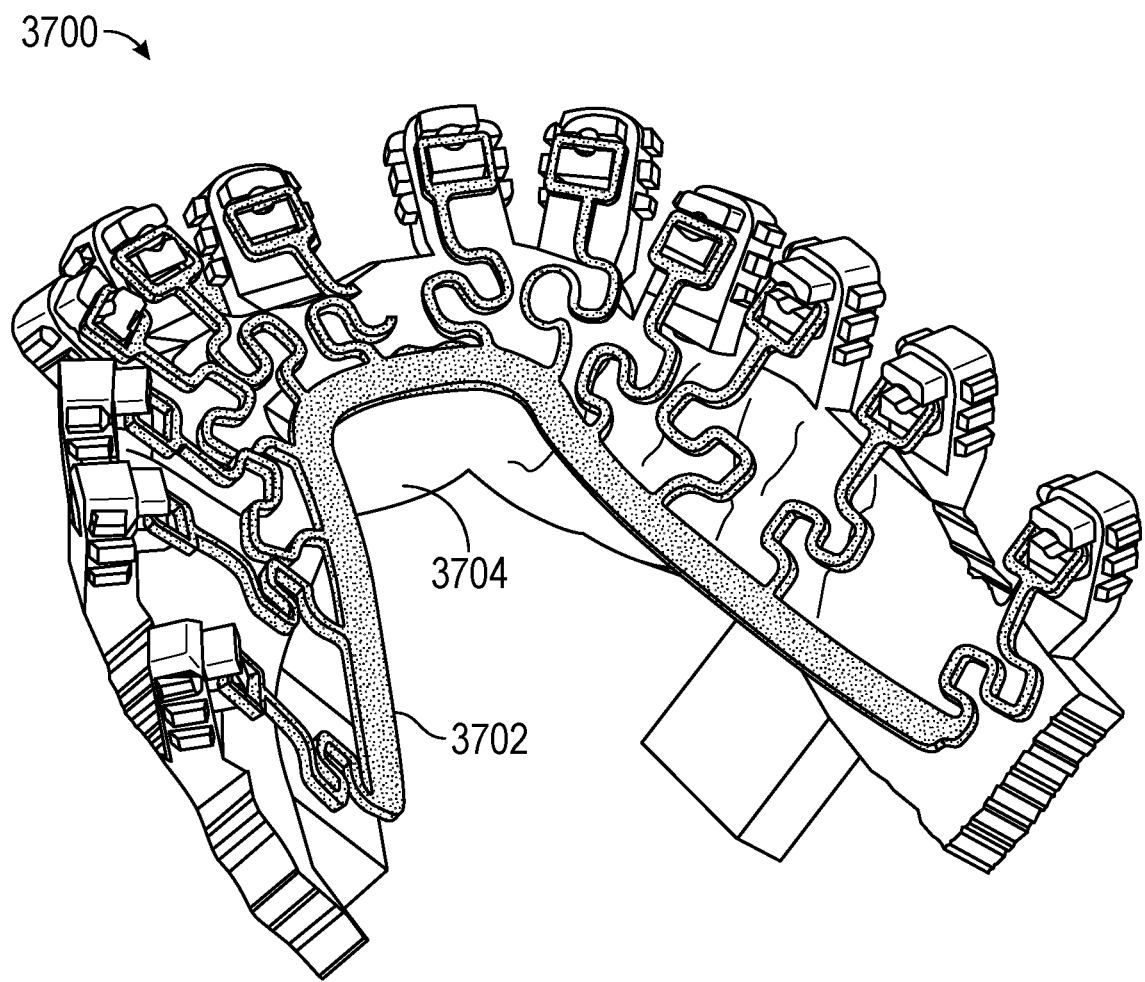
FIG. 37 illustrates an example of an intended appliance digital model obtained by performing a finite element analysis with a planar appliance digital model and a heat treatment fixture digital model.

Referring back to FIG. 36, the process 3600 may continue at process portion 3608 with obtaining an intended appliance digital model virtually representing the appliance in a pre-installation form. FIG. 37 depicts an example of an intended appliance digital model 3702 mated with a shape forming fixture model 3704 as a result of the first FEA (process portion 3606). The intended appliance digital model 3702 obtained in process portion 3608 can be obtained from the first FEA performed in process portion 3606 of the process 3600. In some embodiments, an intended appliance digital model 3702 representing a contoured or 3D configuration of the appliance after manufacturing can be obtained without performing a first FEA. For example, an intended appliance digital model 3702 can be obtained directly from CAD software such as Solidworks®, Autodesk® Inventor, Autodesk® MeshMixer, Creo®, etc. In addition, or alternatively, an intended appliance digital model 3702 can be obtained from a scan of a physical representation of an appliance such as a fabricated appliance, an appliance mold, etc. At process portion 3610 an OTA digital model may be obtained that virtually represents the patient's teeth, gingiva, and/or other anatomical structures in an original arrangement. For example, an OTA digital model with securing members attached thereto, such as digital model 1000, can be used. In some embodiments, the OTA digital model can comprise a modified representation of the patient's teeth and/or gingiva. For example, the OTA digital model can have similar features as the shape forming fixture (e.g., securing portions with channels and/or protrusions, a gingival portion, a stabilizing crossbar, etc.) in place of or in addition to a virtual representation of the patient's actual teeth and/or gingiva. For example, in some embodiments, securing portions located at positions of a patient's teeth in an original arrangement can replace a virtual representation of the patient's actual teeth in an OTA digital model. According to some embodiments, the OTA digital model can comprise a dataset comprising position data characterizing the spatial coordinates of a patient's teeth in an original arrangement.

Figure 38:
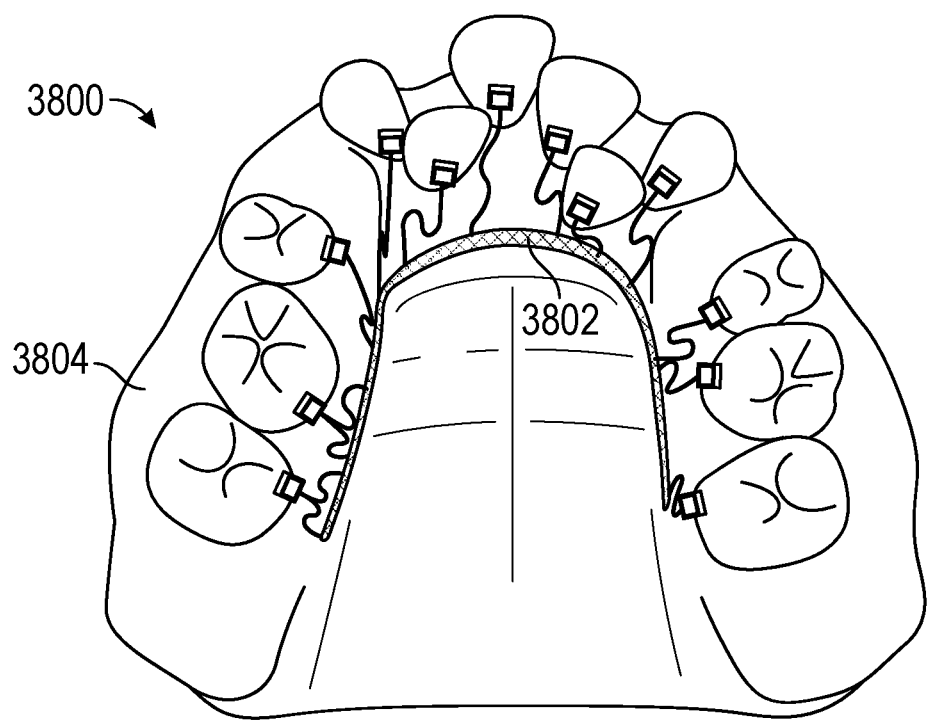
FIG. 38 illustrates an example of a deformed intended appliance digital model obtained by performing a finite element analysis with an intended appliance digital model and an OTA digital model.

Referring back to FIG. 36, the process 3600 may continue with performing a second FEA with the intended appliance digital model (e.g., digital model 3702) and the OTA digital model (e.g., digital model 700, 1000, etc.) at process portion 3612 to produce a deformed intended appliance digital model representing the appliance in an installed form. FIG. 38 illustrates an example of a digital model 3800 that includes a deformed intended appliance digital model 3802 mated with an OTA digital model 3804. The OTA digital model 3804 can be similar to any other OTA digital model disclosed herein (e.g., OTA digital model 700, OTA with securing member digital model 1000, etc.). As shown in FIG. 38, the deformed intended appliance digital model 3802 can virtually represent the appliance in an installed form in the patient's mouth (e.g., in the OTA or ITA). For example, via the second FEA, the intended appliance digital model 3702 (e.g., characterizing the appliance in a pre-installation form) can be virtually deformed into an installed form in which the appliance is mated to a patient's teeth in the OTA (or ITA), as reflected in the OTA digital model 3804. This virtual deformation can produce the deformed intended appliance digital model 3802, which can effectively model the real-world behavior of a fabricated appliance when installed within a patient's mouth. As such, evaluation of the deformed intended appliance digital model 3802 allows a human operator and/or an automated process to assess and/or predict operation and behavior of the appliance when installed within the patient's mouth.

In some embodiments, performing the second FEA can include discretizing the digital model(s), assigning material properties, defining any contact interactions, assigning boundary conditions, defining any analysis parameters, and/or running the FEA until an exit condition is reached as previously described. For example, assigning boundary conditions to perform the second FEA may include determining a displacement of each tooth between the FTA and OTA. As previously described, the displacement of a tooth can be defined using six degrees of freedom by calculating the difference between the location of each tooth in the FTA data and the OTA data. Assigning the boundary conditions can include assigning the displacement of each tooth between the FTA and OTA to a corresponding attachment portion of the intended appliance digital model 3702. Assigning the boundary conditions may comprise assigning constraints to prevent rotation and/or translation of the OTA digital model 3804 and/or one or more portions of the intended appliance digital model 3702.

Referring back to FIG. 36, at process portion 3614 the process 3600 may obtain the deformed intended appliance digital model (see, for example, FIG. 38), and/or an analysis result. The deformed intended appliance digital model 3802 and/or the analysis result can be obtained from the second FEA. The deformed intended appliance digital model 3802 may virtually represent the appliance in an installed form once it has been installed into the patient's mouth (e.g., with the appliance coupled to the patient's teeth in an OTA or ITA). The analysis result can comprise output data from the second FEA. For example, the analysis result may be a measure of position, displacement, rotation, force, moment, stress, or strain in one or more of the digital models used in the second FEA. The process 3600 may continue at process portion 3616 with evaluating the analysis result. In some embodiments, evaluating the analysis result includes comparing the analysis result to one or more predetermined thresholds. Based on the evaluation of the analysis result, the process 3600 may continue to process portion 3618 and modify the planar appliance digital model and/or the shape forming fixture digital model.

In various embodiments, modifying the appliance digital model (e.g., the planar appliance digital model, the intended 3D appliance digital model, etc.) can include modifying the particular shape and/or configuration of an anchor and/or arms of the appliance, the geometry of the 3D pre-installation form of the appliance, and/or the locations of the securing members on the teeth. For example, features of the arm(s) that can be modified include but are not limited to, the overall length of the arm, the shape or configuration of the biasing portion, the shape or configuration of the bracket connector, the width dimension of one or more sections of the arm, the thickness dimension of one or more sections of the arm, or the like. Features of the anchor that can be modified include, but are not limited to the shape, length, thickness, depth, or other properties of the anchor. In some embodiments, a human operator may manually select or revise the design and configuration of the anchor and/or arms as desired. In some embodiments, one or more of the arms can be replaced based on a pre-populated library of arm designs. In some embodiments, fully or partially automated modification of the appliance digital model or the shape forming fixture digital model can be reviewed and/or modified by an operator based on relevant criteria.

Figure 39:
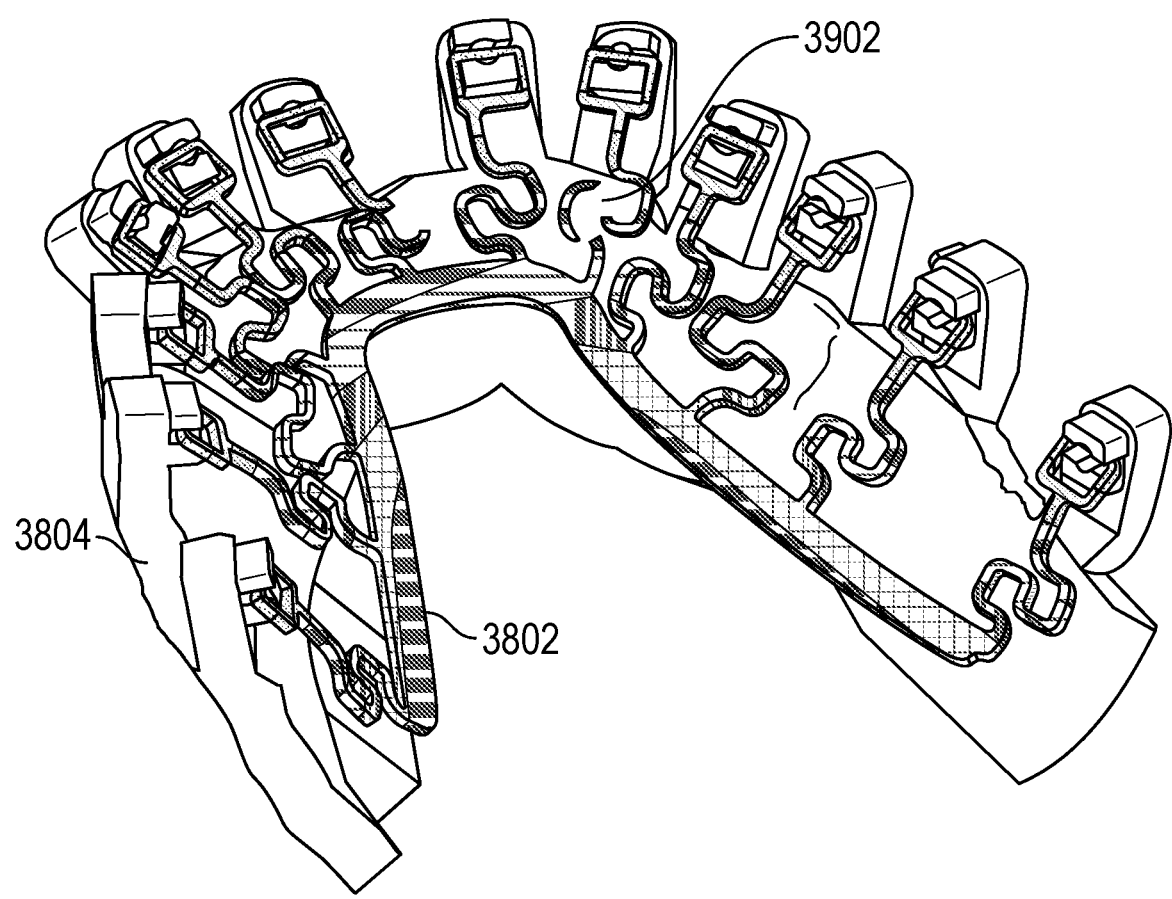
FIG. 39 illustrates an example of a result of a finite element analysis.

FIG. 39 illustrates an example of an analysis result of a deformed intended appliance digital model 3802 in a configuration mated to a patient's teeth, as reflected in the OTA digital model 3804. The analysis result can include a measure of strain in the appliance digital model 3802. The measure of strain may comprise, for example, a single maximum strain in the appliance, a volume of elements exceeding a strain threshold, and/or an average strain of a portion of the appliance. As depicted in FIG. 39, the measure of strain may be displayed by the process 3600 as a heat map superimposed over the appliance digital model 3802. Such a heat map (or other graphical representation) can visually indicate the strain at different regions of the appliance digital model 3802. In some embodiments, the measure of strain may be a number and/or a set of numbers. The process 3600 may compare the measure of strain to a predetermined maximum strain threshold in process portion 3616. In some embodiments, the predetermined maximum strain may be an elastic limit of the appliance material. For example, the predetermined maximum strain for nitinol may between about 4% to about 10%. If the measure of strain exceeds the predetermined maximum strain threshold, the process 3600 may proceed to process portion 3618 and modify the planar appliance digital model. Modifying the planar appliance digital model may include, for example, increasing the thickness of one or more portions of the appliance, selecting a different geometry of an arm or anchor portion of the appliance, etc.

In some embodiments, the analysis result may comprise a force and/or moment in order to evaluate a force and/or moment the appliance applies to a patient's tooth. For example, the analysis result can be a reaction force and/or moment measured at a portion of the anchor of the appliance digital model 3802, a securing member of an OTA digital model 3804, a tooth of the OTA digital model, or any other suitable location. The location the force and/or moment is measured from can be based, at least in part, on the boundary conditions assigned in the second FEA. In some embodiments, evaluating the analysis result (process portion 3616) comprises comparing the force and/or moment to a predetermined value. In some embodiments, the predetermined value may correspond to an intended force and/or moment. A difference between the measured and intended force and/or moment can be obtained and evaluated to determine if a physical appliance based on the intended appliance design will sufficiently apply the intended force and/or moment and perform as intended. In some embodiments, the predetermined value can be a safety threshold corresponding to a maximum allowable force for the appliance and/or the patient's anatomy. According to some embodiments, the predetermined value is a minimum force and/or moment, a range of allowable forces and/or moments, or any other suitable metric. Based on the comparison of the force and/or moment to the predetermined value, the process 3600 may modify one or more parameters of the planar appliance digital model, the shape forming fixture digital model, the intended appliance digital model 3700, or another suitable digital model.

Another example of an analysis result includes identifying portions of the appliance that may impinge on a patient's gingiva. For example, as shown in FIG. 39, in region 3902, a portion of the appliance digital model 3802 has penetrated beneath a gingival surface of the OTA digital model 3804. This may occur as a result of deformation of the model from the intended appliance digital model 3702 to the deformed appliance digital model 3802 described previously. The intersection shown in region 3902 can indicate an area at which a real-world fabricated appliance is at risk of contacting the patient's gingiva when installed. Such contact can be uncomfortable and irritate the patient's gingiva. Accordingly, as a result of identifying such a contact point, the appliance design may be modified (e.g., by modifying the planar appliance digital model), the pre-installation form of the appliance may be modified (e.g., by modifying the shape forming fixture model), or any other suitable modifications, corrections, or compensations may be made.

Figure 40:
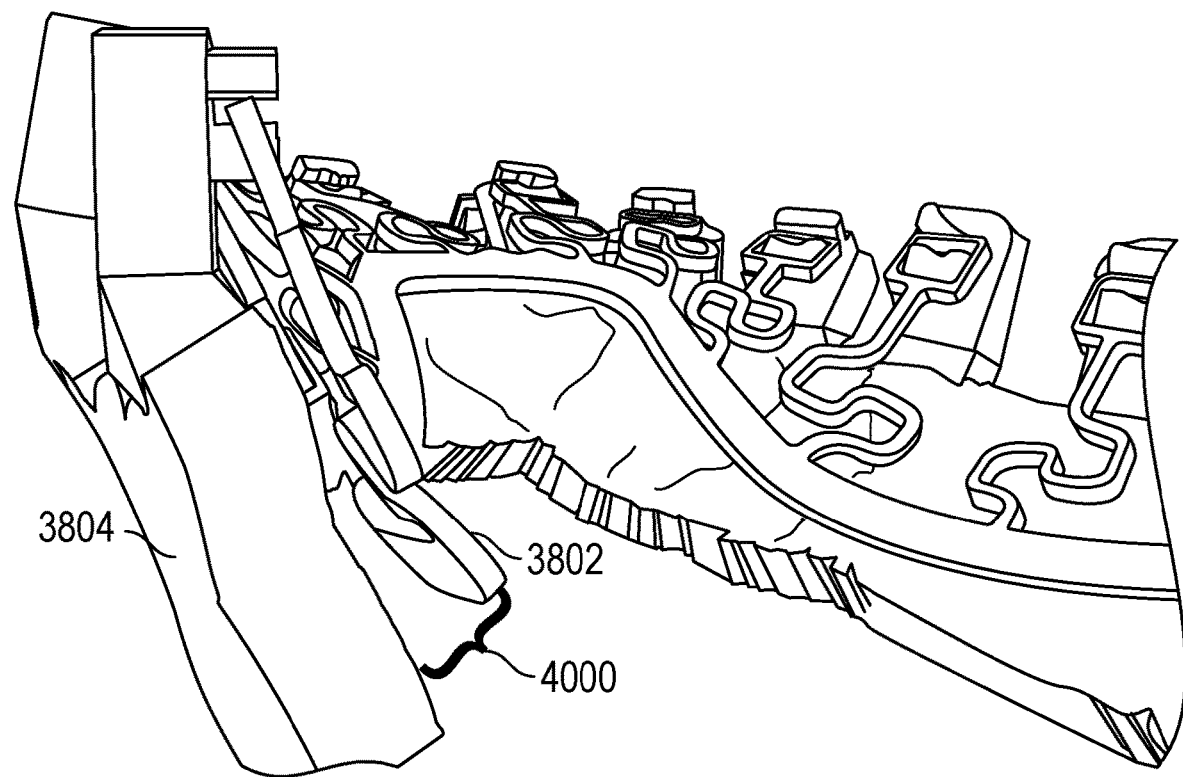
FIG. 40 illustrates another example of an analysis result.

FIG. 40 illustrates another example of an analysis result based on assessment of the relative positions of the deformed appliance digital model 3802 and the OTA digital model 3804. For example, as shown in FIG. 40, a portion of the appliance digital model 3802 is spaced apart from a gingival surface of the OTA digital model 3804 by a local distance 4000 due to a shape set form of the appliance. Too large of a gap between the appliance the patient's gingiva can irritate the patient's tongue and cause pain and/or discomfort for the patient. Therefore, in some embodiments, the analysis can include determining whether a local distance 4000 is greater than a predetermined maximum distance threshold. In the example shown in FIG. 40, the analysis result can comprise a local distance 4000 between a portion of the deformed intended appliance digital model 3802 and a portion of the lingual surface of the patient's gingiva of the OTA digital model 3804 that exceeds a predetermined maximum distance threshold. In some examples, the maximum distance threshold for a local distance between a portion of the deformed intended appliance digital model and a portion of the lingual surface of the patient's gingiva may be between about 0 mm and about 5 mm. If the local distance 4000 is greater than the maximum distance threshold, the process 3600 may modify one or more digital models (process portion 3618) to thereby modify the relative positions of the appliance in the installed form and the patient's gingiva. For example, the thickness of the gingival surface of the shape forming fixture digital model can be increased and/or decreased at one or more locations. The process 3600 may repeat with the modified digital model(s) to determine if the local distance 4000 falls below the maximum distance threshold and whether the modified digital model(s) are more favorable design(s).

It may be favorable to space an anchor of an appliance apart from a patient's gingiva to minimize irritation of the patient's gingiva due to the appliance. Consequently, in some embodiments, the analysis result can comprise a local distance 4000 between a portion of the deformed intended appliance digital model 3802 and a portion of the lingual surface of the patient's gingiva of the OTA digital model 3804 that is less than a predetermined minimum distance threshold. In some examples, the minimum threshold may be between about 0.00 mm and 0.5 mm. If the local distance 4000 is less than the minimum distance threshold, the process 3600 may modify one or more digital model(s) (process portion 3618). For example, the thickness of the gingival surface of the shape forming fixture digital model 1200 may be increased and/or decreased at one or more locations. Such a modification may alter the pre-installation form of the appliance. The process 3600 may repeat with the modified digital model(s) to determine if the local distance falls above the minimum threshold.

Figure 41:
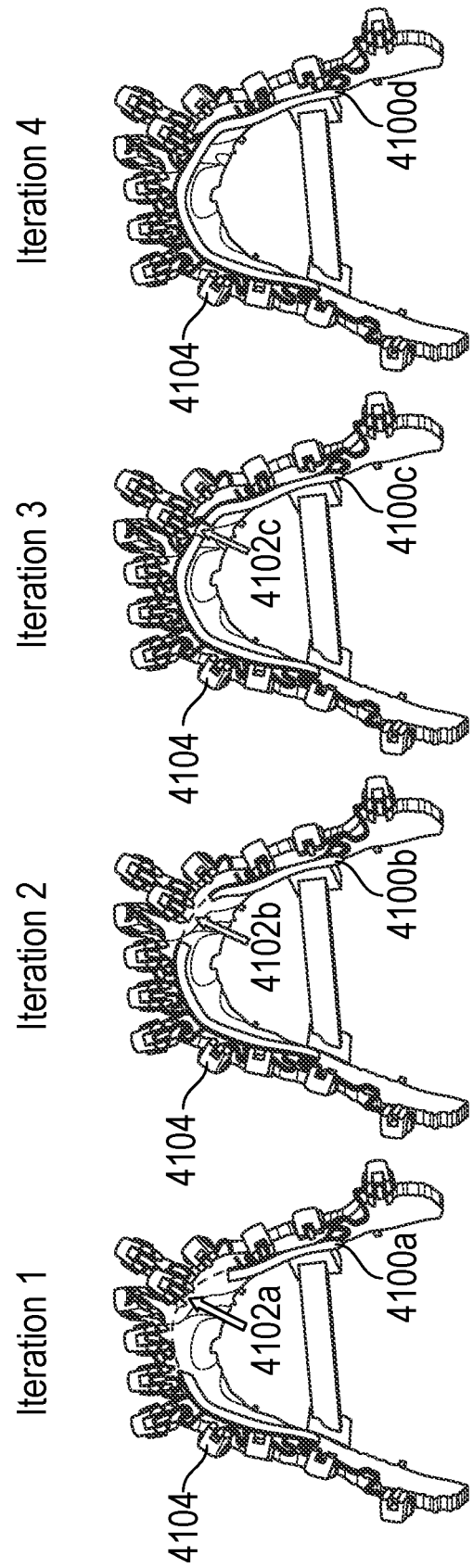
FIG. 41 illustrates an example of results from iterative finite element analyses.

According to some embodiments, the process 3600 can iteratively repeat until a favorable appliance design is obtained. For example, FIG. 41 depicts four deformed intended appliance digital models 4100a, 4100b, 4100c, and 4100d mated to an OTA digital model 4104 representing the patient's teeth in an original arrangement. A first appliance digital model 4100a has penetrated a gingival surface of the OTA digital model 4104 in a first intersecting region 4102a as a result of the second FEA. The process 3600 can modify one or more digital model(s) based on this analysis result (process portion 3618) and repeat process portions 3602 through 3616 with the modified digital model(s) until a finalized appliance design is obtained. For example, FIG. 41 shows a second appliance digital model 4100b that penetrates a gingival surface of the OTA digital model 4104 to a lesser extent than the first appliance digital model 4100a, forming a second intersection region 4102b that is smaller than the first intersection region 4102a. A third appliance digital model 2022c forms a third intersection region 4102c that is smaller than the first and second intersection regions 4102a, 4102b. A fourth appliance digital model 2502d depicted in FIG. 41 does not penetrate a gingival surface of the OTA digital model 4104 and may be a favorable appliance design. Based on the favorable fourth appliance digital model 2502d, the process 3600 can stop iteratively repeating and select a finalized appliance design. In some embodiments, a human operator can select a finalized appliance design. In some embodiments, a finalized appliance design can be selected automatically and/or by a human operator based on a quantitative metric such as, but not limited to, a change in an analysis result between iterations, a comparison of an analysis result to a predetermined threshold or parameter, etc. In addition, or alternatively, the process 3600 may stop repeating and select a finalized appliance design if a predetermined maximum number of iterations has been reached.

In some embodiments, the fixture digital model can be modified based on a final appliance design. For example, the gingiva portion of the fixture digital model can be modified such that the a lingual surface of the gingiva portion is tangent to the gingival-facing surface of the appliance when attachment portions of the appliance are positioned within and tangent to a base plane of securing portions of the fixture digital model.

Upon selection of a final appliance design and/or a final shape forming fixture design, the process 3600 can continue to process portion 3620 and output the planar appliance digital model, the shape forming fixture digital model, and/or the intended appliance digital model 3702. Based on the output in process portion 3620, the appliance and/or the shape forming fixture can be fabricated, for example using any of the techniques described previously herein.

VI. Selected Devices, Systems, and Methods for Manufacturing Orthodontic Appliances Based on Overcorrection and/or Compensation Parameters As previously described, the manufacturing process to create an orthodontic device (e.g., an orthodontic appliance or fixture) according to embodiments of the present technology can include obtaining data corresponding to an OTA of a patient, and then using the data to develop an FTA model in which the patient's teeth are in an optimal position. The FTA model can be used as a basis for creating a fixture (e.g., a heat treatment fixture) that generally corresponds to the FTA, but with one or more modifications (as discussed elsewhere herein). The fixture can then be used to form a 3D configuration of the appliance (e.g., a curved or contoured configuration of the appliance able to urge teeth from the OTA toward the FTA when installed in a patient's mouth). For example, as described elsewhere herein, a substantially planar configuration of the appliance may be manipulated and/or disposed over the fixture and then heat treated on the fixture such that the appliance assumes a 3D shape that generally conforms to the fixture.

Manufacturing the appliance in such a manner should enable the appliance to precisely replicate the FTA described above and, when installed, reposition a patient's teeth from the OTA to the desired FTA. However, in practice, certain factors may cause there to be a discrepancy between the desired FTA and the actual final arrangement of the patient's teeth after repositioning via the appliance. As described in more detail below, this discrepancy can be due to: (a) implementation considerations (e.g., a minimum threshold force needed to move the patient's teeth, and/or free play or tolerance between the appliance and securing member), (b) material properties of the appliance (e.g., plastic deformation, hysteresis, etc.), (c) irregularities associated with the manufacturing process, and/or (d) expected teeth movement (e.g., relapse) after repositioning. To mitigate these issues, embodiments of the present technology can account for these discrepancies and modify design parameters (e.g., via overcorrection or compensation) of the fixture and/or appliance during or prior to manufacturing thereof.

A person of ordinary skill in the art will recognize that while embodiments of the present technology related to overcorrection or compensation are described below as individual parameters or factors, any of the factors described may be combined in a single embodiment. For example, design or manufacturing of an appliance and/or fixture may consider both the minimum threshold force needed to move the patient's teeth as well as irregularities associated with the manufacturing process.

C. Considerations Related to Orthodontic Device Implementation

As previously described, orthodontic appliances of the present technology are generally designed and manufactured based at least in part on the forces (e.g., load/moment/magnitude and/or direction) needed to reposition a patient's teeth (e.g., individual teeth) from the OTA to a desired or optimal FTA. In some embodiments, these appliances may consider external factors acting thereon (e.g., the minimum threshold force needed to move a patient's teeth and/or the free play between the appliance and securing members), which in turn affect the necessary force(s) that the appliance and/or one or more portions thereof must provide on the patient's teeth to cause the desired repositioning to the FTA.

1. Minimum Threshold Force to Move a Patient's Teeth

As previously described, appliances of the present technology are configured to move a patient's teeth from the OTA along a path to a determined FTA. More specifically, individual arms of the appliance are configured to move a respective patient's tooth along a respective path from an original position to a respective final position. The force applied to a patient's teeth via the appliance, or in some embodiments the force applied to a patient's tooth via a corresponding arm of the appliance, is generally highest at or near the OTA, when the appliance is in a loaded or stressed state, and decreases as the patient's teeth approach the FTA, when the appliance is in an unloaded or unstressed state. Accordingly, when the patient's teeth approach the FTA, the appliance will generally be applying some minimal force to the teeth. However, due to various external factors, such as the root of a particular tooth or positioning of a tooth within the gingiva, there can be a minimum threshold force that must be overcome to move each tooth. That is, a force applied via an arm of the appliance on the tooth that is less than the minimum threshold force will not move the tooth. Therefore, if an appliance in its unloaded state is manufactured to resemble or otherwise correspond to the FTA without considering this minimum threshold, movement of the patient's teeth may cease prior to actually reaching the FTA.

Figure 42:
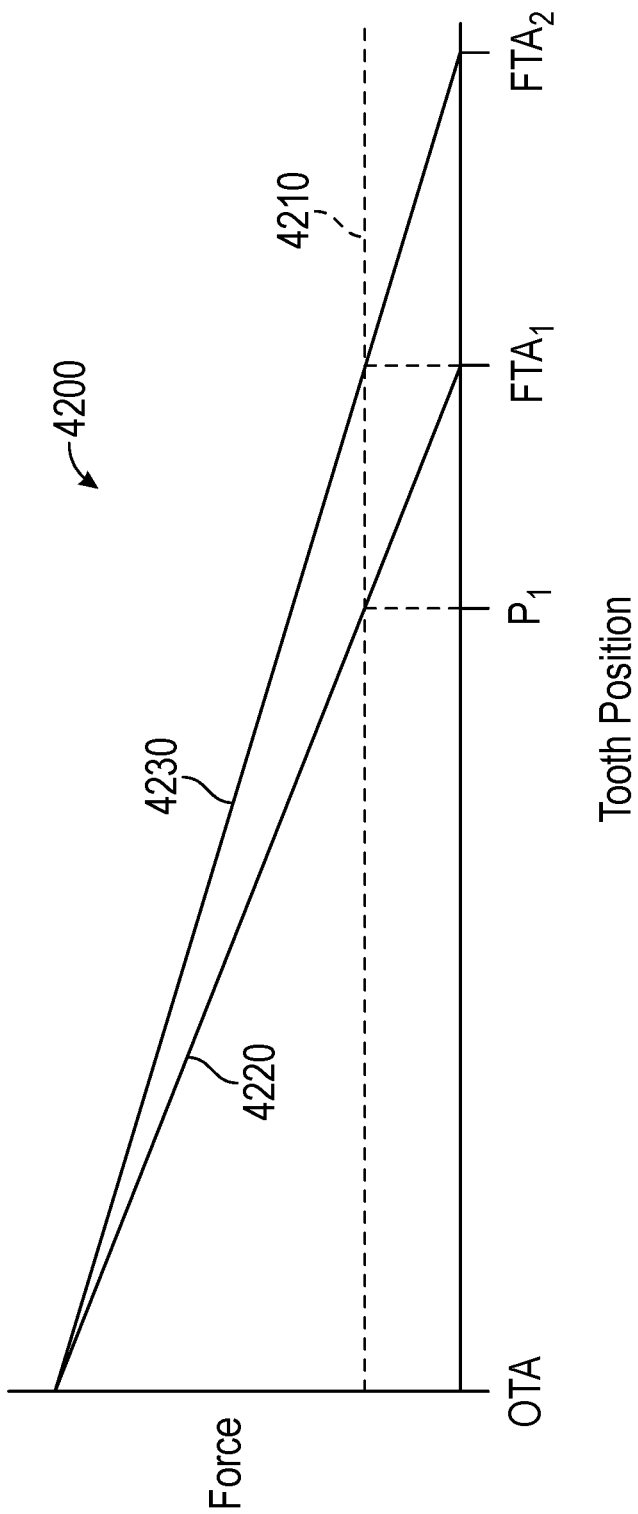
FIG. 42 is a plot showing the relationship between force applied to a patient's teeth and positioning of the patient's teeth.

To further illustrate this point, FIG. 42 is a plot 4200 showing the relationship between force applied to a patient's teeth on the y-axis, and positioning of the patient's teeth on the x-axis. As shown in FIG. 42, line 4210 corresponds to a minimum threshold force needed to move a patient's teeth, line 4220 corresponds to varying forces applied, e.g., via a first appliance, to the patient's teeth during movement from the OTA to a first final tooth arrangement ($FTA_1$), and line 4230 corresponds to varying forces applied, e.g., via a second appliance, to the patient's teeth during movement from the OTA to a second final tooth arrangement ($FTA_2$). In some embodiments, the minimum threshold force may be at least about 5 grams-force (GF), 10 GF, 15 GF, 20 GF, 25 GF, or 50 GF. The first appliance has an unloaded or unstressed state that corresponds to the first final tooth arrangement ($FTA_1$), which is an optimal tooth arrangement determined for the patient, and the second appliance has an unloaded state that corresponds to the second final tooth arrangement ($FTA_2$) different than the first final tooth arrangement ($FTA_1$).

As shown in FIG. 42, lines 4220, 4230 indicate a generally linear relationship between force applied to the patient's teeth and positioning thereof. However, a person of ordinary skill in the art will appreciate that in some embodiments the relationship between the applied force and positioning of the patient's teeth may be non-linear (e.g., exponential, logarithmic, etc.). Additionally or alternatively, in some embodiments the relationship between force applied to the patient's teeth and positioning thereof can be linear, non-linear, and/or constant depending on the strain of the appliance of portions thereof (e.g., the arm(s) of the appliance). For example, with regard to an appliance or arm comprising nitinol, the force applied to the patient's teeth via the nitinol appliance may be constant or nearly constant during a first portion of teeth movement and have a linear of non-linear relationship to the position of the patient's teeth during a second, different portion of teeth movement.

As indicated by line 4220 of FIG. 42, the first appliance (manufactured to have an unloaded configuration corresponding to the first final tooth arrangement ($FTA_1$)) will cause the patient's teeth to reposition from the OTA along a path toward the first final tooth arrangement ($FTA_1$). Such an appliance, when implanted within a patient's mouth and secured to securing members adhered to the patient's teeth (as previously described), will transition from a loaded configuration generally corresponding to the OTA toward an unloaded configuration generally corresponding to the first final tooth arrangement ($FTA_1$). However, due to the minimum threshold force ($T_{MIN}$) needed to move the patient's teeth (as shown by line 4210), the first appliance will be unable to move the patient's teeth all the way to the first final tooth arrangement ($FTA_1$), and instead will move the patient's teeth only until the force provided via the appliance is equal to the minimum threshold force ($T_{MIN}$), as represented by position (Pi) in FIG. 42.

Embodiments of the present technology can mitigate the above described issues by considering the minimum threshold force ($T_{MIN}$) when designing the orthodontic appliance. In some embodiments, an appliance may be designed and/or manufactured to have a second final tooth arrangement ($FTA_2$) in its unloaded configuration that is different that the first final tooth arrangement ($FTA_1$). When implanted within a patient's mouth and secured to securing members adhered to the patient's teeth, the second appliance is configured to reposition the patient's teeth from the OTA toward and/or to the first final tooth arrangement ($FTA_1$). In such embodiments, the second appliance is designed to provide the minimum threshold force ($T_{MIN}$) on the patient's teeth when the second appliance, which has an unloaded configuration corresponding to the second final tooth arrangement ($FTA_2$), assumes a configuration generally corresponding to the first final tooth arrangement ($FTA_1$). As shown in FIG. 42, the second appliance can be manufactured to have an unloaded configuration generally corresponding to the second final tooth arrangement ($FTA_2$). When implanted within a patient's mouth and secured to corresponding securing members, the second appliance will cause the patient's teeth to reposition from the OTA along a path toward the second final tooth arrangement ($FTA_2$), as indicated by line 4230. Due to the minimum threshold force ($T_{MIN}$), movement of the patient's teeth via the second appliance ceases when the second appliance generally assumes the first final tooth arrangement ($FTA_1$) and is providing a force on the patient's teeth approximately equal to the minimum threshold force ($T_{MIN}$). As shown in FIG. 42, such an appliance is configured to apply a nonzero force on the patient's teeth when they become repositioned to the first tooth arrangement ($FTA_1$). The nonzero force may be (i) at least about 5 GF, 10 GF, 15 GF, 20 GF, 25 GF, or 50 GF, and/or (ii) no more than 500 GF, 400 GF, 300 GF, 250 GF, 100 GF, or 50 GF.

The above description regarding the minimum threshold force applies to the appliance and patient's teeth generally, but the same or similar principles also apply to individual arms of the appliance and individual teeth of the patient. For example, each arm of the appliance may be configured to move a corresponding patient tooth such that the force provided via the arm is equal to the minimum threshold force ($T_{MIN}$) when the position of the arm generally corresponds to that of a corresponding arm in the first final tooth arrangement ($FTA_1$). Moreover, the minimum threshold needed to move a particular tooth may be slightly different from other teeth, e.g., depending on the type of tooth (e.g., molar or incisor), the position of the tooth (e.g., relative to the adjacent gingival surface), and/or other factors. As such, the distinct minimum threshold force for individual teeth may each be accounted for when designing the corresponding portions (e.g., arms, biasing portions, attachment portions, etc.) of the appliance.

Figure 43:
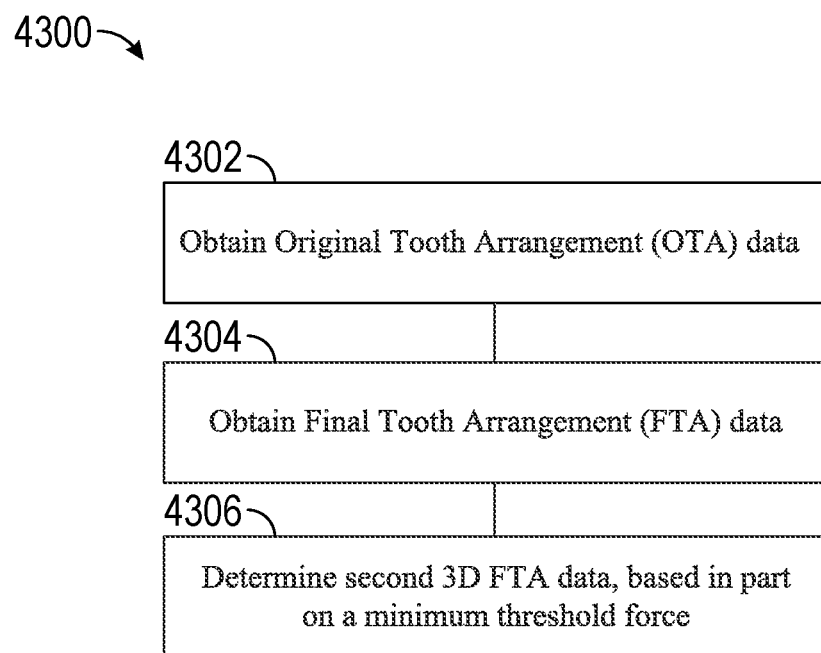
FIG. 43 is a flow diagram of a method for determining data corresponding to an arrangement of an orthodontic device in accordance with embodiments of the present technology.

FIG. 43 is a flow diagram of a method 4300 for determining a dataset associated with an arrangement of an orthodontic device, in accordance with embodiments of the present technology. The method 4300 includes obtaining data (e.g., a first input) corresponding to an OTA of a patient (process portion 4302), and obtaining data (e.g., a second input) corresponding to a first FTA of the patient (process portion 4304). As described elsewhere herein, the OTA can be based on a scan of the patient's teeth, and the FTA can be determined and/or provided by an operator (e.g., a clinician, orthodontist, or technician) based on the OTA and a desired optimal positioning of the teeth.

The method 4300 can further include determining data (e.g., a third input) corresponding to a second FTA (different than the first FTA), based in part on a minimum threshold force needed to move at least one tooth of the patient (process portion 4306). The minimum threshold force may be a predetermined parameter, in that the minimum threshold force is known or can be determined prior to manufacturing of the device. In some embodiments, the minimum threshold force may correspond to a modification applied generally to the appliance (e.g., the same modification is applied to each individual arm), or a plurality of distinct modifications applied to each individual arm of the appliance. Additionally or alternatively, the minimum threshold may be determined based on factors common to all patients generally or on factors unique to a particular patient. For example, in some embodiments the minimum threshold considered may be based on the general anatomy of human teeth, e.g., with molars or larger teeth having a greater minimum threshold than that of incisors or smaller teeth. As another example, in some embodiments the minimum threshold considered may be based on the patient's particular gingiva (e.g., the gingival surface) surrounding individual ones of the patient's teeth.

In some embodiments, the method 4300 may omit process portion 4306 and only include a single FTA that considers the minimum threshold force. In such embodiments, the method 4300 may include obtaining first data corresponding to an OTA of a patient, and providing second data corresponding to an FTA of the patient, where the second data is based at least in part on a minimum threshold force. In some embodiments, the method 4300 can further comprise manufacturing the fixture and/or the appliance according to at least the data corresponding to the second FTA. Such manufacturing of the fixture and/or the appliance can correspond to the manufacturing processes described elsewhere herein.

2. Free Play Between the Appliance and Securing Member

As previously described, appliances of the present technology are configured to move a patient's teeth from the OTA along a path to a determined FTA. More specifically, individual arms of the appliance are configured to move a respective patient's tooth along a respective path from an original position to a respective final position. As also previously described, the individual arms are attached to a corresponding securing member (e.g., a bracket) adhered to individual teeth of the patient. Accordingly, the force applied via the individual arms of the appliance is provided to the corresponding securing member, and therein to the corresponding individual patient's tooth to cause repositioning. In this regard, because the securing members are a separate component from the appliance, there will often be some free play (e.g., gap, wiggle, or misfit, for example due to manufacturing tolerances) between each individual arm and the corresponding securing member. In some embodiments, the free play is the same for each individual arm and corresponding securing member. Moreover, in some embodiments the free play is different for at least one of the individual arms and corresponding securing member relative to other individual arms and corresponding securing members. As a result of the free play, the force provided via the individual arm may not be entirely transferred to the corresponding tooth because a portion of the force is lost via the free play. For example, if an individual arm is configured to move the corresponding tooth a given distance in a particular direction (e.g., the mesial, distal, occlusal, gingival, buccal, and/or lingual direction) and/or a given angle of rotation about a particular axis (e.g., about the mesiodistal axis, occlusogingival axis, and/or buccolingual axis), the free play can prevent the corresponding tooth from moving the full distance and/or the full angle of rotation.

Figure 44C:
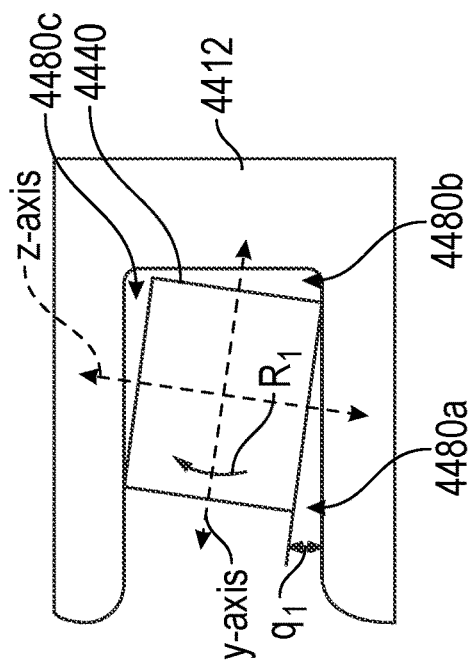
FIG. 44C is an enlarged side view of the securing member and appliance shown in FIG. 44B, in accordance with embodiments of the present technology.
Figure 44B:
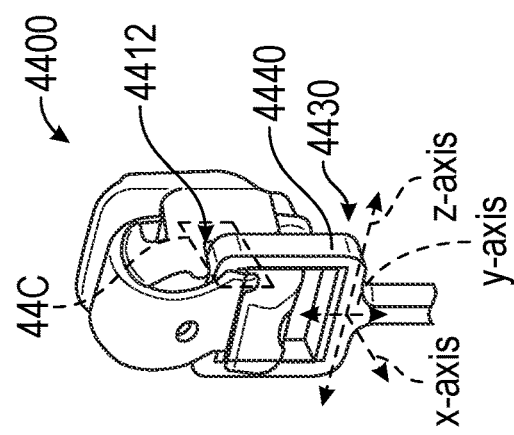
FIG. 44B is a perspective view of a portion of an arm of an orthodontic appliance coupled to the securing member shown in FIG. 44A.
Figure 44A:
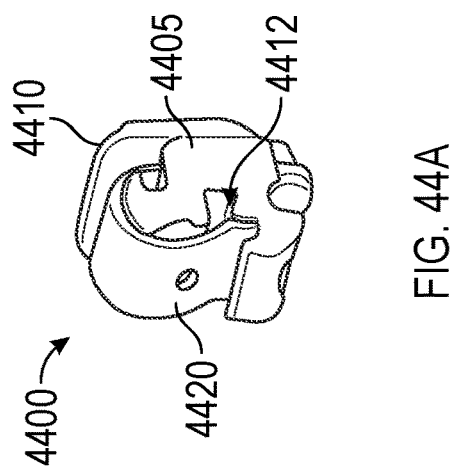
FIG. 44A is a perspective view of a securing member.

FIG. 44A is a perspective view of a securing member 4400, and FIG. 44B is a perspective view of a portion of an arm 4430 of an orthodontic appliance coupled to the securing member 4400 shown in FIG. 44A, in accordance with embodiments of the present technology. As shown in FIG. 44A, the securing member 4400 includes (i) a body region 4405 having a back side or surface 4410 to be attached to a patient's tooth, (ii) a slot or recess 4412 within the body region 4405 and configured to receive a portion of an orthodontic appliance or arm, and (iii) a moveable clip portion 4420 coupled to the body region 4405 configured to secure the portion of the appliance or arm 4430 when positioned within the slot 4412. The slot 4412 can form a three-sided or U-shaped opening. As shown in FIG. 44B, the arm 4430, or more particularly an attachment portion 4440 of the arm 4430, is disposed within the slot 4412. As also shown in FIG. 44B, the x-axis may generally correspond to the buccolingual axis, the y-axis may generally correspond to the occlusogingival axis, and the z-axis may generally correspond to the mesiodistal axis.

FIG. 44C is an enlarged cross-sectional side view of the securing member 4400 and arm 4430 shown in FIG. 44B, and is meant to further illustrate the previously described issue associated with the free play between the securing member 4400 and attachment portion 4440. As shown in FIG. 44C, the attachment portion 4440 is disposed within the slot 4412, but one or more gaps 2880 (individual gaps identified as 4480a-c) exist between the attachment portion 4440 and corresponding adjacent surfaces of the slot 4412. As such, rotation of the attachment portion 4440, e.g., in a first direction ($R_1$) causes the attachment portion 4440 to rotate relative to the slot 4412, and thus relative to the securing member 4400. That is, the initial rotation of the attachment portion 4440, as indicated by ($\theta_1$), is not translated to the securing member 4400 and/or the corresponding tooth of the patient. Such a translation issue may occur (e.g., simultaneously occur) in one or more directions (e.g., the mesial, distal, occlusal, gingival, buccal, and/or lingual directions) and/or about one or more axes (e.g., the mesiodistal axis, occlusogingival axis, and/or buccolingual axis). For example, free play between the attachment portion and securing member may allow some rotation of an attachment portion relative to the securing member about the mesiodistal axis, the occlusogingival axis, and/or the buccolingual axis. As a result, such rotation would not be translated to the corresponding tooth because of the gap between the attachment portion and corresponding securing member. As another example, free play between the attachment portion and securing member may allow some initial movement of the attachment portion relative to the securing member along the mesiodistal axis, the occlusogingival axis, and/or the buccolingual axis. As a result, such movement would not be translated to the corresponding tooth because of the gap between the attachment portion and corresponding securing member.

FIG. 45A is a perspective view of another securing member 4500 configured in accordance with embodiments of the present technology, and is another example of the above-described concepts regarding free play between an arm of an appliance and a securing member. As shown in FIG. 45A, the securing member 4500 includes (i) a body region 2905 having a first, back side or surface to be attached to a patient's tooth and a second, opposing side or surface, and (ii) one or more coupling arms 4510 attached to the second side of the body region 2905. Each coupling arm 4510 can include a first, elongate portion 4512 fixed to the body region 2905, and a second, coupling portion 4514 extending from the first portion 4512 and that is partially spaced apart from the body region 2905. The coupling portion 4514 can define a slot or opening 4515 configured to receive and partially surround a portion of an orthodontic appliance or arm (as shown in FIG. 45B). In some embodiments, the securing member 4500 may be a commercially-available 2D® Lingual Bracket manufactured by Bernhard Foerster GmbH.

FIG. 45B is a perspective view of a portion of an arm 4530 of an orthodontic appliance coupled to the securing member 4500 shown in FIG. 45A. As shown in FIG. 45B, the arm 4530 includes an attachment portion or end portion 4540 having a region or extension 4565 disposed within the slot 4515. As also shown in FIG. 45B, when the arm 4530 and securing member 4500 are installed within a patient's mouth, the x-axis may generally correspond to the buccolingual axis, the y-axis may generally correspond to the occlusogingival axis, and the z-axis may generally correspond to the mesiodistal axis.

FIG. 45C is an enlarged side view of the securing member 4500 and portion of the attachment portion 4540 shown in FIG. 45B, and is meant to further illustrate the previously described issue associated with the free play between the securing member 4500 and arm 4530. As shown in FIG. 45C, the region 4565 of the attachment portion 4540 is disposed adjacent the securing member 4500 such that one or more gaps 2980 (individual gaps identified as 4580a, 4580b, 4580c) exist between the region 4565 and corresponding adjacent surfaces of the coupling arm 4510 of the securing member 4500. As such, free play between the attachment portion 4540 and securing member 4500 may allow some movement of the region 4565 relative to the coupling arm 4510 along the mesiodistal axis, the occlusogingival axis, and/or the buccolingual axis. For example, as shown in FIG. 45C, free play between the attachment portion 4540 and securing member 4500 may allow movement of the region 4565 relative to the coupling arm 4510 by a distance ($D_1$) along the y-axis and/or a distance ($D_2$) along the x-axis. As a result, such movement would not be translated to the corresponding tooth because of the one or more gaps 2980. As another example, rotation of the region 4565 in a first direction ($R_1$) can cause the region 4565 to rotate relative to the coupling arm 4510, and thus the securing member 4500. That is, the initial rotation of the region 4565 may not be translated to the securing member 4500 and/or the corresponding tooth of the patient. Such a translation issue may occur (e.g., simultaneously occur) in one or more directions (e.g., the mesial, distal, occlusal, gingival, buccal, and/or lingual directions) and/or about one or more axes (e.g., the mesiodistal axis, occlusogingival axis, and/or buccolingual axis). For example, free play between the attachment portion 4540 and securing member 4500 may allow some rotation of the attachment portion 4540 relative to the securing member 4500 about the mesiodistal axis, the occlusogingival axis, and/or the buccolingual axis. As a result, such rotation would not be translated to the corresponding tooth because of the gap between the attachment portion 4540 and corresponding securing member 4500.

Figure 46:
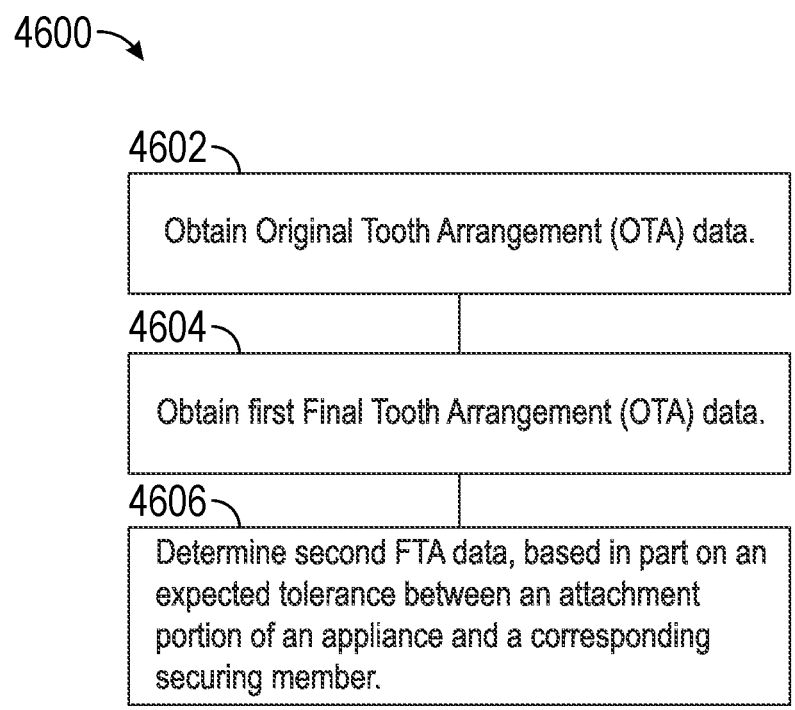
FIG. 46 is a flow diagram of a method for determining data corresponding to an arrangement of an orthodontic device, in accordance with embodiments of the present technology.

Embodiments of the present technology can mitigate this issue (as described with reference to FIGS. 28A-29C) associated with free play between the attachment portion and securing member by considering free play when designing the orthodontic device. FIG. 46 is a flow diagram of a method 4600 for generating design parameters and/or manufacturing an orthodontic appliance or related fixture, in accordance with embodiments of the present technology. The method 4600 includes obtaining data corresponding to an OTA of a patient (process portion 4602), and obtaining data corresponding to a first FTA of the patient (process portion 4604). As described elsewhere herein, the OTA can be based on a scan of the patient's teeth, and the FTA can be determined and/or provided by the operator based on the OTA and a desired optimal positioning of the teeth.

The method 4600 can further include determining data corresponding to a second FTA (different than the first FTA), based in part on an expected free play between an attachment portion of an appliance and a corresponding securing member (process portion 4606). In some embodiments, the expected free play may be a predetermined parameter (e.g., based on the attachment portion and securing member used), in that the expected free play is known or can be determined prior to manufacturing of the appliance. In some embodiments, the expected free play may correspond to a dimension or angle that causes the design (e.g., shape, thickness, type of spring, etc.) of the appliance or portions thereof (e.g., the arms, biasing portions, attachment portions, etc.) to be modified. For example, if the expected free play between an attachment portion and securing member is 15° in a first direction (e.g., a direction about the mesiodistal axis, occlusogingival axis, and/or buccolingual axis) and the total rotation in the first direction required for a particular tooth (e.g., from the OTA to the first FTA) is 45°, then the arm (e.g., the attachment portion) of the appliance may be designed to rotate 60° in the first direction. In doing so, the arm or attachment portion, when coupled to the corresponding tooth via the corresponding securing member, will rotate 15° relative to the corresponding securing member, and then will rotate 45° along with the corresponding securing member and corresponding tooth, as desired. As previously described, the free play may be adjusted in multiple directions and/or about multiple axes simultaneously for an individual arm. Additionally or alternatively, the free play for each arm of the appliance may be uniquely adjusted relative to the other arms.

In some embodiments, the method 4600 may omit process portion 4606 and only include a single FTA that considers the expected free play. In such embodiments, the method 4600 may include receiving first data corresponding to an OTA of a patient, and providing second data corresponding to an FTA of the patient, where the second data is based at least in part on the expected free play between an attachment portion of an appliance and a corresponding securing member or portion thereof.

In some embodiments, the method 4600 can further comprise manufacturing the fixture and/or the appliance according to at least the data corresponding to the second FTA. Such manufacturing of the fixture and/or the appliance can correspond to the manufacturing processes described elsewhere herein.

D. Accounting for Material Properties of the Appliance

Appliances of the present technology are configured to move a patient's teeth from the OTA along a path to a determined and optimal FTA. As previously described, an appliance may be manufactured to have a configuration that in its unloaded or unstressed state generally corresponds to the FTA of the patient's teeth. The appliance is implanted within a patient's mouth and individual arms of the appliance are coupled to corresponding securing members adhered to the patient's teeth. As the individual arms are coupled to the corresponding securing member on the patient's teeth in the OTA, the appliance assumes a loaded or stressed configuration. In this loaded configuration, the appliance is often in its most stressed state and thus is most likely, if at all, to experience plastic deformation. If plastic deformation occurs, the individual arm may not transition from the OTA to the FTA along the desired path and/or may be unable to provide the necessary force upon the corresponding tooth. More generally, plastic deformation will limit treatment efficacy of the patient's teeth and prevent or inhibit the teeth from reaching the FTA.

Embodiments of the present technology can mitigate these issues by considering plastic deformation, or more particularly avoiding plastic deformation, when designing the orthodontic appliance and/or fixture. As previously described, embodiments of the present technology may determine the path of a patient's teeth from the OTA to the FTA. As such, the path of the appliance from a first configuration generally corresponding to the OTA to a second configuration generally corresponding to the FTA is also known. Based on the expected path of the individual arms of the appliance and the material(s) used to form the appliance (e.g., the arms, biasing portions, attachment portion, etc.), embodiments of the present technology can determine, and if necessary avoid, the appliance's yield strength at which plastic deformation occurs for each arm. For example, embodiments of the present technology may be able to simulate the stress to be experienced by individual arms of an appliance when in the first configuration generally corresponding to the OTA, or any other configuration between the OTA and FTA. If the stress experienced by one of the arms in any such a configuration is expected to be above the yield strength for the material of the arm, embodiments of the present technology may then adjust one or more parameters of the arm such that the yield strength is not exceeded. In some embodiments, altering one or more parameters of the arm can include altering the shape, configuration, and/or dimension (e.g., length, width, and/or thickness) of any portion of the appliance (e.g., the anchor, arms, and/or biasing portions). Altering one or more of these parameters can increase the yield strength of the arm to be greater than the highest stress expected to be experienced. As but one example, certain biasing portions (e.g., spring designs) can experience a greater stress than other biasing portions. Accordingly, if movement of an arm from the OTA to the FTA is determined to cause the yield strength of the arm to be exceeded, embodiments of the present technology may alter the biasing portion of the arm to increase its yield strength and thereby avoid plastic deformation.

Additionally or alternatively to altering a portion of the appliance in response to determining that a yield strength may be exceeded, embodiments of the present technology may alter the path of a patient's tooth from the OTA such that the yield strength of the appliance is not exceeded along the path. That is, if moving a patient's tooth from an OTA to an FTA along a first path will result in yield strength being exceeded, embodiments of the present technology may instead alter the appliance, or more particularly the corresponding arm of the appliance, such that the patient's tooth is moved from the OTA to the FTA along a second path, different than the first path, which will result in the yield strength not being exceeded.

Figure 47:
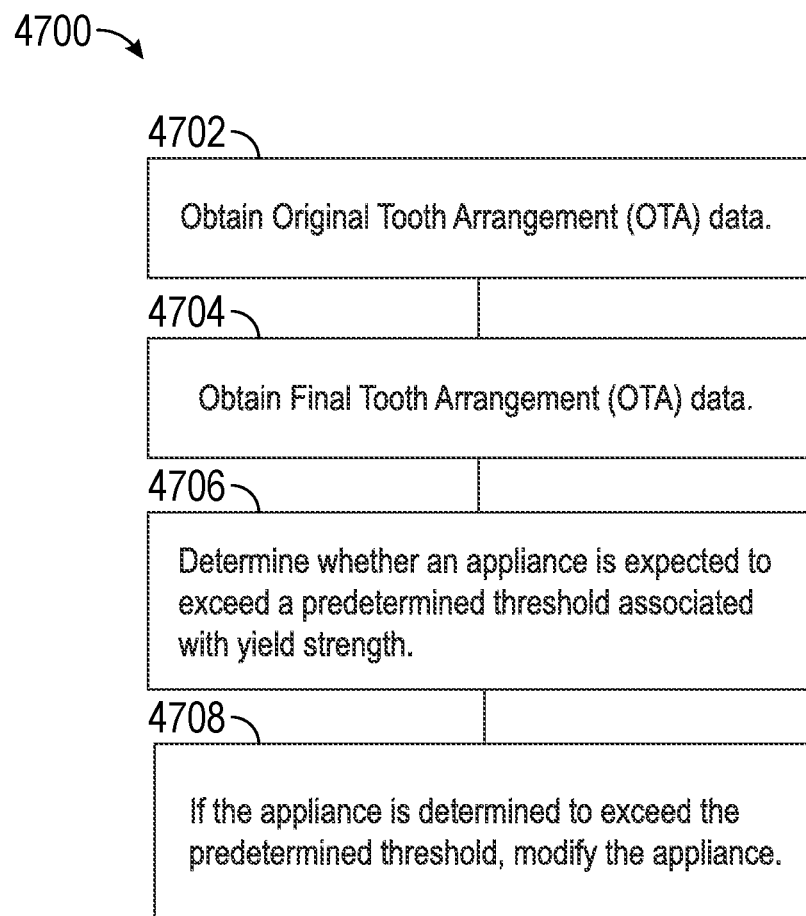
FIG. 47 is a flow diagram of a method for determining data corresponding to an arrangement of an orthodontic device, in accordance with embodiments of the present technology.

FIG. 47 is a flow diagram of a method 4700 for generating design parameters and/or manufacturing an orthodontic appliance or related fixture, in accordance with embodiments of the present technology. The method 4700 includes obtaining data corresponding to an OTA of a patient (process portion 4702), and obtaining data corresponding to an FTA of the patient (process portion 4704). As described elsewhere herein, the OTA can be based on a scan of the patient's teeth, and the FTA can be determined and/or provided by the operator based on the OTA and a desired positioning of the teeth.

The method 4700 can further include determining whether an appliance is expected to exceed a predetermined threshold associated with yield strength (process portion 4706). In some embodiments, process portion 4706 can include determining whether an appliance configured to transition from a first configuration (e.g., corresponding to the OTA) toward a second configuration (e.g., corresponding to the FTA) is expected to exceed a yield strength of the appliance. Additionally or alternatively, determining whether the appliance is expected to exceed the yield strength can include determining whether any portion of the appliance (e.g., individual arms, biasing portions, attachment portions, etc.) is expected to exceed the yield strength. As such, embodiments of the present technology may determine the stress experienced by the appliance or any portion thereof when in the first configuration (e.g., at the OTA), the second configuration (e.g., at the FTA), and/or a plurality of discrete points along the path between the first and second configurations (e.g., at intermediate tooth arrangements (ITA)).

In some embodiments, determining whether the appliance is expected to exceed the yield strength can be based on hysteresis behavior, e.g., of the material(s) forming the appliance. With regard to the present technology, hysteresis can alter the path taken by an arm of the appliance depending on whether the arm is experiencing compression or tension along its path from the OTA to the FTA. For example, an arm comprising Nitinol or nickel-titanium alloy may follow a different stress-strain curve in compression than the arm would in tension. Accordingly, in addition to or in lieu of the determining the expected stress of the appliance or any portion thereof at discrete points between and including the OTA and FTA, embodiments of the present technology may consider the configuration of the appliance or any portion thereof prior to the appliance assuming these discrete points.

In some embodiments, the method 4700 can include, if the appliance is expected to exceed the predetermined threshold, modifying the appliance such that the yield strength is not exceeded (process portion 4708). Modifying the appliance in such a manner can include altering (i) the shape, configuration, and/or dimension (e.g., length, width, and/or thickness) of the appliance (e.g., the anchor, arms, and/or biasing portions), and/or (ii) the material of the arm. Altering one or more of these parameters can increase the yield strength of the arm to be greater than the highest stress expected to be experienced, thereby ensuring the appliance (or any portion thereof) is not plastically deformed in a manner that limits treatment efficacy of the patient's teeth. As an example, if it is determined that an appliance would exceed a predetermined threshold, a single biasing portion (e.g., spring) of the appliance could be replaced with two or more lower load biasing portions. Such a replacement may be performed for each arm of the appliance that is expected to exceed the predetermined threshold.

In some embodiments, the method 4700 can further comprise manufacturing the fixture and/or the appliance. Such manufacturing of the fixture and/or the appliance can correspond to the manufacturing processes described elsewhere herein.

E. Accounting for Manufacturing Irregularities

As previously described, the 3D configuration of the orthodontic appliance can be created by bending a substantially planar configuration of the appliance to assume the 3D configuration that generally corresponds to the FTA. In some embodiments, as described elsewhere herein, this bending is accomplished by attaching (e.g., via ligature wire) a substantially planar configuration of the appliance to a shape forming fixture that generally corresponds to the FTA (potentially with slight modifications, as previously described), and then heat treating the substantially planar configuration such that the appliance assumes and remains in the 3D configuration after heat treatment. In some embodiments, the appliance is made at least in part from a superelastic material (e.g., Nitinol). In such embodiments, the heat treatment process previously described may be relatively mild to ensure the superelastic material after heat treatment substantially maintains its elastic properties. However, as a result of such mild heat treatment, the appliance in the 3D configuration or portions thereof can tend to retract partially back toward the previous substantially planar configuration after the heat treatment process is complete and the appliance is detached from the fixture. For example, individual arms of the appliance in the 3D configuration may move in a direction (e.g., a labial, buccal, gingival, occlusal, mesial, and/or distal direction) or about an axis (e.g., a mesiodistal axis, occlusogingival axis, and/or buccolingual axis) after the appliance is detached from the fixture after heat treatment. As a result, the heat treated 3D configuration of the appliance may not precisely correspond to the shape of the fixture, or more generally, the FTA. Such a discrepancy may cause individual arms of the appliance to apply a force (e.g., a direction and/or magnitude) different than the intended force and thus prevent the patient's teeth from reaching the desired FTA.

Figure 48:
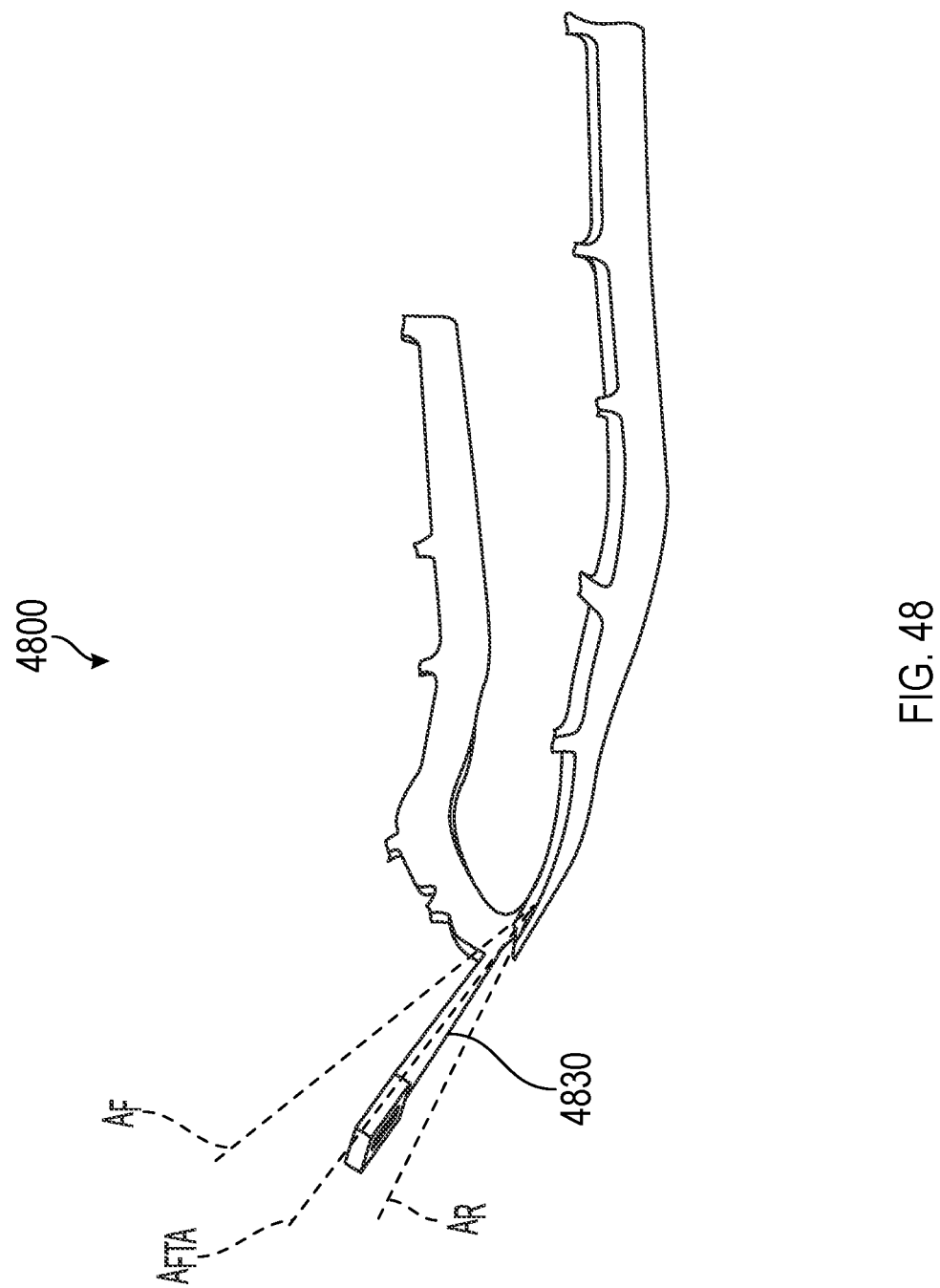
FIG. 48 is a side perspective view of an orthodontic appliance, configured in accordance with embodiments of the present technology, in accordance with embodiments of the present technology.

FIG. 48 is a side perspective view of an orthodontic appliance 4800 in accordance with embodiments of the present technology, and is meant to further illustrate the issue regarding an appliance retracting after heat treatment. For illustrative purposes, only a single arm 4830 of the appliance 4800 is shown, but a person of ordinary skill in the art will appreciate that the principles described herein can apply to any arm 4830 of the appliance (e.g., the appliance 100 shown in FIG. 16). As shown in FIG. 48, the arm 4830 extends along an axis ($A_{FTA}$), which corresponds to the FTA of the patient's teeth. As previously described, due at least in part to the material of the appliance, when the appliance is heat treated over the fixture and detached therefrom, the appliance tends to retract to a previous position other than that of the FTA. As shown in FIG. 48, axis ($A_R$) corresponds to the arrangement the appliance would have after retracting, e.g., from the axis ($A_{FTA}$). That is, if the fixture was heat set while the arm 4830 was positioned along axis $A_{FTA}$, the arm 4830 of the resulting appliance after retraction would be positioned along axis ($A_R$), which is deflected away from the axis ($A_{FTA}$) in which it was heat set and/or toward a more planar configuration. Such an arm, or appliance generally, would be spaced apart from the axis ($A_{FTA}$) and thus, when coupled to a securing member adhered to a patient's tooth, would provide a force different than that intended and thus prevent the patient's teeth from reaching the FTA.

Embodiments of the present technology can mitigate this issue by considering the material properties of the appliance and irregularities associated with heat treatment, or more generally the manufacturing process, when designing the orthodontic appliance and/or fixture. For example, embodiments of the present technology may design and/or manufacture an appliance to have a configuration that retracts after heat treatment to have a configuration generally corresponding to the FTA. As shown in FIG. 48, axis ($A_F$) corresponds to the arrangement of the fixture and/or the appliance after heat treatment and before the appliance is detached from the fixture. After heat treatment and after being detached from the fixture, the arm 4830 of the appliance 4800 may generally retract from the axis ($A_F$) to the axis ($A_{FTA}$), which corresponds to the FTA of the patient's teeth. Accordingly, the axis ($A_F$) can correspond to a position that enables the arm 4830 of the appliance 4800 to have an arrangement corresponding to the FTA for the corresponding tooth after the appliance has been heat treated, while also maintaining the desirable elastic properties of the material, e.g., to reposition the patient's teeth to the FTA. Stated differently, if a fixture is designed to have an arrangement corresponding to the axis ($A_F$), the resulting appliance formed via the fixture after the expected retraction can have an arrangement corresponding to or positioned along the axis ($A_{FTA}$). In some embodiments, the amount of retraction from the axis ($A_F$) to the axis ($A_{FTA}$) may be the same or different than the amount of retraction from the axis ($A_{FTA}$) to the axis ($A_R$). Accordingly, this varying amount of retraction can be considered during the manufacturing process, e.g., when designing the fixture.

Figure 49:
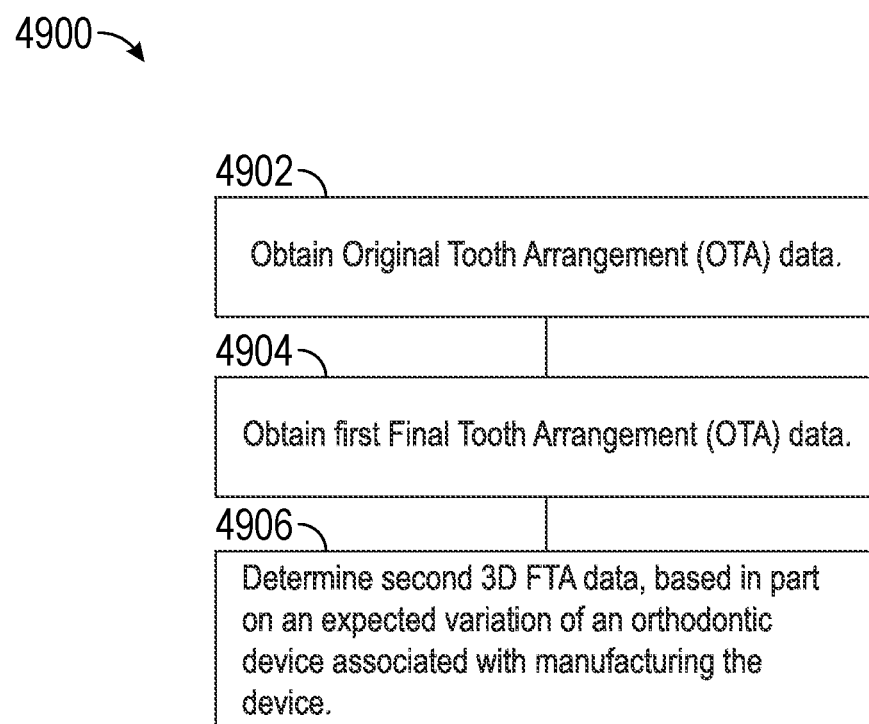
FIG. 49 is a flow diagram of a method for determining data corresponding to an arrangement of an orthodontic device, in accordance with embodiments of the present technology.

FIG. 49 is a flow diagram of a method 4900 for generating design parameters and/or manufacturing an orthodontic appliance or related fixture, in accordance with embodiments of the present technology. The method 4900 includes obtaining data corresponding to an OTA of a patient (process portion 4902), and obtaining data corresponding to a first FTA of the patient (process portion 4904). As described elsewhere herein, the OTA can be based on a scan of the patient's teeth, and the FTA can be determined and/or provided by the operator based on the OTA and a desired positioning of the teeth.

The method 4900 can further include determining data corresponding to a second FTA (different than the first FTA), based on an expected variation of an orthodontic device associated with manufacturing the device (process portion 4906). The expected variation can correspond to the expected different position or arrangement of the retracted appliance after heat treatment (as previously described) relative to the position or arrangement of the FTA. For example, if the position of a particular arm of the retracted appliance is spaced apart (e.g., in a lingual, occlusal, and/or distal direction) from the position of the corresponding arm in the FTA, then the expected variation, and therein the data corresponding to the second FTA, may correspond to the positional difference between the arm in the retracted position and the arm in the second FTA position. The expected variation may be a predetermined parameter, in that the expected variation is known or can be determined prior to manufacturing of the appliance. In some embodiments, the expected variation may be based on one or more factors including (i) the shape, configuration, and/or dimension (e.g., length, width, and/or thickness) of the appliance (e.g., the anchor, arms, and/or biasing portions), (ii) the material(s) of the appliance, (iii) the type of heat treatment applied or expected to be applied (e.g., maximum temperature of the heat treatment, elapsed time of heat treatment, etc.), and/or (iv) other aspects of the particular patient's dentition. In some embodiments, the expected variation may be unique to each arm of the appliance. As such, the expected variation may correspond to different values or modifications made to each arm (e.g., each biasing portion, attachment portion, etc.).

In some embodiments, the method 4900 may omit process portion 4906 and only include a single FTA that considers the expected variation of the appliance. In such embodiments, the method 4900 may include receiving first data corresponding to an OTA of a patient, and providing second data corresponding to an FTA of the patient, where the second data is based in part on the expected variation of the appliance or fixture associated with manufacturing, as described above.

In some embodiments, the method 4900 can further comprise manufacturing the fixture and/or the appliance according to at least the data corresponding to the second FTA. Such manufacturing of the fixture and/or the appliance can correspond to the manufacturing processes described elsewhere herein.

F. Accounting for Expected Teeth Movement after Repositioning

Appliances of the present technology are configured to reposition a patient's teeth from the OTA along a path to a determined and optimal FTA. After reaching the FTA, a patient's teeth may experience orthodontic relapse and move toward their previous position (e.g., the OTA) and thus away from their optimal position. For example, the patient's teeth may generally move in a partial buccal direction and/or a partial occlusal direction after the teeth are repositioned via the appliance to the FTA. As such, the patient's teeth after relapse may no longer resemble the FTA. Retainers or other devices may be used to prevent such relapse, however for multiple reasons (e.g., lack of patient compliance) these devices are often ineffective.

Embodiments of the present technology can mitigate these issues by considering orthodontic relapse when designing the orthodontic appliance and/or fixture. As previously described, the 3D configuration of the orthodontic appliance can be created by bending a substantially planar configuration of the appliance to assume a 3D configuration that generally corresponds to the FTA. In some embodiments, this bending is accomplished by attaching a substantially planar configuration of the appliance to a fixture that generally corresponds to the FTA (with slight modifications, as previously described), and then heat treating the substantially planar configuration such that the appliance assumes and remains in the 3D configuration. In order to account for orthodontic relapse after repositioning a patient's teeth to the FTA, embodiments of the present technology can determine the amount of relapse expected to occur, and alter the design of the appliance and/or fixture accordingly.

Figure 50:
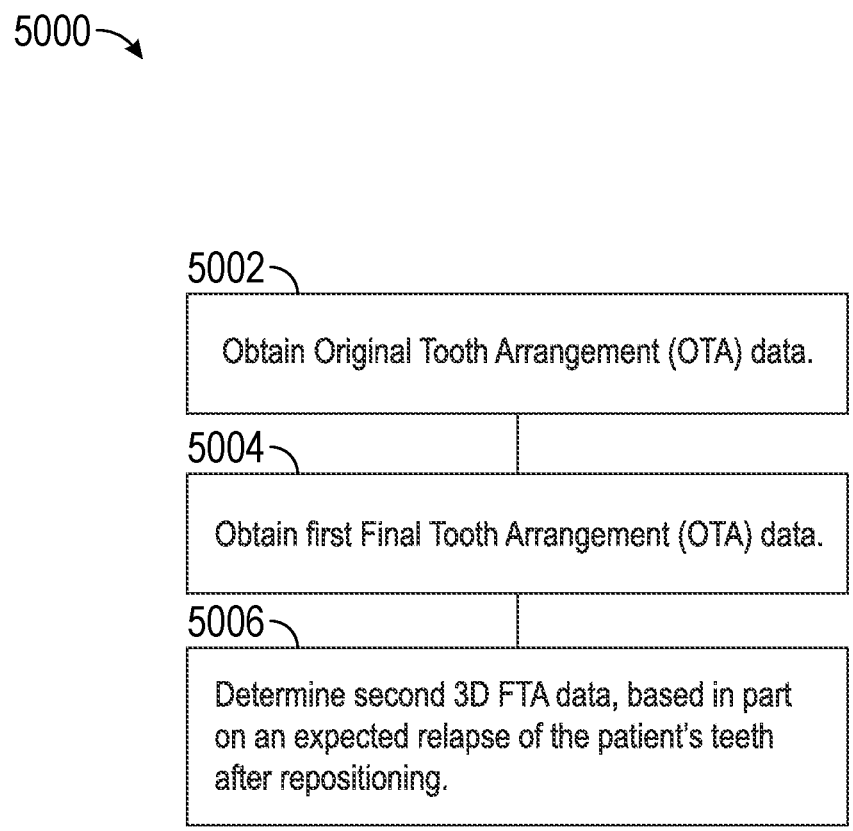
FIG. 50 is a flow diagram of a method for determining data corresponding to an arrangement of an orthodontic device, in accordance with embodiments of the present technology.

FIG. 50 is a flow diagram of a method 5000 for generating design parameters and/or manufacturing an orthodontic appliance or related fixture, in accordance with embodiments of the present technology. The method 5000 includes obtaining data corresponding to an OTA of a patient (process portion 5002), and obtaining data corresponding to a first FTA of the patient (process portion 5004). As described elsewhere herein, the OTA can be based on a scan of the patient's teeth, and the FTA can be determined and/or provided by the operator based on the OTA and a desired optimal positioning of the teeth.

The method 5000 can further include determining data corresponding to a second FTA (different than the first FTA), based in part on an expected relapse of the patient's teeth after repositioning, e.g., to the first FTA and/or second FTA (process portion 5006). The second FTA may correspond to a tooth arrangement wherein the expected relapse causes the patient's teeth to transition from the second FTA to the first FTA, which is the optimal tooth arrangement for the patient. As a result, in some embodiments an appliance having a configuration generally corresponding to the second FTA may have individual arms with positions that are spaced apart in a particular direction (e.g., a labial, buccal, gingival, occlusal, mesial, and/or distal direction) and/or about a particular axis (e.g., a mesiodistal, occlusogingival, and/or buccolingual) from the positions of corresponding individual arms of an appliance having a configuration generally corresponding to the first FTA.

In some embodiments, the expected relapse may be a predetermined parameter, in that the expected relapse is known or can be determined prior to manufacturing the appliance and/or fixture. Determining the expected relapse can be based on the second FTA, the first FTA, the OTA, and/or other factors specific to the patient's dentition. Additionally or alternatively, the expected relapse may differ for each individual tooth. For example, smaller teeth (e.g., incisors) may experience more relapse than larger teeth (e.g., molars). As such, individual portions of the appliance (e.g., the anchor, arms, biasing portions, attachment portions, etc.) and/or the fixture corresponding to individual teeth may be adjusted differently and distinctly based on the expected relapse for that particular portion. For example, modifications made to the smaller teeth, which are expected to experience more relapse, may be smaller than those made to the larger teeth, which are expected to experience less relapse.

In some embodiments, the method 5000 may omit process portion 5006 and only include a single FTA that considers the expected relapse of the appliance. In such embodiments, the method 5000 may include receiving first data corresponding to an OTA of a patient, and providing second data corresponding to an FTA of the patient, where the second data is based in part on the expected relapse of the patient's teeth after repositioning.

In some embodiments, the method 5000 can further comprise manufacturing the fixture and/or the appliance according to at least the data corresponding to the second FTA. Such manufacturing of the fixture and/or the appliance can correspond to the manufacturing processes described elsewhere herein.

Any of the processes detailed herein can be used with any of the other processes detailed herein. For example, any of the processes described with respect to FIGS. 19-25 can be used with any of the processes described with respect to FIGS. 26-34.

As previously noted, an overcorrection process can comprise modifying a design parameter of an appliance configured to move the tooth, a design parameter of a heat treatment fixture configured for use when setting a shape of an appliance, and/or a final position of one or more of the patient's teeth. For example, a position of a securing portion of a shape forming fixture can be modified such that, after the appliance is coupled to the shape forming fixture and heat treated, a position of an attachment portion of the appliance and the position to which the attachment portion moves the tooth are modified.

Figure 51:
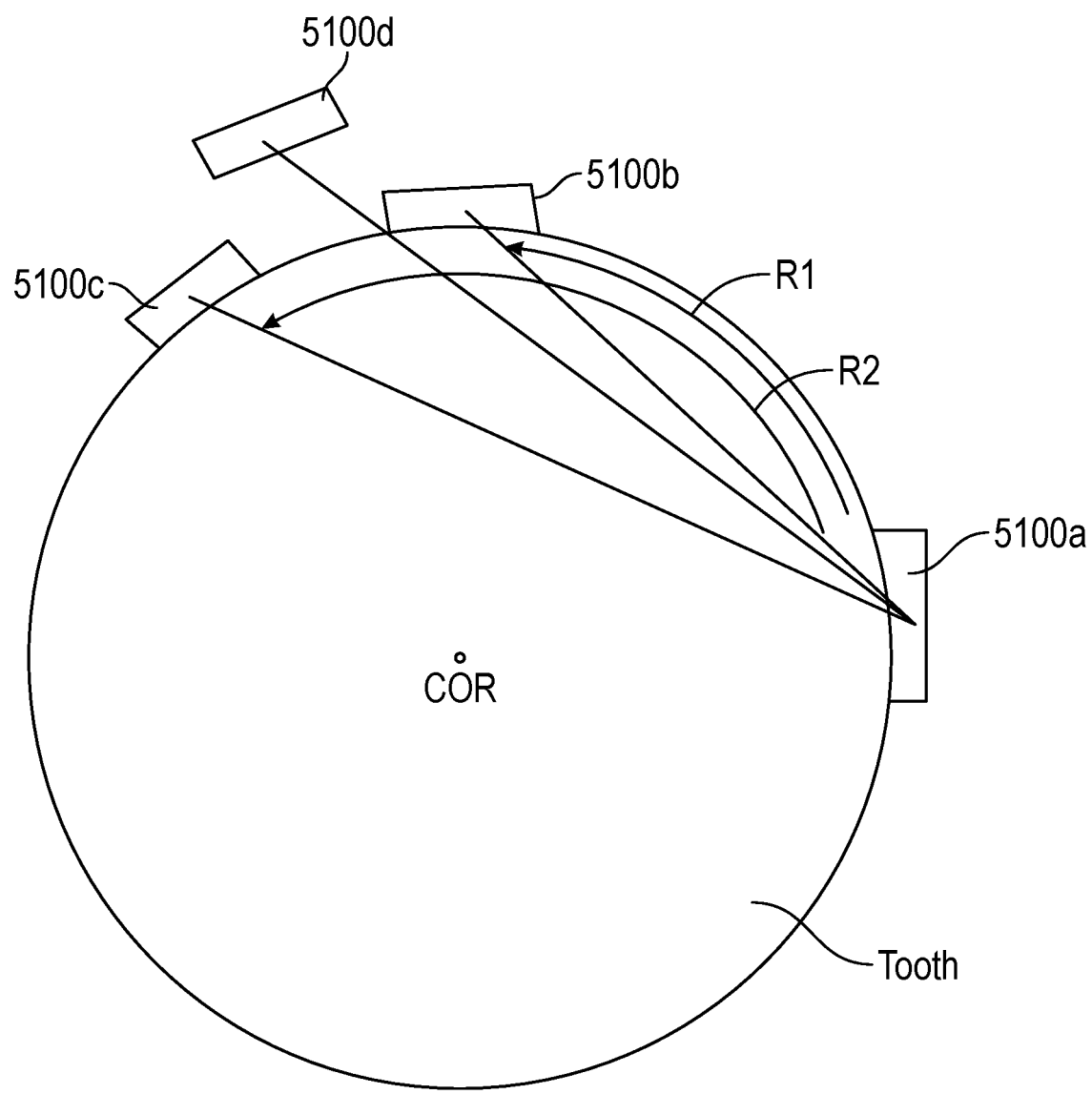
FIG. 51 schematically illustrates overcorrection about various points on a tooth in accordance with embodiments of the present technology.

In any of the embodiments disclosed herein, overcorrection can occur about one or more specific points on or around a tooth. FIG. 51 depicts an example of how selection of the point(s) about which overcorrection is applied influences the design parameters of the appliance and/or shape forming fixture and/or the final position of the tooth. FIG. 51 depicts a transverse view of a tooth with a bracket bonded to the surface of the tooth. FIG. 51 depicts the position of the bracket relative to the tooth when the tooth is in an original position (bracket 5100a), when the tooth is in a preliminary final position (bracket 5100b), when overcorrection has been applied about the center of rotation CoR of the tooth (bracket 5100c), and when overcorrection has been applied at a point on the bracket (bracket 5100d). As shown in FIG. 51, the bracket will move along a straight line from the original position to the final position. Additionally, as shown in FIG. 51, the tooth is configured to be rotated from about its center of rotation by a first rotation R1 from the original position to the preliminary final position. In some embodiments, it may be advantageous to apply overcorrection to rotate the tooth to a greater extent than the first rotation R1. It may be advantageous to rotate the tooth according to the second rotation R2 based on a predicted relapse of the tooth, for example. In some embodiments, overcorrection is applied by rotating the tooth about its center of rotation CoR by a second rotation R2 that is larger than the first rotation R1. However, movement of the tooth is accomplished by an appliance imparting force to the tooth via a connection between the appliance and the bracket. Such connection point is not located at the center of resistance CoR of the tooth. Thus, it may be advantageous to instead apply a rotation and a translation to the position of the attachment portion of the appliance such that the tooth is rotated according to R2.

VII. Communicating the Treatment Plan

Figure 52:
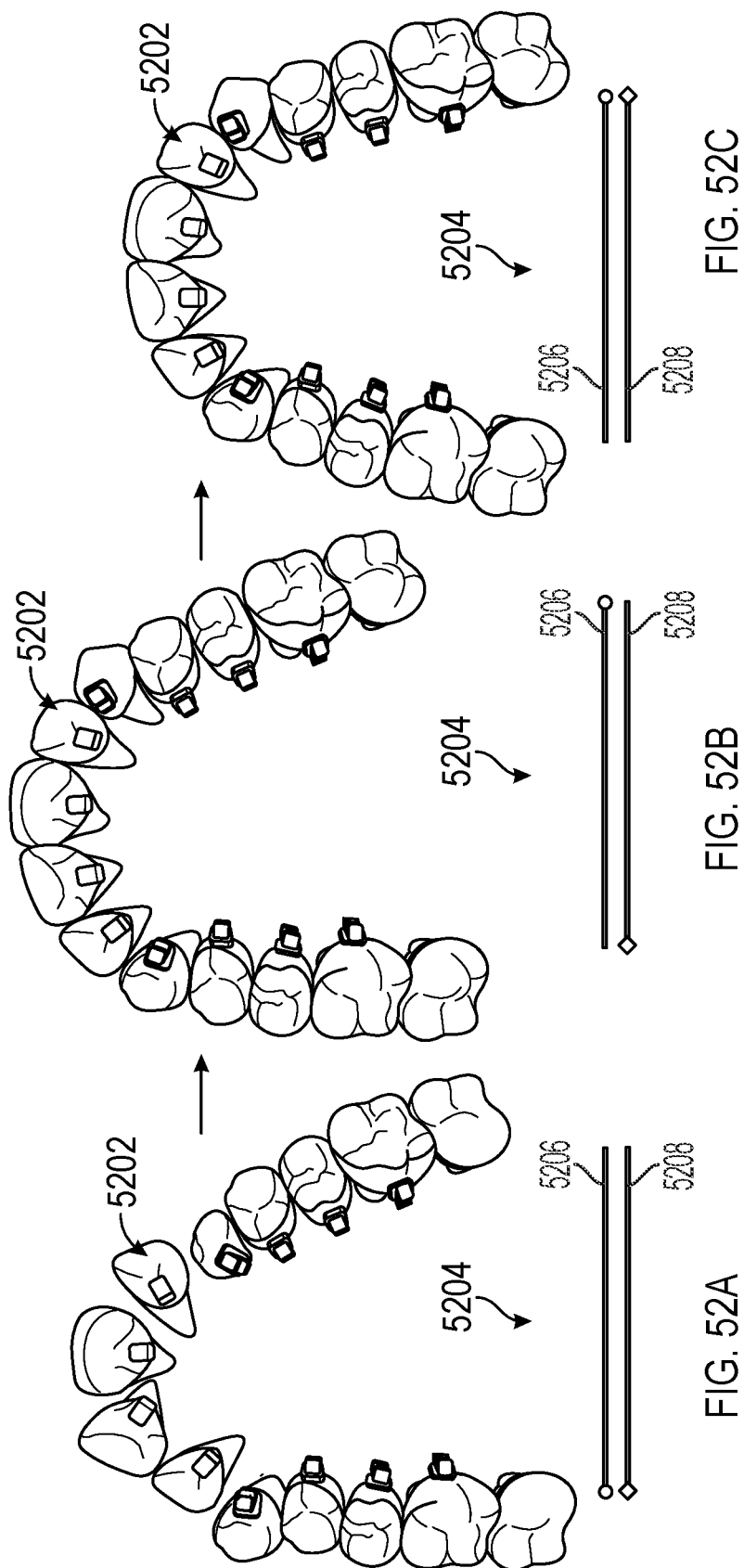
FIGS. 52A-52C depict a user interface illustrating various stages of an animation configured to communicate an orthodontic treatment plan to a human operator in accordance with embodiments of the present technology.

In some embodiments of the present technology an orthodontic treatment plan can be communicated to a clinician such as, but not limited to, an orthodontist, a dentist, or a surgeon. As previously noted, identification of the component tooth movements and suggestions included in the orthodontic treatment plan can facilitation coordination of the orthodontic treatment, management of patient expectations, etc. An orthodontic treatment plan and/or information related to the orthodontic treatment plan (e.g., the first data, the second data, the third data, the common movements, the intraarch movements, the suggestions, etc.) can be communicated visually, in writing, audibly, or via any other suitable form of communication. In some embodiments, orthodontic treatment plan and/or information related to the orthodontic treatment plan can be communicated via a software platform. For example, FIGS. 52A-52C show an animation in a software platform that visually communicates the original, intermediate, and final positions of a patient's teeth (see FIG. 52A, FIG. 52B, and FIG. 52C, respectively). In some embodiments, the software platform can be configured to visually display first movements from the original positions to the intermediate positions (e.g., the intraarch movements) and/or second movements from the intermediate positions to the final positions (e.g., common movements). In the example animation shown in FIGS. 52A-52C, a patient's teeth 5202 are shown in an original arrangement (see FIG. 52A), an intermediate arrangement (see FIG. 52B), and a final arrangement (see FIG. 52C). The animation can include one or more indicators 5204 configured to communicate useful information regarding the arrangement of the teeth 5202 and/or movements of the teeth to an operator. In the example shown in FIGS. 52A-52C, the indicator 5204 can comprise a first bar 5206 representing a magnitude and/or a duration of one or more types of tooth movements and/or a second bar 5208 representing a magnitude and/or a duration of one or more other types of tooth movements. For example, the first bar 5206 can represent the blue movements of a treatment plan and the second bar 5208 can represent the orange and/or purple movements of the treatment plan. In these embodiments and others, the indicators 5204 can include a symbol, character, or other indicia configured to communicate to an operator the portion of the movements represented by the first and second bars 5206, 5208 that the teeth 5202 have been moved by in the arrangement the teeth 5202 are depicted in.

In some embodiments, an orthodontic treatment plan and/or a portion thereof can be communicated to a human operator during any portion of the processes disclosed herein. Communicating the treatment plan can facilitate obtaining the treatment plan and/or modifying the treatment plan such that the treatment plan is achievable and/or realistic. In some cases, the human operator can be an aligning technician responsible for obtaining the second data characterizing the final positions of the patient's teeth based on the original positions and instructions from a clinician. In some cases, the human operator can be a clinician responsible for coordinating the orthodontic treatment. For example, an animation in a software platform, such as the animation described above with respect to FIGS. 52A-52C, can visually communicate an angular displacement between a patient's mandible and maxilla about one or both condyloid processes of the patient's mandible when the patient's teeth are in an original arrangement, a final arrangement, an intermediate arrangement, etc. Communication of the angular displacement(s) can indicate to the operator if there is excessive contact and/or excessive spacing between the patient's teeth. This information can be communicated to the operator such that the operator can approve the orthodontic treatment plan or modify the orthodontic treatment plan (e.g., the final positions of the teeth, the suggested orthodontic interventions, etc.). For example, based on the angular displacement, the operator could determine that a bite plate or splint should be used during surgical intervention or use of an appliance to address, for example, temporomandibular joint issues related to the angular displacement(s).

VIII. Evaluating an Orthodontic Treatment

It can be advantageous to evaluate an orthodontic treatment during and/or after implementation of the treatment to assess the progress of the treatment. If a patient's teeth have not moved as planned, the treatment may need to be modified and/or further treatment may be required to accomplish the objectives of the orthodontic treatment (e.g., proper occlusion, improved aesthetics, etc.). For example, if a patient's teeth are moving slower than anticipated in response to installation of an appliance, the pace of movement may be indicative of the appliance imparting insufficient forces to the teeth to move the teeth to their final positions. In cases in which an orthodontic treatment is not progressing as planned, secondary orthodontic interventions (e.g., additional appliances, new appliances, different types of interventions, etc.) may be required to reposition the patient's teeth to the final positions. It may be beneficial to modify such secondary interventions based on an evaluation of the first intervention. As an example, if rotation of one of a patient's lateral incisors occurred very slowly or to a very small degree, a secondary appliance can be designed to apply larger forces to the lateral incisor to rotate the tooth to a greater degree and/or faster.

Traditionally, evaluation of orthodontic treatment is performed by a human operator (e.g., a clinician, the patient, etc.). An orthodontist can visually inspect a patient's teeth and, using their clinical training and experience, assess how the teeth are moving (e.g., whether the teeth are moving in the desired directions, whether the teeth are moving at a desirable pace, etc.) and determine whether modifications to the treatment and/or further treatment are needed to accomplish the treatment objectives. However, such clinical evaluation is qualitative and relies heavily on the skill of the human operator, and it can be challenging to accurately and precisely identify the magnitude, direction, and pace of movements of the teeth that have occurred and residual movements of the teeth that should be accomplished for the teeth to reach their planned positions. To address these challenges, methods of evaluating orthodontic treatment in accordance with the present technology employ quantitative, numerical processes for identifying current, actual positions of the patient's teeth during and/or after an orthodontic treatment, the actual movements of the teeth that have occurred during the orthodontic treatment, and the residual movements required for the teeth to reach planned, final positions. In various embodiments, a method of evaluating an orthodontic treatment comprises obtaining one or more performance parameters of the treatment (e.g., accuracy, efficiency, etc.), which can be used to determine whether to modify the current treatment, if the treatment is completed or if further treatment is needed and how to proceed with treatment. Additionally or alternatively, aggregation and analysis of the data disclosed herein (e.g., position data, movement data, performance parameter data, etc.) can be used to inform and improve future orthodontic treatments.

Figure 53:
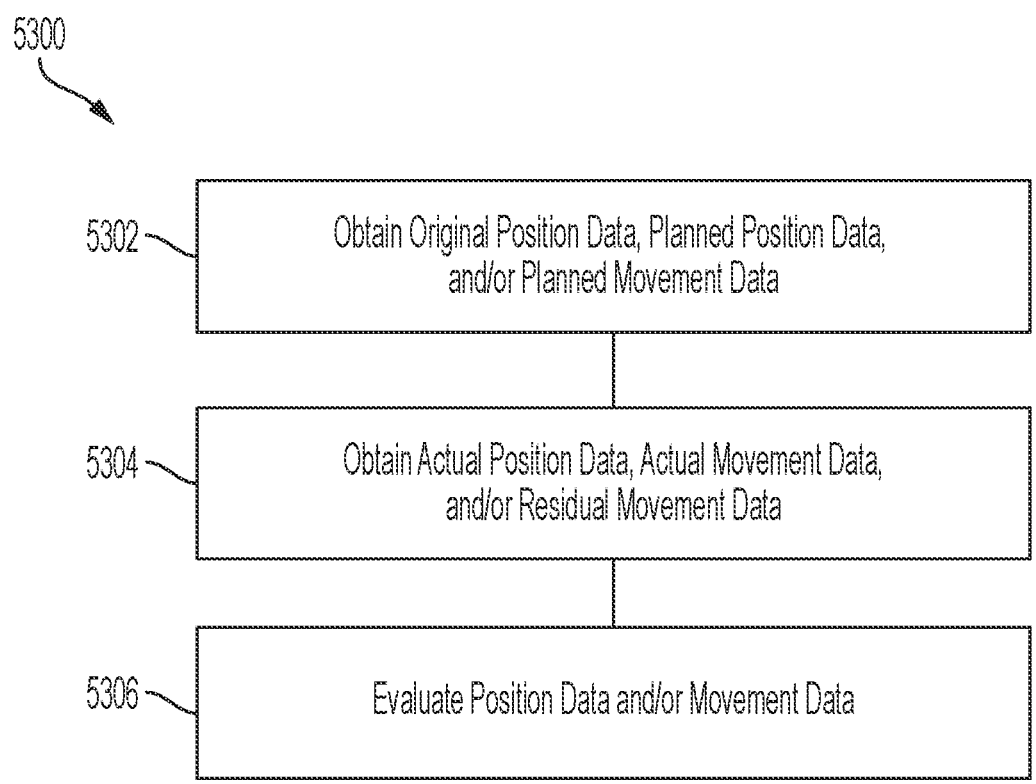
FIG. 53 is a flow diagram of a method for evaluating an orthodontic treatment in accordance with embodiments of the present technology.

FIG. 53 is a flow chart of an example process 5300 for evaluating an orthodontic treatment in accordance with the present technology. At process portion 5302, the process 5300 can comprise obtaining original position data characterizing original positions of a patient's teeth (e.g., when the teeth are in the OTA, prior to implementation of the orthodontic treatment, etc.), planned position data characterizing planned positions of the patient's teeth (e.g., planned final positions, planned intermediate positions, etc.), and/or planned movement data characterizing planned movements of the patient's teeth from the original positions to the planned positions. At process portion 5304, the process 5300 can comprise obtaining actual position data characterizing the patient's anatomy (e.g., teeth, gingiva, skull, etc.) in an actual tooth arrangement (ATA) during and/or after the orthodontic treatment. The process 5300 can also include obtaining actual movement data characterizing actual movements of the patient's teeth from the original positions to the positions of the teeth in the ATA (e.g., actual positions) and/or residual movement data characterizing residual movements of the patient's teeth from the actual positions to the planned positions. The process 5300 can continue at process portion 5306 with comparing the planned and actual position data, comparing the planned and actual movement data, and/or evaluating the residual movement data. Such comparisons and evaluations can be used to determine whether objectives of the orthodontic treatment have been and/or are projected to be accomplished, which can be used to determine whether the treatment should be completed, modified, or extended and/or if and how a secondary treatment should be implemented.

The original position data can characterize original positions of the patient's teeth (e.g., positions of the patient's teeth prior to implementation of some or all of an orthodontic treatment). The original position data can be similar to the OTA data and/or the OTA digital model, as described herein. The original position data can comprise a dataset defining 3D coordinates of one or more portions of the patient's anatomy (e.g., teeth, gingiva, jaw bone, skull, etc.). For example, the original position data can comprise a point cloud defining 3D coordinates of a plurality of points characterizing the surfaces of the teeth. Additionally or alternatively, the original position data can comprise a dataset defining 3D coordinates of a specific reference point (e.g., center of mass, etc.) of one or more of the patient's teeth. In some embodiments, the original position data comprises a digital model of the patient's anatomy. The digital model can comprise a continuous, unsegmented digital model of the teeth, gingiva, jaw bone, skull, or other anatomical structures. Additionally or alternatively, the digital model can comprise one or more individual models (e.g., an individual model of each tooth, an individual model of the gingiva, an individual model of the jaw bone, an individual model of the skull, etc.) produced by segmenting a continuous model of the anatomical structures. As but one example, the original position data can comprise one digital model representing a patient's skull based on CBCT image data, another digital model representing the patient's maxilla based on CBCT image data, a plurality of other digital models each representing one of the patient's teeth based on intraoral scan data, and/or yet another digital model representing the patient's gingiva based on intraoral scan data. Such digital model(s) can comprise a mesh model (e.g., a triangle mesh model, a polygon mesh model, a volumetric mesh model, etc.), a surface model (e.g., a non-uniform rational basis spline (NURBS) surface model, a T-Spline surface model, etc.), a parametric CAD model, or another suitable type of model.

The planned position data can characterize planned positions of the patient's teeth after the patient's teeth have been moved via some or all of an orthodontic treatment. The planned position data can be similar to the FTA data, the ITA data, the FTA digital model, and/or the ITA digital model, as described herein. The planned position data can comprise a dataset defining 3D coordinates of one or more portions of the patient's teeth and/or gingiva. For example, the planned position data can comprise a point cloud defining 3D coordinates of a plurality of points defining the surfaces of the teeth. Additionally or alternatively, the planned position data can comprise a dataset defining 3D coordinates of a reference point (e.g., a center of mass, etc.) of one or more of the patient's teeth. In some embodiments, the planned position data comprises a digital model of the patient's teeth and/or gingiva. The digital model can comprise a continuous, unsegmented digital model of the teeth and/or gingiva. Additionally or alternatively, the digital model can comprise one or more individual models of a tooth or the gingiva produced by segmenting a continuous model of the teeth and/or gingiva. The digital model can comprise a mesh model (e.g., a triangle mesh model, a polygon mesh model, a volumetric mesh model, etc.), a surface model (e.g., a non-uniform rational basis spline (NURBS) surface model, a T-Spline surface model, etc.), a parametric CAD model, or another suitable type of model.

In some embodiments, the planned movements comprise overall movements of the teeth from the original positions to the planned positions. For example, as described herein, an overall movement of a tooth can be defined by a 3D vector characterizing a displacement between a reference point of the tooth (e.g., a center of mass of the tooth, a center of mass of the crown of the tooth, one or more points on a surface of the crown of the tooth, etc.) in the original position and a corresponding reference point of the tooth in the planned position. In some embodiments, the overall movement can be defined by a 3D transformation characterizing a rotation and/or a translation of the tooth as a 3D body from the original position to the planned position. Additionally or alternatively, the planned movements can comprise one or more component movements of the teeth from the original positions to the planned positions. For example, the planned movements can comprise a movement that is unique to each tooth (e.g., a blue movement), a movement that is common to all of the teeth in one of the patient's dental arches (e.g., an orange movement), a movement that is common to all of the teeth in both of the patient's dental arches (e.g., a purple movement), etc.

As previously noted, at process portion 5304 the process 5300 can comprise obtaining actual position data, actual movement data, and/or residual movement data. The actual movement data characterizes actual positions of the patient's teeth at the time that the actual position data is obtained. The actual position data can be obtained at one or more predetermined times during and/or after the treatment. For example, the actual position data can be obtained at regular intervals during the treatment such that progress of the treatment can be monitored while the treatment is ongoing. In some embodiments, the actual position data can be obtained after a predetermined amount of time has passed such that the patient's teeth are expected to be located at their planned positions. For example, the actual position data can be obtained after an estimated duration of the treatment has elapsed to evaluate whether the teeth reached their desired, final positions and if further treatment is beneficial and/or necessary. Additionally or alternatively, a clinician and/or the patient can determine when the actual position data is obtained. For example, a clinician can visually inspect a patient's teeth at an appointment. If the clinician suspects from the visual inspection that the treatment is not progressing as planned, the clinician can determine that the actual position should be obtained, and the progress of the treatment should be evaluated.

The actual position data can comprise a dataset defining 3D coordinates of one or more portions of the patient's teeth and/or gingiva. For example, the actual position data can comprise a point cloud defining 3D coordinates of a plurality of points defining the surfaces of the teeth. Additionally or alternatively, the actual position data can comprise a dataset defining 3D coordinates of a reference point (e.g., a center of mass, etc.) of one or more of the patient's teeth. In some embodiments, the actual position data comprises a digital model of the patient's teeth and/or gingiva. The digital model can comprise a continuous, unsegmented digital model of the teeth and/or gingiva. Additionally or alternatively, the digital model can comprise one or more individual models of a tooth or the gingiva produced by segmenting a continuous model of the teeth and/or gingiva. The digital model can comprise a mesh model (e.g., a triangle mesh model, a polygon mesh model, a volumetric mesh model, etc.), a surface model (e.g., a non-uniform rational basis spline (NURBS) surface model, a T-Spline surface model, etc.), a parametric CAD model, or another suitable type of model.

In some embodiments, the process 5300 includes obtaining actual movement data and/or residual movement data (e.g., at process portion 5304). The actual movement data can characterize actual movements of the teeth from their original positions to their actual positions and the residual movement data can characterize residual movements of the teeth from their actual positions to their planned positions (e.g., movements that have not yet been accomplished). An actual movement and/or a residual movement can be defined by a 3D vector characterizing a distance between corresponding reference points of a tooth in the actual position and the original position or the planned position, respectively. In some embodiments, the actual movement and/or the residual movement can be defined by a 3D transformation characterizing a rotation and/or a translation of the tooth as a 3D body between the actual position and the original position or the planned position, respectively. The actual movements and/or the residual movements can each comprise overall movements and/or one or more component movements.

At process portion 5306, the process 5300 can comprise evaluating the position data and/or the movement data. For example, the process 5300 can comprise comparing the actual positions of the teeth as characterized by the actual position data to the planned positions of the teeth as characterized by the planned position data to determine if the teeth have reached their desired positions. In some embodiments, comparing the actual position data to the planned position data comprises evaluating the residual movement data. For example, evaluating the residual movement data can comprise comparing the residual movement data to a predetermined threshold to determine if the residual movements can be accomplished by a specific type of orthodontic intervention. Additionally or alternatively, the process 5300 can comprise comparing the actual positions of the teeth to the original positions of the teeth and/or evaluating the actual movement data. For example, evaluating the actual movement data can comprise comparing the actual movement data to the planned movement data to determine a percentage of the planned movement data that was accomplished. Such evaluation can provide insight into an accuracy and/or an efficiency of the orthodontic treatment.

Figure 54:
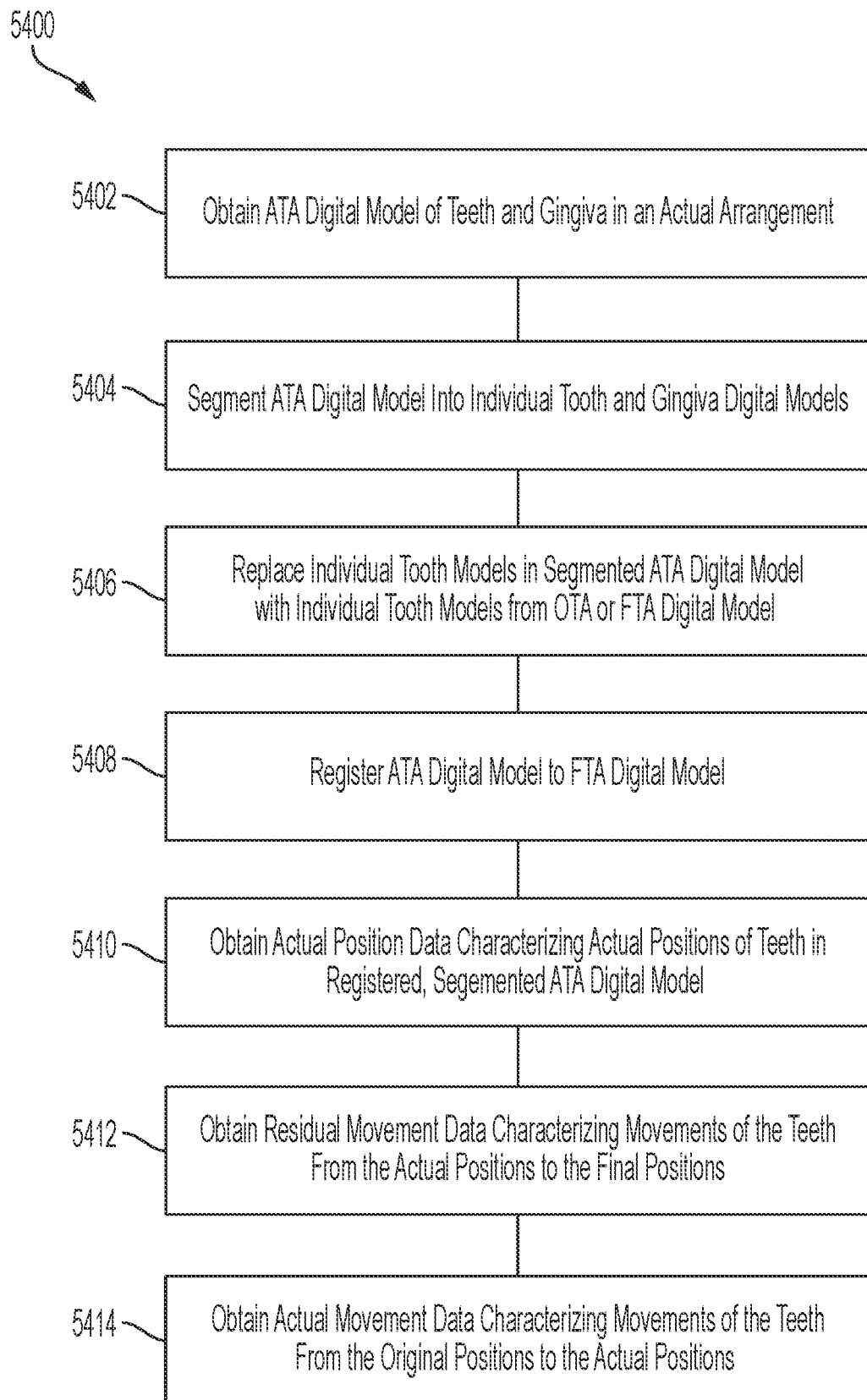
FIG. 54 is a flow diagram of a method for obtaining actual position data, actual movement data, and/or residual movement data in accordance with embodiments of the present technology.

FIG. 54 is a flow chart of an example of a process 5400 for obtaining actual position data, actual movement data, and residual movement data (e.g., process portion 5304 of FIG. 53). As shown in FIG. 54, the process 5400 can comprise obtaining an ATA digital model of a patient's teeth and gingiva in an actual arrangement at process portion 5402. Obtaining the ATA digital model can be similar to obtaining the OTA digital model, as described herein. For example, obtaining the ATA digital model can comprise scanning the patient's oral cavity with an intraoral scanner, imaging the patient's skull, face, and/or jaws with CBCT, etc. In some embodiments, obtaining the ATA digital model comprises obtaining a single, continuous digital model of the patient's teeth and/or gingiva. At process portion 5404, the process 5400 can comprise segmenting the ATA digital model into one or more individual tooth and gingiva models. For example, the ATA digital model can be segmented such that the ATA digital model comprises a plurality of individual digital models each representing one of the patient's teeth or the patient's gingiva.

To compare the actual positions of the patient's teeth to the planned and/or original positions of the patient's teeth, as can be an objective of evaluating an orthodontic treatment, it can be beneficial and/or preferable for a shape (e.g., a surface geometry, etc.) of a tooth in the ATA digital model to be as similar as possible to a shape of the tooth in the OTA or FTA digital model. For example, in some embodiments a position of a tooth is defined at the center of mass of the tooth. Because the coordinates of a body's center of mass are dependent on a geometry of the body, the center of mass of the tooth will have different coordinates in the ATA digital model and the FTA digital model if the shape of the tooth in the ATA digital model differs from the shape of the tooth in the FTA digital model. If the actual and planned positions of the tooth are evaluated at the center of mass of the tooth and the center of mass is different in the ATA and the FTA due to a difference in shape of the tooth, the actual position of the tooth will be different than the planned position of the tooth, even if the actual and planned positions were equivalent. Because the FTA digital model can be obtained by moving the teeth of the OTA digital model, in many cases the teeth in the FTA digital model have the same shape as the teeth in the OTA digital model. However, because the digital models of the teeth in the ATA digital model are obtained from new scan and/or image data obtained after the OTA data has been obtained, one or more of the teeth in the ATA digital model may have a different shape than a shape of a corresponding tooth in the OTA and FTA digital models. For example, an ATA digital model produced from an optical scan may have holes or regions where the patient's anatomy was not sufficiently captured by the scanner. If the ATA digital model comprises a mesh model generated by reconstructing surfaces of the teeth from a point cloud or other image data, errors in the surface reconstruction may cause the shape of the tooth in the ATA digital model to differ from the shape of the tooth in the OTA digital model. In some cases, a patient may have undergone interproximal reduction (IPR) or other dental procedures (e.g., filings, crowns, etc.) that modified a shape of a tooth between obtaining the OTA digital model and obtaining the ATA digital model.

To address the above-noted concerns, the process 5400 for obtaining the actual position data can comprise replacing the individual digital models of the teeth in the ATA digital model with individual digital models of the teeth from the OTA digital model or the FTA digital model (process portion 5406). Because the teeth in the FTA digital model can have the same shape as the teeth in the OTA digital model, either are appropriate to use at process portion 5406. The outcome of process portion 5406 can comprise an ATA digital model comprising individual digital models of the teeth from the OTA or FTA digital model that are each located at the actual position of the corresponding tooth. The new ATA digital model with the OTA or FTA teeth at the actual positions can then be compared to the OTA digital model of the teeth in the original positions and/or the FTA digital model of the teeth in the planned positions because corresponding teeth of each of the models will have the same shape, just different positions. In some embodiments, rather than replacing the individual tooth models of the ATA digital model with individual tooth models from the OTA or FTA digital model, the individual tooth models of the OTA or FTA digital model can be replaced with individual tooth models of the ATA digital model to produce an OTA or FTA digital model comprising individual digital models of the teeth from the ATA digital model located at the original positions or final positions, respectively.

Figure 55C:
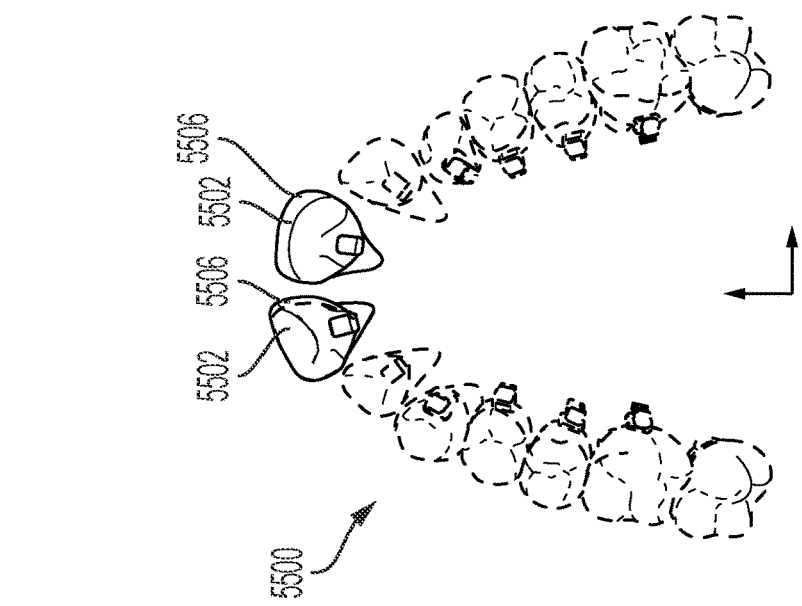
FIG. 55C illustrates two of the patient's teeth from the OTA digital model shown in FIG. 55B aligned with a corresponding ones of the patient's teeth of the ATA digital model shown in FIG. 55A.
Figure 55B:
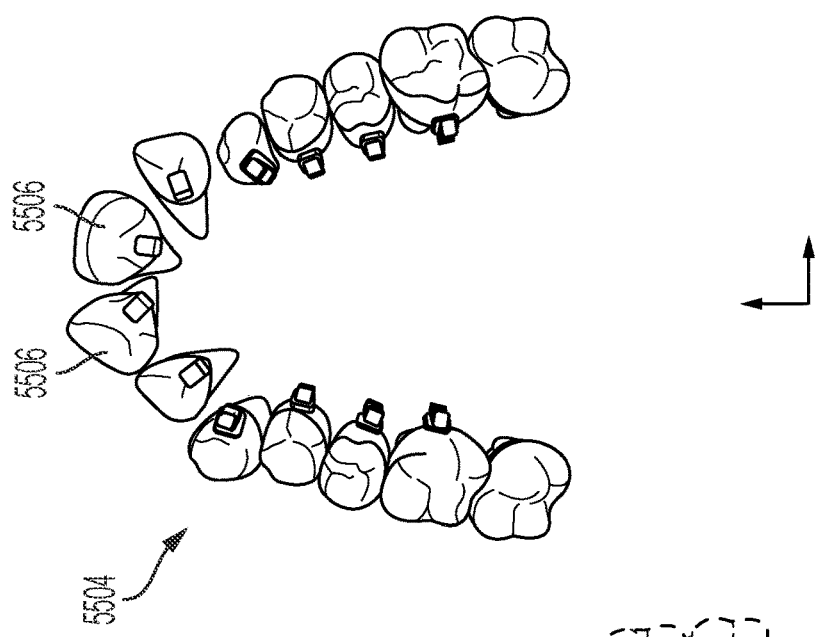
FIGS. 55A and 55B illustrates an example of a digital model of a patient's teeth in an actual tooth arrangement (e.g., an ATA digital model) and an original tooth arrangement (e.g., an OTA digital model), respectively.
Figure 55A:
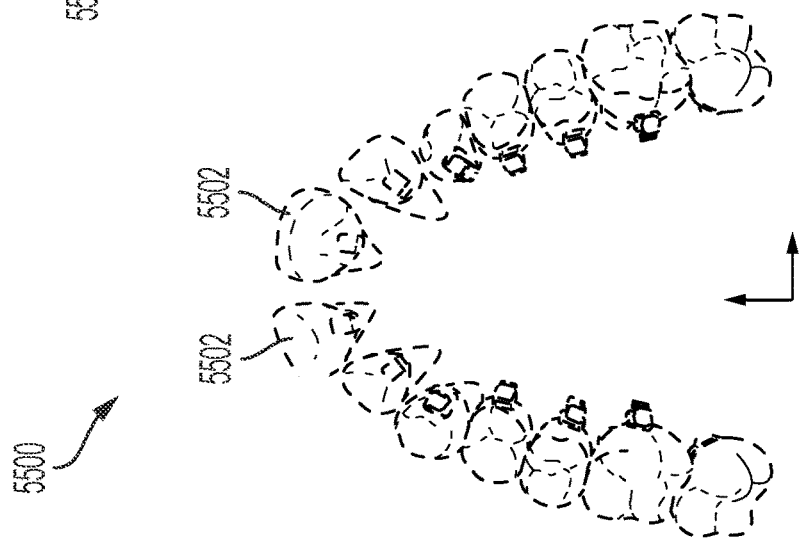

FIGS. 55A-55C illustrate an example of replacing individual teeth models 5502 of an ATA digital model 5500 with individual teeth models 5506 of an OTA digital model 5504 to facilitate understanding of process portion 5406. One or more of the individual teeth models 5502 of the ATA digital model 5500 may, in some cases, have one or more holes, artifacts, or defects such that a shape of the tooth represented by the individual tooth model 5502 of the ATA digital model 5500 differs from a shape of the corresponding individual tooth model 5506 of the OTA digital model 5506. Additionally or alternatively, one or more of the individual teeth models 5502 may characterize a true change in shape of the corresponding tooth.

Process portion 5406 can comprise registering the individual teeth models 5506 in the OTA digital model 5504 to the individual teeth models 5502 in the ATA digital model 5500. In some embodiments, the registration occurs one tooth at a time. For example, a first tooth model 5506 of the OTA digital model 5504 can be registered to a corresponding first tooth model 5502 of the ATA digital model 5500, a second tooth model 5506 of the OTA digital model 5504 can be registered to a corresponding second tooth model 5502 of the ATA digital model 5500, etc. In some embodiments, registering one of the OTA individual teeth models 5506 to a corresponding one of the ATA individual teeth models 5502 comprises transforming the OTA individual tooth model 5506 such that a coordinate system of the OTA individual tooth model 5506 is aligned with a coordinate system of the ATA individual tooth model 5502, a feature of the OTA individual tooth model 5506 is aligned with a corresponding feature of the ATA individual tooth model 5502, a distance between references points of the OTA individual tooth model 5506 and corresponding reference points of the ATA individual tooth model 5502 is reduced or minimized, etc. Registering one of the OTA individual teeth models 5506 to a corresponding one of the ATA individual teeth models 5502 can be an iterative process. Once the OTA individual tooth models 5506 have been registered with the corresponding ATA individual tooth models 5502, the ATA individual tooth models 5502 can be deleted such that the ATA digital model 5500 comprises the OTA individual tooth models 5506 located at the actual positions of the teeth.

In some embodiments, it can be advantageous to evaluate the actual positions at which securing members (e.g., an orthodontic brackets, etc.) were bonded to a patient's teeth in addition to, or in place of, evaluating actual positions of the teeth themselves. The position of a securing member on a tooth can influence the magnitude and/or direction of a force applied to the tooth by an appliance via the securing member. In various cases, an indirect bonding tray can be used to facilitate bonding of the securing members to the patient's teeth. However, errors in positioning of the securing members can still occur due to defects in the bonding tray, clinician inexperience, complex anatomy, and other reasons. Accordingly, it can be useful to evaluate how accurately the securing members were bonded to a patient's teeth which can inform designs of future orthodontic interventions, clinician training, etc.

In some embodiments, an actual position of a securing member can be obtained after the OTA individual tooth models (or FTA individual tooth models) have been aligned with corresponding ATA individual tooth models. As shown in FIGS. 55A-55C, the ATA digital model can be obtained by scanning and/or imaging a patient's teeth while the securing members are secured to the teeth such that the ATA digital model characterizes the securing members. Obtaining an actual position of one of the securing members can comprise obtaining 3D coordinates of one or more reference points of the securing member and/or obtaining a rotation matrix defining an orientation of the securing member, as the securing member is represented in the ATA digital model. An intended position of the securing member can be obtained from a corresponding OTA (or FTA) individual tooth model that is aligned with the ATA individual tooth model such that the actual and intended positions of the securing member are comparable. For example, after aligning individual tooth models 5506 of the OTA digital model 5504 to the individual tooth models 5502 of the ATA digital model 5500 and prior to deleting the individual tooth models 5502 of the ATA digital model 5500 (e.g., such that corresponding individual tooth models 5502, 5506 are aligned) the intended positions of the securing members can be obtained from the individual tooth models 5506 of the OTA digital model 5504 and the actual positions of the securing members can be obtained from the individual tooth models 5502 of the ATA digital model 5500.

Referring back to FIG. 54, the process 5304 for determining actual position data can comprise registering the ATA digital model to the FTA digital model (process portion 5408) and/or to the OTA digital model. To compare the actual positions of a patient's teeth obtained from the ATA digital model to the desired, final positions of the teeth obtained from the FTA digital model, the actual positions and final positions should be measured with reference to the same coordinate system. For example, original positions of the patient's teeth obtained from an OTA digital model and the final positions of the patient's teeth obtained from the FTA digital model may be comparable because the FTA digital model is derived from the OTA digital model and shares the same coordinate system as the OTA digital model. However, because the ATA digital model can be generated independently of the OTA and FTA digital models, the ATA digital model may have a unique coordinate system. Accordingly, methods of the present technology are directed to processes for registering one digital model to another digital model such that the digital models share a common coordinate system.

Figure 56A:
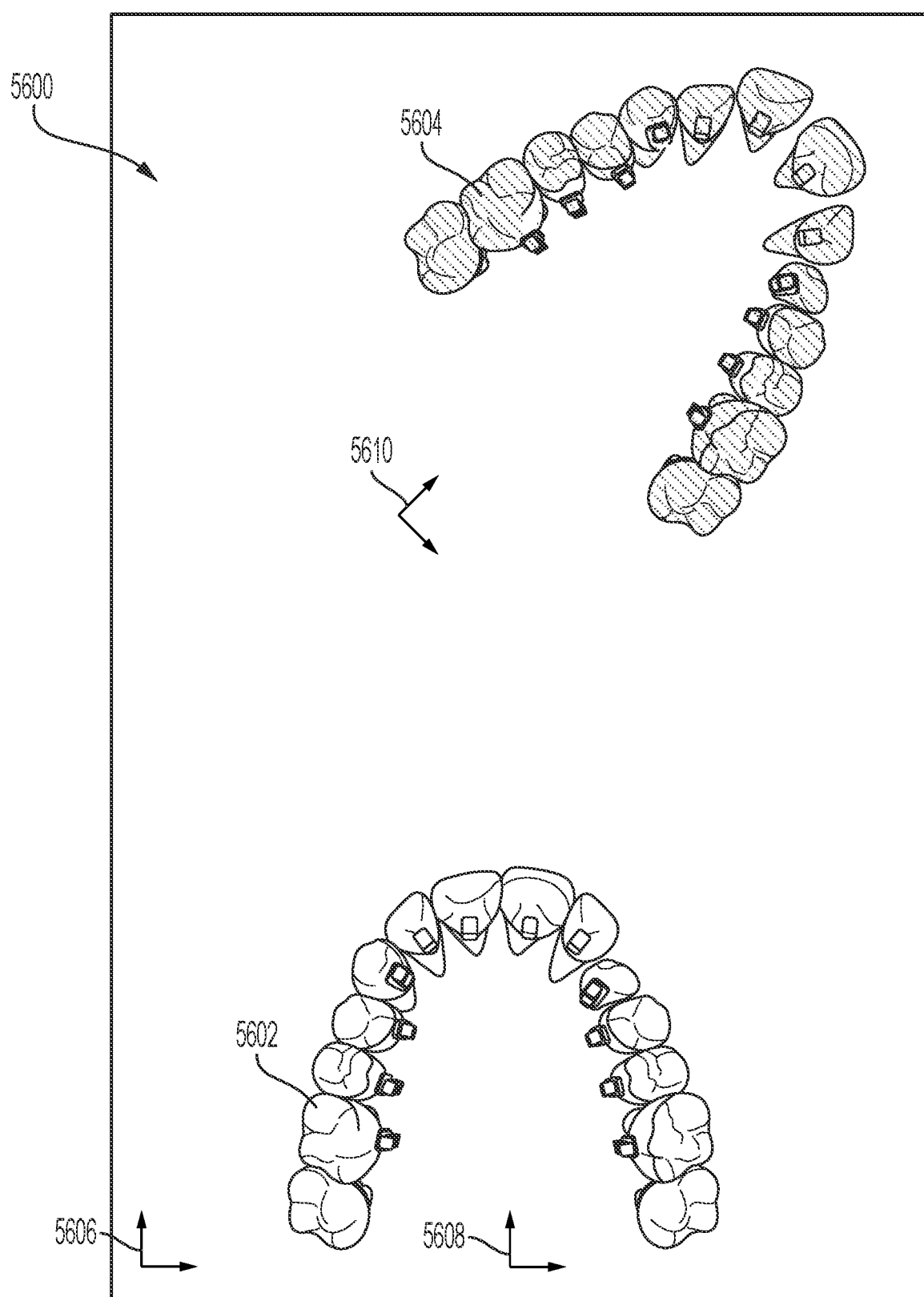
FIG. 56A illustrates an example of a digital model of a patient's teeth in an actual tooth arrangement and an example of a digital model of the patient's teeth in a final tooth arrangement positioned in a digital environment.
Figure 56B:
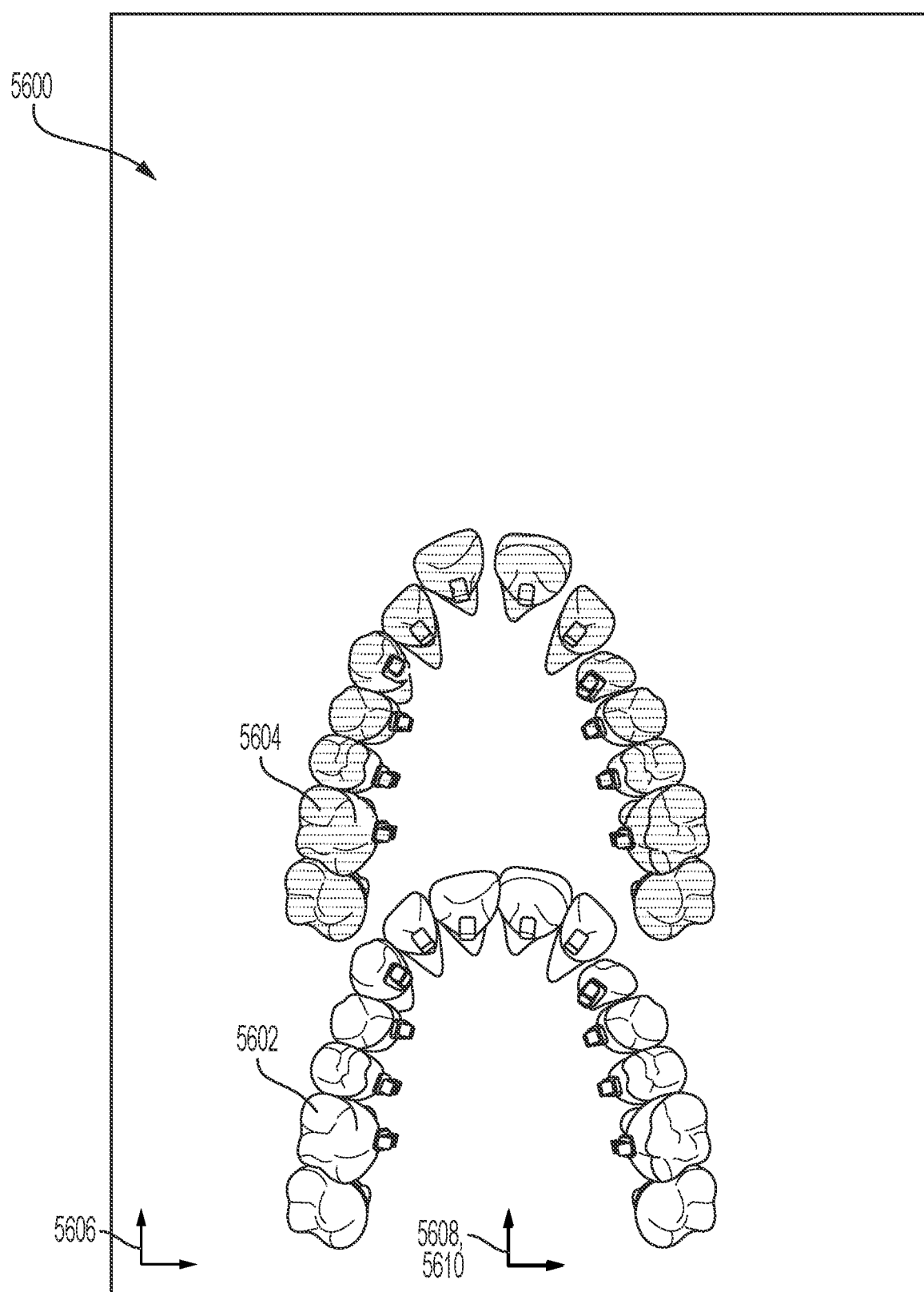
FIG. 56B illustrates the digital model of the patient's teeth in the actual tooth arrangement of FIG. 56A registered to the digital model of the patient's teeth in the final tooth arrangement of FIG. 56A in the digital environment.

FIGS. 56A and 56B illustrate an example of such registration and are provided as visual aids to facilitate the discussion of process portion 5408. Specifically, FIGS. 56A and 56B depict a digital environment 5600 with an FTA digital model 5602 and an ATA digital model 5604 positioned in the digital environment 5600. As shown in FIG. 56A, the digital environment 5600 can comprise an environment coordinate system 5606. Any of the coordinate systems disclosed herein, including the environment coordinate system 5606, can comprise a Cartesian coordinate system with three orthogonal axes and an origin (as shown in FIG. 56A), a cylindrical coordinate system, a spherical coordinate system, etc. The FTA digital model 5602 comprises an FTA coordinate system 5608, which may or may not be aligned with the environment coordinate system 5606, and the ATA digital model 5604 comprises an ATA coordinate system 5610, which, as shown in FIG. 56A, in some cases may not be aligned with FTA coordinate system 5608 and/or the environment coordinate system 5606. For example, as shown in FIG. 56A, the ATA coordinate system 5610 can be rotated and/or translated relative to FTA coordinate system 5608. As a result, a center of mass of a tooth in the ATA digital model 5604 that is measured with respect to the environment coordinate system 5606 and a center of mass of a corresponding tooth in the FTA digital model 5602 that is measured with respect to the environment coordinate system 5606 will be spaced apart by a substantial distance that is not reflective of the true distance between the tooth's actual position and the tooth's planned, final position.

The ATA digital model 5604 can be registered to the FTA digital model 5602 such that coordinates of corresponding features, portions, or points of the digital models 5604, 5602 are comparable. According to various embodiments, registering the ATA digital model 5604 to the FTA digital model 5602 comprises determining the spatial transformation that aligns the ATA digital model 5604 to the FTA digital model 5602 and/or aligns the ATA coordinate system 5610 to the FTA coordinate system 5608. Additionally or alternatively, the ATA digital model can be registered to the OTA digital model (not shown). FIG. 56B illustrates an example of the FTA digital model 5602 and the ATA digital model 5604 positioned in the digital environment 5600 after the ATA digital model 5604 has been registered to the FTA digital model 5602. A variety of methods can be used to register the ATA digital model 5604 to the FTA digital model 5602, which are described in greater detail below.

According to various embodiments, registering the ATA digital model 5604 to the FTA digital model 5602 comprises identifying one or more correspondences on each of the digital models 5602, 5604 and determining the transformation that positions the correspondences relative to one another in a specific manner, for example aligning the correspondences. A correspondence can comprise an anatomical landmark (e.g., a crest of a tooth, a ridge of a tooth, a gingival edge of a crown of a tooth, a portion of a skull, etc.), a point (e.g., a center of mass of the tooth, a center of mass of the crown of the tooth, a point on a surface of a tooth, etc.), a line, a surface, a body, a coordinate system, or another suitable geometric reference. As discussed in greater detail below, correspondences of the digital models 5602, 5604 and/or their positions can be known. Additionally or alternatively, the correspondences may not be known initially, but can be identified through an iterative process.

In some embodiments, registering the ATA digital model 5604 to the FTA digital model 5602 comprises identifying one or more correspondences on each of the digital models 5602, 5604 that is not expected to move over at least a portion of the orthodontic treatment, obtaining the positions of the correspondences, and determining a difference between the positions of the correspondences. The difference in positions can serve as the basis for and/or substantially correspond to a transformation that, when applied to the ATA digital model 5604, minimizes a distance between the correspondences. For example, if each of the FTA digital model and the ATA digital model includes a representation of a skull of a patient (e.g., from CBCT image data), one or more portions of the skull can serve as the correspondence in each of the digital models 5602, 5604. Because the shape and position of the skull are not expected to change during the orthodontic treatment, the position of the skull correspondence of the ATA digital model 5604 should be the same as the position of the skull correspondence of the FTA digital model 5602. Accordingly, a difference in the positions of the correspondences of the ATA digital model 5604 and the FTA digital model 5602 can be obtained. The ATA digital model 5604 can be moved according to a transformation corresponding at least in part to the difference in positions of the correspondences to register the ATA digital model 5604 to the FTA digital model 5602.

Other stationary anatomical features that can be used as known correspondences can include certain soft tissues (e.g., the rugae of the palate, etc.), certain bones of the head, face, jaws, and/or neck, and/or the teeth. For example, if an overall planned movement of a tooth is negligible or non-existent, the position of the tooth in the ATA digital model 5604 should be the same as or similar to the position of the tooth in the FTA digital model 5602.

However, in some cases all a patient's teeth may have non-negligible planned movements. Additionally or alternatively, the digital models 5602, 5604 may not include the stationary anatomical features noted above. For example, CBCT image data might not be obtained for every patient, and intraoral scan data may only include the teeth and gingiva, which can move during treatment. To address these limitations, a method of registering the ATA digital model 5604 to the FTA digital model 5602 can comprise determining a transformation that can be applied to the ATA digital model 5604 to reduce or minimize an error between multiple anatomical features (e.g., all of the teeth, some of the teeth, etc.). As an example, such a method can comprise obtaining actual position data characterizing a position of one or more points per tooth in the ATA digital model 5604 and planned position data characterizing a position of the same one or more points per tooth in the FTA digital model 5602. In some embodiments, the one or more points comprise a center of mass of the tooth, a center of mass of the crown, a point on a surface of the tooth, etc. The actual position data can be symbolically transformed to determine symbolic registered actual position data, and a regression analysis can be performed to determine numerical equivalents of the symbolic transformation and the symbolic registered actual position data based on one or more cost functions (e.g., a loss function, an error function, an objective function, etc.). For example, a transformation can be identified such that an error parameter characterizing a difference between the registered actual position data and the planned position data is minimized. The error parameter can comprise a measure of the distances between corresponding teeth. For example, the error parameter can comprise a sum of the squared distance between the registered actual position and the planned position of each tooth, summed over all of the teeth. In some embodiments, registering the ATA digital model 5604 to the FTA digital model 5602 comprises a process that is the same as, or similar to, the processes described in reference to FIGS. 26-32E.

In some embodiments, an optimization-based registration can be performed to register the ATA digital model 5604 to the FTA digital model 5602. For example, the ATA digital model 5604 can be transformed to obtain a registered ATA digital model 5604, an error parameter can be evaluated to characterize a difference in position between one or more portions of the ATA digital model 5604 and the FTA digital model 5602, and the transformation and error evaluation can be repeated until the error falls within a desirable range or a maximum number of iterations has been reached. In these and other embodiments, the correspondences may not be known between the ATA digital model 5604 and the FTA digital model 5602. For example, registering the ATA digital model 5604 to the FTA digital model 5602 can comprise an iterative closest point (ICP) algorithm in which an initial set of correspondences is identified. The correspondences can be identified by selecting a number of reference points on one of the digital models and identifying the closest point on the other digital model to each of the reference points A transformation can be applied to the ATA digital model 5604 to obtain a registered ATA digital model and an error parameter between the registered ATA digital model and the FTA digital model 5604 can be obtained. The previous process portions, including identifying the correspondences, can be repeated one or more times.

In one example, registering the ATA digital model 5604 to the FTA digital model 5602 comprises aligning the ATA coordinate system 5610 to the FTA coordinate system 5608. In embodiments in which the ATA and FTA coordinate systems 5610, 5608 comprise Cartesian coordinate systems with three orthogonal axes (e.g., as shown in FIGS. 56A and 56B, etc.), aligning the coordinate systems 5608, 5610 can comprise rotating and/or translating one of the coordinate systems 5608, 5610 such that corresponding axes of the coordinate systems 5608, 5610 extend in the same direction. In some embodiments, aligning the coordinate systems 5608, 5610 comprises positioning an origin of one of the coordinate systems 5608, 5610 at the same position as an origin of the other of the coordinate systems 5608, 5610.

Referring back to FIG. 54, once the ATA digital model 5604 has been aligned to the FTA digital model 5602, the actual positions of the teeth in the reference coordinate system can be obtained (process portion 5410). In some embodiments, the actual positions are defined by 3D coordinates of one or more points for each tooth in the ATA digital model 5604. In some embodiments, the one or more points comprise a center of mass of the tooth, a point on a surface of the tooth, or another suitable reference point. Additionally or alternatively, an orientation of the tooth in the ATA digital model 5604 can be defined by a rotation matrix defining angles of rotation of the tooth about the axes of the reference coordinate system.

At process portion 5412, residual movement data can be obtained by determining a residual movement (e.g., a displacement) of one or more of the teeth between the actual position of the tooth and the planned, final position of the tooth. In various embodiments, the residual movement comprises a movement that should preferably be completed for the objectives of the orthodontic treatment to be achieved (e.g., such that the teeth reach their desired, final positions). In some embodiments, a residual movement of a tooth comprises a 3D vector defining a difference between the 3D coordinates of a reference point of the tooth in the actual position and the 3D coordinates of a corresponding reference point of the tooth in the final position. Additionally or alternatively, a residual movement of a tooth can comprise a transformation matrix defining a translation and a rotation of the tooth between its actual position and its final position. For example, the transformation matrix can comprise a 4×4 matrix including a 3D rotation matrix and a 3D displacement vector. The transformation defining the residual movement between the actual and final positions of the tooth can be affine, rigid, or nonrigid.

In some embodiments, it can be useful to decompose the overall residual movements (e.g., displacements between the actual and final positions of the teeth) into one or more component movements. As described herein, for example with reference to FIGS. 22A-24C, a component movement can include movement of all of a patient's teeth within both of the patient's dental arches according to the same transformation (e.g., a purple movement), movement of all of a patient's teeth within one of the patient's dental arches according to the same transformation (e.g., an orange movement), movement of the patient's teeth within one dental arch relative to one another (e.g., a blue movement), etc. If the orthodontic treatment comprises the use of multiple orthodontic interventions to accomplish different component movements (e.g., elastics to accomplish interarch movements with an appliance to accomplish intraarch movements, surgery to accomplish purple movements with an appliance to accomplish blue movements, etc.) it can be advantageous to evaluate the degree to which each individual intervention has accomplished each component movement. As one example, if an appliance has accomplished all of the planned intraarch movements of a treatment plan but the elastics have only accomplished half of the planned interarch movements of a treatment plan, the decisions made with regards to how to proceed with treatment to accomplish the residual movements that still need to be completed may differ drastically from the decisions made with regards to how to proceed with treatment if the elastics have accomplished all of the interarch movements but the appliance has only accomplished half of the intraarch movement. For example, one or more orthodontic interventions can be discontinued once the associated component movements to be accomplished by the intervention have been completed.

Decomposing the overall residual movements can be similar to the processes disclosed herein, for example with reference to FIGS. 30-32E, for decomposing overall planned movements. For example, decomposing the overall residual movements can comprise performing a tooth registration to obtain a unique movement of each tooth (e.g., a blue movement) and a common movement of all of the teeth (e.g., an orange movement). Decomposing the overall residual movements comprises determining a transformation that can be applied to the teeth in the ATA digital model and/or the teeth in the FTA digital model such that an error parameter defining a difference between the spatial positions of the digital models is reduced or minimized. In some embodiments, the overall residual movements can be decomposed to determine intermediate positions of the teeth corresponding to positions of the teeth after the blue movements have been applied to the teeth in their actual positions. As a visual example of various tooth arrangements after overall and component movements, FIG. 57 illustrates a digital environment 5700 comprising a digital model of the patient's teeth in an original arrangement 5702, a digital model of the patient's teeth in a final arrangement 5704, and a digital model of the patient's teeth in an actual arrangement 5706, and a digital model of the patient's teeth in such an intermediate arrangement 5708.

Figure 57:
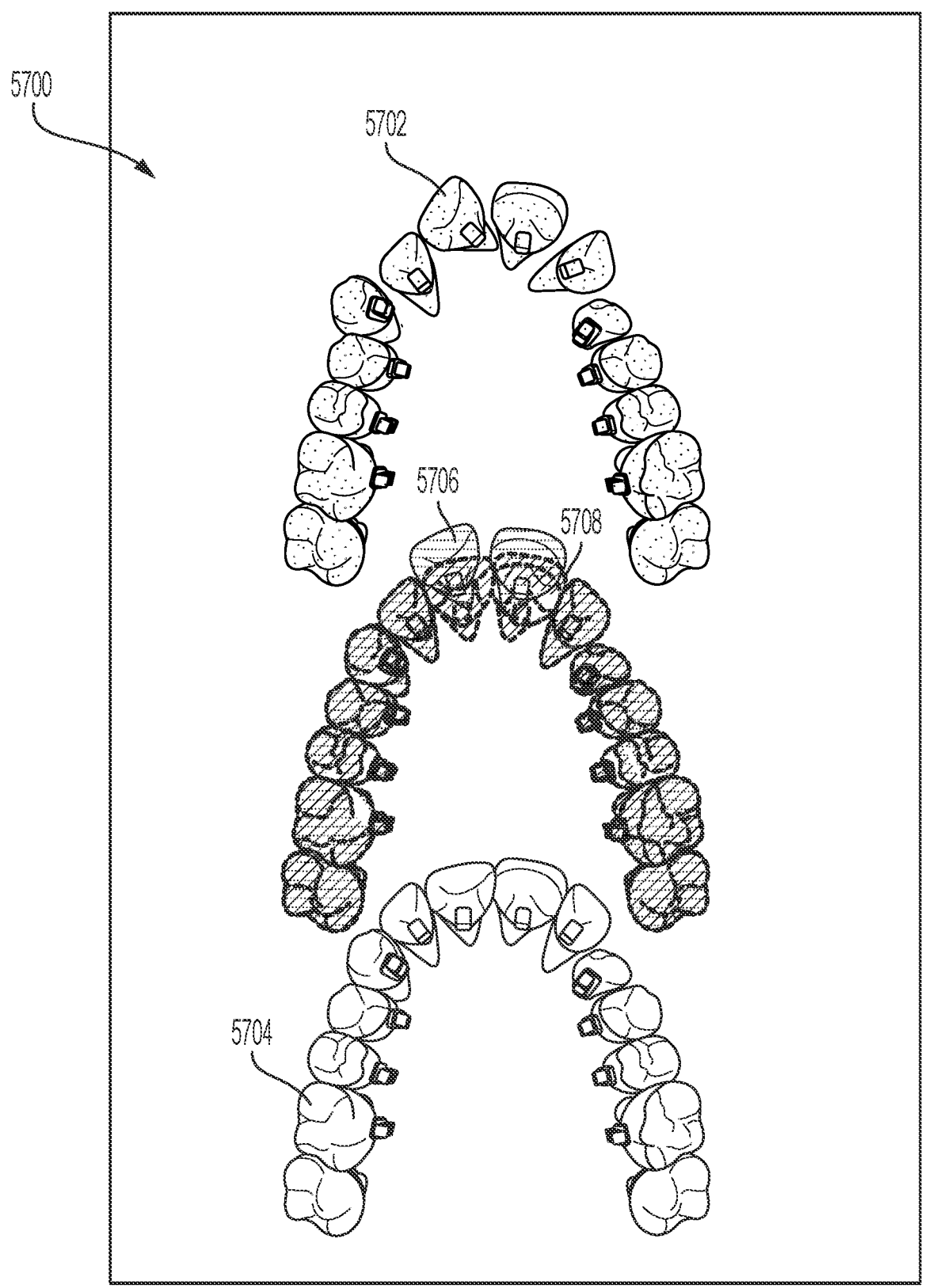
FIG. 57 illustrates a digital model of the patient's teeth in an original arrangement, a digital model of the patient's teeth in a final arrangement, and a digital model of the patient's teeth in an actual arrangement, and a digital model of the patient's teeth in an intermediate arrangement in a digital environment.

As shown in FIG. 57, moving the patient's teeth from the original arrangement 5702 to the final arrangement 5704 can comprise moving the teeth according to blue movements (e.g., to improve an alignment of the teeth in one arch) and orange movements (e.g., to improve an occlusion by moving all of the teeth in one arch). In the actual arrangement 5706 shown in FIG. 57, neither the blue movements nor the orange movements have been entirely accomplished. Specifically, the central incisors are not properly aligned with the other teeth in the dental arch, and all of the teeth in the dental arch need to move according to a common, orange movement to reach the final arrangement 5704. It can be beneficial to evaluate the progress of various types of orthodontic tooth movements, as well as evaluating an overall progress of the treatment. In some embodiments, various types of movements to be accomplished during an orthodontic treatment can occur at varying magnitudes and rates. For example, if one type of movement is to be accomplished by an orthodontic intervention whose efficacy is heavily reliant on patient compliance (e.g., orange movements accomplished by removable elastics, etc.), that type of movement may occur at a slower rate if patient compliance is poor. Evaluating the independent progress of various interventions and tooth movements can help guide future treatment decisions for an individual patient and/or a population of patients.

As previously noted, the residual movement data can characterize differences in the actual and planned positions of a patient's teeth, and thereby the movements that should be accomplished for the teeth to reach the planned positions. In some embodiments, it may be beneficial to evaluate the movements that have been accomplished, instead of or in addition to the portions of the planned movements that have not yet been accomplished. Therefore as shown in FIG. 54, the process 5304 can comprise obtaining actual movement data (process portion 5414) characterizing the actual movements that have occurred. An actual movement can be defined as the difference between the actual position of a tooth and the original position of the tooth. To obtain the actual movement data, the residual movement data can be subtracted from the planned movement data. Overall actual movement data can be obtained by subtracting the overall residual movement data from the overall planned movement data and/or component actual movement data can be obtained by subtracting the corresponding component residual movement data from the corresponding component planned movement data. Additionally or alternatively, the process 5304 shown in FIG. 54 can be performed with the OTA digital model in place of the FTA digital model to obtain actual movement data, and the residual movement data can be obtained by subtracting the actual movement data from the planned movement data.

As previously noted, the process of evaluating an orthodontic treatment 5300 includes evaluating the position data and/or the movement data (process portion 5306) obtained via process portion 5304. Process portion 5306 can comprise evaluating the position and/or movement data for a single tooth, one tooth in one dental arch, multiple teeth in one dental arch, all teeth in one dental arch, one teeth in both dental arches, multiple teeth in both dental arches, and/or all teeth in both dental arches. The position and/or movement data can be evaluated along one translational dimension, two translational dimensions, three translational dimensions, one rotational dimension, two rotational dimensions, and/or three rotational dimensions. In some embodiments, evaluating the position and/or movement data comprises obtaining a performance parameter, which can comprise a magnitude of a movement, a direction of a movement, a speed of a movement, a percentage of a planned movement that was accomplished, a percentage of a planned movement that has not yet been accomplished, and/or others. For example, a performance parameter can comprise a Euclidian distance between an actual position of a tooth and a planned position of the tooth to characterize a magnitude of a 3D translation of the tooth according to the residual movement data. Additionally or alternatively, a performance parameter can comprise an axis-angle representation (e.g., a rotation vector, an Euler vector, etc.) to characterize a magnitude and an angle of a 3D rotation of a tooth from an original position to an actual position according to the actual movement data.

As but one example for a single tooth, the performance parameters can comprise a completed percentage of a planned overall movement, a completed percentage of a planned blue movement, and/or a completed percentage of a planned orange movement. For each overall movement and each component movement, the performance parameter can characterize the movement along one or more translational directions and/or one or more rotational directions. For example, a completed percentage of a planned overall movement can comprise a Euclidean distance between a center of mass of the tooth in an actual position and the center of mass of the tooth in an original position divided by a Euclidean distance between the center of mass of the tooth in the original position and the center of mass of the tooth in the planned position.

In various embodiments, evaluating the position and/or movement data (process portion 5306) comprises obtaining a performance parameter summarizing performance parameters of multiple teeth. For example, in some embodiments a performance parameter comprises an average of the actual overall movements of two or more of the patient's teeth divided by an average of the planned overall movements of corresponding ones of the patient's teeth. In various embodiments, it may be useful to evaluate corresponding performance parameters of various teeth. For example, a performance parameter can be evaluated and compared across all teeth, and the tooth with the worst of the performance parameters can be used to determine an accuracy, efficiency, etc. of the treatment.

Evaluating the position and/or movement data can comprise comparing the position and/or movement data to a predetermined threshold. In some embodiments, a measure of the actual movement data relative to the planned movement data can be evaluated against a completion threshold. For example, if the average actual overall movements of all of the teeth divided by the average planned overall movements of all of the teeth is greater than the completion threshold, the treatment can be considered complete, and any active orthodontic interventions can be discontinued. Such completion threshold can be, for example about 0.8, about 0.85, about 0.90, about 0.95, about 0.99, no less than 0.8, no less than 0.85, no less than 0.90, no less than 0.95, or no less than 0.99. Additionally or alternatively, a measure of the residual movement data relative to the planned movement data can be evaluated against a residual threshold. For example, if a residual overall movement of one of the teeth along a mesiodistal direction divided by a planned overall movement of the tooth along the mesiodistal direction is less than the residual threshold, the treatment can be considered complete, and any active orthodontic interventions can be discontinued. Such residual threshold can be, for example about 0.05, about 0.1, about 0.15, about 0.2, about 0.25, no more than 0.05, no more than 0.1, no more than 0.15, no more than 0.2, or no more than 0.25.

Based on the evaluation of the orthodontic treatment, a human operator and/or an automated process can determine if and/or how treatment should proceed. For example, if, based on the evaluation, it is determined that the patient's teeth are at or sufficiently close to their desired, final positions, the treatment can be concluded in its entirety. Additionally or alternatively, as previously noted, in some cases certain planned component movements may be accomplished at varying rates. If a first component movement is sufficiently accomplished by a first orthodontic intervention but a second component movement to be accomplished by a second orthodontic intervention has not been sufficiently completed, the first orthodontic intervention can be discontinued while the second orthodontic intervention continues to be employed to move the patient's teeth. In some embodiments, it may be advantageous to modify an orthodontic treatment and/or intervention prior to its completion. As an example, if it is determined that a patient's teeth are moving much slower in response to forces applied by orthodontic elastics than anticipated, it may be beneficial to replace the patient's current elastics with elastics configured to apply greater forces and thereby move the patient's teeth more quickly to reduce the duration of the orthodontic treatment.

As shown in FIG. 19, based on the evaluation the process 1900 for orthodontically treating a patient can repeat, starting with obtaining movement data. In this example, and in other examples, the actual movements accomplished compared to the planned movements may not have sufficiently moved the patient's teeth to the desired, final positions and additional treatment and/or a new or modified treatment may be desirable or required. For example, if an appliance has been installed in a patient's mouth for a sufficient duration of time such that the treatment should be completed, but the patient's teeth are not sufficiently close to the planned, final positions, additional treatment may be required and/or desired to move the patient's teeth closer to the planned, final positions. In these and other embodiments, the evaluation of the position data and/or the movement data can inform the next steps in planning and implementing further orthodontic treatment. For example, based on the types, magnitudes, and directions of the residual movements, it may be beneficial to complete the treatment using a polymeric aligner that is quick and inexpensive to fabricate. However, if large and/or difficult movements are still needed to move the teeth to their final positions, it may be beneficial to design and manufacture an appliance that is better suited to accomplish such movements (e.g., appliances 100, 3802, etc. as disclosed herein).

If further treatment is desired and/or needed, the process 1900 can repeat with obtaining new movement data, obtaining a new treatment plan, communicating the new movement data and/or treatment plan, implementing the new treatment, and/or evaluating the new treatment. In some embodiments, the ATA digital model can be used as the OTA digital model when obtaining new movement data. Additionally or alternatively, the previous FTA digital model can be used as the new FTA digital model. In many cases, the previous or original FTA will not change after some or all of an original treatment has been implemented, because the originally-determined final positions of the teeth will remain the positions at which the teeth function optionally and are aesthetic. In some cases, it may be useful to modify the FTA based on specific challenges that occurred during the previous treatment. Obtaining the new movement data can comprise decomposing overall movements into one or more component movements, as described herein.

In some embodiments, it may be advantageous to select and/or modify an orthodontic intervention for accomplishing the new movements of the teeth. For example, if the planned intraarch movements were sufficiently accomplished during the previous treatment but the planned interarch movements were not, it may be preferable to replace an appliance that was used to accomplish the intraarch movements with a retainer configured to maintain the intraarch relationship of the teeth and to secure the retainer to orthodontic elastics for further modification of the patient's interarch arrangement of the teeth. Additionally or alternatively, if an actual movement of a tooth was significantly less than the planned movement, it may be advantageous to design an appliance such that the appliance is configured to impart a much greater force and/or moment to the tooth such that the residual movement of the tooth can be accomplished.

In some embodiments, a shape forming fixture of the present technology (e.g., fixture 1700, fixture 3300, etc.) can be modified based on evaluation of the data. If one or more additional appliances should be manufactured to further reposition a patient's teeth, it can be advantageous to modify the shape forming fixture based on the evaluation of the position and/or movement data. As discussed herein, positions of securing members of the shape forming fixture can be based on intermediate positions of the patient's teeth (e.g., positions of the patient's teeth after blue, intraarch movements, etc.). Thus, positions of the securing portions of a secondary shape forming fixture can be based on the actual, intermediate positions of the teeth based on the decomposition of the actual overall movement. Additionally or alternatively, the positions of the securing portions of the secondary shape forming fixture can be modified based on the evaluation of the data. For example, if one of the patient's canine teeth moved much slower than the other teeth, the canine may be overcorrected to a greater degree. In such example, the position of the securing member of the shape forming fixture that corresponds to the problematic canine can be moved such that an appliance formed with the shape forming fixture is configured to move the canine to an overcorrected final position. Additionally or alternatively, securing portions of the secondary shape forming fixture can be modified based on the evaluation of the actual positions of the securing members. If a securing member was inaccurately bonded to a patient's tooth such that the actual position of the securing member differs from its intended position, it can be beneficial to modify the position of the securing portion of the fixture to reflect the actual position of the securing member.

As previously noted, it can be useful for an evaluation of a preceding orthodontic treatment to inform a subsequent orthodontic treatment for the patient. Additionally or alternatively, evaluation of orthodontic treatment of one or more patient can inform orthodontic treatment of other future patients. Position data (e.g., original position data, final position data, intermediate position data, actual position data, etc.) and/or movement data (e.g., planned overall movement data, planned component movement data, actual overall movement data, actual component movement data, residual overall movement data, residual component movement data, etc.) associated with multiple patients can be stored in a database. Other information such as patient demographic information, clinical information, orthodontic intervention information, etc. can be stored in the database. The data stored in the database can comprise categorical variables (e.g., sex, age group, ethnicity, type of intervention, tooth type, jaw, appliance geometric design, etc.) and/or continuous variables (e.g., residual overall movement of a tooth, percentage of planned component movements that was completed, force to be imparted on a tooth by an appliance, speed of tooth movement, etc.).

The data stored in the database can be evaluated to assess relationships between variables. For example, the data can be statistically analyzed to determine how types of orthodontic interventions are related to percentages of planned component movements that are accomplished, to determine if and/or how age group of the patient is related to a maximum residual overall movement after use of a first orthodontic intervention, determine how a force to be imparted to a tooth by an appliance and the type of tooth is related to movement speed, etc. The statistical analysis of the data can comprise a univariate analysis, a bivariate analysis, or a multivariate analysis. The analysis can comprise a regression (e.g., linear, logarithmic, multiple, etc.), an analysis of variance (e.g., ANOVA, MANOVA, etc.), a factor analysis, a cluster analysis, a discriminant analysis, a conjoint analysis, a canonical correlation analysis, structural equation modeling, multidimensional scaling, a t-test, a chi-squared test, or another suitable analysis.

A treatment plan of a patient, including movement data, intervention selections, appliance designs, estimated treatment time, etc., can be based at least in part on an evaluation of data stored in the database. For example, if evaluation of the data inversely correlates age with tooth movement speed, an appliance designed for an older patient may be configured to apply greater forces to the patient's teeth than an appliance designed for a younger patient. In one example, if evaluation of the data indicates that teeth moved by an appliance having a specific design are associated with lower percentage completion of planned overall movements, a design of the appliance can be modified.

Figure 58:
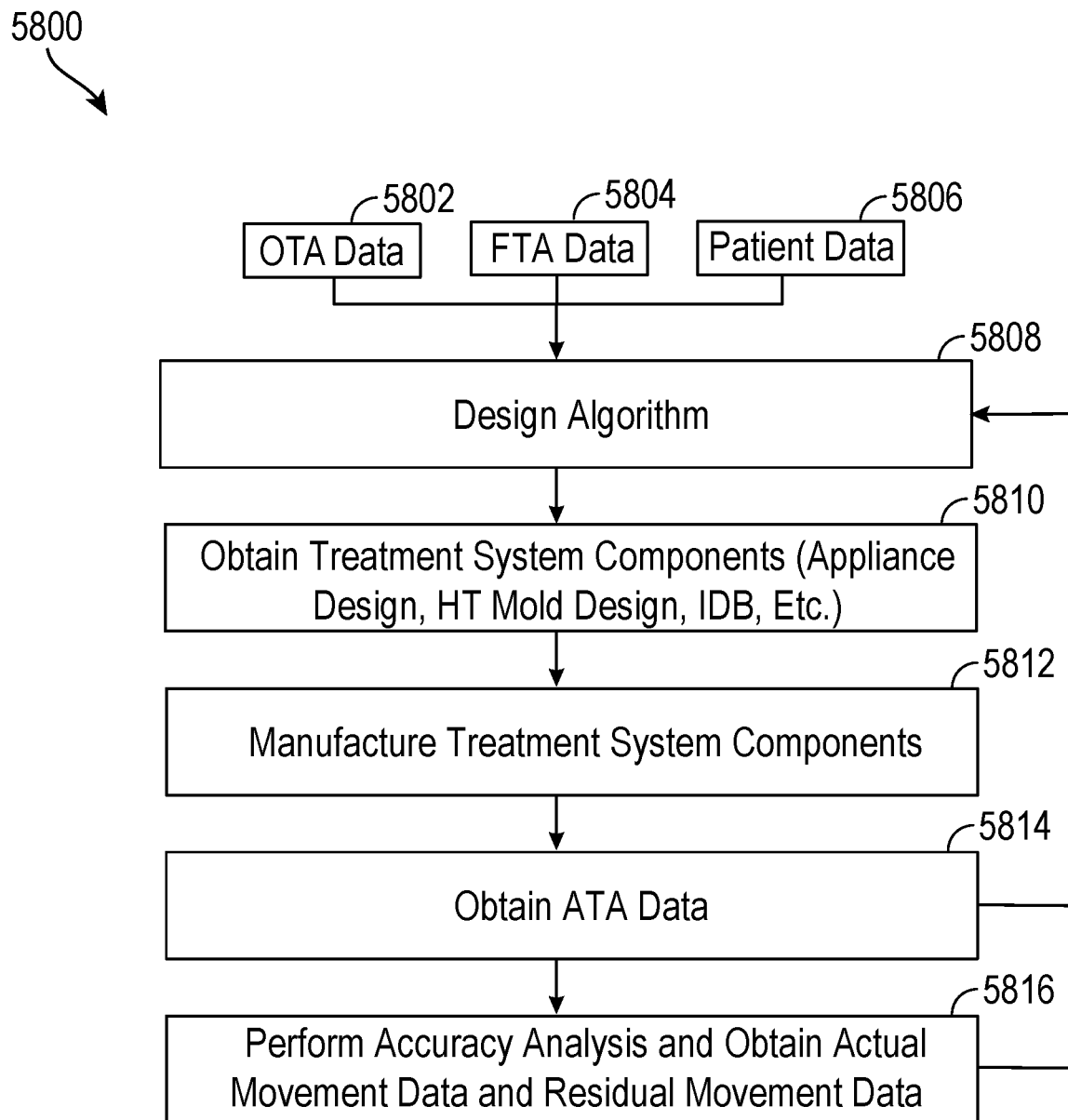
FIG. 58 is a flow diagram of an example process for designing an orthodontic treatment plan and/or system in accordance with embodiments of the present technology.

FIG. 58 shows a process 5800 for designing an orthodontic treatment plan and/or system in accordance with several embodiments of the present technology. The process 5800 can include running a design algorithm to design one or more aspects of the appliance and/or manufacturing assembly (such as a shape setting fixture). The process 5800 can be configured to modify and/or train the algorithm (via machine learning, neural networks, etc.) any time the process 5800 receives ATA data, actual movement data, and/or residual movement data. In some embodiments, the process 5800 comprises obtaining one or more inputs, such as OTA data (5802), FTA data (5804), patient data (5806) (e.g., age, ethnicity, etc. as described herein), and/or other data. The process 5800 proceeds with running a design algorithm 5808. The design algorithm 5808 can output an appliance design, a fixture design, an IDB design, and/or another treatment system component (5810). Next, the one or more treatment system components can be manufactured in their physical forms (5812). The process 5800 continues with obtaining ATA data (5814) and performing an accuracy analysis to obtain actual movement data and/or residual movement data (5816). The ATA data, actual movement data, and/or residual movement data can then be fed back into the design algorithm to improve the design of future treatment components.

CONCLUSION

Although many of the embodiments are described above with respect to systems, devices, and methods for orthodontic treatment, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-58.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method comprising:
    obtaining first data characterizing original positions of a patient's teeth;
    obtaining second data characterizing planned positions of the teeth;
    for each tooth in one jaw of a patient, determining a planned displacement between the corresponding original position and the corresponding planned position based on the first and second data;
    for each planned displacement,
        determining a first portion of the planned displacement unique to the tooth associated with the planned displacement, and
        determining a second portion of the planned displacement shared by all of the planned displacements;
    obtaining third data characterizing actual positions of the teeth after the teeth have been at least partially repositioned by the orthodontic treatment;
    for each tooth in the one jaw of the patient, determining a residual displacement between the corresponding actual position and the corresponding planned position based on the second and third data;
    for each residual displacement,
        determining a first portion of the residual displacement unique to the tooth associated with the residual displacement, and
        determining a second portion of the residual displacement shared by all of the residual displacements;
    comparing the first portion of the residual displacement to the first portion of the planned displacement and comparing the second portion of the residual displacement to the second portion of the planned displacement;
    based at least in part on the comparison, indicating if further orthodontic treatment is recommended; and
    if further orthodontic treatment is recommended, manufacturing an orthodontic appliance configured to accomplish at least one of the first portion of the residual displacement or the second portion of the residual displacement.

2. The method of claim 1, wherein the indication includes one or more suggested orthodontic interventions to accomplish one or more portions of the residual displacements.

3. The method of claim 1, wherein comparing a corresponding portion of the planned and residual displacements comprises determining a remaining percentage of the corresponding portion of the planned displacement.

4. The method of claim 3, wherein further orthodontic treatment is recommended if the percentage remaining of the planned displacement for one of the teeth is greater than a predetermined threshold.

5. The method of claim 3, wherein registering the third data to the second data comprises identifying a rigid transformation that, when applied to the third data, reduces an error parameter characterizing a difference between the third data and the second data.

6. The method of claim 1, wherein further orthodontic treatment is recommended if a magnitude of the residual displacement for one of the teeth is greater than a predetermined threshold.

7. The method of claim 1, further comprising, before determining the residual displacements, registering the third data to the second data.

8. The method of claim 1, further comprising:
    for each tooth in the one jaw of the patient, determining an actual displacement between the corresponding original position and the corresponding actual position based on the first and third data;
    for each actual displacement,
        determining a first portion of the actual displacement unique to the tooth associated with the actual displacement, and
        determining a second portion of the actual displacement shared by all of the actual displacements.

9. A method comprising:
    obtaining first data characterizing original positions of teeth of a patient;
    obtaining second data characterizing final positions of the patient's teeth;
    based on the first and second data, determining planned movement data characterizing a planned movement of each of the patient's teeth from the original position to the final position;
    decomposing the planned movement data into first planned movement data and second planned movement data, wherein the first planned movement data characterizes a first component of the planned movement achievable by a first orthodontic intervention, and wherein the second planned movement data characterizes a second component of the planned movement achievable by a second orthodontic intervention that is a different type of orthodontic intervention than the first orthodontic intervention;
    obtaining third data characterizing actual positions of the patient's teeth after at least one of the first orthodontic intervention or the second orthodontic intervention has been at least partially implemented;

based on first and third data, determining actual movement data characterizing an actual movement of each of the patient's teeth from the original position to the actual position;

decomposing the actual movement data into first actual movement data and second actual movement data, wherein the first actual movement data characterizes a first component of the actual movement achieved by the first orthodontic intervention, and wherein the second actual movement data characterizes a second component of the actual movement achieved by the second orthodontic intervention;

comparing the first actual movement data to the first planned movement data and comparing the second actual movement data to the second planned movement data;

based at least in part on the comparison, indicating whether further orthodontic treatment is recommended; and if further orthodontic treatment is recommended, obtaining an orthodontic appliance configured to achieve a residual movement of at least one of the patient's teeth, the residual movement comprising a difference between the first planned movement and the first actual movement or a difference between the second planned movement and the second actual movement.

10. The method of claim 9, wherein comparing the first actual movement data to the first planned movement data comprises determining a percentage of the first portion of the planned movement that has been achieved by the first orthodontic intervention.

11. The method of claim 9, wherein comparing the second actual movement data to the second planned movement data comprises determining a percentage of the second portion of the planned movement that has been achieved by the second orthodontic intervention.

12. The method of claim 9, wherein obtaining the third data comprises obtaining image data characterizing the patient's teeth after at least one of the first orthodontic intervention or the second orthodontic intervention has been at least partially implemented.

13. The method of claim 9, wherein:
the first orthodontic intervention comprises an appliance including a plurality of attachment portions each configured to secure to one of the patient's teeth and a connector extending between adjacent ones of the attachment portions; and
the second orthodontic intervention comprises at least one of an elastic, a temporary anchorage device, a platform, or surgery.

14. The method of claim 9, wherein the orthodontic appliance comprises a plurality of attachment portions each configured to secure to one of the patient's teeth and a connector extending between adjacent ones of the attachment portions.

15. The method of claim 9, wherein the first planned movement is unique to the tooth associated with the first planned movement and the second planned movement is shared by all of the planned movements.

16. The method of claim 9, wherein a first duration of treatment during which the first orthodontic intervention is implemented at least partially overlaps with a second duration of treatment during which the second orthodontic intervention is implemented.

17. A method comprising:
obtaining an original tooth arrangement (OTA) digital model characterizing original positions of a patient's teeth in a jaw of the patient;
obtaining a final tooth arrangement (FTA) digital model characterizing desired, final positions of the patient's teeth in the jaw;
based on the OTA and FTA digital models, determining planned displacement data characterizing a planned movement of each of the patient's teeth from the original position to the final position, wherein each planned movement has a first portion unique to the tooth associated with the planned movement and a second portion shared by all of the planned movements;
obtaining an actual tooth arrangement (ATA) digital model characterizing actual positions of the patient's teeth in the jaw;
registering the ATA digital model to the FTA digital model;
based on the registered ATA digital model and the FTA digital model, determining residual movement data characterizing a residual movement of each of the patient's teeth from the actual position to the final position, wherein each residual movement has a first portion unique to the tooth associated with the residual movement and a second portion shared by all of the residual movements;
comparing the first portions of the planned and residual movements and comparing the second portions of the planned and residual movements;
based on the comparison, indicating whether further orthodontic treatment is recommended; and
if further orthodontic treatment is recommended, obtaining an orthodontic appliance configured to accomplish the first portion of the residual movement or the second portion of the residual movement.

18. The method of claim 17, wherein at least one of the OTA digital model, the FTA digital model, or the ATA digital model is segmented and comprises a plurality of distinct tooth models.

19. The method of claim 18, wherein obtaining the ATA digital model comprises, for each of the teeth in the ATA digital model, positioning a corresponding one of the distinct tooth models from the OTA digital model or the FTA digital model at the corresponding actual position of the tooth as characterized by the ATA digital model.

* * * * *